United States Patent
Avniel et al.

(10) Patent No.: US 10,683,505 B2
(45) Date of Patent: Jun. 16, 2020

(54) METHODS OF INTRODUCING DSRNA TO PLANT SEEDS FOR MODULATING GENE EXPRESSION

(71) Applicant: A.B. Seeds Ltd., Lod (IL)

(72) Inventors: Amir Avniel, Tel-Aviv (IL); Efrat Lidor-Nili, Nes Ziona (IL); Rudy Maor, Rechovot (IL); Ofir Meir, Doar-Na Emek Soreq (IL); Orly Noivirt-Brik, Givataim (IL)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 848 days.

(21) Appl. No.: 14/143,836

(22) Filed: Dec. 30, 2013

(65) Prior Publication Data

US 2014/0230090 A1    Aug. 14, 2014

Related U.S. Application Data

(60) Provisional application No. 61/748,095, filed on Jan. 1, 2013, provisional application No. 61/748,101, filed on Jan. 1, 2013, provisional application No. 61/748,094, filed on Jan. 1, 2013, provisional application No. 61/748,099, filed on Jan. 1, 2013, provisional application No. 61/814,888, filed on Apr. 23, 2013, provisional application No. 61/814,892, filed on Apr. 23, 2013, provisional application No. 61/814,899, filed on Apr. 23, 2013, provisional application No. 61/814,890, filed on Apr. 23, 2013, provisional application No. 61/908,865, filed on Nov. 26, 2013, provisional application No. 61/908,855, filed on Nov. 26, 2013.

(51) Int. Cl.
*C12N 15/82* (2006.01)
*C12N 15/113* (2010.01)

(52) U.S. Cl.
CPC ........ *C12N 15/1137* (2013.01); *C12N 15/113* (2013.01); *C12N 15/8218* (2013.01); *C12N 15/8279* (2013.01); *C12N 15/8283* (2013.01); *C12N 15/8286* (2013.01); *C12N 15/1131* (2013.01); *C12N 2310/14* (2013.01); *C12N 2320/32* (2013.01); *Y02A 40/162* (2018.01)

(58) Field of Classification Search
CPC .............. C12N 15/1137; C12N 15/113; C12N 15/8218; C12N 15/8286
See application file for complete search history.

(56) References Cited

U.S. PATENT DOCUMENTS

| | | |
|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |

(Continued)

FOREIGN PATENT DOCUMENTS

AU    2008258254 B2    7/2014
AU    2014262189 B2    11/2014
(Continued)

OTHER PUBLICATIONS

Friedberg, Iddo. "Automated protein function prediction—the genomic challenge." Briefings in bioinformatics 7.3 (2006): 225-242.*
Ulrich, Julia, et al. "Large scale RNAi screen in Tribolium reveals novel target genes for pest control and the proteasome as prime target." BMC genomics 16.1 (2015): 674 (Year: 2015).*
Zotti, M. J., and Guy Smagghe. "RNAi technology for insect management and protection of beneficial insects from diseases: lessons,challenges and risk assessments." Neotropical entomology 44.3 (2015):197-213 (Year: 2015).*
Christiaens, Olivier, and Guy Smagghe. "The challenge of RNAi-mediated control of hemipterans." Current Opinion in Insect Science 6 (2014): 15-21 (Year: 2014).*

(Continued)

*Primary Examiner* — Weihua Fan
(74) *Attorney, Agent, or Firm* — Arnold & Porter Kaye Scholer LLP; Amanda Carmany-Rampey; David R. Marsh

(57) ABSTRACT

A method of introducing an exogenous non-transcribable polynucleotide trigger, for example dsRNA, molecule into a seed is provided. The method comprises contacting the seed with the exogenous non-transcribable polynucleotide trigger, for example dsRNA, molecule under conditions which allow penetration of the exogenous non-transcribable polynucleotide trigger, for example dsRNA, molecule into the seed, thereby introducing the exogenous non-transcribable polynucleotide trigger, for example dsRNA, molecule into the seed.

12 Claims, 65 Drawing Sheets

Specification includes a Sequence Listing.

(56) References Cited

U.S. PATENT DOCUMENTS

| | | |
|---|---|---|
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 7/2002 | McElroy et al. |
| 6,437,217 B1 | 8/2002 | McElroy et al. |

(56) References Cited

U.S. PATENT DOCUMENTS

| | | |
|---|---|---|
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Antoni et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 9,777,288 B2 | 10/2017 | Beattie et al. |
| 9,850,496 B2 | 12/2017 | Beattie et al. |
| 9,856,495 B2 | 1/2018 | Beattie et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1 | 11/2003 | Rottman et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0127444 A1 | 7/2004 | Spradling et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1 | 10/2005 | Clinton et al. |
| 2005/0246784 A1 | 11/2005 | Plesch et al. |
| 2005/0250647 A1 | 11/2005 | Hills et al. |
| 2005/0289664 A1 | 12/2005 | Moshiri et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Racmackers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |

(56) References Cited

U.S. PATENT DOCUMENTS

| | | |
|---|---|---|
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0203013 A1 | 8/2011 | Peterson et al. |
| 2011/0296555 A1 | 12/2011 | Ivashuta et al. |
| 2011/0296556 A1* | 12/2011 | Sammons ............... A01N 63/02 800/298 |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1* | 6/2012 | Baum ..................... A01N 63/02 424/409 |
| 2012/0174262 A1 | 7/2012 | Azhakanandam et al. |
| 2012/0185967 A1 | 7/2012 | Sela et al. |
| 2012/0198586 A1* | 8/2012 | Narva ............... C07K 14/43563 800/279 |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| CN | 101279950 A | 10/2008 |
| CN | 101279951 A | 10/2008 |
| CN | 101892247 A | 11/2010 |
| CN | 101914540 A | 12/2010 |
| CN | 102154364 A | 8/2011 |
| CN | 102481311 A | 5/2012 |
| CN | 102822350 A | 12/2012 |
| CN | 102906263 A | 1/2013 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| RU | 2 291 613 C1 | 1/2007 |
| RU | 2 337 529 C1 | 11/2008 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/14348 A1 | 3/1999 |
| WO | WO 99/024585 A1 | 5/1999 |
| WO | WO 99/26467 | 6/1999 |
| WO | WO 99/26467 A1 | 6/1999 |
| WO | WO 99/27116 A2 | 6/1999 |
| WO | WO 99/32619 | 7/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |

(56) References Cited

FOREIGN PATENT DOCUMENTS

| | | |
|---|---|---|
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A2 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/153607 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A2 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 * | 1/2011 ............. C12N 15/82 |
| WO | WO-2011/001434 A1 * | 1/2011 ............. C12N 15/82 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A1 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |

(56) References Cited

FOREIGN PATENT DOCUMENTS

| | | |
|---|---|---|
| WO | WO 2012/156342 A1 | 11/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Li, H., et al. "Long dsRNA but not siRNA initiates RNAi in western corn rootworm larvae and adults." Journal of Applied Entomology 139.6 (2015): 432-445 (Year: 2015).*

Friedberg, Iddo. "Automated protein function prediction—the genomic challenge." Briefings in bioinformatics 7.3 (2006): 225-242. (Year: 2006).*

Töpfer, Reinhard, et al. "Uptake and transient expression of chimeric genes in seed-derived embryos." The Plant Cell;1.1 (1989): 133-139. (Year: 1989).*

Chee et al., "Transformation of Soybean (*Glycine max*) by Infecting Germination Seeds With *Agrobacterium tumefaciens*," *Plant Physiology*, 91:1212-1218 (1989).

Dalmay et al., "An RNA-Dependent RNA Polymerase Gene in *Arabidopsis* Is Required for Posttranscriptional Gene Silencing Mediated by a Transgene But Not by a Virus," *Cell*, 101(5):543-553 (2000).

International Search Report and the Written Opinion dated Oct. 1, 2013 From the International Searching Authority Re. Application No. PCT/IL2013/050447.

Alarcón-Reverte et al., "Resistance to ACCase-inhibiting herbicides in the weed *Lolium multiflorum*," *Comm. Appl. Biol. Sci.*, 73(4):899-902 (2008).

Amarzguioui et al., "An algorithm for selection of functional siRNA sequences," *Biochemical and Biophysical Research Communications*, 316:1050-1058 (2004).

Ambrus et al., "The Diverse Roles of RNA Helicases in RNAi," *Cell Cycle*, 8(21):3500-3505 (2009).

An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).

Andersson et al., "A novel selection system for potato transformation using a mutated AHAS gene," *Plant Cell Reports*, 22(4):261-267 (2003).

Anonymous, "A handbook for high-level expression and purification of 6xHis-tagged proteins," *The QUIexpressionist*, (2003).

Anonymous, "Agronomy Facts 37: Adjuvants for enhancing herbicide performance," *n.p.*, 1-8, (Jan. 26, 2000), *Web*, (Jan. 21, 2014).

Anonymous, "Devgen, The mini-Monsanto," KBC Securities (2006).

Anonymous, "Do Monsanto have the next big thing?," *Australian Herbicide Resistance Initiative (AHRI)*, (Apr. 23, 2013) *Web*. (Jan. 19, 2015).

Aoki et al., "In Vivo Transfer Efficiency of Antisense Oligonucleotides into the Myocardium Using HVJ-Liposome Method," *Biochem Biophys Res Commun*, 231:540-545 (1997).

Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).

Artmymovich, "Using RNA interference to increase crop yield and decrease pest damage," *MMG 445 Basic Biotech.*, 5(1):7-12 (2009).

Australian Patent Examination report No. 1 dated Nov. 11, 2013, in Australian Application No. 2011224570.

Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).

Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).

Baulcombe, "RNA silencing and heritable epigenetic effects in tomato and *Arabidopsis*," Abstract 13$^{th}$ Annual Fall Symposium, Plant Genomes to Phenomes, Donald Danforth Plant Science Center, 28-30 (2011).

Bayer et al., "Programmable ligand-controlled riboregulators of eukaryotic gene expression," *Nature Biotechnol.*, 23(3):337-343 (2005).

Beal, et al., "Second Structural Motif for Recognition of DNA by Oligonucleotide-Directed Triple-Helix Formation," *Science*, 251:1360-1363 (1992).

Becker et al., "Fertile transgenic wheat from microprojectile bombardment of scutellar tissue," *The Plant Journal*, 5(2):299-307 (1994).

Bhargava et al., "Long double-stranded RNA-mediated RNA interference as a tool to achieve site-specific silencing of hypothalamic neuropeptides," *Brain Research Protocols*, 13:115-125 (2004).

Boletta et al., "High Efficient Non-Viral Gene Delivery to the Rat Kidney by Novel Polycationic Vectors," *J. Am Soc. Nephrol.*, 7:1728 (1996).

Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).

Bolter et al., "A chloroplastic inner envelope membrane protease is essential for plant development," *FEBS Letters*, 580:789-794 (2006).

Breaker et al., "A DNA enzyme with $Mg^{2+}$-dependent RNA phosphoesterase activity," *Chemistry and Biology*, 2:655-660 (1995).

Brodersen et al., "The diversity of RNA silencing pathways in plants," *Trends in Genetics*, 22(5):268-280 (2006).

Busi et al., "Gene flow increases the initial frequency of herbicide resistance alleles in unselectedpopulations," *Agriculture, Ecosystems and Environments*, Elsevier, Amsterdam, NL, 142(3):403-409 (2011).

Butler et al., "Priming and re-drying improve the survival of mature seeds of *Digitalis purpurea* during storage," *Annals of Botany*, 103:1261-1270 (2009).

Bytebier et al., "T-DNA organization in tumor cultures and transgenic plants of the monocotyledon *Asparagus officinalis*," *Proc. Natl. Acad. Sci. U.S.A.*, 84:5345-5349 (1987).

Chabbouh et al., "Cucumber mosaic virus in artichoke," *FAO Plant Protection Bulletin*, 38:52-53 (1990).

Chakravarty et al., "Genetic Transformation in Potato: Approaches and Strategies," *Amer J Potato Res*, 84:301 311 (2007).

Chen et al., "In Vivo Analysis of the Role of atTic20 in Protein Import into Chloroplasts," *The Plant Cell*, 14:641-654 (2002).

Cheng et al., "Production of fertile transgenic peanut (*Arachis hypogaea* L.) plants using *Agrobacterium tumefaciens*," *Plant Cell Reports*, 15:653-657 (1996).

Chi et al., "The Function of RH22, a Dead RNA Helicase, in the Biogenesis of the 50S Ribosomal Subunits of *Arabidopsis* Chloroplasts," *Plant Physiology*, 158:693-707 (2012).

Chinese Office Action dated Aug. 28, 2013 in Chinese Application No. 201180012795.2.

Clough et al., "Floral dip: a simplified method for Agrobacterium-mediated transformation of *Arabidopsis thaliana*," *The Plant Journal*, 16(6):735-743 (1998).

CN101914540 Patent Diclosure, "Introduction of RNA into plant by interference," (2010).

Colbourne et al., "The Ecoresponsive Genome of Daphnia pulex," *Science*, 331(6017):555-561 (2011).

(56) References Cited

OTHER PUBLICATIONS

Colombian Office Action dated Aug. 2, 2013 in Application No. 12 152898.
Colombian Office Action dated Feb. 21, 2014 in Application No. 12 152898.
Cooney et al., "Site-Specific Oligonucleotide Binding Represses Transcription of the Human c-myc Gene in Vitro," *Science*, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
Della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Dietemann et al., "*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Feb. 2, 2015, in European Patent Application No. 12 830 932.5.
Extended European Search Report dated Feb. 3, 2015, in European Patent Application No. 12 831 945.6.
Extended European Search Report dated Feb. 27, 2015, in European Patent Application No. 12 832 160.1.
Extended European Search Report dated Mar. 3, 2015, in European Patent Application No. 12 831 166.9.
Extended European Search Report dated Mar. 17, 2015, in European Patent Application No. 12 831 684.1.
Partial Supplementary European Search Report dated Mar. 2, 2015, in European Patent Application No. 12 831 494.5.
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
First Examination Report dated Apr. 23, 2013, in New Zealand Patent Application No. 601784.
Fukuhara et al., "The wide distribution of endornaviruses, large double-stranded RNA replicons with plasmid-like properties," *Archives of Virology*, 151:995-1002 (2006).

Further Examination Report issued in New Zealand Patent Application No. 601784 dated May 16, 2014.
Gaines et al., "Gene amplification confers glyphosate resistance in *Amaranthus palmeri*," *Proc. Natl. Acad. Sci. USA*, 107(3):1029-1034 (2010).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. AY545657.1, published 2004.
GenBank accession No. GI:186478573, published Jan. 22, 2014.
GenEmbl FJ861243, published Feb. 3, 2010.
Gong et al., "Silencing of Rieske iron-sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus?*," *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and- independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).

(56) References Cited

OTHER PUBLICATIONS

Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability dated Sep. 11, 2014, in International Application No. PCT/IL13/50447.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).

Kirkwood, "Use and Mode of Action of Adjuvants for Herbicides: A Review of some Current Work," *Pestic Sci.*, 38:93-102 (1993).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kusaba et al., "Low glutelin content1: A Dominant Mutation That Suppresses the Glutelin Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of *Arabidopsis* and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Masoud et al., "Constitutive expression of an inducible β-1,3-glucanase in alfalfa reduces disease severity caused by the oomycete pathogen *Phytophthora megasperma* f. sp medicaginis, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).

(56) References Cited

OTHER PUBLICATIONS

Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Misawa et al., "Expression of an Erwinia phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis yellow variegated* Mutants," *The Plant Cell*, 19:1313-1328 (2007).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action dated Jan. 6, 2015, in Japanese Patent Application No. 2012-557165.
Office Action dated Nov. 19, 2014, in Eurasian Patent Application No. 201201264/28.
Ongvarrasopone et al., "A Simple and Cost Effective Method to Generate dsRNA for RNAi Studies in Invertebrates," *Science Asia*, 33:35-39 (2007).
Ouellet et al., "Members of the Acetohydroxyacid Synthase Muligene Family of *Brassica napus* Have Divergent Patterns of Expression," *The Plant Journal*, Blackwell Scientific Publications, Oxford, GB, 2(3):321-330 (1992).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of Shrunken-2 Corn," *J. Amer. Soc. Hort. Sci.*, 119(3):629-635 (1994).
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by *Arabidopsis* induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).

Qiwei, "Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That Is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Sharma et al., "A simple and efficient *Agrobacterium*-mediated procedure for transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Temple et al., "Can glutamine synthetase activity levels be modulated in transgenic plants by the use of recombinant DNA technology?" *Transgenic Plants and Plant Biochemistry*, 22:915-920 (1994).

(56) References Cited

OTHER PUBLICATIONS

Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "Clustal W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Tran et al., "Control of specific gene expression in mammalian cells by co-expression of long complementary RNAs," *FEBS Lett.*;573(1-3):127-134 (2004).
Turina et al., "Tospoviruses in the Mediterranean Area," *Advances in Virus Research*, 84:403-437 (2012).
Tuschl, "RNA Interference and Small Interfering RNAs," *ChemBiochem*. 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).
Van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants Is Initiated by Localized Introduction of Ectopic Promoterless DNA," *Cell*, 95:177-187 (1998).

Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol*. 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al.,"An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "Agrobacterium-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al.,"*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).
Agrios, *Plant Pathology* (Second Edition), 2:466-470 (1978).
Bai et al., "Naturally Occurring Broad-Spectrum Powdery Mildew Resistance in a Central American Tomato Accession Is Caused by Loss of Mlo Function," *MPMI*, 21(1):30-39 (2008).
Bourgeois et al., "Field and producer survey of ACCase resistant wild oat in Manitoba," *Canadian Journal of Plant Science*, 709-715 (1997).
Brugière et al., "Glutamine Synthetase in the Phloem Plays a Major Role in Controlling Proline Production," *The Plant Cell*, 11:1995-2011 (1999).
Chang et al., "Cellular Internalization of Fluorescent Proteins via Arginine-rich Intracellular Delivery Peptide in Plant Cells," *Plant Cell Physiol.*, 46(3):482-488 (2005).

(56) References Cited

OTHER PUBLICATIONS

Communication pursuant to Article 94(3) EPC dated Jun. 26, 2015, as received in European Patent Application No. 11 753 916.3.
Communication pursuant to Article 94(3) EPC dated Oct. 23, 2015, as received in European Patent Application No. 12 831 945.6.
Desai et al., "Reduction in deformed wing virus infection in larval and adult honey bees (Apis mellifera L.) by double-stranded RNA ingestion," Insect Molecular Biology, 21(4):446-455 (2012).
Emery et al., "Radial Patterning of Arabidopsis Shoots by Class III HD-ZIP and KANADI Genes," Current Biology, 13:1768-1774 (2003).
Final Office Action dated Nov. 10, 2015, in U.S. Appl. No. 13/612,985.
Final Office Action dated Nov. 7, 2013, in U.S. Appl. No. 13/042,856.
Final Office Action dated Nov. 30, 2015, in U.S. Appl. No. 13/612,948.
International Preliminary Report on Patentability (Chapter II) dated Jul. 24, 2015, in International Application No. PCT/US2014/047204.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated Nov. 24, 2015, in International Application No. PCT/US2015/037522.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Kim et al., "Synthetic dsRNA Dicer substrates enhance RNAi potency and efficacy," Nature Biotechnology, 23(2):222-226 (2005).
Lein et al., "Target discovery of novel herbicides," Current Opinion in Plant Biology, 7:219-225 (2004).
MacKenzie et al., "Transgenic Nicotiana debneyii expressing viral coat protein are resistant to potato virus S infection," Journal of General Virology, 71:2167-2170 (1990).
Maori et al., "IAPV, a bee-affecting virus associated with Colony Collapse Disorder can be silenced by dsRNA ingestion," Insect Molecular Biology, 18(1):55-60 (2009).
Molina et al., "Inhibition of protoporphyrinogen oxidase expression in Arabidopsis causes a lesion-mimic phenotype that induces system acquired resistance," The Plant Journal, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (Lolium perenne L.)," Plant Cell Reports, 28(10):1549-1562 (2009).
Notice of Allowance dated Oct. 5, 2015, in U.S. Appl. No. 13/583,302.
Office Action dated Jul. 23, 2015, in Ukrainian Patent Application No. 201211548.
Office Action dated Oct. 5, 2015, in Eurasian Patent Application No. 201201264/28.
Office Action dated Sep. 9, 2015, in Chinese Patent Application No. 201280055409.2.
Orbović et al., "Foliar-Applied Surfactants and Urea Temporarily Reduce Carbon Assimilation of Grapefruit Leaves," J. Amer. Soc. Hort. Sci., 126(4):486-490 (2001).
Pratt et al., "Amaranthus rudis and A. tuberculatus, One Species or Two?," Journal of the Torrey Botanical Society, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (Amaranthus tuberculatus) using GS-FLX 454 pyrosequencing and its application for studies of herbicide target-site genes," Pest Manag. Sci., 66:1042-1052 (2010).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Schweizer et al., "Double-stranded RNA interferes with gene function at the single-cell level in cereals," The Plant Journal, 24(6):895-903 (2000).
Senthil-Kumar et al., "A systematic study to determine the extent of gene silencing in Nicotiana benthamiana and other Solanaceae species when heterologous gene sequences are used for virus-induced gene silencing," New Phytologist, 176:782-791 (2007).
Snead et al., "Molecular basis for improved gene silencing by Dicer substrate interfering RNA compared with other siRNA variants," Nucleic Acids Research, 41(12):6209-6221 (2013).
Stevens et al., "New Formulation Technology—SILWET® Organosilicone Surfactants Have Physical and Physiological Properties Which Enhance the Performance of Sprays," Proceedings of the 9th Australian Weeds Conference, pp. 327-331 (1990).
Street, "Why is DNA (and not RNA) a stable storage form for genetic information?," Biochemistry Revisited, pp. 1-4 (2008).
Sutton et al., "Activity of mesotrione on resistant weeds in maize," Pest Manag. Sci., 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Tranel et al., "Resistance of weeds to ALS-inhibiting herbicides: what have we learned?," Weed Science, 50:700-712 (2002).
Tsugawa et al., "Efficient transformation of rice protoplasts mediated by a synthetic polycationic amino polymer," Theor Appl Genet, 97:1019-1026 (1998).
Vermeulen et al., "The contributions of dsRNA structure to Dicer specificity and efficiency," RNA, 11(5):674-682 (2005).
Wang et al., "Foliar uptake of pesticides—Present status and future challenge," ScienceDirect, 87:1-8 (2007).
Written Opinion dated May 8, 2014, in International Application No. PCT/IL2013/050447.

(56) References Cited

OTHER PUBLICATIONS

Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus-elicited suppression of a 35S promoter-regulated transgene," *Nature Biotechnology*, 18:995-999 (2000).
Balibrea et al., "Extracellular Invertase is an Essential Component of Cytokinin-Mediated Delay of Senescence," *The Plant Cell*, 16(5):1276-1287 (2004).
Bart et al., "A novel system for gene silencing using siRNAs in rice leaf and stem-derived protoplasts," *Plant Methods*, 2(13):1-9 (2006).
Basu et al., "Weed genomics: new tools to understand weed biology," *TRENDS in Plant Science*, 9(8):391-398 (2004).
Busch et al., "RNAi for discovery of novel crop protection products," *Pflanzenschutz-Nachrichten Bayer*, 58(1):34-50 (2005).
Chabannes et al., "In situ analysis of lignins in transgenic tobacco reveals a differential impact of individual transformations on the spatial patterns of lignin deposition at the cellular and subcellular levels," *The Plant Journal*, 28(3):271-282 (2001).
Chen et al., "Transfection and Expression of Plasmid DNA in Plant Cells by an Arginine-Rich Intracellular Delivery Peptide without Protoplast Preparation," *FEBS Letters 581*, pp. 1891-1897 (2007).
Colliver et al., "Differential modification of flavonoid and isoflavonoid biosynthesis with an antisense chalcone synthase construct in transgenic *Lotus corniculatus*," *Plant Molecular Biology*, 35:509-522 (1997).
Communication pursuant to Article 94(3) EPC dated Jan. 14, 2016, in European Patent Application No. 12 832 415.9.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Concise Descriptions of Relevance filed by a third party on Nov. 29, 2012, in U.S. Appl. No. 13/042,856.
Dawson et al., "cDNA cloning of the complete genome of tobacco mosaic virus and production of infectious transcripts," *Proc. Natl. Acad. Sci. USA*, 83:1832-1836(1986).
Extended European Search Report dated Jan. 20, 2016, in European Patent Application No. 13 794 339.5.
Feuillet et al., "Crop genome sequencing: lessons and rationales," *Trends Plant Sci.*, 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Sep. 9, 2016, in U.S. Appl. No. 13/612,954.
Final Office Action dated Nov. 19, 2015, in U.S. Appl. No. 13/612,941.
Final Office Action dated Sep. 9, 2016, in U.S. Appl. No. 14/608,951.
Final Office Action dated Sep. 9, 2016, in U.S. Appl. No. 14/603,347.
Final Office Action dated Oct. 20, 2016, in U.S. Appl. No. 14/480,199.
Final Office Action dated Oct. 22, 2015, in U.S. Appl. No. 14/608,951.
First Office Action dated Feb. 2, 2016, in Chinese Patent Application No. 201380039346.6.
Fraley et al., "Liposome-mediated delivery of tobacco mosaic virus RNA into tobacco protoplasts: A sensitive assay for monitoring liposome-protoplast interactions," *Proc Natl Acad Sci U S A.*, 79(6):1859-1863 (1982).
Fukunaga et al., "dsRNA with 5' overhangs v contributes to endogenous and antiviral RNA silencing pathways in plants," *The EMBO Journal*, 28(5):545-555 (2009).
Gan et al., "Inhibition of Leaf Senescence by Autoregulated Production of Cytokinin," *Science*, 270:1986-1988 (1995).
Gao et al., "Nonviral Methods for siRNA Delivery," *Molecular Pharmaceutics*, 6(3):651-658 (2008).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. EW765249, "STO20010B10C12 Normalized and subtracted western corn rootworm female head cDNA library Diabrotica virgifera virgifera cDNA clone STO20010B10C12 5-, mRNA sequence," (2007).
GenBank Accession No. EW771198, "STO20010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulcx_Chosen_One_Library_2 Daphnia pulex cDNA clone CBIB7954 5', mRNA sequence" (2011).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
Gossamer Threads, Compendium of Herbicide Adjuvants: Organo-Silicone Surfactant, p. 1-4 (1998).
Gudkov, "Minireview: The L7/L12 ribosomal domain of the ribosome: structural and functional studies," *FEBS Letters*, 407:253-256 (1997).
Hajirezaei et al., "Impact of elevated cytosolic and apoplastic invertase activity on carbon metabolism during potato tuber development," *Journal of Experimental Botany*, 51:439-445 (2000).
Heffer et al., "Rapid isolation of gene homologs across taxa: Efficient identification and isolation of gene orthologs from non-model organism genomes, a technical report," *EvoDevo Journal*, 2(7):1-5 (2011).
Holtra et al., "Assessment of the Physiological Condition of *Salvinia natans* L. Exposed to Copper(II) Ions," *Environ. Protect. Eng.*, 41:147-158 (2015).
International Preliminary Report on Patentability dated Sep. 11, 2012, in International Application No. PCT/US2011/027528.
International Rice Genome Sequencing Project, The map-based sequence of the rice genome, *Nature*, 436(11):793-800 (2005).
International Search Report and the Written Opinion dated May 10, 2011, in International Application No. PCT/US2011/027528.
International Search Report and Written Opinion dated May 26, 2016, in International Application No. PCT/US2016/014344.
International Search Report and Written Opinion dated Nov. 27, 2015, in International Application No. PCT/US2015/037015.
Jin el al., "Posttranslational Elevation of Cell Wall Invertase Activity by Silencing its Inhibitor in Tomato Delays Leaf Senescence and Increases Seed Weight and Fruit Hexose Level," *The Plant Cell*, 21:2072-2089 (2009).
Kaloumenos et al., "Identification of a Johnsongrass (*Sorghum halepense*) Biotype Resistant to ACCase-Inhibiting Herbicides in Northern Greece," *Weed Technol*, 23:470-476 (2009).
Kambiranda et al., "Relationship Between Acid Invertase Activity and Sugar Content in Grape Species," *Journal of Food Biochemistry*, 35:1646-1652 (2011).
Kim et al., "Optimization of Conditions for Transient Agrobacterium-Mediated Gene Expression Assays in *Arabidopsis*," *Plant Cell Reports*, 28:1159-1167 (2009).
Kirkwood, "Herbicides and Plants," *Botanical Journal of Scotland*, 46(3):447-462 (1993).
Knudsen, "Promoter2.0: for the recognition of Poll promoter sequences," *Bioniformatics*, 15(5):356-361 (1999).
Liu et al., "Identification and Application of a Rice Senescence-Associated Promoter," *Plant Physiology*, 153:1239-1249 (2010).

(56) References Cited

OTHER PUBLICATIONS

Liu, "Influence of Sugars on the Foliar Uptake of Bentazone and Glyphosate," *New Zealand Plant Protection*, 55:159-162 (2002).
Migge et al., "Greenhouse-grown conditionally lethal tobacco plants obtained by expression of plastidic glutamine synthetase antisense RNA may contribute to biological safety," *Plant Science* 153:107-112 (2000).
Mora et al., "How Many Species Are There on Earth and in the Ocean?," *PLOS Biol.*, 9(8):e100127, p. 1-8 (2011).
Mount el al., "Gene and Metabolite Regulatory Network Analysis of Early Developing Fruit Tissues Highlights New Candidate Genes for the Control of Tomato Fruit Composition and Development," *Plant Physiology*, 149:1505-1528 (2009).
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Sep. 6, 2016, in U.S. Appl. No. 14/335,135.
Non-Final Office Action dated Mar. 1, 2016, in U.S. Appl. No. 13/612,954.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Nookaraju et al., "Molecular approaches for enhancing sweetness in fruits and vegetables," *Scientia Horticulture*, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Apr. 13, 2016, in Chinese Patent Application No. 201280053985.3.
Office Action dated Jul. 18, 2016, in Indonesian Patent Application No. W00201203610.
Office Action dated Jun. 20, 2016, in Chinese Patent Application No. 201280054819.5.
Office Action dated Jun. 24, 2016, in Chinese Patent Application No. 201280053984.9.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Restriction Requirement dated Jul. 15, 2016, in U.S. Appl. No. 14/143,748.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," *Plant Methods*, 1(12):1-3 (2005).
Robson et al., "Leaf senescence is delayed in maize expressing the Agrobacterium IPT gene under the control of a novel maize senescence-enhanced promoter," *Plant Biotechnology Journal*, 2:101-112 (2004).
Roitsch et al., "Extracellular invertase: key metabolic enzyme and PR protein," *Journal of Experimental Botany*, 54(382):513-524 (2003).
Roitsch et al., "Function and regulation of plant invertases: sweet sensations," *Trades in Plant Science*, 9(12):606-613 (2004).
Ruan et al., "Suppression of Sucrose Synthase Gene Expression Represses Cotton Fiber Cell Initiation, Elongation, and Seed Development," *The Plant Cell*, 15:952-964 (2003).
Salanenka et al., "Seedcoat Permeability: Uptake and Post-germination Transport of Applied Model Tracer Compounds," *HortScience*, 46(4):622-626 (2011).
Scott et al., "Botanical Insecticides for Controlling Agricultural Pests: Piperamides and the Colorado Potato Beetle *Leptinotarsa decemlineata* Say (Coleoptera: Chrysomelidae), *Archives of Insect Biochemistry and Physiology*, 54:212-225 (2003).
Second Office Action dated Feb. 25, 2016, in Chinese Patent Application No. 201280054179.8.
Second Office Action dated Mar. 4, 2016, in Chinese Patent Application No. 201280054820.8.
Shintani et al., "Antisense Expression and Overexpression of Biotin Carboxylase in Tobacco Leaves," *Plant Physiol.*, 114:881-886 (1997).
Showalter, "Structure and Function of Plant Cell Wall Proteins," *The Plant Cell*, 5:9-23 (1993).
Song et al. "Herbicide," *New Heterocyclic Pesticide*, Chemical Industry Press, 354-356 (2011).
Tang et al., "Efficient delivery of small interfering RNA to plant cells by a nanosecond pulsed laser-induced stress wave for post-transcriptional gene silencing," *Plant Science*, 171:375-381 (2006).
Tenllado et al., "Double-Stranded RNA-Mediated Interference with Plant Virus Infection," *Journal of Virology*, 75(24):12288-12297 (2001).
Thomas et al., "Size constraints for targeting post-transcriptional gene silencing and for RNA-directed methylation in *Nicotiana benthcuniana* using a potato virus X vector," *The Plant Journal*, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," *Journal of Experimental Botany*, 55(406):2291-2303 (2004).
Widholm et al., "Glyphosate selection of gene amplification in suspension cultures of 3 plant species," *Phyisologia Plantarum*, 112:540-545 (2001).
Wiesman et al., "Novel cationic vesicle platform derived from vernonia oil for efficient delivery of DNA through plant cuticle membranes," *Journal of Biotechnology*, 130:85-94 (2007).
Written Opinion dated Apr. 7, 2016, in Singapore Patent Application No. 201206152-9.

(56) References Cited

OTHER PUBLICATIONS

Zhang et al., "Chapter 10: New Characteristics of Pesticide Research & Development," *New Progress of the world agriculture chemicals*, p. 209 (2010).
Adenosine Triphosphatases, MeSH Descriptor Data 2017, U.S. National Library of Medicine.
Andersen et al., "Delivery of siRNA from lyophilized polymeric surfaces," Biomaterials, 29:506-512 (2008).
Anonymous, "A handbook for high-level expression and purification of 6xHis-tagged proteins," The QiaExpressionist, (2003).
Artymovich, "Using RNA interference to increase crop yield and decrease pest damage," MMG 445 Basic Biotech., 5(1):7-12 (2009).
Axtell et al., "A Two-Hit Trigger for siRNA Biogenesis in Plants," Cell, 127:565-577 (2006).
Campbell et al., "Gene-knockdown in the honey bee mite *Varroa destructor* by a non-invasive approach: studies on a glutathione S-transferase," Parasites & Vectors, 3(1):73,pp. 1-10 (2010).
Chee et al., "Transformation of Soybean (*Glycine max*) by Infecting Germinating Seeds with Agrobacterium tumefaciens," Plant Physiol., 91:1212-1218 (1989).
Chupp et al., "Chapter 8: White Rust," Vegetable Diseases and Their Control, The Ronald Press Company, New York, pp. 267-269 (1960).
Communication pursuant to Article 94(3) EPC dated Jun. 26, 2015, in European Patent Application No. 11 753 916.3.
Communication pursuant to Article 94(3) EPC dated Oct. 23, 2015, in European Patent Application No. 12 831 945.6.
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Dependent RNA Polymerase Gene in *Arabidopsis* Is Required for Posttranscriptional Gene Silencing Mediated by a Transgene but Not by a Virus," Cell, 101:543-553 (2000).
Extended European Search Report dated Jun. 29, 2015, in European Patent Application No. 12 831 494.5.
Extended European Search Report dated Oct. 8, 2013, in European Patent Application No. 11753916.3.
Extended European Search Report dated Sep. 29, 2016, in European Patent Application No. 14778840.
Final Office Action dated Nov. 10, 2016, in U.S. Appl. No. 13/583,302.
First Examination Report dated Apr. 23, 2013, in New Zealand Patent Applicant No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Further Examination Report dated May 16, 2014, in New Zealand Patent Application No. 601784.
GenBank Accession No. AY545657.1 (2004).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenEmbl Accession No. FJ861243 (2010).
International Preliminary Report on Patentability dated Sep. 11, 2014, in International Application No. PCT/IL2013/050447.
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report dated Mar. 12, 2013, in International Application No. PCT/US2012/054789.
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Khan et al., "Matriconditioning of Vegetable Seeds to Improve Stand Establishment in Early Field Plantings," J. Amer. Soc. Hort. Sci., 117(1):41-47 (1992).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Leopold et al., "Chapter 4: Moisture as a Regulator of Physiological Reaction in Seeds," Seed Moisture, CSSA Special Publication No. 14, pp. 51-69 (1989).
Luque et al., "Water Permeability of Isolated Cuticular Membranes: A Structural Analysis," Archives of Biochemistry and Biophysics, 317(2):417-422 (1995).
Moriyama et al., "Double-stranded RNA in rice: a novel RNA replicon in plants," Molecular & General Genetics, 248(3):364-369 (1995).
Non-Final Office Action dated Nov. 9, 2016, in U.S. Appl. No. 14/901,003.
Office Action dated Aug. 28, 2013, in Chinese Patent Application No. 201180012795.2.
Office Action dated Sep. 5, 2016, in Ukrainian Patent Application No. a 2014 03846.
Office Action dated Aug. 25, 2016, in Eurasian Patent Application No. 201201264.
Office Action dated Feb. 24, 2014, in Eurasian Patent Application No. 201201264.
Office Action dated Nov. 3, 2014, in Chinese Patent Application No. 201180012795.2.

(56) References Cited

OTHER PUBLICATIONS

Office Action dated Nov. 15, 2016, in Mexican Patent Application. No. MX/a/2014/003068.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 13, 2016, in Ukrainian Patent Application No. a 2014 03843.
Office Action dated Dec. 15, 2016, in Ukrainian Patent Application No. a 2014 03849.
Office Action dated Dec. 14, 2016, in Ukrainian Patent Application No. a 2014 03850.
Office Action dated Dec. 27, 2016, in Ukrainian Patent Application No. a 2012 11548.
Orbović et al., "Foliar-Applied Surfactants and Urea Temporarily Reduce Carbon Assimilation of Grapefruit Leaves," J. Amer. Soc. Hort. Sci., 126(4):486-490 (2001).
Patent Examination Report No. 1 dated Nov. 11, 2013, in Australian Patent Application No. 2011224570.
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Second Chinese Office Action dated Jun. 10, 2014, in Chinese Patent Application No. 201180012795.2.
Temple et al., "Can glutamine synthetase activity levels be modulated in transgenic plants by the use of recombinant DNA technology?" Transgenic Plants and Plant Biochemistry, 22(4):915-920 (1994).
Unniraman et al., "Conserved Economics of Transcription Termination in Eubacteria," Nucleic Acids Research, 30(3):675-684 (2002).
Voinnet et al., "Systemic Spread of Sequence-Specific Transgene RNA Degradation in Plants Is Initiated by Localized Introduction of Ectopic Promoterless DNA," Cell, 95:177-187 (1998).
Wild Carrot, Noxious Weed Control Board (NWCB) of Washington State (2010) <www.nwcb.wa.gov/detail.asp?weed=46>.
Sakthivel, "ATP-ase as a Potential Drug Target for Cancer, Tumor Growth and Cellular Functions," *Int J Hum Genet*, 12(3):151-156 (2012).
Shaoquan, "The action target of herbicide and the innovation of a new variety," Chemical Industry Press, pp. 23-24 (2001).
Adams et al., "The Genome Sequence of *Drosophila melanogaster*," Science, 287:2185-2195 (2000).
Arensburger et al., "Sequencing of Culex quinquefasciatus establishes a platform for mosquito comparative genomics," Science, 330:86-88 (2010).
Ascencio-Ibanez et al., "DNA abrasion onto plants is an effective method for geminivirus infection and virus-induced gene silencing," Journal of Virological Methods, 142:198-203 (2007).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Bedell et al., "Sorghum Genome Sequencing by Methylation Filtration," PLOS Biology, 3(1):E13/104-115 (2005).
Brenchley et al., "Analysis of the bread wheat genome using whole-genome shotgun sequencing," Nature, 491:705-710 (2012).
Eamens et al., "RNA Silencing in Plants: Yesterday, Today, and Tomorrow," Plant Physiology, 147(2):456-468 (2008).
Fassler, BLAST Glossary, National Center for Biotechnology Information (2011).
GenBank Accession No. EF143582 (2007).
Goff et al., "A Draft Sequence of the Rice Genome (*Oryza sativa* L. ssp. *japonica*)," Science, 296:92-100 (2002).
Huang et al., "The genome of the cucumber, *Cucumis sativus* L.," Nature Genetics, 41:1275-1283 (2009).
Kornyshev et al., "Helical Structure Determines Different Susceptibilities of dsDNA, dsRNA, and tsDNA to Counterion-Induced Condensation," Biophysical Journal, 104:2031-2041 (2013).
Nene et al., "Genome sequence of Aedes aegypti, a major arbovirus vector," Science, 316:1718-1723 (2007).
Nygaard et al., "The genome of the leaf-cutting ant Acromyrmex echinatior suggests key adaptations to advanced social life and fungus farming," Genome Research, 21:1339-1348 (2011).
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5.
Office Action dated Aug. 3, 2017, in European Patent Application No. 12 831 684.1.
Office Action dated Aug. 8, 2017, in Chilean Patent Application No. 201501874.
Office Action dated Jul. 11, 2017, in Mexican Patent Application No. MX/a/2015/013118.
Office Action dated Jul. 3, 2017, in Mexican Patent Application No. MX/a/2015/012632.
Office Action dated Jul. 6, 2017, in Mexican Patent Application No. MX/a/2015/013103.
Office Action dated Mar. 16, 2017, in Chinese Patent Application No. 201280054819.5.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 6, 2017, in Chinese Patent Application No. 2014800154012 (with English translation).
Patent Examination Report No. 1 dated Jun. 8, 2017, in Australian Patent Application No. 2012308686.
Powles et al., "Evolution in Action: Plants Resistant to Herbicides," Annual Review of Plant Biology, 61(1):317-347 (2010).
Schmutz et al., "Genome sequence of the palaeopolyploid soybean," Nature, 463:178-183 (2010).
Schnable et al., "The B73 Maize Genome: Complexity, Diversity, and Dynamics," Science, 326:1112-1115 (2009).
Search Report dated Jul. 24, 2017, in Chinese Patent Application No. 201480014392.5.
Statement of Grounds and Particulars dated Sep. 1, 2017, in Australian Patent No. 2014262189.
Stevens, "Organosilicone Surfactants as Adjuvants for Agrochemicals," New Zealand Journal of Forestry Science, 24:27-34 (1994).
Suen et al., "The Genome Sequence of the Leaf-Cutter Ant Atta cephalotes Reveals Insights into Its Obligate Symbiotic Lifestyle," PLoS Genetics, 7:e1002007 (2011).
The International Aphid Genomics Consortium, "Genome Sequence of the Pea Aphid Acyrthosiphon pisum," PLoS Biology, 8:e1000313 (2010).
The Tomato Genome Consortium, "The tomato genome sequence provides insights into fleshy fruit evolution," Nature, 485:635-641 (2012).
Tribolium Genome Sequencing Consortium, "The genome of the model beetle and pest *Tribolium castaneum*," Nature, 452:949-955 (2008).
Voinnet, "Origin, Biogenesis, and Activity of Plant MicroRNAs," Cell, 136:669-687 (2009).
Wool et al., "Structure and evolution of mammalian ribosomal proteins," Biochem. Cell Biol., 73:933-947 (1995).
Written Opinion dated Mar. 6, 2017, in Singaporean Patent Application No. 2012061529.
Wurm et al., "The genome of the fire ant *Solenopsis invicta*," PNAS, 108:5679-5684(2011).
Xu et al., "Characterization and Functional Analysis of the Calmodulin-Binding Domain of Rac1 GTPase," PLoS One, 7(8):e42975 (2012).
Zhang, Chapter 10: New Characteristics of Pesticide Research & Development, p. 209 (2010).
Boutros el al., "Genome-Wide RNAi Analysis of Growth and Viability in *Drosophila* Cells," Science, 303:832-835 (2004).
Dietzl et al., "A genome-wide transgenic RNAi library for conditional gene inactivation in *Drosophila*," Nature, 448:151-156 (2007).

(56) References Cited

OTHER PUBLICATIONS

Dow et al., "Molecular genetic analysis of V-ATPase function in *Drosophila melanogaster,*" *Journal of Experimental Biology*, 200:237-245 (1997).
Dow, "The multifunctional *Drosophila melanogaster* V-ATPase is encoded by a multigene family," *J. Bioenerg. Biomembr.*, 31:75-83 (1999).
European Search Report dated Sep. 7, 2017, in European Patent Application No. 17152830.0.
Extended European Search Report dated Nov. 7, 2017, in European Patent Application No. 15811092.4.
Extended European Search Report dated Nov. 8, 2017, in European Patent Application No. 15737282.2.
Hoermann et al., "Tic32, as Essential Component in Chloroplast Biogenesis," *The Journal of Biological Chemistry*, 279(33):34756-34762 (2004).
Lee et al., "A systematic RNAi screen identifies a critical role for mitochondria in C. elegans longevity," *Nature Genetics*, 33:40-48 (2002).
Legeai et al., "An Expressed Sequence Tag collection from the male antennae of the Noctuid moth *Spodoptera littoralis*: a resource for olfactory and pheromone detection research," *BMC Genomics*, 12:86 (2011).
Miller et al., "Genes, gene flow and adaptation of Diabrotica virgifera virgifera," *Agricultural and Forest Entomology*, 11:47-60 (2009).
Nègre et al., "SPODOBASE: an EST database for the lepidopteran crop pest Spodoptera," *BMC Bioinformatics*, 7:322 (2006).
Office Action dated Dec. 5, 2017, in Japanese Patent Application No. 2016-502033.
Office Action dated Feb. 21, 2018, in Mexican Patent Application No. MX/a/2015/012632 (with English translation).
Partial European Search Report dated Dec. 6, 2017, in European Patent Application No. 17181861.0.
Partial Supplementary European Search Report dated Jan. 11, 2018, in European Patent Application No. 15812530.0.
Qichuan et al., Seed Science, *China Agriculture Press*, pp. 101-103, Tables 2-37.
Restriction Requirement dated Jul. 18, 2016, in U.S. Appl. No. 14/143,836.
Siegfried et al., "Expressed sequence tags from Diabrotica virgifera virgifera midgut identify a coleopteran cadherin and a diversity of cathepsins," *Insect Molecular Biology*, 14:137-143 (2005).
Summons to Attend Oral Proceedings Pursuant to Rule 115(1) EPC, dated Aug. 7, 2017, in European Patent Application No. 12832160.1.
Sun et al.,"Antisense oligodeoxynucleotide inhibition as a potentstrategy in plant biology: identification of SUSIBA2 as atranscriptional activator in plant sugar signalling," *The Plant Journal*, 44:128-138 (2005).
Zaimin et al., Botany, *Northwest A&F University Press*, pp. 87-92.
Zhao et al., "Vegetable Standardized Production Technology," *Hangzhou Zhejiang Science and Technology Press*, p. 19 (2008).
Anonymous, "Resistant Weeds Spur Research Into New Technologies," *Grains Research & Development Corporation* (2013).
Asad et al. ,"Silicon Carbide Whisker-mediated Plant Transformation," *Properties and Applicants of Silicon Carbide*, pp. 345-358 (2011).
Baker, "Chlorophyll Fluorescence: A Probe of Photosynthesis in Vivo," *Annu. Rev. Plant Biol.*, 59:89-113 (2008).
Bauer et al., "The major protein import receptor of plastids is essential for chloroplast biogenesis," *Nature*, 403:203-207 (2000).
Baulcombe, "RNA silencing in plants," *Nature*, 431:356-363 (2004).
Baum et al., "Progress Towards RNAi-Mediated Insect Pest Management," *Advances in Insect Physiology*, 47:249-295 (2014).
Belhadj et al., "Methyl Jasmonate Induces Defense Responses in Grapevine and Triggers Protection against Erysiphe necator," *J. Agric Food Chem.*, 54:9119-9125 (2006).
Burgos et al., "Review: Confirmation of Resistance to Herbicides and Evaluation of Resistance Levels," *Weed Science*, 61 (1):4-20 (2013).
Burleigh, "Relative quantitative RT-PCR to study the expression of plant nutrient transporters in arbuscular mycorrhizas," *Plant Science*, 160:899-904 (2001).
Chang et al., "Dual-target gene silencing by using long, sythetic siRNA duplexes without triggering antiviral responses," *Molecules and Cells*, 27(6) 689-695 (2009).
Chen et al., "Exploring MicroRNA-Like Small RNAs in the Filamentous Fungus Fusarium oxysporum," *PLOS One*, 9(8):e104956:1-10 (2014).
Cheng et al., "Transient Expression of Minimum Linear Gene Cassettes in Onion Epidermal Cells Via Direct Transformation," *Appl Biochem Biotechnol*, 159:739-749 (2009).
Christiaens et al., "The challenge of RNAi-mediated control of hemipterans," *Current Opinion in Insect Science*, 6:15-21 (2014).
Communication Pursuant to Article 94(3) EPC dated Sep. 5, 2018, in European Patent Application No. 17152830.0.
Cong et al., "Multiplex Genome Engineering Using CRISPR/Cas Systems," *Science*, 339:819-823 (2013).
Constan et al., "An outer envelope membrane component of the plastid protein import apparatus plays an essential role in Arabidopsis," *The Plant Journal*, 38:93-106 (2004).
Danka et al., "Field Test of Resistance to Acarapis woodi (Acari: Tarsonemidae) and of Colony Production by Four Stocks of Honey Bees (Hymenoptera: Apidae)" *Journal of Economic Entomology*, 88(3):584-591 (1995).
Database EMBL XP-002781749(BG442539) dated Mar. 20, 2001.
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Delye et al., "PCR-based detection of resistance to acetyl-CoA carboxylase-inhibiting herbicides in black-grass (Alopecurus myosuroides Huds) and ryegrass (Lolium rigidum Gaud)," *Pest Management Science*, 58:474-478 (2002).
Delye et al., "Variation in the gene encoding acetolactate-synthase in *Lolium* species and proactive detection of mutant, herbicide-resistant alleles," *Weed Research*, 49:326-336 (2009).
Desveaux et al., "PBF-2 Is a Novel Single-Stranded DNA Binding Factor Implicated in PR-10a Gene Activation in Potato," *The Plant Cell*, 12:1477-1489 (2000).
Di Stilio et al., "Virus-Induced Gene Silencing as a Tool for Comparative Functional Studies in Thalictrum," *PLoS One*, 5(8):e12064 (2010).
Dietzgen et al., "Transgenic gene silencing strategies for virus control," *Australasian Plant Pathology*, 35:605-618 (2006).
Dilpreet et al., "Glyphosate Rsistance in a Johnsongrass (*Sorghum halepense*) Biotype from Arkansas," *Weed Science*, 59(3):299-304 (2011).
Downey et al., "Single and dual parasitic mite infestations on the honey bee, Apis mellifera L.," *Insectes Sociaux*, 47(2):171-176 (2000).
Drobyazko R.V., "Reliable and environmentally friendly insecticide," *Protection and quarantine of plants*, 2012 (pp. 52, 53) (in Russian).
Duhoux et al., "Reference Genes to Study Herbicide Stress Response in *Lolium* sp.: Up-Regulation of P3450 Genes in Plants Resistant to Acetolactate-Synthase Inhibitors," *PLOS One*, 8(5):e63576 (2013) Herewith.
Egli et al., "A Maize Acetyl-Coenzyme a Carboxylase cDNA Sequence," *Plant Physiol.*, 108: 1299-1300 (1995).
Eudes et al., "Cell-penetrating peptides," *Plant Signaling & Behavior*, 3(8):549-5550 (2008).

(56) References Cited

OTHER PUBLICATIONS

Extended European Search Report dated Dec. 19, 2018, in European Patent Application No. 16804395.8.
Extended European Search Report dated Nov. 16, 2018, in European Patent Application No. 18182238.8.
Extended European Search Report dated Nov. 21, 2018, in European Patent Application No. 18175809.5.
Extended European Search Report dated Sep. 28, 2018, in European Patent Application No. 16740770.9.
Fernandez et al., "Uptake of Hydrophilic Solutes Through Plant Leaves: Current State of Knowledge and Perspectives of Foliar Fertilization," *Critical Reviews in Plant Sciences*, 28:36-38 (2009).
Funke et al., "Molecular basis for herbicide resistance in Roundup Ready crops," *PNAS*, 103:13010-13015 (2006).
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 29(11):1261-1268 (2010).
Gao et al., "DNA-guided genome editing using the Natronobacterium gregoryi Argonaute," *Nature Biotechnology*, 34(7):768-773 (2016).
Gaskin et al., "Novel organosillicone adjuvants to reduce agrochemical spray volumes on row crops," *New Zealand Plant Protection*, 53:350-354 (2000).
Gasser et al., "Structure, Expression, and Evolution of the 5-Enolpyruvylshikimate-3-phosphate Synthase Genes of Petunia and Tomato," *J. Biol. Chem.*, 263: 4280-4287 (1988).
Gilmer et al., "Latent Viruses of Apple I. Detection with Woody Indicators," *Plant Pathology*, 1(10):1-9 (1971).
Gomez-Zurita et al., "Recalibrated Tree of Leaf Beetles (*Chrysomelidae*) Indicates Independent Diversification of Angiosperms and Their Insect Herbivores," *PLoS One*, 4(e360):1-8 (2007).
Guttieri et al., "DNA Sequence Variation in Domain a of the Acetolactate Synthase Genes of Herbicide-Resistant and -Susceptible Weed Biotypes," *Weed Science*, 40:670-679 (1992).
Hagio, "Chapter 25: Direct Gene Transfer into Plant Mature Seeds via Electroporation After Vacuum Treatment," *Electroporation and Sonoporation in Developmental Biology*, p. 285-293 (2009).
Hess, "Surfactants and Additives," *1999 Proceedings of the California Weed Science Society*, 51:156-172 (1999).
Hörmann et al., "Tic32, as Essential Component in Chloroplast Biogenesis," *The Journal of Biological Chemistry*, 279(33):34756-34762 (2004).
Horsch et al., "Inheritance of Functional Foreign Genes in Plants," *Science*, 223:496-498 (1984).
Hsu et al., "DNA targeting specificity of RNA-guided Cas9 nucleases," *Nature Biotechnology*, 31:827-832 (2013).
Hu et al., "High efficiency transport of quantum dots into plant roots with the aid of silwet L-77," *Plant Physiology and Biochemistry*, 48:703-709 (2010) Herewith.
Huang et al., "In Vivo Analyses of the Roles of Essential Omp85-Related Proteins in the Chloroplast Outer Envelope Membrane," *Plant Physiol.*, 157:147-159 (2011).
Huggett et al., "Real-time RT-PCR normalisation; strategies and considerations," *Genes and Immunity*, 6:279-284 (2005).
Inaba et al., "Arabidopsis Tic110 Is Essential for the Assembly and Function of the Protein Import Machinery of Plastids," *The Plant Cell*, 17:1482-1496(2005).
International Search Report dated Oct. 13, 2016, in International Patent Application No. PCT/US2016/35500.
Ivanova et al., "Members of the Toc159 Import Receptor Family Represent Distinct Pathways for Protein Targeting to Plastids," *Molecular Biology of the Cell*, 15:3379-3392 (2004).
Jacque et al., "Modulation of HIV-1 replication by RNA interference," *Nature*, 418, 435-438 (2002).
Jang et al., "Resistance to herbicides caused by single amino acid mutations in acetyl-CoA carboxylase in resistant populations of grassy weeds," *New Phytologist*, 197(4):1110-1116 (2013).
Jarvis et al, "An *arabidopsis* mutant defective in the plastid general protein import apparatus," *Science*, 282:100-103 (1998).

Khanbekova et al., The defeat of the honey bee apis melifera caucasica Gorb. By viruses and parasites, and condition of bee colonies in different ecogeographical conditions of Greater Caucasus, *Agricultural Biology*, 2013 (p. 43) (in Russian).
Kikkert et al., "Stable Transformation of Plant Cells by Particle Bombardment/Biolistics," *Methods in Molecular Biology*, 286:61-78 (2005).
Kim et al., "Synthesis and characterization of mannosylated pegylated polyethylenimine as a carrier for siRNA," *International Journal of Pharmaceutics*, 427:123-133 (2012).
Kirkwood, "Recent developments in our understanding of the plant cuticle as a barrier to the foliar uptake of pesticides," *Pestic Sci*, 55:69-77 (1999).
Kovacheva et al., "Further in vivo studies on the role of the molecular chaperone, Hsp93, in plastid protein import," *The Plant Journal*, 50:364-379 (2007).
Kovacheva et al., "In vivo studies on the roles of Tic100, Tic40 and Hsp93 during chloroplast protein import," *The Plant Journal*, 41:412-428 (2005).
Kumar et al., "Sequencing, De Novo Assembly and Annotation of the Colorado Potato Beetle, *Leptinotarsa decemlineata*, Transcriptome," *PLoS One*, 9(1):e86012 (2014).
Li et at., "Long dsRNA but not siRNA initiates RNAi in western corn rootworm larvae and adults," *Journal of Applied Entomology*, 139(6):432-445 (2015).
Liu et al, "The Helicase and RNaseIIIa Domains of *Arabidopsis* Dicer-Like 1 Modulate Catalytic Parameters during MicroRNA Biogenesis," *Plant Physiology*, 159:748-758 (2012).
Liu, "Calmodulin and Cell Cycle," *Foreign Medical Sciences Section of Pathophysiology and Clinical Medicine*, 18(4):322-324 (1998).
Liu, "Confocal laser scanning microscopy—an attractive tool for studying the uptake of xenobiotics into plant foliage," *Journal of Microscopy*, 213(Pt 2):87-93 (2004).
Liu, "The Transformation of Nucleic Acid Degradants in Plants," *China Organic Fertilizers, Agriculture Press*, ISBN: 7-1091634 (1991) (with English translation).
Lodish et al., Molecular Cell Biology, *Fourth Edition*, p. 210 (2000).
Lucas et al., "Plasmodesmata—bridging the gap between neighboring plant cells," *Trends in Cell Biology*, 19:495-503 (2009).
Masoud, "Constitutive expression of an inducible β-1,3-glucanase in alfalfa reduces disease severity caused by the oomycete pathogen *Phytophthora megasperma* f. sp *medicaginis* . . . ," *Trans Res*, 5:313-323 (1996).
McGinnis, "RNAi for functional genomics in plants," *Brief Funct Genomics*, 9(2):111-7 (2010).
Misawa, "Expression of an Erwinia phytoene desaturase gene not only confers multiple resistance to herbicides interfering with carotenoid biosynthesis but also alters xanthophyll metabolism . . . ," *The Plant Jrnl*, 6(4):481-489 (1994).
Misawa, "Functional expression of the Erwinia uredovora carotenoid biosynthesis gene crtI in transgenic plants showing an increase of β-carotene biosynthesis activity and resistance . . . ," *The Plant Jrnl*, 4(5):833-840 (1993).
Morozov et al., "Evaluation of Preemergence Herbicides for Control of Diclofop-resistant Italian Ryegrass (*Lolium multiflorum*) in Virginia," *Virginia Polytechnic Institute and State University*, pp. 4371 (2004).
Nemeth, "Virus, mycoplasma and rickettsia diseases of fruit trees," *Martinus Nijhoff Publishers*, 197-204 (1986).
N-TER Nanoparticle siRNA, Sigma Aldrich TM website, Web. Nov. 20, 2018 <https://www.sigmaaldrich.com/life-science/custom-oligos/sirna-oligos/n-ter-nanoparticle.html>.
Office Action dated Aug. 9, 2018, in Canadian Patent Application No. 2,848,371.
Office Action dated Jul. 30, 2018, in Canadian Patent Application No. 2,848,576.
Office Action dated Mar. 8, 2018 (with English translation), in Chilean Patent Application No. 201403192.
Office Action dated Sep. 20, 2018, in Chilean Patent Application No. 201601440 (with English translation).

(56) References Cited

OTHER PUBLICATIONS

Paddison et al., "Stable suppression of gene expression by RNAi in mammalian cells," *Proc. Natl Acad. Sci. USA*, 99(3):1443-1448 (2002).
Partial European Search Report dated Jun. 29, 2018, in European Patent Application No. 18157745.3.
Partial Supplementary European Search Report dated Jan. 11, 2018, in European Patent Application No. 15812530.2.
Pratt et al., "Sorghum Expressed Sequence Tags Identify Signature Genes for Drought, Pathogenesis, and Skotomorphogenesis from a Milestone Set of 16,801 Unique Transcripts," *Plant Physiology*, 139:869-884 (2005).
Qi et al., "RNA processing enables predictable programming of gene expression," *Nature Biotechnology*, 30:1002-1007 (2012).
Rakoczy-Trojanowska, "Alternative Methods of Plant Transformation—a short review," *Cellular & Molecular Biology Letters*, 7:849-858 (2002).
Regalado, "The Next Great GMO Debate," *MIT Technology Review*,pp. 1-19 (2015) <https://www.technologyreview.com/s/540136/the-next-great-gmo-debate/>.
Reverdatto et al., "A Multisubunit Acetyl Coenzyme a Carboxylase from Soybean," *Plant Physiol.*, 119: 961-978 (1999).
Richardson et al., "Targeting and assembly of components of the TOC protein import complex at the chloroplast outer envelope membrane," *Frontiers in Plant Science*, 5:1-14 (2014).
Sammataro et al., "Some Volatile Plant Oils as Potential Control Agents for Varroa Mites (Acari: *Varroidae*) in Honey Bee Colonies (Hymenoptera: *Apidae*)," *American Bee Journal*, 138(9):681-685 (1998).
Schönherr et al., "Size selectivity of aqueous pores in astomatous cuticular membranes isolated from *Populus canescens* (Aiton) Sm. Leaves," *Planta*, 219:405-411 (2004) Herewith.
Simeoni et al., "Insight into the mechanism of the peptide-based gene delivery system MPG: implications for delivery of siRNA into mammalian cells," *Nucleic Acids Research*, 31(11):2717-2724 (2003).
Small, "RNAi for revealing and engineering plant gene functions," *Current Opinion in Biotechnology*, 18:148-153 (2007).
Stevens, "Formulation of Sprays to Improve the Efficacy of Foliar Fertilisers," *New Zealand Journal of Forestry Science*, 24(1):27-34 (1994).
Stevens, "Organosilicone Surfactants as Adjuvants for Agrochemicals," *Journal of Pesticide Science*, 38:103-122 (1993).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Swarts et al., "Argonaute of the archaeon Pyrococcus furiosus is a DNA-guided nuclease that targets cognate DNA," *Nucleic Acid Res.*, 43(10):5120-5129 (2015).
Swarts et al., "DNA-guided DNA interference by a prokaryotic Argonaute," *Nature*, 507(7490):258-61 (2014).
Teng et al., "Tic21 Is an Essential Translocon Component for Protein Translocation across the Chloroplast Inner Envelope Membrane," *The Plant Cell*, 18:2247-2257 (2006).
Tenllado et al., "Crude extracts of bacterially expressed dsRNA can be used to protect plants against virus infections," *BMC Biotechnology*, 3:1-11 (2003).
Tice, "Selecting the right compounds for screening: does Lipinski's Rule of 5 for pharmaceuticals apply to agrochemicals?" *Pest Management Science*, 57(1):3-16 (2001).
Tomlinson, "Evidence that the hexose-to-sucrose ratio does not control the switch to storage product accumulation in oilseeds: analysis of tobacco seed development and effects...,"*Jrnl of Exper Bot*, 55(406):2291-2303 (2004).
Toriyama et al., "Transgenic Rice Plants After Direct Gene Transfer Into Protoplasts," *Bio/Technology*, 6:1072-1074 (1988).
Townsend et al., "High frequency modification of plant genes using engineered zinc finger nucleases," *Nature*, 459:442-445 (2009).

TransIT-TKO® Transfection Reagent, Frequently Asked Questions, Web. 2019 <https://www.mirusbio.com/tech-resources/faqs/transit-tko-faqs>.
Trucco et al., "*Amaranthus hybridus* can be pollinated frequently by *A. tuberculatus* under filed conditions," *Heredity*, 94:64-70 (2005).
Ulrich et al., "Large scale RNAi screen in Tribolium reveals novel target genes for pest control and the proteasome as prime target," *BMC genomics*, 16(1):671 (2015).
Van der Meer et al., "Promoted analysis of the chalcone synthase (chs A) gene of Petunia hybrid: a 67 bp promoter region directs flower-specific expression," *Plant Mol. Biol.*, 15:95-109 (1990).
Wang et al., "Principle and technology of genetic engineering in plants," in Plant genetic engineering principles and techniques, Beijing: Science Press, pp. 313-315 (1998).
Watson et al., "RNA silencing platforms in plants," *FEBS Letters*, 579:5982-5987 (2005).
Yu et al., "Diversity of Acetyl-Coenzyme A Carboxylase Mutations in Resistant Lolium Populations: Evaluation Using Clethodim," *Plant Physiology*, 145:547-558 (2007).
Yu et al., "Glyphosate, paraquat and ACCase multiple herbicide resistance evolved in a Lolium rigidum biotype," *Planta*, 225:499-513 (2007).
Zabkiewicz, "Adjuvants and herbicidal efficacy—present status and future prospects," *Weed Research*, 40:139-149 (2000).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," *Toxicological Sciences*, 95(2):356-368 (2007).
Zhang et al., "Progress in research of honey bee mite Varro destructor," *Journal of Environmental Entomology*, 34(3):345-353 (2012).
Zhang, "Artificial trans-acting small interfering RNA: a tool for plant biology study and crop improvements," *Planta*, 239:1139-1146 (2014).
Zhao et al., "Ps0rl, a potential target for RNA interference-based pest management," *Insect Molecular Biology*, 20(1):97-104 (2011).
Zhong et al., "A forward genetic screen to explore chloroplast protein import in vivo identifies Moco sulfurase, pivotal for ABA and IAA biosynthesis and purine turnover," *The Plant Journal*, 63:44-59 (2010).
Zhong et al., "A pea antisense gene for the chloroplast stromal processing peptidase yields seedling lethals in *Arabidopsis*: survivors show defective GFP import in vivo," *The Plant Journal*, 34:802-812 (2003).
Zidack et al., "Promotion of Bacterial Infection of Leaves by an Organosilicone Surfactant: Implications for Biological Weed Control," *Biological Control*, 2:111-117 (1992).
Zipperian et al., "Silicon Carbide Abrasive Grinding," Quality Matters Newsletter, PACE Technologies 1(2):1-3 (2002).
Zotti et al., "RNAi technology for insect management and protection of beneficial insects from diseases: lessons, challenges and risk assessments," *Neotropical Entomology*, 44(3):197-213 (2015).
Search Report dated Oct. 20, 2017, in Chinese Patent Application No. 201380039346.6.
Jiang et al., Chapter III Seeds and Seedlings, Botany, Northwest A&F University Press, pp. 87-92 (2009).
Yan et al., Seed Science, China Agriculture Press, pp. 101-103, Tables 2-37 (2001).
Zhao et al., "Vegetable Statdardized Production Technology," Hangzhou: Zhejiang Science and Technology Press, p. 19 (2008).
Li et al., "A Simplified Seed Transformation Method for Obtaining Transgenic *Brassica napus* Plants," Agricultural Sciences in China, 8(6):658-663 (2009).
Friedberg, "Automated protein function prediction—the genomic challenge," Briefings in Bioinformatics, 7(3):225-242 (2006).
Hagio, "Chapter 25: Direct Gene Transfer into Plant Mature Seeds via Electroporation After Vacuum Treatment," Electroporation and Sonoporation in Developmental Biology, p. 285-293 (2009) Herewith.

* cited by examiner

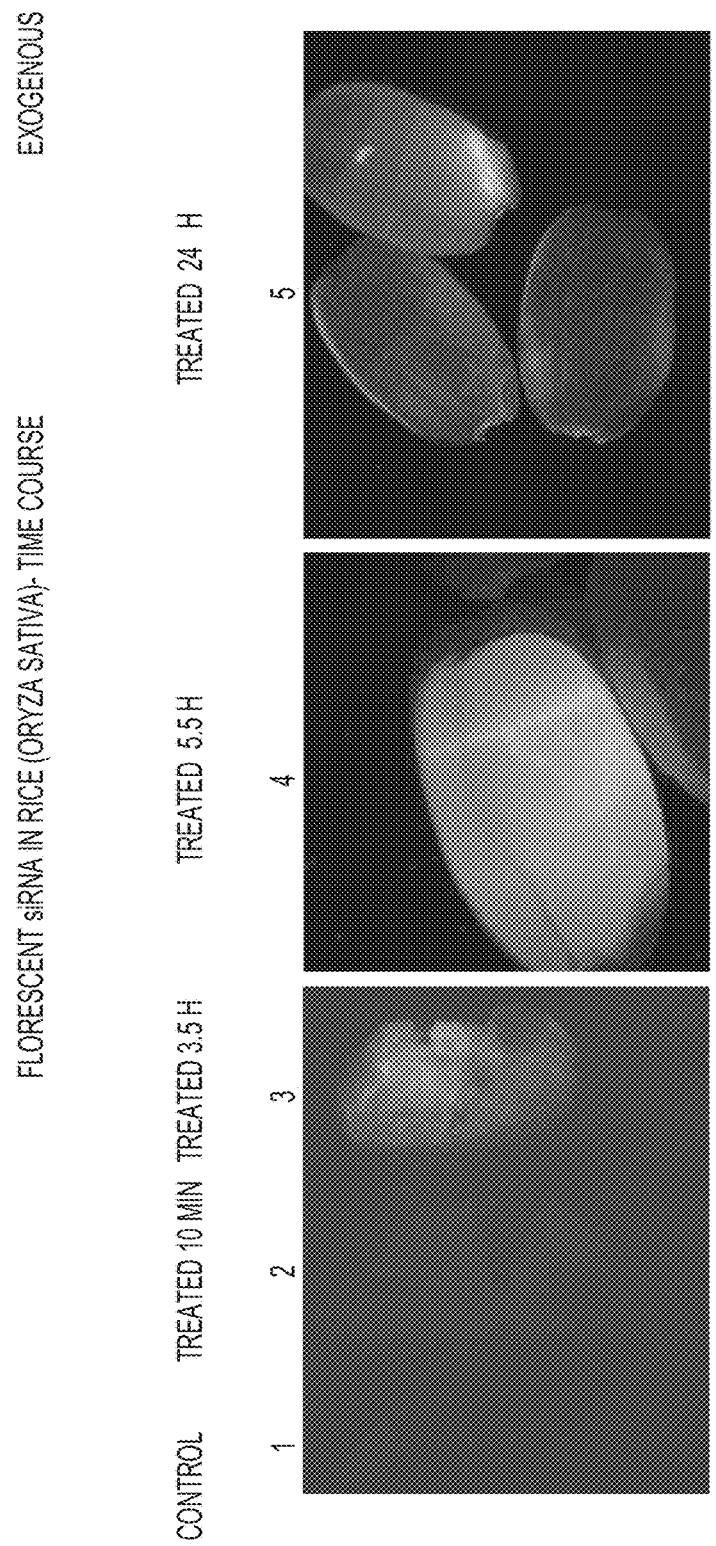

NADPH-DS#1

SCORE         EXPECT    IDENTITIES   GAPS      STRAND      FRAME
64.4 BITS(70) 3E-09()   58/71(82%)   4/71(5%)  PLUS/PLUS

FEATURES:

QUERY   27   TTGGGCTTGGAGATGATGACGCTAAT--ATTGAAGATGACTTTATCACCTGGAAAGAAAA
             |||| ||||||||||||||| |||    ||||||||||||| |||| ||||||||| ||
SBJCT   864  TTGGTCTTGGAGATGATGA---CCAATGCATTGAGGATGACTTCAACACATGGAAAGAAAC
        921

QUERY   85   GTTCTGGCCAG   95
             | ||||||||||
SBJCT   922  TCTCTGGCCAG   932

NADPH-DS2

SCORE         EXPECT    IDENTITIES   GAPS      STRAND      FRAME
46.4 BITS(50) 8e-04()   31/35(89%)   0/35(0%)  PLUS/PLUS

FEATURES:

QUERY   351  CCTCGCCTACAACCAAGATACTACTCCATCTCATC   385
             |||||||| |||||||||||||||| || |||||||
SBJCT   1604 CCTCGCCTTCAACCAAGATACTACTATTCATTTCATC  1638

FIG. 9A

ATPASE-DS1

| SCORE | EXPECT | IDENTITIES | GAPS | STRAND | FRAME |
|---|---|---|---|---|---|
| 251 BITS(278) | 1E-65(1) | 348/484(72%) | 10/484(2%) | PLUS/PLUS | |

FEATURES:

```
QUERY  27   GGAAAGCCCATTGACAAGGGTCCCCCAATCCTCGCCGAGGACTTCTTGACATCCAGGGA  86
            |||||| ||||||||||||| |||||||||||| ||||||||| ||||||||||||| ||
SBJCT  462  GGAAAACCTATTGACAAATGGCCCCCGATATTACCTGAAGCTACTTGGATATCTCTGGA  521

QUERY  87   CAGCCCATCAACCCATGGTCCCGTATCTACCCGAGGAGATGATCCAGACTGGTATCTCC  146
            |||||||||| |||| || ||||||||| || |||| |||||| ||||| ||||||  |
SBJCT  522  AGTTCTATTAATCCCAGTGAGAGAGAACCTATCCAGAGGAGATGATCCAAACTGGGATATCC  581

QUERY  147  GCTATCGACGTGATGAACTCCATTGCTCGTGGTCAGAAGATCCCCATCTTCTCTGCCGCT  206
            ||||| ||||||||||||||||||||| || ||||| |||||||||| |||| |||| |
SBJCT  582  ACCATTGATGTGATGAACTCCATTGCTCGTCGTGGGCAAAAAAATCCCCTATTTTCTGCTGCT  641

QUERY  207  GGTCTGCCCCCACAATGAAATTGCCGCCCAGATCGTAGACAGGCGGTCTTGTTAAGATC  266
            |||||||||  ||||||||||||| ||||| || ||||| ||| ||  |||  |||
SBJCT  642  GGACTCCCTCACAATGAAATTGCTGCTCAGATCGTGCTCAGATCGTGTCGGCCTGGCCTTGTGAAGACA  701
```

*FIG. 9B*

| | | |
|---|---|---|
| QUERY 267 | CCCG------GCAAATCA-GTGTTGGATGACCACGAGGACAACTTGCCATCGTATTCGCA | 320 |
| SBJCT 702 | TTGGAGAAAGGAAAGCATGCAGAGGGTGTGAAGATGACAACTTGCTATTGTGTTTGCT | 761 |
| QUERY 321 | GCTATGGGTGTGAACATGGAAACCGCCCGGTTCTTCAAACAGGACTTCGAAGAGAACGGT | 380 |
| SBJCT 762 | GCTATGGGAGTGAACATGGAAACAGCTCAATTCTTCAAACGTCATTTTGAAGAGAACGGT | 821 |
| QUERY 381 | TCTATGGAGAACGTGT--GCCTGTTCTTTGAACTTGGCCAATGACCCCACTATTGAGAGAA | 438 |
| SBJCT 822 | TCCATG--GAACGGGTCACCCTTTTTCTGAATCTGGCTAATGATCCACCATTGAACGTA | 879 |
| QUERY 439 | TTATCACACCCCGTCTTGCTTTGACTGCTGCCGAGTTCTTGGCCTACCAGTGCCGAGAAAC | 498 |
| SBJCT 880 | TTATCACCCCTCGGATTGCTCTAACAACAGCAGAATATTTGGCATATGAATGTGGGAAGC | 939 |
| QUERY 499 | ACGT | 502 |
| SBJCT 940 | ATGT | 943 |

*FIG. 9B CONTINUED*

IAP-DS1

| SCORE | EXPECT | IDENTITIES | GAPS | STRAND | FRAME |
|---|---|---|---|---|---|
| 37.4 BITS(40) | 0.43() | 22/23(96%) | 0/23(0%) | PLUS/PLUS | |

FEATURES:

```
QUERY  2    TAATACGACTCACTATAGGGAGA  24
            |||||||||||||||||||| ||
SBJCT  441  TAATACGACTCACTATAGGGCGA  463
```

IAP-DS2

| SCORE | EXPECT | IDENTITIES | GAPS | STRAND | FRAME |
|---|---|---|---|---|---|
| 35.6 BITS(38) | 1.5() | 19/19(100%) | 0/19(0%) | PLUS/PLUS | |

FEATURES:

```
QUERY  444  CCGGTACCTCTCCGCCACG  462
            |||||||||||||||||||
SBJCT  607  CCGGTACCTCTCCGCCACG  625
```

FIG. 9C

NADPH-DS1

| SCORE | EXPECT | IDENTITIES | GAPS | STRAND | FRAME |
|---|---|---|---|---|---|
| 42.8 BITS(46) | 0.021() | 28/30(93%) | 1/30(3%) | PLUS/PLUS | |

FEATURES:
```
QUERY  2      TAATACGACTCACTATAGGGAGAACTTGGG   31
              ||||||||||||||||||||| ||| |||||
SBJCT  283    TAATACGACTCACTATAGGGCGAA-TTGGG   311
```

ANOTHER SEGMENT:

| SCORE | EXPECT | IDENTITIES | GAPS | STRAND | FRAME |
|---|---|---|---|---|---|
| 37.4 BITS(40) | 0.91() | 20/20(100%) | 0/20(0%) | PLUS/PLUS | |

FEATURES:
```
QUERY  523    CCCTATAGTGAGTCGTATTA   542
              ||||||||||||||||||||
SBJCT  755    CCCTATAGTGAGTCGTATTA   774
```

NADPH-DS2

| SCORE | EXPECT | IDENTITIES | GAPS | STRAND | FRAME |
|---|---|---|---|---|---|
| 39.2 BITS(42) | 0.26() | 21/21(100%) | 0/21(0%) | PLUS/PLUS | |

FEATURES:
```
QUERY  189     GATGAAGAAGACAAAAAGAAA   209
               |||||||||||||||||||||
SBJCT  42818   GATGAAGAAGACAAAAAGAAA   42838
```

ATPASE-DS1

| SCORE | EXPECT | IDENTITIES | GAPS | STRAND | FRAME |
|---|---|---|---|---|---|
| 214 BITS(236) | 6e-54() | 263/359(73%) | 9/359(2%) | PLUS/PLUS | |

FEATURES:

```
QUERY  114  TACCCCGAGGAGATGATCCAGATGGTATCCCGTATCGAGCTGAGAACTCCATTGCT  173
            |||||| |||||||||||||||| |||  ||||| |||||||||| |||| ||||||
SBJCT  487  TATCCTGAAGAAATGATACAGACAGGAAATTCCACAGTAGACGTCATGAATTCAATTGCT  546

QUERY  174  CGTGGTCAGAGATCCCCATCTTCTGCCGGTGTCTGCCCACAGAATGAAATTGCCGCC    233
            ||| |||||||| ||||||| || |||| |||||  ||||||| |||||||||| ||
SBJCT  547  AGAGGGCAGAAGATTCCTCTTTTCTGCTGGTGTCTCCTCATAATGAAATTGCAGCC    606

QUERY  234  CAGATCTGTAGACAGGCCGGTCTTGTTAAGATCCCGGCAAATCAG------TGTTG--   284
            |||||||||| ||||| ||||| ||||| ||||| ||||||||||      |||||
SBJCT  607  CAGATCTGTCGTCAGGCTGGACTGGACTGGTGAAAGAGAGTTGGAAAAAATCGACAACTTCTTGAG  666

QUERY  285  GATGACCACGAGGACAACTTCGCCATCGTATTCGCAGTGACTTCGTGAACATGGAAACC  344
            |||||||| |||||||||| ||||| ||| ||||| ||| | ||||||||||||| ||
SBJCT  667  GGTGGTGAAGAGACAATTTGCCATAGTCTTGCTGCCATGGGAGTCAACATGGAAACA    726

QUERY  345  GCCCGGTTCTTCAAACAGGACTTCGAACAGAACGGTTCTATGGAGAACGTGTGCCTGTTC  404
            |||| |||| ||||||| |||| |||||| ||| | |||||||||| |||| ||||||
SBJCT  727  GCACAATTTTTCAAACGTGATTTTGAGGAAAAATGAACTATGGACATCATGGACACTTTTC  786

QUERY  405  TTGAACTTGGCCAATGACCCCACTATTGAGAGAATTATCACACCCGTCTTGCTTTGAC    463
            ||||||||||||||||||||| ||||||||||  ||| |||||||||||| |||||||
SBJCT  787  TTAAACTTGGCCAATGATCCTACTACTATAGAGGGTATTATTACTCCCAGGATTGCTCTGAC  845
```

IAP1-DS1

| SCORE | EXPECT | IDENTITIES | GAPS | STRAND | FRAME |
|---|---|---|---|---|---|
| 37.4 BITS(40) | 0.91(0) | 22/23(96%) | 0/23(0%) | PLUS/PLUS | |

FEATURES:

```
QUERY 501   TCTCCCTATAGTGAGTCGTATTA  523
            || |||||||||||||||||||||
SBJCT 90683 TCGCCCTATAGTGAGTCGTATTA  90705
```

FIG. 10C

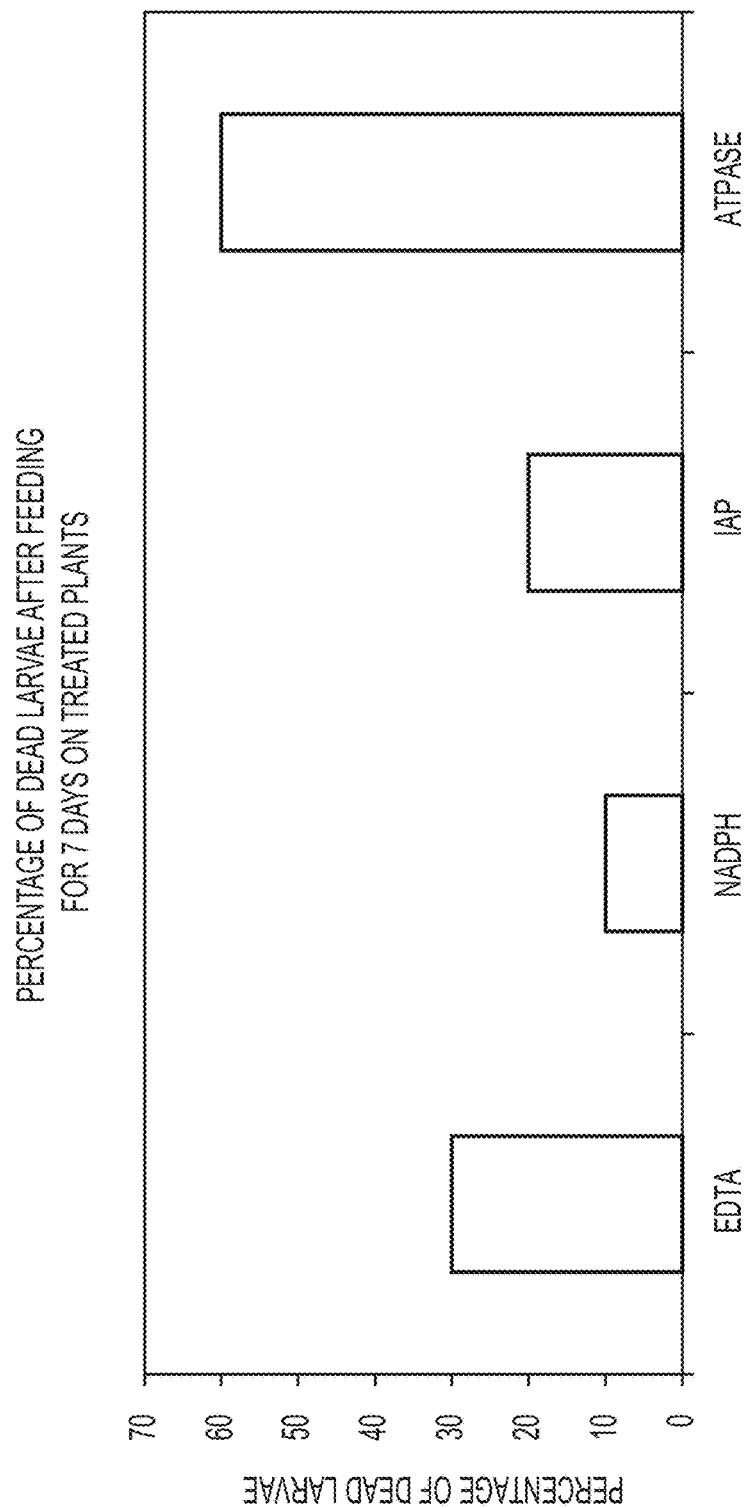

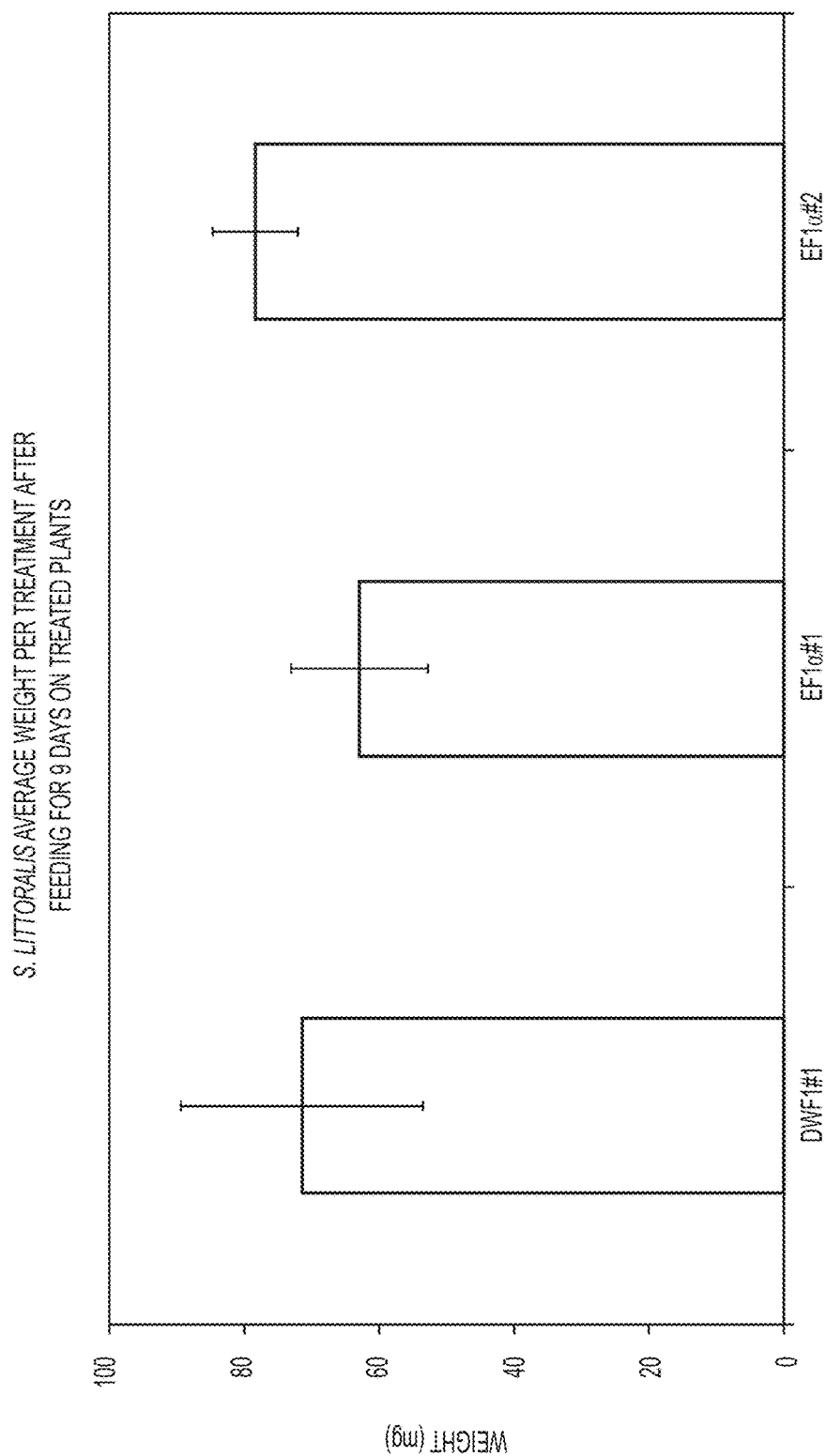

| SCORE | EXPECT | IDENTITIES | GAPS | STRAND |
|---|---|---|---|---|
| 264 BITS (292) | 2e-69 | 298/400(75%) | 0/400(0%) | PLUS/PLUS |

```
QUERY   124   CCCACAGACAAGCCCTCGTCTTCCCCTCCAGGACGTATACAAAATCGTGGTATTGGT   183   SEQ. ID NO. 221
              ||| |  ||||||||  ||||||  ||||  |||||| ||||| |||| ||||| ||
SBJCT   837   CCCTCGGACAAGCCCCTCGTCTCCCCCTCCAGGATGTGTACAAGATTGTGGTATTGGA   896   SEQ. ID NO. 222

QUERY   184   ACGGTGCCCGTAGGCAGAGTTGAAACTGTATCCTCAAGCCTGGTACCATCGTCGTCTTC   243
              |||||||||||| ||||||||  ||||| || || |||||||||| || |||| ||| 
SBJCT   897   ACTGTGCCAGTTGGTCGTGTGGAGACTGTGGTCATCAACCCTGGTATGTTGTCACCTTT   956

QUERY   244   GCCCCCCGCCAACATCACCACTGAAGTCAAGTCTGTGGAGATGCACCACGAAGCTCTCCAA   303
              ||  || |||||||| ||||||||  |||| ||||| ||  ||||||| ||||||| ||
SBJCT   957   GGTCCAACTGGCCTGACTACTGAGGTGAAGTCTGTTGAGGATGATGCACCATGAGGCTCTTCAG   1016

QUERY   304   GAGGCCCGTACCCGGTGCAACGTTGGTTTCAACGTAAAGAACGTTTCCGTCAAGGAGTTG   363
              |||||||| ||||||||||| |||||| ||||   || |||   ||||||||||||| |
SBJCT   1017  GAGGCCCTTCCTGGTGGTACAAGTTGGCTTCAACGTTGGCTTGTGAAGGATTC   1076

QUERY   364   CGTCGTGGTTACGTCGTCGGTGACTCCAAGAACAACCCCAAGGGGCCCCGCCGATTTC   423
              || |||||||| ||||||||   ||||||||||| ||| ||||||  || |||||| 
SBJCT   1077  AAGCGTGGTTATGTGGCCTCCAACTCCAAGGATGACCCTGCCAAGGAGGCTGCCAGCTTC   1136

QUERY   424   ACAGCACAGGTCATCATCGTCTCTCAACCACCCTGGTCAAATCTCAAACGGATACACACCTGTG   483
              |||||||| ||||| ||||| |||||||||||||||| || |  ||| |||| || |||||| 
SBJCT   1137  ACTCCCAGTCATCATCATGAACCACACCCTGGGCAGATCGGTAACGGTTATGCCCCAGTG   1196

QUERY   484   CTGGATTCCACACAGCCCACACTTGCCTGCAAGTTCGCTG   523
              ||||| | ||||  ||| ||| ||||| ||||||||||||
SBJCT   1197  CTGGACTGCCACACCTCCATATTGCTGTCAAGTTGCTG   1236
```

FIG. 31A

```
SCORE         EXPECT    IDENTITIES     GAPS        STRAND
300 BITS(332) 2e-80     335/446(75%)   6/446(1%)   PLUS/PLUS

QUERY   32  GAAATGGGTAAGGGTTCCTTCAAATACGCCTGGGTATTGGACAAACTGAAGGCTGAGCGT  91   SEQ. ID NO. 223
            |||||||| ||| |||| |||||||| || ||||| || |||||||||||||||||||||
SBJCT  218  GAAATGAATAAGCGGTCCTTCAAGTACGCGTGGGTGCTCGACAAGCTCAAGGCTGAGCGT  277  SEQ. ID NO. 224

QUERY   92  GAACGTGGTATCACCATTGATATTGCTCTCTGTGGAAGTTCGAAACCGCTAAATACTATGTC 151
            |||||||||||||||||||||||||||||||||||||||||||||||| ||||| |||||
SBJCT  278  GAGAGAGGTATCACCATTGATATTGCTCTGTGTGGAAGTTGAGACCAAGTACTACTGC    337

QUERY  152  ACCATTATTGACGCTCCCGGACACAGAGATTTCATCAAGAACATGATCATGATCGAACCTCC 211
            ||||||||||| |||| |||| ||| |||||||||||||||||||||||||||||||||||
SBJCT  338  ACGGTCATTGATGCCCCTGGACACCACCCTGATGACTTGACTTCATCAAGAACATGATCATGATCACTGGTACCTCC 397

QUERY  212  CAGGCCCGATTGCGCCGTAC---TCATTGTCGCCGCTGGTACCGGTGAATTCGAGGCTGGT  268
            ||||| | ||| ||||| ||   |||||  |||  |||     ||||||||||||||||
SBJCT  398  CAGGCTGACTGTGCTGTCCTTATCATTGACTCCAC---CACTGGTGGTTTTGAGGCTGGT  454

QUERY  269  ATCTCGAAGAACGACAGACCCGTCAGCACGCTCTGCTTCCTGCTGTTCACACTCGGTGTCAAG 328
            |||| |||||| ||||||||||| |||||| |||||| || |  |||||||||  ||||||
SBJCT  455  ATCTCCAAGATGGCCAGACCCGTGAACACATGCTCTCCTTGCGTTCACCCTTGGAGTGAAG    514

QUERY  329  CAGCTGATTGTGGGCGTCAACAAAATGGACTCCACTGAGCCCCCCATACAGCGAATCCCGT  388
            ||||||||||||  |||||||||| |||  |||| ||||| |||||||||||| |||||
SBJCT  515  CAGATGATTTGCTGCTGCAACAAGATGATGCAACCACTCCCAAATACTCCAAGGCACGT    574

QUERY  389  TTCGAGGAAATCAAGAAGGAAGTGTCCTCTACATCAAGAAGATCGGTTACAACCCAGCT  448
            ||||||||||||||||| |||||||||||||| ||||||||||||| | |||||||||
SBJCT  575  TTCGAGGAAATCAAGAAGGAAGTCTCATCCTCCTACCTCAAGAAGTTGGGTACAACCCTGAT  634

QUERY  449  GCTGTCGCTTTCGTACCCATTTCTGG  474
            |||||| || |||| |||||||||||
SBJCT  635  AAGATTGCCTTTGTCCCCATTTCTGG  660
```

FIG. 31B

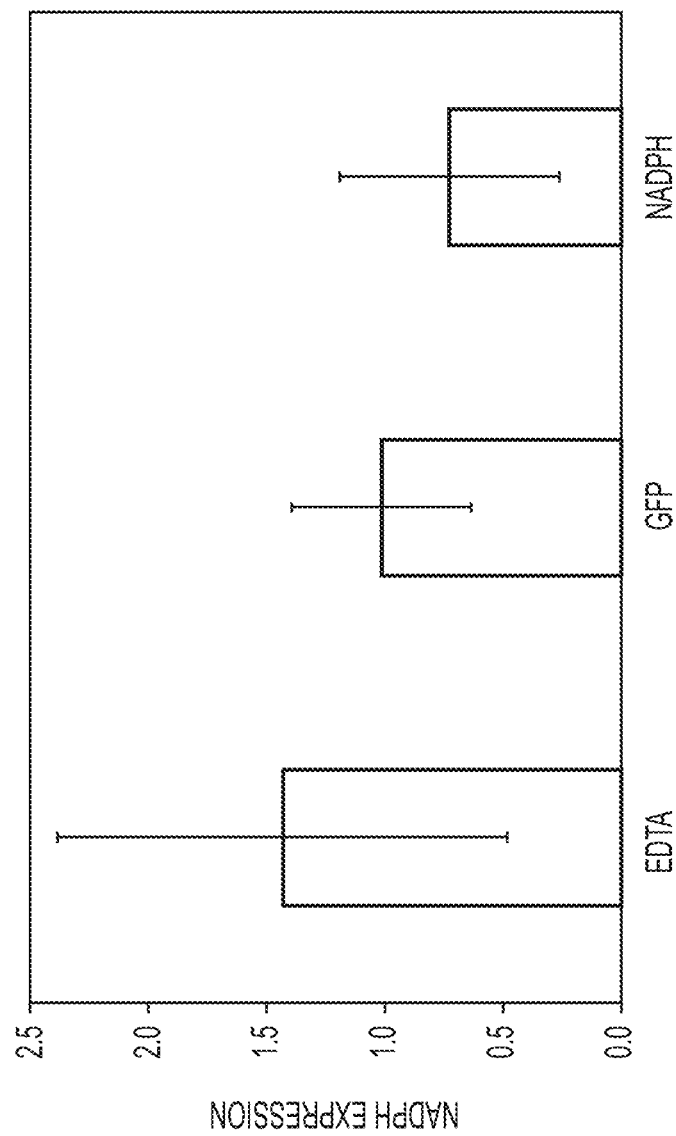

METHODS OF INTRODUCING DSRNA TO PLANT SEEDS FOR MODULATING GENE EXPRESSION

CROSS REFERENCE TO RELATED APPLICATIONS

This application claims benefit of provisional applications 61/748,095, filed Jan. 1, 2013, 61/748,101, filed Jan. 1, 2013, 61/748,094, filed Jan. 1, 2013, 61/748,099, filed Jan. 1, 2013, 61/814,888, filed Apr. 23, 2013, 61/814,892, filed Apr. 23, 2013, 61/814,899, filed Apr. 23, 2013, 61/814,890, filed Apr. 23, 2013, 61/908,965, filed Nov. 26, 2013, and 61/908,855, filed Nov. 26, 2013, each of which is herein incorporated by reference.

INCORPORATION OF SEQUENCE LISTING

The ASCII file, entitled P34098_05-01-2014_ST25.txt, created on Apr. 10, 2014, comprising 112,075 bytes, is incorporated herein by reference.

FIELD OF THE DISCLOSURE

Methods and compositions for improving plant resistance to insect pests are provided. Methods and compositions for improving plant resistance to viral pathogens are also provided.

BACKGROUND

With a growing world population, increasing demand for food, fuel and fiber, and a changing climate, agriculture faces unprecedented challenges. Development of plants with improved traits is highly desirable, with some of the major traits that are of major interest to farmers and seed companies include improved abiotic stress tolerance, fertilizer use efficiency, disease resistance, yield and more.

Plant trait improvement is typically performed by either genetic engineering or classical breeding. New methods for trait improvement through specific gene alteration are highly desirable. These include methods for over-expression of genes or gene silencing. A powerful technique for sequence-specific gene silencing is through RNA interference (RNAi). First discovered in the nematode C. elegans (Fire et al. 1998, Nature, 391:806-811), RNAi is a mechanism in which expression of an individual gene can be specifically silenced by introducing a double-stranded RNA (dsRNA) that is homologous to the selected gene into cells. Inside the cell, dsRNA molecules are cut into shorter fragments of 21-27 nucleotides by an RNase III-related enzyme (Dicer). These fragments, called small interfering RNAs (siRNAs), get incorporated into the RNA-induced silencing complex (RISC). After additional processing, the siRNAs are transformed into single-stranded RNAs that act as guide sequences to eventually cleave target messenger RNAs. By using RNAi to specifically silence relevant target genes, one can alter basic traits of an organism. Specifically for plants, it holds incredible potential for modifications that may lead to increased stress resistance and better crop yield.

In plants, RNAi is typically performed by producing transgenic plants that over-express a DNA fragment that is transcribed to produce a dsRNA. This dsRNA is then processed into siRNAs that mediate the cleavage and silencing of target genes.

The major technical limitation for this technology is that many important plant crop species are difficult or impossible to transform, precluding the constitutive expression of constructs directing production of dsRNA. Moreover, questions concerning the potential ecological impact of virus-resistant transgenic plants have so far significantly limited their use (Tepfer, 2002, Annu Rev. Phytopathol. 40, 467-491). An additional hurdle for obtaining transgenic plants is attributed to the difficulty of having the transformation and regeneration events occur in the same cell types.

Therefore the development of a method for obtaining transformed seeds which is independent of the methods inherent to tissue culture procedures is at the cutting edge of plant molecular biology research.

SUMMARY OF THE INVENTION

According to an aspect of some embodiments of the present invention there is provided a method of introducing naked dsRNA into a seed, the method comprising contacting the seed with the naked dsRNA under conditions which allow penetration of the dsRNA into the seed, thereby introducing the dsRNA into the seed.

According to an aspect of some embodiments of the present invention there is provided an isolated seed comprising an exogenous naked dsRNA, wherein the seed is devoid of a heterologous promoter for driving expression of the dsRNA in the plant.

According to an aspect of some embodiments of the present invention there is provided an isolated seed comprising an exogenous naked dsRNA3.

According to an aspect of some embodiments of the present invention there is provided a plant or plant part comprising an exogenous naked dsRNA and being devoid of a heterologous promoter for driving expression of the dsRNA in the plant.

According to an aspect of some embodiments of the present invention there is provided a seed containing device comprising a plurality of the seeds.

According to an aspect of some embodiments of the present invention there is provided a sown field comprising a plurality of the seeds.

According to an aspect of some embodiments of the present invention there is provided a method of producing a plant, the method comprising:
  (a) providing the seed; and
  (b) germinating the seed so as to produce the plant.

According to an aspect of some embodiments of the present invention there is provided a method of modulating gene expression, the method comprising:
  (a) contacting a seed of a plant with a naked dsRNA, under conditions which allow penetration of the dsRNA into the seed, thereby introducing the dsRNA into the seed; and optionally
  (b) generating a plant of the seed.

According to some embodiments of the invention, the naked dsRNA is designed for down regulating expression of a gene of the plant.

According to some embodiments of the invention, the naked dsRNA is designed for down regulating expression of a gene of a phytopathogen.

According to some embodiments of the invention, the penetration is to an endosperm and alternatively or additionally an embryo of the seed.

According to some embodiments of the invention, the naked dsRNA does not integrate into the genome of the seeds.

According to some embodiments of the invention, the conditions result in presence of the dsRNA in the plant for at least 10 days following germination.

According to an aspect of some embodiments of the present invention there is provided a method of inhibiting expression of a target gene in a phytopathogenic organism, the method comprising providing to the phytopathogenic organism the plant or plant part, thereby inhibiting expression of a target gene in the phytopathogenic organism.

According to some embodiments of the invention, the phytopathogenic organism is selected from the group consisting of a fungus, a nematode and an insect.

According to some embodiments of the invention, the method further comprises observing death or growth inhibition of the phytopathogen following the providing.

According to an aspect of some embodiments of the present invention there is provided a kit for introducing naked dsRNA to seeds comprising:

(i) naked dsRNA; and
(ii) a priming solution.

According to some embodiments of the invention, the naked dsRNA and the priming solutions are comprised in separate containers.

According to some embodiments of the invention, the dsRNA comprises siRNA.

According to some embodiments of the invention, the dsRNA comprises siRNA and dsRNA.

According to some embodiments of the invention, the contacting is effected by inoculating the seed with the dsRNA.

According to some embodiments of the invention, the method further comprises priming the seed prior to the contacting.

According to some embodiments of the invention, the priming is effected by:

(i) washing the seed prior to the contacting; and
(ii) drying the seed following step (i).

According to some embodiments of the invention, the washing is effected in the presence of double deionized water.

According to some embodiments of the invention, the washing is effected for 2-6 hours.

According to some embodiments of the invention, the washing is effected at 4-28° C.

According to some embodiments of the invention, the drying is effected at 25-30° C. for 10-16 hours.

According to some embodiments of the invention, the contacting is effected in a presence of the naked dsRNA at a final concentration of 0.1-100 µg/µl.

According to some embodiments of the invention, the contacting is effected in a presence of the naked dsRNA at a final concentration of 0.1-0.5 µg/µl.

According to some embodiments of the invention, the method further comprises treating the seed with an agent selected from the group consisting of a pesticide, a fungicide, an insecticide, a fertilizer, a coating agent and a coloring agent following the contacting.

According to some embodiments of the invention, the treating comprises coating the seed with the agent.

According to some embodiments of the invention, the seed is free of an agent selected from the group consisting of a pesticide, a fungicide, an insecticide, a fertilizer, a coating agent and a coloring agent.

According to some embodiments of the invention, the dsRNA is for down regulating expression of a coding gene.

According to some embodiments of the invention, the dsRNA is for down regulating expression of a non-coding gene.

According to some embodiments of the invention, the seed is of the Viridiplantae super-family.

According to some embodiments of the invention, the conditions allow accumulation of the dsRNA in the endosperm and alternatively or additionally embryo of the seed.

According to some embodiments of the invention, a concentration of the naked dsRNA is adjusted according to a parameter selected from the group consisting of seed size, seed weight, seed volume, seed surface area, seed density and seed permeability.

According to some embodiments of the invention, the contacting is effected prior to breaking of seed dormancy and embryo emergence.

According to some embodiments of the invention, the seed is a primed seed.

According to some embodiments of the invention, the seed or the plant comprises RNA dependent RNA polymerase activity for amplifying expression of the dsRNA.

According to some embodiments of the invention, the seed is a hybrid seed.

According some embodiments, there is provided an isolated dsRNA comprising a nucleic acid sequence having:

(i) a homology level to a plant gene sufficient to induce amplification of secondary siRNA products of the dsRNA in a plant cell comprising same and wherein down-regulation of the plant gene by the dsRNA does not substantially affect any of biomass, vigor or yield of the plant; and (ii) a homology level to a gene of a phytopathogenic organism sufficient to induce degradation of the gene of the phytopathogenic organism, wherein the phytopathogenic organism depends on the plant for growth and wherein the degradation induces a growth arrest or death of the phytopathogenic organism. According to some embodiments, the nucleic acid sequence is at least 25 bp long. According to some embodiments, the nucleic acid sequence is 25-70 bp long. According to some embodiments, the dsRNA wherein the nucleic acid sequence is at least 80% identical to the plant gene. According to some embodiments, the nucleic acid sequence is more than 70 bp. According to some embodiments, the nucleic acid sequence comprises a nucleic acid segment at least 70 bp in length which is at least 65% identical to the plant gene, and/or a second nucleic acid segment at least 17 bp in length which is at least 85% identical to the plant gene. According to some embodiments, the first nucleic acid segment and the second nucleic acid segment overlap. According to some embodiments, the first nucleic acid segment and the second nucleic acid segment are in no overlap. According to some embodiments, the plant gene is expressed in most plant organs starting from germination. According to some embodiments of the invention, the isolated dsRNA is at least 80% homologous to the gene of the phytopathogen.

Several embodiments relate to a method of providing a plant having improved resistance to an insect pest, comprising: growing a plant from a seed, wherein the seed has been contacted with an exogenous dsRNA molecule comprising a sequence that is essentially identical or essentially complementary to at least 18 contiguous nucleotides of a gene of the insect pest or to the sequence of an RNA transcribed from said gene, wherein the plant exhibits improved resistance to the insect pest relative to a control plant, wherein the control plant is grown from a seed not contacted with the exogenous dsRNA molecule. In some embodiments, the plant is maize, soybean, rice, wheat, tomato, cucumber, lettuce, cotton or rapeseed. In some embodiments, the insect pest is *Spodoptera littoralis, Diabrotica virgifera virgifera* or *Leptinotarsa decemlineata*. In some embodiments, the insect pest gene is selected from the group consisting of ATPase, NADPH Cytochrome P450 Oxidoreductase, IAP, Chitin Synthase, EF1α, and β-actin. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent.

Several embodiments relate to a plant provided by a method comprising: growing a plant from a seed, wherein the seed has been contacted with an exogenous dsRNA molecule comprising a sequence that is essentially identical or essentially complementary to at least 18 contiguous nucleotides of a gene of the insect pest or to the sequence of an RNA transcribed from said gene, wherein the plant exhibits improved resistance to the insect pest relative to a control plant, wherein the control plant is grown from a seed not contacted with the exogenous dsRNA molecule. In some embodiments, the plant is maize, soybean, rice, wheat, tomato, cucumber, lettuce, cotton or rapeseed. In some embodiments, the insect pest is *Spodoptera littoralis, Diabrotica virgifera virgifera* or *Leptinotarsa decemlineata*. In some embodiments, the insect pest gene is selected from the group consisting of ATPase, NADPH Cytochrome P450 Oxidoreductase, IAP, Chitin Synthase, EF1α, and β-actin. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent. In some embodiments, the plant does not comprise detectable levels of the exogenous dsRNA molecule.

Several embodiments relate to a method of providing a plant having improved resistance to an insect pest, comprising growing the plant from a seed, wherein the seed comprises an exogenous dsRNA molecule comprising a sequence that is essentially identical or essentially complementary to at least 18 contiguous nucleotides of a gene of the insect pest or to the sequence of an RNA transcribed from said gene, wherein the seed is devoid of a heterologous promoter for driving expression of the exogenous dsRNA molecule, and wherein the plant exhibits improved resistance to the insect pest relative to a control plant, wherein the control plant is grown from a seed not comprising the exogenous dsRNA molecule. In some embodiments, the plant is maize, soybean, rice, wheat, tomato, cucumber, lettuce, cotton or rapeseed. In some embodiments, the insect pest is *Spodoptera littoralis, Diabrotica virgifera virgifera* or *Leptinotarsa decemlineata*. In some embodiments, the insect pest gene is selected from the group consisting of ATPase, NADPH Cytochrome P450 Oxidoreductase, IAP, Chitin Synthase, EF1α, and β-actin. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent. In some embodiments, the plant does not comprise detectable levels of the exogenous dsRNA molecule.

Several embodiments relate to a method for generating a plant having insect resistance, the method comprising: a) introducing a non-transcribable trigger molecule comprising at least one polynucleotide strand comprising at least one segment of 18 or more contiguous nucleotides of an insect pest gene in either anti-sense or sense orientation into an ungerminated seed and b) germinating the seed to generate a plant exhibiting insect resistance after emerging from said seed. In some embodiments, the plant does not comprise detectable levels of the trigger molecule after emerging from the seed. In some embodiments, the non-transcribable trigger molecule is dsRNA. In some embodiments, the insect pest gene is selected from the group consisting of ATPase, NADPH Cytochrome P450 Oxidoreductase, IAP, Chitin Synthase, EF1α, and β-actin. In some embodiments, the plant is resistant to *Spodoptera littoralis, Diabrotica virgifera virgifera* or *Leptinotarsa decemlineata* infestation. In some embodiments, the non-transcribable trigger molecule comprises a sequence that is essentially identical or essentially complementary to at least 18 contiguous nucleotides of SEQ ID Nos.: 21-26, 31, 34, 37, 38, 131-133, 144 or 145. In some embodiments, the non-transcribable trigger molecule comprises a sequence that is essentially identical or essentially complementary to at least 18 contiguous nucleotides of SEQ ID Nos.: 146-190. In some embodiments, the non-transcribable trigger molecule is at least 80% identical to an endogenous plant gene over at least 25 consecutive bp. In some embodiments, the seed is primed prior to introducing the non-transcribable trigger molecule. In some embodiments, the priming is effected by: (i) washing the seed prior to said contacting; and (ii) drying the seed following step (i).

Several embodiments relate to a method of treating a seed to improve insect resistance of a plant grown from the seed, the method comprising: introducing an exogenous dsRNA molecule comprising a sequence that is essentially identical or essentially complementary to at least 18 contiguous nucleotides of an insect pest gene or to the sequence of an RNA transcribed from the insect pest gene into the seed, wherein the plant grown from the seed exhibits improved insect resistance relative to a control plant. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the seed is primed prior to introducing the exogenous dsRNA molecule. In some embodiments, the priming is effected by: (i) washing the seed prior to said contacting; and (ii) drying the seed following step (i). In some embodiments, the seed is washed in double deionized water. In some embodiments, the seed is washed for 2-6 hours. In some embodiments, the seed is washed at 4-28° C. In some embodiments, the seed is dried at 25-30° C. for 10-16 hours. In some embodiments, the dsRNA molecule is provided to the seed at a concentration of 20-150 μg/ml. In some embodiments, the dsRNA molecule is provided to the seed in a solution comprising 0.1 mM EDTA. In some embodiments, the dsRNA molecule is provided to the seed in the presence of a physical agent. In some embodiments, the physical agent is PEG-modified carbon nanotubes.

Several embodiments relate to a seed provided by a method comprising introducing an exogenous dsRNA molecule comprising a sequence that is essentially identical or essentially complementary to at least 18 contiguous nucleotides of an insect pest gene or to the sequence of an RNA transcribed from the insect pest gene into the seed, wherein the plant grown from the seed exhibits improved insect resistance relative to a control plant. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the seed is primed prior to introducing the exogenous dsRNA molecule. In some embodiments, the priming is effected by: (i) washing the seed prior to said contacting; and (ii) drying the seed following step (i). In some embodiments, the seed is washed in double deionized water. In some embodiments, the seed is washed for 2-6 hours. In some embodiments, the seed is washed at 4-28° C. In some embodiments, the seed is dried at 25-30° C. for 10-16 hours. In some embodiments, the dsRNA molecule is provided to the seed at a concentration of 20-150 μg/ml. In some embodiments, the dsRNA molecule is provided to the seed in a solution comprising 0.1 mM EDTA. In some embodiments, the dsRNA molecule is provided to the seed in the presence of a physical agent. In some embodiments, the physical agent is PEG-modified carbon nanotubes. Several embodiments relate to a seed containing device comprising one or more of the seeds. Several embodiments relate to a sown field comprising a plurality of the seeds.

Several embodiments relate to a seed comprising an exogenous dsRNA molecule comprising a sequence that is essentially identical or essentially complementary to at least 18 contiguous nucleotides of an insect pest gene or to the sequence of an RNA transcribed from the insect pest gene, wherein the seed is devoid of a heterologous promoter for driving expression of said dsRNA molecule and wherein the exogenous dsRNA does not integrate into the genome of the seed. In some embodiments, the exogenous dsRNA molecule is present in an endosperm of the seed. In some embodiments, the exogenous dsRNA molecule comprises a sequence that is essentially identical or essentially complementary to at least 18 contiguous nucleotides of SEQ ID Nos.: 21-26, 31, 34, 37, 38, 131-133, 144 or 145. In some embodiments, the exogenous dsRNA molecule comprises a sequence that is essentially identical or essentially complementary to at least 18 contiguous nucleotides of SEQ ID Nos.: 146-190. In some embodiments, the exogenous dsRNA molecule is present in an embryo of the seed. In some embodiments, the exogenous dsRNA molecule is present at a similar concentration in an embryo and an endosperm of the seed. In some embodiments, the exogenous dsRNA molecule is present at a higher concentration in an endosperm than an embryo and of the seed. In some embodiments, the insect pest gene is selected from the group consisting of ATPase, NADPH Cytochrome P450 Oxidoreductase, IAP, Chitin Synthase, EF1α, and β-actin. In some embodiments, the insect pest is *Spodoptera littoralis, Diabrotica virgifera virgifera* or *Leptinotarsa decemlineata*. In some embodiments, the exogenous dsRNA molecule comprises a nucleic acid sequence that is at least 80% identical over at least 25 consecutive bp to an endogenous gene of the seed. In some embodiments, the seed is treated with an agent selected from the group consisting of a pesticide, a fungicide, an insecticide, a fertilizer, a coating agent and a coloring agent. In some embodiments, the seed is a primed seed. Several embodiments relate to a seed containing device comprising one or more of the seeds. Several embodiments relate to a sown field comprising a plurality of the seeds.

Several embodiments relate to a plant exhibiting insect resistance after emerging from a seed, wherein a non-transcribable trigger molecule comprising at least one polynucleotide strand comprising at least one segment of 18 or more contiguous nucleotides of an insect pest gene in either anti-sense or sense orientation is introduced into an ungerminated seed that gives rise to said plant. In some embodiments, the plant is selected from the group consisting of maize, soybean, rice, wheat, tomato, cucumber, lettuce, cotton and rapeseed. In some embodiments, the plant does not comprise a detectable level of the non-transcribable trigger molecule. In some embodiments, the insect pest gene is selected from the group consisting of ATPase, NADPH Cytochrome P450 Oxidoreductase, IAP, Chitin Synthase, EF1α, and β-actin. In some embodiments, the non-transcribable trigger molecule comprises a sequence that is essentially identical or essentially complementary to at least 18 contiguous nucleotides of SEQ ID Nos.: 21-26, 31, 34, 37, 38, 131-133, 144 or 145. In some embodiments, the non-transcribable trigger molecule comprises a sequence that is essentially identical or essentially complementary to at least 18 contiguous nucleotides of SEQ ID Nos.: 146-190. In some embodiments, the non-transcribable trigger molecule comprises a nucleic acid sequence that is at least 80% identical over at least 25 consecutive bp to an endogenous gene of the seed. In some embodiments, the non-transcribable trigger molecule comprises a nucleic acid sequence that is at least 17 bp in length and at least 85% identical to an endogenous gene of the seed. In some embodiments, the non-transcribable trigger molecule comprises a nucleic acid sequence that is at least 70 bp in length and at least 65% identical to an endogenous gene of the seed.

Several embodiments relate to a plant comprising a nucleic acid molecule for suppressing an insect pest gene, wherein the nucleic acid molecule is not integrated into a chromosome of the plant, wherein the nucleic acid molecule is not transcribed from a heterologous transgene integrated into a chromosome of the plant, and wherein the insect pest gene is suppressed by introduction of a trigger molecule comprising at least one polynucleotide strand comprising at least one segment of 18 or more contiguous nucleotides of an insect pest gene in either anti-sense or sense orientation into an ungerminated seed giving rise to the plant. In some embodiments, the plant is selected from the group consisting of maize, soybean, rice, wheat, tomato, cucumber, lettuce, cotton and rapeseed. In some embodiments, the trigger molecule is dsRNA. In some embodiments, the insect pest gene is selected from the group consisting of ATPase, NADPH Cytochrome P450 Oxidoreductase, IAP, Chitin Synthase, EF1α, and β-actin. In some embodiments, the trigger molecule comprises a sequence that is essentially identical or essentially complementary to at least 18 contiguous nucleotides of SEQ ID Nos.: 21-26, 31, 34, 37, 38, 131-133, 144 or 145. In some embodiments, the trigger molecule comprises a sequence that is essentially identical or essentially complementary to at least 18 contiguous nucleotides of SEQ ID Nos.: 146-190. In some embodiments, the trigger molecule comprises a nucleic acid sequence that is at least 80% identical over at least 25 consecutive bp to an endogenous gene of the seed giving rise to the plant. In some embodiments, the trigger molecule comprises a nucleic acid sequence that is at least 17 bp in length and at least 85% identical to an endogenous gene of the seed giving rise to the plant. In some embodiments, the trigger molecule comprises a nucleic acid sequence that is at least 70 bp in length and at least 65% identical to an endogenous gene of the seed giving rise to the plant. In some embodiments, the plant does not comprise a detectable level of the trigger molecule.

Several embodiments relate to a method of reducing corn root worm pressure on a corn plant, the method comprising: a) introducing a trigger molecule comprising at least one polynucleotide strand comprising at least one segment of 18 or more contiguous nucleotides of a corn root worm gene in either anti-sense or sense orientation into an ungerminated corn seed and b) germinating the corn seed to generate a corn plant. In some embodiments, the trigger molecule is dsRNA. In some embodiments, the trigger molecule comprises at least one segment of 18 or more contiguous nucleotides of SEQ ID No. 144. In some embodiments, the trigger molecule comprises at least one segment of 18 or more contiguous nucleotides of SEQ ID Nos.: 146-190. In some embodiments, the ungerminated corn seed is primed prior to introducing the trigger molecule. In some embodiments, the seed is primed by: (i) washing the seed prior to said contacting; and (ii) drying the seed following step (i). In some embodiments, the seed is washed in double deionized water.

Several embodiments relate to a method of providing a plant having improved viral resistance, comprising: growing a plant from a seed, wherein the seed has been contacted with an exogenous dsRNA molecule comprising a sequence that is essentially identical or essentially complementary to at least 18 contiguous nucleotides of a viral gene or to the sequence of an RNA transcribed from said gene, wherein the plant exhibits improved viral resistance relative to a control plant, wherein the control plant is grown from a seed not contacted with the exogenous dsRNA molecule. In some embodiments, the plant is maize, soybean, rice, wheat, tomato, cucumber, lettuce, cotton or rapeseed. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the exogenous dsRNA molecule comprises a sequence that is essentially identical or essentially complementary to at least 18 contiguous nucleotides of SEQ ID Nos.: 8, 11 or 185-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent.

Several embodiments relate to a plant provided by a method comprising: growing a plant from a seed, wherein the seed has been contacted with an exogenous dsRNA molecule comprising a sequence that is essentially identical or essentially complementary to at least 18 contiguous nucleotides of a viral gene or to the sequence of an RNA transcribed from said gene, wherein the plant exhibits improved resistance to the virus relative to a control plant, wherein the control plant is grown from a seed not contacted with the exogenous dsRNA molecule. In some embodiments, the plant is maize, soybean, rice, wheat, tomato, cucumber, lettuce, cotton or rapeseed. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the exogenous dsRNA molecule comprises a sequence that is essentially identical or essentially complementary to at least 18 contiguous nucleotides of SEQ ID Nos.: 8, 11 or 185-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent. In some embodiments, the plant does not comprise detectable levels of the exogenous dsRNA molecule.

Several embodiments relate to a method of providing a plant having improved viral resistance, comprising growing the plant from a seed, wherein the seed comprises an exogenous dsRNA molecule comprising a sequence that is essentially identical or essentially complementary to at least 18 contiguous nucleotides of a viral gene or to the sequence of an RNA transcribed from said gene, wherein the seed is devoid of a heterologous promoter for driving expression of the exogenous dsRNA molecule, and wherein the plant exhibits improved viral resistance relative to a control plant, wherein the control plant is grown from a seed not comprising the exogenous dsRNA molecule. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the exogenous dsRNA molecule comprises a sequence that is essentially identical or essentially complementary to at least 18 contiguous nucleotides of SEQ ID Nos.: 8, 11 or 185-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent.

Several embodiments relate to a plant provided by a method comprising growing the plant from a seed, wherein the seed comprises an exogenous dsRNA molecule comprising a sequence that is essentially identical or essentially complementary to at least 18 contiguous nucleotides of a viral gene or to the sequence of an RNA transcribed from said gene, wherein the seed is devoid of a heterologous promoter for driving expression of the exogenous dsRNA molecule, and wherein the plant exhibits improved viral resistance relative to a control plant, wherein the control plant is grown from a seed not comprising the exogenous dsRNA molecule. In some embodiments, the plant is maize, soybean, rice, wheat, tomato, cucumber, lettuce, cotton or rapeseed. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the exogenous dsRNA molecule comprises a sequence that is essentially identical or essentially complementary to at least 18 contiguous nucleotides of SEQ ID Nos.: 8, 11 or 185-190. In some embodiments, the exogenous dsRNA molecule comprises a nucleic acid sequence that is at least 80% identical to an endogenous plant gene over at least 25 consecutive bp. In some embodiments, the seed is further treated with an agent selected from the group consisting of a pesticide, a fungicide, an insecticide, a fertilizer, a coating agent and a coloring agent. In some embodiments, the plant does not comprise detectable levels of the exogenous dsRNA molecule.

Several embodiments relate to a method for generating a plant having viral resistance, the method comprising: a) introducing a non-transcribable trigger molecule comprising at least one polynucleotide strand comprising at least one segment of 18 or more contiguous nucleotides of an viral gene in either anti-sense or sense orientation into an ungerminated seed and b) germinating the seed to generate a plant exhibiting viral resistance after emerging from said seed. In some embodiments, the plant does not comprise detectable levels of the trigger molecule after emerging from the seed. In some embodiments, the non-transcribable trigger molecule is dsRNA. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the non-transcribable trigger molecule comprises a sequence that is essentially identical or essentially complementary to at least 18 contiguous nucleotides of SEQ ID Nos.: 8, 11 or 185-190. In some embodiments, the non-transcribable trigger molecule is at least 80% identical to an endogenous plant gene over at least 25 consecutive bp. In some embodiments, the seed is primed prior to introducing the non-transcribable trigger molecule. In some embodiments, the priming is effected by: (i) washing the seed prior to said contacting; and (ii) drying the seed following step (i).

Several embodiments relate to a method of treating a seed to improve viral resistance of a plant grown from the seed, the method comprising: introducing an exogenous dsRNA molecule comprising a sequence that is essentially identical or essentially complementary to at least 18 contiguous nucleotides of a viral gene or to the sequence of an RNA transcribed from the viral gene into the seed, wherein the plant grown from the seed exhibits improved viral resistance relative to a control plant. In some embodiments, the exogenous dsRNA molecule comprises a sequence that is essentially identical or essentially complementary to at least 18 contiguous nucleotides of SEQ ID Nos.: 8, 11 or 185-190. In some embodiments, the seed is primed prior to introducing the exogenous dsRNA molecule. In some embodiments, the priming is effected by: (i) washing the seed prior to said contacting; and (ii) drying the seed following step (i). In some embodiments, the seed is washed in double deionized water. In some embodiments, the seed is washed for 2-6 hours. In some embodiments, the seed is washed at 4-28° C. In some embodiments, the seed is dried at 25-30° C. for 10-16 hours. In some embodiments, the dsRNA molecule is provided to the seed at a concentration of 20-150 µg/ml. In some embodiments, the dsRNA molecule is provided to the seed in a solution comprising 0.1 mM EDTA. In some embodiments, the dsRNA molecule is provided to the seed in the presence of a physical agent. In some embodiments, the physical agent is PEG-modified carbon nanotubes.

Several embodiments relate to a seed provided by a method comprising introducing an exogenous dsRNA molecule comprising a sequence that is essentially identical or essentially complementary to at least 18 contiguous nucleotides of a viral gene or to the sequence of an RNA transcribed from the viral gene into the seed, wherein the plant grown from the seed exhibits improved viral resistance relative to a control plant. In some embodiments, the exogenous dsRNA molecule comprises a sequence that is essentially identical or essentially complementary to at least 18 contiguous nucleotides of SEQ ID Nos.: 8, 11 or 185-190. In some embodiments, the seed is primed prior to introducing the exogenous dsRNA molecule. In some embodiments, the priming is effected by: (i) washing the seed prior to said contacting; and (ii) drying the seed following step (i). In some embodiments, the seed is washed in double deionized water. In some embodiments, the seed is washed for 2-6 hours. In some embodiments, the seed is washed at 4-28° C. In some embodiments, the seed is dried at 25-30° C. for 10-16 hours. In some embodiments, the dsRNA molecule is provided to the seed at a concentration of 20-150 µg/ml. In some embodiments, the dsRNA molecule is provided to the seed in a solution comprising 0.1 mM EDTA. In some embodiments, the dsRNA molecule is provided to the seed in the presence of a physical agent. In some embodiments, the physical agent is PEG-modified carbon nanotubes. Several embodiments relate to a seed containing device comprising one or more of the seeds. Several embodiments relate to a sown field comprising a plurality of the seeds.

Several embodiments relate to a seed comprising an exogenous dsRNA molecule comprising a sequence that is essentially identical or essentially complementary to at least 18 contiguous nucleotides of a viral gene or to the sequence of an RNA transcribed from the viral gene, wherein the seed is devoid of a heterologous promoter for driving expression of said dsRNA molecule and wherein the exogenous dsRNA does not integrate into the genome of the seed. In some embodiments, the exogenous dsRNA molecule is present in an endosperm of the seed. In some embodiments, the exogenous dsRNA molecule is present in an embryo of the seed. In some embodiments, the exogenous dsRNA molecule is present at a similar concentration in an embryo and an endosperm of the seed. In some embodiments, the exogenous dsRNA molecule is present at a higher concentration in an endosperm than an embryo and of the seed. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the exogenous dsRNA molecule comprises a sequence that is essentially identical or essentially complementary to at least 18 contiguous nucleotides of SEQ ID Nos.: 8, 11 or 185-190. In some embodiments, the exogenous dsRNA molecule comprises a nucleic acid sequence that is at least 80% identical over at least 25 consecutive bp to an endogenous gene of the seed. In some embodiments, the seed is treated with an agent selected from the group consisting of a pesticide, a fungicide, an insecticide, a fertilizer, a coating agent and a coloring agent. In some embodiments, the seed is a primed seed. Several embodiments relate to a seed containing device comprising one or more of the seeds. Several embodiments relate to a sown field comprising a plurality of the seeds.

Several embodiments relate to a plant exhibiting viral resistance after emerging from a seed, wherein a non-transcribable trigger molecule comprising at least one polynucleotide strand comprising at least one segment of 18 or more contiguous nucleotides of a viral gene in either anti-sense or sense orientation is introduced into an ungerminated seed that gives rise to said plant. In some embodiments, the plant is selected from the group consisting of maize, soybean, rice, wheat, tomato, cucumber, lettuce, cotton and rapeseed. In some embodiments, the plant does not comprise a detectable level of the non-transcribable trigger molecule. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the non-transcribable trigger molecule comprises a sequence that is essentially identical or essentially complementary to at least 18 contiguous nucleotides of SEQ ID Nos.: 8, 11 or 185-190. In some embodiments, the non-transcribable trigger molecule comprises a nucleic acid sequence that is at least 80% identical over at least 25 consecutive bp to an endogenous gene of the seed. In some embodiments, the non-transcribable trigger molecule comprises a nucleic acid sequence that is at least 17 bp in length and at least 85% identical to an endogenous gene of the seed. In some embodiments, the non-transcribable trigger molecule comprises a nucleic acid sequence that is at least 70 bp in length and at least 65% identical to an endogenous gene of the seed.

Several embodiments relate to a plant comprising a nucleic acid molecule for suppressing a viral gene, wherein the nucleic acid molecule is not integrated into a chromosome of the plant, wherein the nucleic acid molecule is not transcribed from a heterologous transgene integrated into a chromosome of the plant, and wherein the viral gene is suppressed by introduction of a trigger molecule comprising at least one polynucleotide strand comprising at least one segment of 18 or more contiguous nucleotides of a viral gene in either anti-sense or sense orientation into an ungerminated seed giving rise to the plant. In some embodiments, the plant is selected from the group consisting of maize, soybean, rice, wheat, tomato, cucumber, lettuce, cotton and rapeseed. In some embodiments, the trigger molecule is dsRNA. In some embodiments, the virus is Tomato golden mottle virus (ToGMoV), Cucumber Mosaic Virus (CMV) or Tomato Spotted Wilt Virus (TSWV). In some embodiments, the viral gene is selected from the group consisting of a ToGMoV gene, a CMV gene and a TSWV gene. In some embodiments, the viral gene is selected from the group consisting of Nucleocapsid (N) gene, a Replicase gene, a Coat gene and the AC1 gene. In some embodiments, the trigger molecule comprises a sequence that is essentially identical or essentially complementary to at least 18 contiguous nucleotides of SEQ ID Nos.: 8, 11 or 185-190. In some embodiments, the trigger molecule comprises a nucleic acid sequence that is at least 80% identical over at least 25 consecutive bp to an endogenous gene of the seed giving rise to the plant. In some embodiments, the trigger molecule comprises a nucleic acid sequence that is at least 17 bp in length and at least 85% identical to an endogenous gene of the seed giving rise to the plant. In some embodiments, the trigger molecule comprises a nucleic acid sequence that is at least 70 bp in length and at least 65% identical to an endogenous gene of the seed giving rise to the plant. In some embodiments, the plant does not comprise a detectable level of the trigger molecule.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, examples of methods and/or materials are described below.

In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1 shows a time-course siGLO-treatment results on rice seeds. The effect of incubation time with siGLO dsRNA on fluorescence intensity, indicating quantity and quality of dsRNA penetration, was tested. Control seeds that were left untreated (1), were imaged along with seeds treated with siGLO dsRNA for four different incubation times; 10 min (2), 3.5 hours (3), 5.5 hours (4), and 24 hours (5).

FIG. 2A—A picture of germinated rice seeds 5 days after treatment, control on the left. FIG. 2B—A picture of germinated rice seeds 7 days after treatment, control on the bottom.

FIG. 3A is a picture of germinated rice seeds 7 days after treatment, control on the bottom. FIG. 3B—A picture of planted rice seeds 5 weeks after treatment, the control plant is on the left and has a darker green color compared to PDS-1 silenced plant. FIG. 3C—RNA was extracted from control and PDS-1 silenced plants and PDS-1 expression levels were checked by Real Time PCR. UBQ5 expression levels were served as normalizers and the PDS-1 expression levels in the control plants served as calibrators and got a value of 1.

FIG. 4A presents the height distribution of control plants (blue bars) and FIG. 4B shows the height distribution of treated plants (yellow bars).

FIG. 5D shows the average height of control plants compared with that of treated plants 62 days following treatment.

FIG. 6A shows the fold change of FW2.2 expression in control (shown in red bars) and dsRNA-treated (shown in blue bars) plants, which was plotted for each individual plant to demonstrate the variation in expression level of FW2.2 gene in the two plant groups. FIG. 6B shows the average expression of FW2.2 in control (red bar) compared to treated plants (blue bar). Down-regulation in expression level of FW2.2 gene is evident in treated plants compared to control plants.

FIG. 9A-C show the homology between the *Spodoptera littoralis* genes used for seed treatment and the corn genome. FIG. 9A—NADPH gene, sequence 1 (top panel, SEQ ID NO: 14 and 22) and sequence 2 (bottom panel, SEQ ID NO: 23 and 24) showing 82% identity over 71 nucleotides and 89% identity over 35 nucleotides respectively, FIG. 9B—ATPase (SEQ ID NOs: 25 and 26) showing 72% identity over 484 nucleotides, and FIG. 9C—IAP, sequence 1 (top panel, SEQ ID NO: 27 and 28) and sequence 2 (bottom panel, SEQ ID NO: 29 and 30) showing 81% identity over 36 nucleotides and 87% identity over 31 nucleotides respectively. "Query" stands for *S. littoralis* sequences and "Subject" stands for corn sequences.

FIGS. 10A-C show the homology between the *Spodoptera littoralis* genes used for seed treatment and the tomato genome. FIG. 10A—NADPH gene, sequence 1 (top panel, SEQ ID NO: 31 and 32) showing 93% identity over 30 nucleotides and 88% identity over 25 nucleotides respectively and sequence 2 (bottom panel, SEQ ID NO: 33 and 34) FIG. 10B—ATPase (SEQ ID NOs. 35 and 36) showing 73% identity over 359 nucleotides, and FIG. 10C—IAP (SEQ ID NOs. 37 and 38) showing 93% identity over 28 nucleotides. "Query" stands for *S. littoralis* sequences and "Subject" stands for tomato sequences.

FIG. 11A shows percentage of dead worms eight days after feeding on three 43-day-old ATPase dsRNA trigger-treated and control corn plants. FIG. 11B shows average weight of live *S. littoralis* larvae at the same time point. FIG. 11C is a bar graph showing percentage of dead *S. littoralis* larvae three days after feeding on 85-days old ATPase-treated and control corn plants. FIG. 11D is a bar graph showing percentage of dead *S. littoralis* larvae seven days after feeding on 91-day-old ATPase dsRNA trigger-treated and control corn plants.

FIG. 12 is a bar graph showing percentage of dead *S. littoralis* larvae seven days after feeding on 67-day-old dsRNA trigger treated (NADPH, IAP, and ATPase) and control (EDTA) corn plants.

FIG. 13A is a bar graph showing average weight of live *S. littoralis* larvae eight days after feeding on 43-day-old EF1α dsRNA trigger-treated and control (EDTA) corn plants. FIG. 13B is a bar graph showing percentage of dead *S. littoralis* larvae five days after feeding on 87-day-old EF1α dsRNA trigger-treated and control (EDTA) corn plants.

FIG. 15A is a bar graph showing average weight of live *S. littoralis* larvae eight days after feeding on 43-day-old NADPH dsRNA trigger-treated and control (EDTA) corn plants. FIG. 15B is a bar graph showing percentage of dead *S. littoralis* larvae seven days after feeding on 91-day-old NADPH dsRNA trigger-treated and control (EDTA) corn plants.

FIG. 5A shows average weight per repeat and FIG. 16B shows average weight per treatment.

FIGS. 17A-B are bar graphs showing average weight of live *S. littoralis* larvae after feeding on EF1α dsRNA trigger-treated corn plants. FIG. 17A shows average weight nine days after feeding on 35-day-old plants. Error bars represent standard deviation for each treatment. FIG. 17B shows average weight five days after feeding on 36-day-old plants. Error bars represent standard deviation for each plant.

FIG. 18A is a bar graph showing percentage of dead *S. littoralis* larvae 12 days after feeding on 56-day-old ATPase dsRNA trigger-treated and control (GUS) corn plants. FIG. 18B is a bar graph showing percentage of dead *S. littoralis* larvae four days after feeding on 57-day-old ATPase dsRNA trigger-treated and control (GUS) corn plants.

FIG. 19A is a bar graph showing average weight of live *S. littoralis* larvae ten days after feeding on 24-day-old dsRNA trigger-treated and control (EDTA, EDTA/CNTP and GFP) corn plants. Error bars represent standard deviation for each plant. FIG. 19B is a bar graph showing average weight of live *S. littoralis* larvae ten days after feeding on 25-day-old dsRNA trigger-treated and control (EDTA, EDTA/CNTP and GFP/CNTP) corn plants. Error bars represent standard deviation for each plant.

FIG. 20A shows average weight of *S. littoralis* larvae per plant and FIG. 20B shows average weight of *S. littoralis* larvae per treatment. Error bars represent standard deviation of the data.

FIG. 23A is a bar graph showing weight of *S. littoralis* larvae after feeding for six days on 85-day-old ATPase dsRNA trigger-treated and control (EDTA) tomato plants relative to their initial weight before feeding. FIG. 23B is a bar graph showing average weight of live *S. littoralis* larvae after feeding for five days on 88-day-old ATPase dsRNA trigger-treated and control (EDTA) tomato plants.

FIG. 24A is a bar graph showing average weight of *S. littoralis* larvae after feeding for four days on 95-day-old NADPH dsRNA trigger-treated and control (EDTA) tomato plants. FIG. 24B is a bar graph showing average weight of *S. littoralis* larvae after feeding for seven days on 95-day-old NADPH dsRNA trigger-treated and control (ARF8) tomato plants.

FIGS. 25A and C are bar graphs showing percentage of dead *S. littoralis* larvae per plant eight and ten days, respectively, after feeding on 31-day-old dsRNA trigger-treated (EF1α#1, EF1α#2, ATPase and NADPH) and control (EDTA and GFP) corn plants. FIGS. 25 B and D are bar graphs combining the data shown in FIGS. 25 A and C into treatments. FIG. 25E is a bar graph showing average weight of live *S. littoralis* larvae 11 days after feeding on treated and control corn plants. Error bars represent standard deviation of the data. FIG. 25F is a bar graph showing average weight of live *S. littoralis* larvae after feeding for eight and nine days on 32-days old treated and control corn plants. Weight scored after eight days is shown in dark colors and weight scored after nine days is shown in bright colors. Error bars represent standard deviation of the data.

FIG. 26A is a bar graph showing the percentage of larval recovery after 4 weeks. FIG. 26B is a bar graph showing the total weight of WCR larvae recovered after 4 weeks. FIG. 26C is a bar graph showing the average weight of the WCR larvae recovered after 4 weeks.

FIG. 27A shows the average defoliation of the T6593 treated and control (formulation and GFP) tomato plant by CPB. FIG. 27B shows the percentage of CPB larvae recovered. FIG. 27C shows the average weight of WCR larvae recovered from the treated plants.

FIG. 28 shows the results of the Quantigene analysis on plants treated with the Tomato golden mottle virus (ToGMoV) after seed imbibition with dsRNA polynucleotide sequences. FIG. 28A shows the results after treatment with the 5'AC1 dsRNA polynucleotide (5') compared to the GUS treated control (NTrC). FIG. 28B shows the results after treatment with the 3'AC1 dsRNA polynucleotide (3') compared to the GUS treated control (NTrC).

FIG. 29 shows the results of the Quantigene analysis on plants treated with the Cucumber Mosaic Virus (CMV) after seed imbibitions with the dsRNA polynucleotide sequences. FIG. 28A shows the results after treatment with the 5' NC dsRNA polynucleotide (5') compared to the GUS treated control (NTrC). FIG. 29B shows the result after treatment with the 3'NC dsRNA polynucleotide (3') compared to the GUS control (NTrC).

FIGS. 31A-B show the homology between the *Spodoptera littoralis* EF1α gene used for seed treatment and the corn genome. FIG. 31A—EF1α gene, sequence 1 showing 75% identity over 400 nucleotides. FIG. 31B—EF1α gene, sequence 2 showing 75% identity over 446 nucleotides. "Query" stands for *S. littoralis* sequences (SEQ ID NOS: 221, 223) and "Subject" stands for corn sequences (SEQ ID NOs: 222, 224).

FIG. 32A shows fold change in corn EF1α mRNA expression following treatment with *S. littoralis* EF1α dsRNA for which GFP dsRNA treatment was used as control baseline. Expression values per individual plants were normalized to the median expression of all plants treated with GFP dsRNA. The difference in expression relative to control group had a p-value of 0.016. FIG. 32B shows fold change in corn EF1α mRNA expression following treatment with a mixture of the same dsRNAs as in FIG. 32A and PEG-modified carbon nanotubes (CNTP). Expression values per individual plants were normalized to the median expression of all plants treated with GFP dsRNA\CNTP. The difference in expression relative to control group had a p-value of 0.003. FIG. 32C shows fold change in the same corn plants 48 days post seed treatment. Expression values per individual plants were normalized to the median expression of all plants treated with GFP dsRNA\CNTP. The difference in expression relative to control group had a p-value of 0.07.

FIG. 34A shows fold change in corn EF1α mRNA expression with respect to the GUS dsRNA treatment. FIG. 34B shows the average fold change in corn EF1α mRNA expression for all plants treated with EF1α dsRNA (both dsRNA #1 and #2, with and without CNTP), GUS dsRNA (with and without CNTP) and EDTA (with and without CNTP). Error bars represent standard deviation of the data.

FIGS. 35A-C are bar graphs showing real-time PCR analyses of corn ATPase and NADPH mRNA expression in 27-days old corn plants germinated from seeds treated with 160 µg/ml dsRNA for 2 hours. FIG. 35A shows the average fold change in corn ATPase mRNA expression. FIGS. 35B and 35C shows the average fold change in corn NADPH mRNA expression. Expression values were normalized to the average expression of plants treated with GFP dsRNA (FIGS. 35A and 35B) or to the average expression of EDTA-treated control plants (FIG. 35C). Error bars represent standard deviation of the data.

DETAILED DESCRIPTION

Figure 2B:
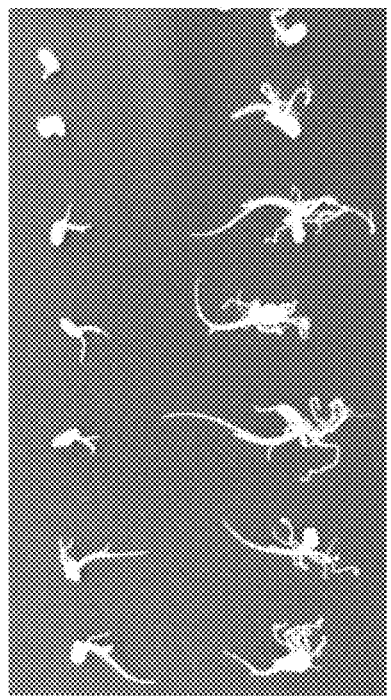
FIGS. 2A-B show silencing the PDS-1 gene in rice by a dsRNA/siRNA mixture.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Further, disclosure of a nucleic acid sequence discloses the sequence of its reverse complement, as one necessarily defines the other, as is known by one of ordinary skill in the art. Where a term is provided in the singular, the inventors also contemplate aspects of the invention described by the plural of that term.

Before explaining embodiments of the invention in detail, it is to be understood that the invention is not necessarily limited in its application to the details set forth in the following description or exemplified by the Examples. The invention is capable of other embodiments or of being practiced or carried out in various ways.

With the extensive growth of the world-population and the limited habitats for plant growth and cultivation, there is an urgent need to improve plant yields under these changing conditions. RNAi has emerged as a powerful tool for modulating gene expression which can be used for generating plants with improved stress tolerance. In plants, RNAi is typically performed by producing transgenic plants that comprise a DNA fragment that is transcribed to produce a dsRNA. This dsRNA is then processed into siRNAs that mediate the silencing of target genes, typically by targeting cleavage of the target gene by an RNA Induced Silencing Complex (RISC) or by translational repression. The major technical limitation for this technology is that many important plant crop species are difficult or impossible to transform, precluding the constitutive expression of constructs directing production of dsRNA. Moreover, questions concerning the potential ecological impact of virus-resistant transgenic plants have so far significantly limited their use (Tepfer, 2002, Annu Rev. Phytopathol. 40, 467-491).

The present embodiments include methods of introducing exogenous non-transcribable polynucleotide trigger, for example dsRNA, molecules into plant seeds for modulating gene expression in a plant grown from the seed and/or in a phytopathic organism that feeds on or infects a plant grown from the treated seed. Several embodiments relate to methods of introducing exogenous non-transcribable polynucleotide triggers into plant seeds for controlling insect pest infestation and/or viral infection of plants grown from the seeds. Ingestion of plant material produced from seeds treated with exogenous non-transcribable polynucleotide trigger, for example dsRNA, molecules according to the present embodiments results in the cessation of feeding, growth, development, reproduction, infectivity, and eventually may result in the death of the phytopathogen. In some embodiments, the exogenous non-transcribable polynucleotide triggers are designed to silence a target gene of an insect pest or viral pathogen. The polynucleotide triggers can be single- or double-stranded RNA or single- or double-stranded DNA or double-stranded DNA/RNA hybrids or modified analogues thereof, and can be of oligonucleotide lengths or longer. Several embodiments relate to methods of introducing dsRNA to plant seeds for modulating gene expression.

The present inventors have now devised a novel technology for introducing exogenous non-transcribable polynucleotide triggers, for example dsRNA molecules, directly to the plant seed. These non-transcribable polynucleotide trigger, for example dsRNA, molecules enter seeds and start a silencing process, which is continued during the life cycle of the plant, resulting in a plant with an improved trait of interest. The introduced polynucleotide triggers are naked and as such no exogenous transcription regulatory elements are introduced into the plant thus lowering the environmental concerns associated with transgenic plants. In some embodiments, the introduced polynucleotide trigger is naked dsRNA and as such no exogenous transcription regulatory elements are introduced into the plant. In addition, the modified seed can be germinated to generate a plant without the need of going through the laborious and cumbersome steps of tissue culture regeneration.

The present embodiments provide, in part, a delivery system for the delivery of pest control agents to pests through their exposure to a diet containing plant material produced from seeds treated with exogenous non-transcribable polynucleotide trigger, for example dsRNA, molecules according to the present embodiments.

As is illustrated herein below and in the Examples section which follows, the present embodiments include configuring the conditions necessary to introduce exogenous non-transcribable polynucleotide triggers, for example naked dsRNA, into the seeds (see e.g., Example 1). The exogenous non-transcribable polynucleotide trigger, for example naked dsRNA, does not integrate into the genome and is highly stable in the plant and in solution (see Examples 2-4). The exogenous non-transcribable polynucleotide trigger, for example naked dsRNA, penetrates through the seed coat (testa) of both monocot and dicot plants and distributes in the endosperm and seed embryo (Examples 5-6). In one aspect, the present embodiments include altering expression of endogenous genes (Examples 8-15). In some embodiments, the endogenous gene whose expression is altered is an ortholog of a targeted pest gene. In another aspect, the present embodiments include introducing into seeds exogenous non-transcribable polynucleotide triggers, for example dsRNA, directed to exogenous genes (e.g., insect pest genes or viral genes). These results are reproduced over a number of plants of both monocot and dicot groups. In a further aspect, the present embodiments include introducing into seeds exogenous non-transcribable polynucleotide triggers, for example dsRNA, directed to essential genes of insect pests or viral pathogens in a wide range of doses and kinetics which resulted in a significant alteration of gene expression. Interestingly, the dsRNA introduced according to the present embodiments is able to down-regulate essential genes in a phytopathogen which feeds on or infects a plant grown from a treated seed (e.g., *Spodoptera littoralis*, Example 7). Thus, the present results are sufficient to show that the present teachings provide a cost-effective treatment of plant seeds to achieve a desired agricultural and horticultural phenotype, such as resistance to insect pests and viral pathogens.

Provided herein are compositions and methods for inducing systemic regulation (e.g., systemic suppression or silencing) of a target gene in a plant or phytopathogen by application to the plant seed of a polynucleotide trigger molecule with a segment in a nucleotide sequence essentially identical to, or essentially complementary to, a sequence of 18 or more contiguous nucleotides in either the target gene or RNA transcribed from the target gene, whereby the composition permeates the interior of the plant seed and induces systemic regulation of the target gene in the plant grown from the seed or in a phytopathogen of the plant grown from the seed. The polynucleotide trigger molecule can be one or more polynucleotide molecules with a single such segment, multiples of such a segment, multiple different such segments, or a combination thereof.

Without being bound by a particular theory, it is suggested that the newly suggested transformation modality and modulation of gene expression is associated with:

(i) Introduction of an exogenous non-transcribable polynucleotide trigger molecule, for example naked dsRNA, into the interior of seeds (as opposed to mere seed coating). The introduction is effected by soaking the seeds in a solution which comprises the exogenous non-transcribable polynucleotide trigger, for example dsRNA, such that the exogenous non-transcribable polynucleotide trigger penetrates through the seed coat or by dipping such that the exogenous non-transcribable polynucleotide trigger coats the seed and penetrates through the coat after sowing;

(ii) Amplification of the signal generated by the exogenous non-transcribable polynucleotide trigger, for example dsRNA; and (iii) Spreading of the signal throughout the plant.

The first step occurs only once, during and shortly after the initial seed treatment, while the second and third steps occur in a repetitive loop for as long as the silencing signal remains active in the plant.

Without being bound by theory, a suggested unbinding mode of action for the described invention is based on each step:

Introduction of an exogenous non-transcribable polynucleotide trigger, for example dsRNA, into seeds.

A typical mature seed consists of an embryo encapsulated within a maternal seed coat (testa) and an abundant layer of endosperm tissue between the embryo and seed coat. The endosperm serves as a nutrient source for the embryo during seed development, germination and seedling establishment.

Seed germination typically begins with exposure of the seeds to water, which is absorbed by the embryo and endosperm. The endosperm then expands in volume, with the endosperm of some plant species being able to grow several-fold from their original volume. The embryo, which was dormant until this stage, is now released from dormancy and cell division, expansion and differentiation begin. The endosperm feeds the developing embryo until it is developed enough to begin photosynthesis and autotrophic growth.

Based on these known mechanisms of seed germination, two possible modes of action for the initial step of "Introduction of the exogenous non-transcribable polynucleotide trigger, for example dsRNA, into seeds" are suggested:

The exogenous non-transcribable polynucleotide trigger, for example dsRNA, molecules enter the embryo directly, carried by the water-based solution which is used for the seed treatment.

The exogenous non-transcribable polynucleotide trigger, for example dsRNA, molecules enter the endosperm as part of the endosperm's water-absorption process. These molecules then feed the embryo as it develops as part of the nutrient flow from the endosperm during germination and seed development.

Based on the results described in FIGS. 7-13, it is estimated that a combination of the two options takes place. That is, some of the dsRNA enters the embryo directly and some is retained in the endosperm and feeds the developing embryo during seed germination.

Amplification of the Signal

Once dsRNA molecules enter the embryo, they are recognized and processed by RNAse III-like enzymes such as Dicer or Dicer-like (DCL) enzymes. DCL enzymes process the long dsRNA molecules into short, double strand RNAs (known as siRNAs or shRNAs), which are typically 21-24 nucleotides (nt) long. One of the siRNA strands is typically rapidly degraded and the second one can be incorporated in RISC (RNA Induced Silencing Complex) protein complexes, which contain an Argonaute (AGO) protein. AGO proteins contain a PIWI domain to bind siRNAs and a PAZ domain with RNAse activity. Subsequently, the siRNA/AGO complex identifies an mRNA molecule, which is complementary to the siRNA and results in its silencing by cleavage or translational repression.

The siRNA is then released from the RISC complex and can now act as a primer for an RNA-Dependant RNA Polymerase (RDRP), this is an enzyme which is unique to the plant kingdom and can generate amplification of the silencing signal by generating new dsRNA molecules (secondary siRNA). These newly-synthesized dsRNAs can be processed again as described above, therefore maintaining and amplifying the silencing signal.

Spreading of the Silencing Signal

Silencing spreading is a known and well-understood phenomenon in plants. Not wishing to be bound by a particular theory, it is believed that short distance, cell-to-cell spreading occurs through plasmodesmata. This process is thought to be mediated by a 21 nt-long siRNA, which is the product of a DCL enzyme. Additionally, systemic spreading is achieved through the phloem across the entire plant from source to sink.

Without being bound by particular theory, it is suggested that in the described methodology, spreading of the silencing signal occurs once the silencing signal begins and is amplified as described above. This may include both short-distance and systematic spreading by various siRNA signal molecules.

According to one embodiment, there is provided a method of introducing an exogenous non-transcribable polynucleotide trigger, for example naked double-stranded RNA (dsRNA), into a seed, the method comprising contacting the seed with the exogenous non-transcribable polynucleotide trigger, for example naked dsRNA, under conditions which allow penetration of the exogenous non-transcribable polynucleotide trigger, for example naked dsRNA into the seed, thereby introducing the dsRNA into the seed.

Several embodiments described herein relate to a method of generating a plant having a desirable phenotype, comprising a) contacting an ungerminated seed with an exogenous non-transcribable polynucleotide trigger molecule under conditions which allow penetration of said trigger molecule into the seed and b) germinating said seed to generate a plant exhibiting the desired phenotype after emerging from said seed. In some embodiments, the desirable phenotype is insect resistance. In some embodiments, the desirable phenotype is viral resistance.

As used herein, the term "trigger" or "trigger polynucleotide" refers to a bioactive polynucleotide molecule that is substantially homologous or complementary to a polynucleotide sequence of a target gene or an RNA expressed from the target gene or a fragment thereof and functions to suppress the expression of the target gene or produce a knock-down phenotype. Trigger polynucleotides are generally described in relation to their "target sequence." Trigger polynucleotides may be single-stranded DNA (ssDNA), single-stranded RNA (ssRNA), double-stranded RNA (dsRNA), double-stranded DNA (dsDNA), or double-stranded DNA/RNA hybrids. Trigger polynucleotides may comprise naturally-occurring nucleotides, modified nucleotides, nucleotide analogues or any combination thereof. In some embodiments, a trigger polynucleotide may be incorporated within a larger polynucleotide, for example in a pri-miRNA molecule. In some embodiments, a trigger polynucleotide may be processed into a small interfering RNA (siRNA).

As used herein, the term "target sequence" refers to a nucleotide sequence that occurs in a gene or gene product against which a trigger polynucleotide is directed. In this context, the term "gene" means a locatable region of genomic sequence, corresponding to a unit of inheritance, which includes regulatory regions, such as promoters, enhancers, 5' untranslated regions, intron regions, 3' untranslated regions, transcribed regions, and other functional sequence regions that may exist as native genes or transgenes in a plant genome. Depending upon the circumstances, the term target sequence can refer to the full-length nucleotide sequence of the gene or gene product targeted for suppression or the nucleotide sequence of a portion of the gene or gene product targeted for suppression.

As used herein, the term "derived from" refers to a specified nucleotide sequence that may be obtained from a particular specified source or species, albeit not necessarily directly from that specified source or species.

As used herein, the terms "sequence," "nucleotide sequence" or "polynucleotide sequence" refer to the nucleotide sequence of a DNA molecule, an RNA molecule or a portion thereof.

The term "polynucleotide" refers to any polymer of mononucleotides that are linked by internucleotide bonds. Polynucleotides may be composed of naturally-occurring ribonucleotides, naturally-occurring deoxyribonucleotides, analogs of naturally-occurring nucleotides (e.g., enantiomeric forms of naturally-occurring nucleotides), or any combination thereof. Where a polynucleotide is single-stranded, its length can be described in terms of the number of nucleotides. Where a polynucleotide is double-stranded, its length can be described in terms of the number of base pairs.

As used herein, the term "non-transcribable polynucleotide" refers to a polynucleotide that does not comprise a complete polymerase II transcription unit.

The term "gene expression" refers to the process of converting genetic information encoded in genomic DNA into RNA (e.g., mRNA, rRNA, tRNA, or snRNA) through transcription of the gene via the enzymatic action of an RNA polymerase, and into protein, through translation of mRNA. Gene expression can be regulated at many stages in the process.

As used herein, the phrases "inhibition of gene expression" or "gene suppression" or "silencing a target gene" and similar terms and phrases refer to the absence or observable reduction in the level of protein and/or mRNA product from the target gene. The consequences of inhibition, suppression, or silencing can be confirmed by examination of the outward properties of a cell or organism or by biochemical techniques.

As used herein, the term "sequence identity," "sequence similarity" or "homology" is used to describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

By "essentially identical" or "essentially complementary" is meant that the bioactive polynucleotide trigger (or at least one strand of a double-stranded polynucleotide or portion thereof, or a portion of a single strand polynucleotide) hybridizes under physiological conditions to the endogenous gene, an RNA transcribed there from, or a fragment thereof, to effect regulation or suppression of the endogenous gene. For example, in some embodiments, a bioactive polynucleotide trigger has 100 percent sequence identity or at least about 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence complementarity or at least about 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a bioactive polynucleotide trigger has 100 percent sequence identity with or complementarity to one allele or one family member of a given target gene (coding or non-coding sequence of a gene). In some embodiments, a bioactive polynucleotide trigger has at least about 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a bioactive polynucleotide trigger has 100 percent sequence identity with or complementarity to multiple alleles or family members of a given target gene.

As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is completely complementary to a reference nucleotide sequence will exhibit a sequence identical to the reverse complement sequence of the reference nucleotide sequence.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

As used herein, the terms "exogenous polynucleotide" and "exogenous nucleic acid molecule" relative to an organisms refer to a heterologous nucleic acid sequence which is not naturally expressed within that organism, for example a plant. An exogenous nucleic acid molecule may comprise a nucleic acid sequence which is identical or partially homologous to an endogenous nucleic acid sequence of the organism.

As used herein, the terms "endogenous polynucleotide" and "endogenous nucleic acid" refers to nucleic acid sequences that are found in an organism's cell. In certain aspects, an endogenous nucleic acid may be part of the nuclear genome or the plastid genome. As used herein, endogenous nucleic acids do not include viral, parasite or pathogen nucleic acids, for example an endovirus sequence.

As used herein the phrase "naked dsRNA" refers to a dsRNA nucleic acid molecule which is non-transcribable in a plant cell. Thus, the naked dsRNA molecule is not comprised in a nucleic acid expression construct such as a viral vector. According to some embodiments of the invention, the naked dsRNA molecule is not derived from a viral vector. According to some embodiments, the dsRNA is not a product of a natural pathogenic or viral infection. According to some embodiments, the naked dsRNA may comprise regulatory elements for in-vitro transcription, such as the T7 promoter. According to some embodiments of the invention, the naked dsRNA may be modified e.g., chemically modified, to confer higher bioavailability, penetration into the seeds and/or improved shelf-life.

As used herein the term "dsRNA" relates to two strands of anti-parallel polyribonucleic acids held together by base pairing. The dsRNA molecule may be formed by intramolecular hybridization or intermolecular hybridization. In some embodiments, the dsRNA may comprise a single strand of RNA that self-hybridizes to form a hairpin structure having an at least partially double-stranded structure including at least one segment that will hybridize to an RNA transcribed from the gene targeted for suppression. In some embodiments, the dsRNA may comprise two separate strands of RNA that hybridize through complementary base pairing. The RNA strands may or may not be polyadenylated; the RNA strands may or may not be capable of being translated into a polypeptide by a cell's translational apparatus. The two strands can be of identical length or of different lengths provided there is enough sequence homology between the two strands that a double stranded structure is formed with at least 80%, 90%, 95% or 100% complementarity over the entire length. According to an embodiment of the invention, there are no overhangs for the dsRNA molecule. According to another embodiment of the invention, the dsRNA molecule comprises overhangs. According to other embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed.

As will be appreciated by one of ordinary skill in the art, a dsRNA molecule of the present disclosure may refer to either strand of the anti-parallel nucleic acids. As will also be appreciated by one of ordinary skill in the art, a dsRNA molecule of the present disclosure includes both a 'sense' and 'antisense' strand and that the sense and antisense strands are reverse complements of each other in a region of base pairing. As used herein the sequence of a dsRNA molecule for regulating a target gene of interest is provided as the 'sense' orientation with respect to the target gene of interest. As used herein, "the reverse complement of a dsRNA molecule for regulating a target gene of interest" refers to a nucleic acid sequence in the 'antisense' orientation.

As mentioned, any dsRNA molecule can be used in accordance with the present teachings. In some embodiments, dsRNA used in the present application is subject to amplification by RNA-Dependant RNA Polymerase (RDRP). Without being limited, dsRNA can be siRNA, shRNA, pre-miRNA, or pri-miRNA.

The polynucleotides, DNA, RNA, dsRNA, siRNA, shRNA, pre-miRNA, pri-miRNA or miRNA of the present embodiments may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874, 5,698,425, 5,712, 135, 5,789,214, and 5,804,693). If synthesized chemically or by in vitro enzymatic synthesis, the RNA may be purified prior to introduction into the seed. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

The present teachings relate to various lengths of dsRNA, whereby the shorter version i.e., x is shorter or equals 50 bp (e.g., 17-50), is referred to as siRNA or miRNA. Longer dsRNA molecules of 51-600 or more than 600 bp are referred to herein as dsRNA, which can be further processed for siRNA molecules.

In one embodiment, the dsRNA in the present application is between 20 and 100 bp, between 25 and 90 bp, between 30 and 80 bp, between 30 and 70 bp, between 30 and 60 bp, or between 30 and 50 bp. In another embodiment, the dsRNA in the present application is about 50 bp. In a further embodiment, the dsRNA comprises 1-base, 2-base or 3-base 5'-overhangs on one or both termini. In another embodiment, the dsRNA does not comprise 1-base, 2-base or 3-base 5'-overhangs on one or both termini. In a further embodiment, the dsRNA comprises 1-base, 2-base or 3-base 3'-overhangs on one or both termini. In another embodiment, the dsRNA does not comprise 1-base, 2-base or 3-base 3'-overhangs on one or both termini.

In another embodiment, the dsRNA in the present application is between 100 and 1,000 bp, between 200 and 900 bp, between 300 and 800 bp, between 400 and 700 bp, between 400 and 600 bp, or between 400 and 500 bp. In another embodiment, the dsRNA in the present application is about 450 bp. In another embodiment, the dsRNA in the present application is about 550 bp. In another embodiment, the dsRNA in the present application is about 650 bp. In another embodiment, the dsRNA in the present application is about 750 bp. In another embodiment, the dsRNA in the present application is about 850 bp. In a further embodiment, the dsRNA comprises 1-base, 2-base or 3-base 5'-overhangs on one or both termini. In another embodiment, the dsRNA does not comprise 1-base, 2-base or 3-base 5'-overhangs on one or both termini. In a further embodiment, the dsRNA comprises 1-base, 2-base or 3-base 3'-overhangs on one or both termini. In another embodiment, the dsRNA does not comprise 1-base, 2-base or 3-base 3'-overhangs on one or both termini.

In one embodiment, the dsRNA in the present application is between 15 and 500 bp, between 15 and 450 bp, between 15 and 400 bp, between 15 and 350 bp, between 15 and 300 bp, between 15 and 250 bp, between 15 and 200 bp, between 15 and 150 bp, between 15 and 100 bp, between 15 and 90 bp, between 15 and 80 bp, between 15 and 70 bp, between 15 and 60 bp, between 15 and 50 bp, between 15 and 40 bp, between 15 and 35 bp, between 15 and 30 bp, or between 15 and 25 bp. In another embodiment, the dsRNA in the present application is at least about 20, 25, 30, 35, 40, 45, 50, 75, 100, 150, 200, 250, 300, 350, 400, 500, 600, 800, 900, 1000 bp long. In a further embodiment, the dsRNA in the present application is between 100 and 1000 bp, between 200 and 1000 bp, between 300 and 1000 bp, between 400 and 1000 bp, between 500 and 1000 bp, between 600 and 1000 bp, between 700 and 1000 bp, between 800 and 1000 bp, or between 900 and 1000 bp.

The term "siRNA" refers to small inhibitory RNA duplexes (generally between 17-30 basepairs, but also longer e.g., 31-50 bp) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned the RNA silencing agent of some embodiments of the invention may also be a short hairpin RNA (shRNA).

The term "shRNA," as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence essentially complementary to the nucleotide sequence of the miRNA molecule.

Typically, a miRNA molecule is processed from a "pre-miRNA" or as used herein a precursor of a pre-miRNA molecule by proteins, such as DCL proteins, present in any plant cell and loaded onto a RISC complex where it can guide the cleavage of the target RNA molecules.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising an imperfect double stranded RNA stem and a single stranded RNA loop (also referred to as "hairpin") and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g., between 30 and 50 nt in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex); it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong than between G and C involving three hydrogen bounds. Examples of hairpin sequences are provided in Tables 3, 4, 6, 7, 13, 18, 26, 27, 28, 34, 35, 36, and 37 below.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the dsRNA molecules may be naturally occurring or synthetic.

The dsRNA can be a mixture of long and short dsRNA molecules such as, dsRNA, siRNA, siRNA+dsRNA, siRNA+miRNA, or any combination of same. According to a specific embodiment, the dsRNA is a siRNA (100%). According to a specific embodiment the dsRNA is a siRNA+dsRNA combination in various ratios. Any dsRNA to siRNA ratio can be used for the siRNA+dsRNA combination. For example, a ratio of 1 to 1: one dsRNA mixed with the same sequence after RNAse III treatment. According to another embodiment, the dsRNA to siRNA ratio is 2:1, 1.5:1, 1.3:1, 1:0.01, 1:0.05 or 1:0.1. According to a further embodiment, the dsRNA to siRNA ratio is 2:1 to 1:0.1. According to a specific embodiment, the dsRNA is purified dsRNA (100%). According to another embodiment, the dsRNA to siRNA ratio is 1:2, 1:5, 1:10, 1:20, or 1:50. According to a further embodiment, the dsRNA is purified siRNA (100%).

The dsRNA molecule can be designed for specifically targeting a target gene of interest. In some embodiments, the target gene is an essential gene of an insect pest. In some embodiments, the target gene is a viral gene. It will be appreciated that the dsRNA can be used to down-regulate one or more target genes. If a number of target genes are targeted, a heterogenic composition which comprises a plurality of dsRNA molecules for targeting a number of target genes is used. Alternatively, said plurality of dsRNA molecules are separately applied to the seeds (but not as a single composition). According to a specific embodiment, a number of distinct dsRNA molecules for a single target are used, which may be separately or simultaneously (e.g., co-formulation) applied.

According to one embodiment, the target gene is endogenous to the plant. Down regulating such a gene is typically important for conferring the plant with an improved, agricultural, horticultural, nutritional trait ("improvement" or an "increase" is further defined herein below). It will be appreciated that the treatment with the dsRNA may result in an up-regulation of the target gene (which follows a suggested mechanism that is provided herein below) however such an up-regulation may be transient.

According to another embodiment, the target gene is exogenous to the plant. In some embodiments, the target gene is an insect pest gene. In some embodiments, the target gene is a viral gene. It will further be appreciated that the treatment with the dsRNA may result in an up-regulation of a plant ortholog of the target gene.

Several embodiments described herein relate to guidelines for the design and selection of non-transcribable polynucleotide trigger, for example dsRNA, molecules for efficient RNA silencing in phytopathogens, which nourish or depend on a plant for growth/replication and/or survival. Not wishing to be bound by a particular theory, non-transcribable polynucleotide trigger, for example dsRNA, molecules having a sufficient level of homology to an endogenous plant gene allows for degradation and amplification of the primary siRNAs (those which are triggered by Dicer processing) to generate secondary siRNAs formed by Dicer-Like 4 (DCL4). Such non-transcribable polynucleotide trigger, for example dsRNA, molecules can be selected for having minimal effect on the plant growth and viability. In some embodiments, the secondary siRNAs are of sufficient homology to a gene of a phytopathogen so as allow the degradation of the targeted phytopathogen gene via an RNA interference mode. In some embodiments, a phytopathogen provided with a plant material grown from a seed treated with a non-transcribable polynucleotide trigger, for example dsRNA, molecule as described herein will lose viability either by the induction of growth arrest or death. Such non-transcribable polynucleotide trigger, for example dsRNA molecules are considered as valuable pesticides and can have wide applications in agriculture and horticulture.

Without being bound by particular theory, it is suggested that one mode of modulation of gene expression is associated with: (i) introduction of non-transcribable polynucleotide trigger, for example dsRNA, molecules into the interior of seeds (as opposed to mere seed coating); (ii) amplification of the signal produced from introduction of the non-transcribable polynucleotide trigger, for example dsRNA, molecule; and spreading of the signal throughout the plant. The first step occurs only once, during and shortly after the initial seed treatment, while the second and third steps occur in a repetitive loop for as long as the silencing signal remains active in the plant. As mentioned, introduction of the compositions of the present invention can also be performed to other organs/cells of the plant (as opposed to seeds) using conventional delivery methods such as particle bombardment, grafting, soaking, topical application with a transfer agent and the like. Thus steps (i) and (ii), defined above, are shared also by this mode of administration.

A phytopathogen feeding-on or infecting a plant which comprises any of the dsRNA, primary siRNA or secondary siRNAs which target an essential gene of the phytopathogen will exhibit a growth arrest or death, thereby reducing its injurious effect on the plant or plant product.

In some embodiments, there is provided a method of introducing naked double-stranded RNA (dsRNA) into a seed, the method comprising contacting the seed with the naked dsRNA under conditions which allow penetration of a nucleic acid sequence having: a homology level to a gene of a phytopathogenic organism sufficient to induce degradation of said gene of said phytopathogenic organism, wherein said phytopathogenic organism depends on said plant for growth and wherein said degradation induces a growth arrest or death of said phytopathogenic organism. In some embodiments, the dsRNA targets a gene that contains regions that are poorly conserved between individual phytopathogenic organisms, or between the phytopathogenic organism and the host plant. In certain embodiments it may be desirable to target a gene in a phytopathogenic organism that has no known homologs in other organisms, such as the host plant.

In some embodiments, a non-transcribable polynucleotide trigger, for example dsRNA, molecule is selected of sufficient homology to a plant gene to mediate its degradation in an RNA interference mediated function.

According to one embodiment, there is provided a method of introducing naked double-stranded RNA (dsRNA) into a seed, the method comprising contacting the seed with the naked dsRNA under conditions which allow penetration of a nucleic acid sequence having:

(i) a homology level to a plant gene sufficient to induce amplification of secondary siRNA products of said dsRNA in a plant cell comprising the same and wherein modification of the expression of the plant gene by said dsRNA does not substantially affect any of biomass, vigor or yield of said plant; and (ii) a homology level to a gene of a phytopathogenic organism sufficient to induce degradation of said gene of said phytopathogenic organism, wherein said phytopathogenic organism depends on said plant for growth and wherein said degradation induces a growth arrest or death of said phytopathogenic organism.

In some embodiments, the dsRNA has a homology level to a plant gene sufficient to induce amplification of secondary siRNA products of said dsRNA in a plant cell comprising the dsRNA and wherein altering expression of the plant gene by said dsRNA does not substantially affect any of biomass, vigor or yield of said plant. The plant gene can be naturally expressed in the plant (endogenous) or a result of genetic transformation (transgenic plant).

In some embodiments, the dsRNA has a homology level to a plant gene that:

(i) is expressed in all or most plant organs, starting from germination;

(ii) is a non-vital gene, such that its down regulation or up regulation does not affect the plant or any of the plant's biomass, yield, vigor; and/or (iii) is not associated with endurance of abiotic or biotic stress.

The plant gene can be selected having at least one of the above characteristics i.e., (i), (ii) or (iii). Alternatively, the plant gene fulfils two criteria such as (i) and (ii), (i) and (iii) or (ii) and (iii). Alternatively all the three criteria prevail i.e., (i), (ii) and (iii). In some embodiments, the dsRNA has a homology level to a plant gene that does not affect the biomass, yield, and/or vigor of the plant when measures are taken to grow the plant under optima/normal conditions or conditions which do not require function of the gene for optimal growth, vigor, biomass, and/or yield. As used herein the phrase "does not substantially affect" refers to no effect as compared to the same characteristic in an isogenic plant of the same developmental stage and growth conditions. Alternatively, said characteristic is only slightly affected by no more than 10%, 8%, 7c %, 6%, 5%, 4%, 3%, 2% or 1%.

According to some embodiments, the nucleic acid sequence of the non-transcribable polynucleotide trigger, for example dsRNA, molecule is selected so as to exhibit sufficient homology to recruit the RDR6 system and generate secondary siRNA transcripts. Such a homology level is typically at least 80% identity to an endogenous plant gene over at least 25 consecutive bp. According to an alternative embodiment, the homology level of the non-transcribable polynucleotide trigger, for example dsRNA, molecule is at least 85% identity to a plant gene over at least 25 consecutive bp. According to an alternative embodiment, the homology level of the non-transcribable polynucleotide trigger, for example dsRNA, molecule is at least 88% identity to the plant gene over at least 25 consecutive bp. According to an alternative embodiment, the homology level of the non-transcribable polynucleotide trigger, for example dsRNA, molecule is at least 90% identity to the plant gene over at least 25 consecutive bp of the target gene. According to an alternative embodiment, the homology level of the non-transcribable polynucleotide trigger, for example dsRNA, molecule is at least 92% identity to the plant gene over at least 25 consecutive bp. According to an alternative embodiment, the homology level of the non-transcribable polynucleotide trigger, for example dsRNA, molecule is at least 95% identity to the plant gene over at least 25 consecutive bp. According to an alternative embodiment, the homology level of the non-transcribable polynucleotide trigger, for example dsRNA, molecule is at least 25 consecutive bp.

According to some embodiments, the non-transcribable polynucleotide trigger, for example dsRNA, molecule is at least is 70 bp or longer say 70-700, 70-600, 70-500, 70-400, 70-300, 70-200, 70-100 bp.

According to some embodiments, the non-transcribable polynucleotide trigger, for example dsRNA, molecule comprises a nucleic acid segment at least 70 bp in length which is at least 65% identical to the plant gene. According to a specific embodiment, the nucleic acid sequence comprises a nucleic acid segment at least 70 bp in length which is at least 70% identical (over the entire sequence) to the plant gene. According to a specific embodiment, the nucleic acid sequence comprises a nucleic acid segment at least 70 bp in length which is at least 75% identical (over the entire sequence) to the plant gene. According to a specific embodiment, the nucleic acid sequence comprises a nucleic acid segment at least 70 bp in length which is at least 80% identical (over the entire sequence) to the plant gene. According to a specific embodiment, the nucleic acid sequence comprises a nucleic acid segment at least 70 bp in length which is at least 85% identical (over the entire sequence) to the plant gene. According to a specific embodiment, the nucleic acid sequence comprises a nucleic acid segment at least 70 bp in length which is at least 90% identical (over the entire sequence) to the plant gene. According to a specific embodiment, the nucleic acid sequence comprises a nucleic acid segment at least 70 bp in length which is at least 95% identical (over the entire sequence) to the plant gene. According to a specific embodiment, the nucleic acid sequence comprises a nucleic acid segment at least 70 bp in length which is % identical (over the entire sequence) to the plant gene.

In some embodiments, the nucleic acid sequence of the non-transcribable polynucleotide trigger, for example dsRNA, molecule comprises a second nucleic acid segment at least 17 bp in length (over at least 17 consecutive bp) which is at least 85% identical to a plant gene. According to a specific embodiment, the nucleic acid sequence of the non-transcribable polynucleotide trigger, for example dsRNA, molecule comprises a second nucleic acid segment at least 17 bp in length (over at least 17 consecutive bp) which is at least 90% identical to a plant gene. According to a specific embodiment, the nucleic acid sequence of the non-transcribable polynucleotide trigger, for example dsRNA, molecule comprises a second nucleic acid segment at least 17 bp in length (over at least 17 consecutive bp) which is at least 95% identical to a plant gene. According to a specific embodiment, the nucleic acid sequence of the non-transcribable polynucleotide trigger, for example dsRNA, molecule comprises a second nucleic acid segment at least 17 bp in length (over at least 17 consecutive bp) which is 100% identical to a plant gene.

According to a specific embodiment, the first nucleic acid segment and the second nucleic acid segment overlap (by at least 5%, 10%, 20%, 40%, 50% or more). According to a specific embodiment, the overlap is by 5-99%, 5-95%, 5-90%, 5-80%, 5-70%, 5-60%. According to a specific embodiment, the first nucleic acid segment and the second nucleic acid segment are in no overlap.

In some embodiments, the nucleic acid sequence of the non-transcribable polynucleotide trigger, for example dsRNA, molecule is selected having a homology level to a gene of a phytopathogenic organism sufficient to induce degradation of the gene of the phytopathogenic organism, wherein the phytopathogenic organism depends on the plant for growth and wherein the degradation induces a growth arrest or death of the phytopathogenic organism.

Thus, the non-transcribable polynucleotide trigger, for example dsRNA, molecule exhibits at least 80%, 85%, 88%, 90%, 91%, 92%, 93%, 94%, 95%, 96%, 97%, 98%, 99% or even 100% identity to the gene of the phytopathogen.

In some embodiments, the non-transcribable polynucleotide trigger, for example dsRNA, molecule can be designed for specifically targeting a target gene of interest. It will be appreciated that the non-transcribable polynucleotide trigger, for example dsRNA, molecule can be used to down-regulate one or more target genes of the phytopathogen or plant (in the latter case to increase the amplification). If a number of target genes are targeted, a heterogenic composition which comprises a plurality of non-transcribable polynucleotide trigger, for example dsRNA, molecules for targeting a number of target genes is used. Alternatively said plurality of non-transcribable polynucleotide trigger, for example dsRNA molecules are separately applied to the seeds (but not as a single composition).

Down-regulation of the target gene may be important for conferring improved tolerance to biotic stress induced by phytopathogen. The biotic stress can affect any of the plant's biomass, vigor or yield, as well as tolerance to abiotic stress and nitrogen use efficiency. The target gene (plant of phytopathogen) may comprise a nucleic acid sequence which is transcribed to an mRNA which codes for a polypeptide.

As used herein, the term "endogenous" refers to a gene whose expression (mRNA or protein) takes place in the plant. Typically, the endogenous gene is naturally expressed in the plant or originates from the plant. Thus, the plant may be a wild-type plant. However, the plant may also be a genetically modified plant (transgenic).

As used herein the term "isolated" refers to the isolation from the physiological, natural environment. In the case of dsRNA, isolation from cellular organelles, such as the cytosol or nucleus. In the case of a seed, isolation from other plant parts such as the fruit. According to a specific embodiment, an isolated dsRNA molecule is in a form of naked RNA.

Down regulation of the target gene may be important for conferring improved one of—, or at least one of (e.g., two of—or more), biomass, vigor, yield, abiotic stress tolerance, biotic stress tolerance or improved nitrogen use efficiency.

Examples of target genes include, but are not limited to, an enzyme, a structural protein, a plant regulatory protein, a miRNA target gene, or a non-coding RNA such as a miRNA of the plant. WO2011067745, WO 2009125401 and WO 2012056401 provide examples of miRNA sequences or targets of miRNAs (e.g., mRNA167, miRNA 156, miR164 and targets thereof NFY, SPL17 and NAC, respectively) which expression can be silenced to improve a plant trait. Other examples of target genes which may be subject to modulation according to the present teachings are described in the Examples section which follows.

The target gene may comprise a nucleic acid sequence which is transcribed to an mRNA which codes for a polypeptide. Alternatively, the target gene can be a non-coding gene such as a miRNA or a siRNA.

For example, in order to silence the expression of an mRNA of interest, synthesis of the dsRNA suitable for use with some embodiments of the invention can be selected as follows. First, the mRNA sequence is scanned including the 3' UTR and the 5' UTR.

Second, the mRNA sequence is compared to an appropriate genomic database using any sequence alignment software, such as the BLAST software available from the NCBI server (wwwdotncbidotnlmdotnihdotgov/BLAST/). Putative regions in the mRNA sequence which exhibit significant homology to other coding sequences are filtered out.

Qualifying target sequences are selected as template for dsRNA synthesis. Preferred sequences are those that have as little homology to other genes in the genome to reduce an "off-target" effect.

In one embodiment, the dsRNA may comprise a target sequence in an intron, exon, 3' UTR, 5' UTR, or a regulatory element of a target gene, or combinations thereof. In one embodiment, the dsRNA of the present application may comprise a target site residing in a promoter.

It will be appreciated that the RNA silencing agent of some embodiments of the invention need not be limited to those molecules containing only RNA, but further encompasses chemically-modified nucleotides and non-nucleotides.

The dsRNA may be synthesized using any method known in the art, including either enzymatic syntheses or solid-phase syntheses. These are especially useful in the case of short polynucleotide sequences with or without modifications as explained above. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g., cyanoethyl phosphoramidite followed by deprotection, desalting, and purification by, for example, an automated trityl-on method or HPLC.

As mentioned, the naked dsRNA molecule is directly contacted with the seed.

The seed may be of any plant, such as of the Viridiplantae super family including monocotyledon and dicotyledon plants. Other plants are listed herein below. According to an embodiment of the invention, the cells of the plant comprise RNA dependent RNA polymerase activity and the target RNA molecule of the dsRNA to ensure amplification of the dsRNA.

The term "plant" as used herein encompasses whole plants, ancestors and progeny of the plants and plant parts, including seeds, shoots, stems, roots (including tubers), and isolated plant cells, tissues and organs. The plant may be in any form including suspension cultures, embryos, meristematic regions, callus tissue, leaves, gametophytes, sporophytes, pollen, and microspores. It will be appreciated, that the plant or seed thereof may be transgenic plants.

As used herein the phrase "plant cell" refers to plant cells which are derived and isolated from disintegrated plant cell tissue or plant cell cultures. Plant cells may be reproductive cells (i.e., cells from a tissue contributing directly to the sexual reproduction of a plant) or non-reproductive cells (i.e., cells from a tissue not involved in the sexual reproduction of a plant). Plant cells may be cells that are capable of regenerating into a whole plant or cells that cannot regenerate into a whole plant, for example, enucleated mature sieve tube cells.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present invention may comprise a particular type of a plant cell or a plurality of different types of plant cells. It should be noted that optionally plant cultures featuring a particular type of plant cell may be originally derived from a plurality of different types of such plant cells.

Any commercially or scientifically valuable plant is envisaged in accordance with some embodiments of the invention. Plants that are particularly useful in the methods of the invention include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cyclonia oblonga, Cryptomeria japonica, Cymbopogon* spp., *Cynthea dealbata, Cyclonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squamosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, sorghum, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, quinoa, spinach, squash, onion, leek, tobacco, potato, sugarbeet, papaya, pineapple, mango, *Arabidopsis thaliana*, and also plants used in horticulture, floriculture or forestry, such as, but not limited to, poplar, fir, eucalyptus, pine, an ornamental plant, a perennial grass and a forage crop, coniferous plants, moss, algae, as well as other plants listed in World Wide Web (dot) nationmaster (dot) com/encyclopedia/Plantae.

According to a specific embodiment, the plant is selected from the group consisting of corn, rice, wheat, tomato, cotton and sorghum.

According to a specific embodiment, the seed is an uncoated or fresh seed that hasn't been subjected to chemical/physical treatments.

In some embodiments, washing of the seeds is effected for 30 minutes to 4 hours. Other examples of wash ranges are 1 minute to 10 minutes, 10 minutes to 30 minutes. According to some embodiments, washing of the seeds can be as short as 5, 10, 20, 30, 45, or 60 seconds. The wash solution may include a weak detergent such as Tween-20. The concentration of the detergent may be 0.01-0.2% or 0.2-1%. According to another embodiment, the detergent concentration can be about 0.001%, 0.005%, 0.01%, 0.05%, 0.1%, 0.5%, 1% or higher.

The seed may be subjected to priming or washing prior to contacting with the dsRNA.

As used herein the term "priming" refers to controlling the hydration level within seeds so that the metabolic activity necessary for germination can occur but radicle emergence is prevented. Different physiological activities within the seed occur at different moisture levels (Leopold and Vertucci, 1989; Taylor, 1997). The last physiological activity in the germination process is radicle emergence. The initiation of radicle emergence requires a high seed water content. By limiting seed water content, all the metabolic steps necessary for germination can occur without the irreversible act of radicle emergence. Prior to radicle emergence, the seed is considered desiccation tolerant, thus the primed seed moisture content can be decreased by drying. After drying, primed seeds can be stored until time of sowing.

Several different priming methods are used commercially. Among them, liquid or osmotic priming and solid matrix priming appear to have the greatest following (Khan et al., 1991).

According to an embodiment of the invention, priming is effected in the presence of salt, a chelating agent, polyethylene glycol or a combination of same (e.g., chelating agent and salt).

Alternatively, priming is effected in the presence of water such as deionized water or double deionized water. According to a specific embodiment, the priming is effected in the presence of 100% ddW.

Several types of seed priming are commonly used:

Osmopriming (osmoconditioning)—is the standard priming technique. Seeds are incubated in well aerated solutions with a low water potential, and afterwards washes and dried. The low water potential of the solutions can be achieved by adding osmotica like mannitol, polyethyleneglycol (PEG) or salts like KCl.

Hydropriming (drum priming)—is achieved by continuous or successive addition of a limited amount of water to the seeds. A drum is used for this purpose and the water can also be applied by humid air. 'On-farm steeping' is a cheap and useful technique that is practiced by incubating seeds (cereals, legumes) for a limited time in warm water.

Matrixpriming (matriconditioning)—is the incubation of seeds in a solid, insoluble matrix (vermiculite, diatomaceous earth, cross-linked highly water-absorbent polymers) with a limited amount of water. This method confers a slow imbibition.

Pregerminated seeds—is only possible with a few species. In contrast to normal priming, seeds are allowed to perform radicle protrusion. This is followed by sorting for specific stages, a treatment that reinduces desiccation tolerance, and drying. The use of pregerminated seeds causes rapid and uniform seedling development.

Thus, according to one embodiment, the seeds are primed seeds.

Of note, it may be possible that the seeds are treated with water (double-distilled water, ddW), prior to contacting with the dsRNA without effecting any priming on the seeds. For instance, treatment for a short while with water (e.g., 30 seconds to 1 hour, 30 seconds to 0.5 hour, 30 seconds to 10 minutes, 30 seconds to 5 minutes or 45 seconds to 5 minutes). According to some embodiments, treatment with water can be as short as 5, 10, 20, or 30 seconds.

It will be appreciated that the non-transcribable polynucleotide trigger, for example dsRNA, molecule can be comprised in water (e.g., tap water, distilled water or double distilled water) i.e., free of any of the above mentioned priming effective concentration of salts, a chelating agents, polyethylene glycol or combinations of same (e.g., chelating agent and salt). In some embodiments, the non-transcribable polynucleotide trigger, for example dsRNA, molecule is provided to the seed in a buffer solution, such as EDTA.

In some embodiments, the seeds are non-primed seeds.

A non-limiting method of introducing the dsRNA into the seed is provided in Example 1, which is considered as an integral part of the specification.

The temperature at the washing/priming and drying steps may be the same or differ.

According to one embodiment, the washing/priming is effected at 4-28° C.

According to one embodiment, the priming/washing solution or the dsRNA containing solution is devoid of a solid carrier.

According to one embodiment, the priming/washing solution or the dsRNA containing solution is devoid of a transferring agent such as a surfactant or a salt.

According to a further embodiment of the invention, the seeds subject to contacting with the dsRNA molecule are washed in order to remove agents, to which the seeds have been subjected, such as a pesticide, a fungicide, an insecticide, a fertilizer, a coating agent and a coloring agent.

Thus, according to one embodiment, the seeds (prior to treatment with dsRNA) are substantially free (i.e., do not comprise effective amounts) of pesticide, a fungicide, an insecticide, a fertilizer, a coating agent and a coloring agent.

The seeds are then subjected to drying. In some embodiments, drying is optional.

According to one embodiment, the drying is effected at 20-37° C., 20-30° C., 22-37° C., 15-22° C. or 20-25° C. for 10-20 hours, 10-16 hours or even 2-5 hours.

Various considerations are to be taken when calculating the concentration of the dsRNA in the contacting solution. These are dependent on at least one of seed size, seed weight, seed volume, seed surface area, seed density and seed permeability.

For example, related to seed size, weight, volume and surface area, it is estimated that corn seeds will require longer treatment than *Arabidopsis* and tomato seeds. Regarding permeability and density, it is estimated that wheat seeds will require longer treatments at higher concentrations than tomato seeds.

Examples of concentrations of dsRNA in the treating solution include, but are not limited to, 0.01-0.3 µg/µl, 0.01-0.15 µg/µl, 0.04-0.15 µg/µl, 0.1-100 µg/µl; 0.1-50 µg/µl, 0.1-10, µg/µl, 0.1-5 µg/µl, 0.1-1 µg/µl, 0.1-0.5 µg/µl, 0.15-0.5 µg/µl, 0.1-0.3 µg/µl, 0.01-0.1 µg/µl, 0.01-0.05 µg/µl, 0.02-0.04 µg/µl, 0.001-0.02 µg/µl. According to a specific embodiment, the concentration of the dsRNA in the treating solution is 0.01-0.15 or 0.04-0.15 µg/µl.

In one embodiment, the dsRNA concentration in the treating solution is 0.01-0.3 µg/ml, 0.01-0.15 µg/ml, 0.04-0.15 µg/ml, 0.1-100 µg/ml; 0.1-50 µg/ml, 0.1-10 µg/ml, 0.1-5 µg/ml, 0.1-1 µg/ml, 0.1-0.5 µg/ml, 0.15-0.5 µg/ml, 0.1-0.3 µg/ml, 0.01-0.1 µg/ml, 0.01-0.05 µg/ml, 0.02-0.04 µg/ml, or 0.001-0.02 µg/ml.

In another embodiment, the dsRNA concentration in the treating solution is about 5-10 µg/ml, 10-15 µg/ml, 15-20

μg/ml, 20-25 μg/ml; 25-30 μg/ml, 30-35 μg/ml, 35-40 μg/ml, 40-45 μg/ml, 45-50 μg/ml, 50-55 μg/ml, 55-60 μg/ml, 60-65 μg/ml, 65-70 μg/ml, 70-75 μg/ml, 75-80 μg/ml, 80-85 μg/ml, 85-90 μg/ml, 90-95 μg/ml, 95-100 μg/ml, 100-105 μg/ml, 105-110 μg/ml, 110-115 μg/ml, 115-120 μg/ml, 120-125 μg/ml; 125-130 μg/ml, 130-135 μg/ml, 135-140 μg/ml, 140-145 μg/ml, 145-150 μg/ml, 150-155 μg/ml, 155-160 μg/ml, 160-165 μg/ml, 165-170 μg/ml, 170-175 μg/ml, 175-180 μg/ml, 180-185 μg/ml, 185-190 μg/ml, 190-195 μg/ml, 195-200 μg/ml, 200-210 μg/ml, 210-220 μg/ml, 220-230 μg/ml, 230-240 μg/ml, 240-250 μg/ml, 250-260 μg/ml, 260-270 μg/ml, 270-280 μg/ml, 280-290 μg/ml, 290-300 μg/ml, 300-310 μg/ml, 310-320 μg/ml, 320-330 μg/ml, 330-340 μg/ml, 340-350 μg/ml, 350-360 μg/ml, 360-370 μg/ml, 370-380 μg/ml, 380-390 μg/ml, 390-400 μg/ml, 400-410 μg/ml, 410-420 μg/ml, 420-430 μg/ml, 430-440 μg/ml, 440-450 μg/ml, 450-460 μg/ml, 460-470 μg/ml, 470-480 μg/ml, 480-490 μg/ml, or about 490-500 μg/ml.

In another embodiment, the dsRNA concentration in the treating solution is 0.0001-3 μg/μl, 0.0001-2.5 μg/μl, 0.0001-2 μg/μl, 0.0001-1.5 μg/μl, 0.0001-1 μg/μl, 0.0001-0.9 μg/μl, 0.0001-0.8 μg/μl, 0.0001-0.7 μg/μl, 0.0001-0.6 μg/μl, 0.0001-0.5 μg/μl, 0.0001-0.4 μg/μl, 0.0001-0.3 μg/μl, 0.0001-0.2 μg/μl, 0.0001-0.1 μg/μl, 0.0001-0.05 μg/μl, 0.0001-0.02 μg/μl, 0.0001-0.01 μg/μl, 0.0001-0.005 μg/μl, 0.0001-0.001 μg/μl, or 0.0001-0.0005 μg/μl.

In another embodiment, the dsRNA concentration in the treating solution is 0.0001-3 μg/μl, 0.0005-3 μg/μl, 0.001-3 μg/μl, 0.005-3 μg/μl, 0.01-3 μg/μl, 0.05-3 μg/μl, 0.1-3 μg/μl, 0.2-3 μg/μl, 0.3-3 μg/μl, 0.4-3 μg/μl, 0.5-3 μg/μl, 0.6-3 μg/μl, 0.7-3 μg/μl, 0.8- 3 μg/μl, 0.9-3 μg/μl, 1-3 μg/μl, or 2-3 μg/μl.

In another embodiment, the dsRNA concentration in the treating solution is 0.0001-3 μg/μl, 0.0005-2.5 μg/μl, 0.001-2 μg/μl, 0.005-1.5 μg/μl, 0.01-1 μg/μl, 0.05-0.5 μg/μl, 0.1-0.4 μg/μl, or 0.2-0.3 μg/μl.

According to a specific embodiment, the contacting with the dsRNA is effected in the presence of a chelating agent such as EDTA or another chelating agent such as DTPA (0.01-0.1 mM).

In some embodiments, the treating solution may comprise a transferring agent such as a surfactant or a salt. Examples of such transferring agents include but are not limited salts such as sodium or lithium salts of fatty acids (such as tallow or tallowamines or phospholipids lipofectamine or lipofectin (1-20 nM, or 0.1-1 nM)) and organosilicone surfactants. Other useful surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet™ L-77 surfactant having CAS Number 27306-78-1 and EPA Number: CAL.REG.NO. 5905-50073-AA, currently available from Momentive Performance Materials, Albany, N.Y.).

In some embodiments, the treating solution may comprise a physical agent. Examples of physical agents include: (a) abrasives such as carborundum, corundum, sand, calcite, pumice, garnet, and the like, (b) nanoparticles such as carbon nanotubes and (c) a physical force. Carbon nanotubes are disclosed by Kam et al. (2004) J. Am. Chem. Soc., 126 (22):6850-6851, Liu et al. (2009) Nano Lett., 9(3):1007-1010, and Khodakovskaya et al. (2009) ACS Nano, 3(10): 3221-3227. Physical force agents can include heating, chilling, the application of positive pressure, or ultrasound treatment. Agents for laboratory conditioning of a plant to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

Contacting of the seeds with the dsRNA can be effected using any method known in the art as long as an effective amount of the dsRNA enters the seeds. These examples include, but are not limited to, soaking, spraying or coating with powder, emulsion, suspension, or solution; similarly, the polynucleotide molecules are applied to the plant by any convenient method, e.g., spraying or wiping a solution, emulsion, or suspension.

As used herein "an effective amount" refers to an amount of dsRNA which is sufficient to down regulate the target gene by at least 20%, 30%, 40%, 50%, or more, say 60%, 70%, 80%, 90% or more even 100%. The effective amount can be a result of the formation of amplification in the plant or the phytopathogen.

According to a specific embodiment contacting may be effected by soaking (i.e., inoculation) so that shaking the seeds with the treating solution may improve penetration and soaking and therefore reduce treatment time. Shaking is typically performed at 50-150 RPM and depends on the volume of the treating solution. Shaking may be effected for 4-24 hours (1-4 hours, 10 minutes to 1 hour or 30 seconds to 10 minutes). The present teachings further envisage short incubation time such as up to 10 minutes. Examples include but are not limited to 30 seconds to 7 minutes, to 30 seconds to 5 minutes, to 30 seconds to 3 minutes, to 30 seconds to 2 minutes, to 30 seconds to 1 minute, 1 minute to 10 minutes or to 1 minute to 5 minutes.

In one embodiment, the incubation time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 seconds.

In another embodiment, the incubation time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 minutes.

Dipping is also considered under the scope of the present embodiments. Thus, the seeds are dipped into the dsRNA solution for seconds e.g., 1-10 seconds, 1-5 seconds, 1-3 seconds or 1-2 seconds. During this period, the dsRNA may adsorb on the seed surface. The adsorbed dsRNA, which coats the seed, may penetrate the seed or the seedling during germination. The incubation takes place in the dark at 4-28° C. or 15-22° C. (e.g., 8-15° C., 4-8° C., 22-28° C.).

In one embodiment, the dipping time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 minutes.

In one embodiment, the dipping time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 seconds.

According to a specific embodiment, contacting occurs prior to breaking of seed dormancy and embryo emergence.

Following contacting, preferably prior to breaking of seed dormancy and embryo emergence, the seeds may be subjected to treatments (e.g., coating) with the above agents (e.g., pesticide, fungicide etc.).

Contacting is effected such that the dsRNA enters the embryo, endosperm, the coat, or a combination of the three.

After contacting with the treatment solution, the seeds may be subjected to drying for up to 30 hours at 25-37° C. For example, the seeds may be dried for 16 hours at 30° C.

According to a specific embodiment, the seed (e.g., isolated seed) comprises the exogenous naked dsRNA and wherein at least 10 or 20 molecules of the dsRNA are in the endosperm of the isolated seed.

As used herein the term "isolated" refers to separation from the natural physiological environment. In the case of seed, the isolated seed is separated from other parts of the plant. In the case of a nucleic acid molecule (e.g., dsRNA) separated from the cytoplasm.

According to a specific embodiment, the dsRNA is not expressed from the plant genome, thereby not being an integral part of the genome.

According to a specific embodiment there is provided an isolated seed comprising an exogenous dsRNA being present at a similar concentration (e.g., about 1:1, 2:1 or 1:2) in an embryo and an endosperm of the seed. It is suggested that the direct introduction of the naked dsRNA to the seed results in higher concentration of the dsRNA in the endosperm than that observed when the dsRNA is expressed from a nucleic acid expression construct.

According to a specific embodiment there is provided an isolated seed comprising an exogenous dsRNA being spatially distributed in an embryo and an endosperm of the plant seed in a spatial distribution that differs from a spatial distribution of the exogenous dsRNA in a seed derived from a transgenic plant that recombinantly expresses said exogenous dsRNA.

Methods of measuring the localization of RNA molecules in the seed are well known in the art. The use of siGlo as described in the Examples section is an example for such.

According to an alternative or an additional embodiment, there is provided an isolated seed comprising an exogenous dsRNA, wherein a concentration ratio of said exogenous dsRNA to siRNA maturing there from is higher in the seed as compared to a transgenic seed recombinantly expressing said exogenous dsRNA.

As used herein the term "higher" refers to at least about 3%, 5%, 7%, 10%, 15%, 20%, 25%, 30%, 50%, 60%, 70%, 80%, 90% or even a few folds higher.

According to an alternative or an additional embodiment, there is provided an isolated seed comprising an exogenous dsRNA, wherein the plant seed is devoid of a heterologous promoter for driving expression of said exogenous dsRNA, wherein a spatial distribution of said exogenous dsRNA and/or siRNA maturing there from is altered in the seed as compared to same in a transgenic seed recombinantly expressing said exogenous dsRNA.

The term "recombinantly expressing" refers to an expression from a nucleic acid construct.

According to a further embodiment there is provided a plant seed obtainable (or obtained) by any of the methods described herein.

Methods of qualifying successful introduction of the dsRNA include but are not limited to, RT-PCR (e.g., quantifying the level of the target gene or the naked dsRNA), phenotypic analysis such as biomass, vigor, yield and stress tolerance, root architecture, leaf dimensions, grain size and weight, oil content, cellulose, as well as cell biology techniques.

According to some embodiments, an alteration of the expression level of the plant ortholog of the insect pest gene targeted by the seed treatment, as described herein, is observed. See for instance Examples 45 and 46 of the Examples section which follows.

Seeds may be stored for 1 day to several months prior to planting (e.g., at 4-10° C.).

The resultant seed can be germinated in the dark so as to produce a plant.

Thus there is provided a plant or plant part comprising an exogenous naked dsRNA and devoid of a heterologous promoter for driving expression of the dsRNA in the plant.

As used herein "devoid of a heterologous promoter for driving expression of the dsRNA" means that the plant or plant cell doesn't include a cis-acting regulatory sequence (e.g., heterologous) transcribing the dsRNA in the plant. As used herein the term "heterologous" refers to exogenous, not-naturally occurring within the native plant cell (such as by position of integration, or being non-naturally found within the plant cell). Thus the isolated seed in the absence of a heterologous promoter sequence for driving expression of the dsRNA in the plant, comprises a homogenic (prior to amplification) or heterogenic (secondary siRNAs, following amplification) population of plant non-transcribable dsRNA.

The present methodology can be used for modulating gene expression such as in a plant, the method comprising:

(a) contacting a seed of the plant with a naked dsRNA, under conditions which allow penetration of the dsRNA into the seed, thereby introducing the dsRNA into the seed; and optionally (b) generating a plant of the seed.

When used for down-regulating a plant gene, the naked dsRNA is designed of the desired specificity using bioinformatic tools which are well known in the art (e.g., BLAST).

This methodology can be used in various applications starting from basic research such as in order to assess gene function and lasting in generating plants with altered traits which have valuable commercial use.

Such plants can exhibit agricultural beneficial traits including altered morphology, altered flowering, altered tolerance to stress (i.e., biotic and/or abiotic), altered biomass vigor and/or yield and the like.

The phrase "abiotic stress" as used herein refers to any adverse effect on metabolism, growth, viability and/or reproduction of a plant. Abiotic stress can be induced by any of suboptimal environmental growth conditions such as, for example, water deficit or drought, flooding, freezing, low or high temperature, strong winds, heavy metal toxicity, anaerobiosis, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present invention contemplates situations in which there is a single abiotic stress condition or alternatively situations in which two or more abiotic stresses occur.

According to one embodiment, the abiotic stress refers to salinity.

According to another embodiment, the abiotic stress refers to drought.

According to another embodiment, the abiotic stress refers to a temperature stress.

As used herein the phrase "abiotic stress tolerance" refers to the ability of a plant to endure an abiotic stress without exhibiting substantial physiological or physical damage (e.g. alteration in metabolism, growth, viability and/or reproducibility of the plant).

As used herein the phrase "nitrogen use efficiency (NUE)" refers to a measure of crop production per unit of nitrogen fertilizer input. Fertilizer use efficiency (FUE) is a measure of NUE. Crop production can be measured by biomass, vigor or yield. The plant's nitrogen use efficiency is typically a result of an alteration in at least one of the uptake, spread, absorbance, accumulation, relocation (within the plant) and use of nitrogen absorbed by the plant. Improved NUE is with respect to that of a non-transgenic plant (i.e., lacking the transgene of the transgenic plant) of the same species and of the same developmental stage and grown under the same conditions.

As used herein the phrase "nitrogen-limiting conditions" refers to growth conditions which include a level (e.g., concentration) of nitrogen (e.g., ammonium or nitrate) applied which is below the level needed for optimal plant metabolism, growth, reproduction and/or viability.

As used herein the term/phrase "biomass", "biomass of a plant" or "plant biomass" refers to the amount (e.g., measured in grams of air-dry tissue) of a tissue produced from the plant in a growing season. An increase in plant biomass can be in the whole plant or in parts thereof such as aboveground (e.g. harvestable) parts, vegetative biomass, roots and/or seeds or contents thereof (e.g., oil, starch etc.).

As used herein the term/phrase "vigor", "vigor of a plant" or "plant vigor" refers to the amount (e.g., measured by weight) of tissue produced by the plant in a given time. Increased vigor could determine or affect the plant yield or the yield per growing time or growing area. In addition, early vigor (e.g. seed and/or seedling) results in improved field stand.

As used herein the term/phrase "yield", "yield of a plant" or "plant yield" refers to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

According to one embodiment, the yield is measured by cellulose content, oil content, starch content and the like.

According to another embodiment, the yield is measured by oil content.

According to another embodiment, the yield is measured by protein content.

According to another embodiment, the yield is measured by seed number, seed weight, fruit number or fruit weight per plant or part thereof (e.g., kernel, bean).

A plant yield can be affected by various parameters including, but not limited to, plant biomass; plant vigor; plant growth rate; seed yield; seed or grain quantity; seed or grain quality; oil yield; content of oil, starch and/or protein in harvested organs (e.g., seeds or vegetative parts of the plant); number of flowers (e.g. florets) per panicle (e.g. expressed as a ratio of number of filled seeds over number of primary panicles); harvest index; number of plants grown per area; number and size of harvested organs per plant and per area; number of plants per growing area (e.g. density); number of harvested organs in field; total leaf area; carbon assimilation and carbon partitioning (e.g. the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

Improved plant NUE is translated in the field into either harvesting similar quantities of yield, while implementing less fertilizers, or increased yields gained by implementing the same levels of fertilizers. Thus, improved NUE or FUE has a direct effect on plant yield in the field.

As used herein "biotic stress" refers stress that occurs as a result of damage done to plants by other living organisms, such as bacteria, viruses, fungi, parasites, beneficial and harmful insects, weeds, and cultivated or native plants. Examples 7, and 20-38 of the Examples section which follows, describes implementation the present teachings towards conferring resistance to *Spodoptera littoralis*. Examples 38 and 39 of the Examples section which follows, describes implementation the present teachings towards conferring resistance to *Coleopteran* pests. Examples 40-52 of the Examples section which follows, describes implementation the present teachings towards conferring resistance to viral infection.

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in NUE, in tolerance to stress, in yield, in biomass or in vigor of a plant, as compared to a native or wild-type plants [i.e., isogenic plants (not grown from seeds treated with dsRNA) of the present embodiments].

In some embodiments, the target gene of the dsRNA may not be an endogenous plant gene but rather a gene exogenous to the plant, such as a gene of a phytopathogenic organism which feeds on the plant or depends thereon for growth/replication (e.g., bacteria or viruses) and/or survival. In some embodiments, the target gene is an essential gene of an insect pest. In some embodiments, the target gene is a viral gene.

As used herein, the term "phytopathogen" refers to an organism that benefits from an interaction with a plant, and has a negative effect on that plant. The term "phytopathogen" includes insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like that may ingest or contact one or more cells, tissues, or fluids produced by a plant.

The methods described herein can be used to generate a plant that is resistant to one or more phytopathogens. In some embodiments, the phytopathogen is an insect pest. When an insect is the target pest for the present invention, such pests include but are not limited to: from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp, *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantiria cunea*, *Keiferia lycopersicella*, *Leucoptera scitella*,

*Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia Nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; from the order Coleoptera, for example, *Agriotes* spp., *Anthonomus* spp., *Atomaria linearis*, *Chaetocnema tibialis*, *Cosmopolites* spp., *Curculio* spp., *Denrmestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.; from the order Orthoptera, for example, *Blatta* spp., *Blattella* spp., *Gryllotalpa* spp., *Leucophaea maderae*, *Locusta* spp., *Periplaneta* ssp., and *Schistocerca* spp.; from the order Isoptera, for example, *Reticulitemes* ssp.; from the order Psocoptera, for example, *Liposcelis* spp.; from the order Anoplura, for example, *Haematopinus* spp., *Linognathus* spp., *Pediculus* spp., *Pemphigus* spp. and *Phylloxera* spp.; from the order Mallophaga, for example, *Damalinea* spp. and *Trichodectes* spp.; from the order Thysanoptera, for example, *Franklinella* spp., *Hercinothrips* spp., *Taeniothrips* spp., *Thrips palmi*, *Thrips tabaci* and *Scirtothrips aurantii*; from the order Heteroptera, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp., *Triatoma* spp., Miridae family spp. such as *Lygus hesperus* and *Lygus lineoloris*, Lygaeidae family spp. such as *Blissus leucopterus*, and Pentatomidae family spp.; from the order Homoptera, for example, *Aleurothrixus floccosus*, *Aleyrodes brassicae*, *Aonidiella* spp., Aphididae, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lacanium corni*, *Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*; from the order Hymenoptera, for example, *Acromyrmex*, *Atta* spp., *Cephus* spp., *Diprion* spp., Diprionidae, *Gilpinia polytoma*, *Hoplocampa* spp., *Lasius* spp., *Monoimorium pharaonis*, *Neodiprion* spp., *Solenopis* spp. and *Vespa* ssp.; from the order Diptera, for example, *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella fit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp., from the order Siphonaptera, for example, *Ceratophyllus* spp. and *Xenopsylla cheopis* and from the order Thysanura, for example, *Lepisma saccharina*. Thus, according to one embodiment, there is provided a method of inhibiting expression of a target gene in a phytopathogenic organism, the method comprising providing (e.g., feeding or contacting under infecting conditions) to the phytopathogenic organism the plant as described herein (at least part thereof includes the naked dsRNA), thereby inhibiting expression of a target gene in the phytopathogenic organism. In some embodiments, the target gene is an "essential gene." As used herein, the term "essential gene" refers to a gene of an organism that is essential for its survival or reproduction. In some embodiments, the target gene is expressed in the insect gut, for example, V-ATPase. Target genes for use in the present invention may include, for example, those that share substantial homologies to the nucleotide sequences of known gut-expressed genes that encode protein components of the plasma membrane proton V-ATPase (Dow et al., 1997, J. Exp. Biol., 200:237-245; Dow, Bioenerg. Biomemb., 1999, 31:75-83). This protein complex is the sole energizer of epithelial ion transport and is responsible for alkalinization of the midgut lumen. The V-ATPase is also expressed in the Malpighian tubule, an outgrowth of the insect hindgut that functions in fluid balance and detoxification of foreign compounds in a manner analogous to a kidney organ of a mammal. In some embodiments, the target gene is involved in the growth, development, and reproduction of an insect. Examples of such genes include, but are not limited to, CHD3 gene and a beta-tubulin gene.

The gene targeted for suppression, or the function in a pest cell or as a physiological or metabolic aspect of the pest that is enabled by the expression of the gene targeted for suppression, can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

The phytopathogenic organism refers to a multicellular organism e.g., insects, fungi, animals or a microorganism that can cause plant disease, including viruses, bacteria, fungi as well as oomycetes, chytrids, algae, and nematodes.

Reference herein to a "nematode" refers to a member of the phylum Nematoda. Members of the family Heteroderidae are sedentary parasites that form elaborate permanent associations with the target host organism. They deprive nutrients from cells of an infected organism through a specialized stylet. The cyst nematodes (genera *Heterodera* and *Globodera*) and root-knot nematodes (genus *Meliodogyne*), in particular, cause significant economic loss in plants, especially crop plants. Examples of cyst nematodes include, inter alia, *H. avenae* (cereal cyst nematodes), *H. glycines* (beet cyst nematode) and *G. pallida* (potato cyst nematode). Root-knot nematodes include, for example, *M. javanica*, *M. incognita* and *M. arenaria*. These pathogens establish "feeding sites" in the plant, by causing the morphological transformation of root cells into giant cells. Hence, nematode "infestation" or "infection" refers to invasion of and feeding upon the tissues of the host plant. Other nematodes that cause significant damage include the lesion nematodes such as *Pratylenchus*, particularly *P. penetrans*, which infects maize, rice and vegetables, *P. brachyurus* which infects pineapple and *P. thornei* which infects inter alia, wheat.

Several embodiments relate to a method of inhibiting expression of a target gene in an insect pest, the method comprising providing (e.g., feeding) to the insect pest a plant grown from a seed treated with an exogenous dsRNA as described herein, thereby inhibiting expression of the target gene in the insect pest. Insects that may cause damage and disease in plants belong to three categories, according to their method of feeding: chewing, sucking and boring. Major damage is caused by chewing insects that eat plant tissue, such as leaves, flowers, buds and twigs. Examples from this large insect category include beetles and their larvae (grubs), web-worms, bagworms and larvae of moths and sawflies (caterpillars). By comparison, sucking insects insert their mouth parts into the tissues of leaves, twigs, branches, flowers or fruit and suck out the plant's juices. Typical examples of sucking insects include but are not limited to aphids, mealy bugs, thrips and leaf-hoppers. Damage caused by these pests is often indicated by discoloration, drooping, wilting and general lack of vigor in the affected plant.

Several embodiments relate to a method of providing resistance to an insect pest, the method comprising growing a plant from a seed treated with an exogenous dsRNA as described herein. In some embodiments, the insect pest is selected from the orders Coleoptera, Lepidoptera, Diptera, Orthoptera, Heteroptera, Ctenophalides, Arachnidiae, and Hymenoptera. In some embodiments, the insect pest is a beetle or larvae. According to a specific embodiment, the phytopathogen is prodentia of the family Noctuidae e.g., *Spodoptera littoralis*.

Examples of significant bacterial plant pathogens include, but are not limited to, *Burkholderia*, Proteobacteria (*Xanthomonas* spp. and *Pseudomonas* spp., *Pseudomonas syringae* pv. tomato).

A number of virus genera are transmitted, both persistently and non-persistently, by soil borne zoosporic protozoa. These protozoa are not phytopathogenic themselves, but parasitic. Transmission of the virus takes place when they become associated with the plant roots. Examples include *Polymyxa graminis*, which has been shown to transmit plant viral diseases in cereal crops and *Polymyxa betae* which transmits Beet necrotic yellow vein virus. Plasmodiophorids also create wounds in the plant's root through which other viruses can enter.

Specific examples of viruses which can be targeted according to the present teachings include, but are not limited to:

(1) Tobacco mosaic virus (TMV, RNA virus) which infects plants, especially tobacco and other members of the family Solanaceae.

(2) Tomato spotted wilt virus (TSWV, RNA virus) which causes serious diseases of many economically important plants representing 35 plant families, including dicots and monocots. This wide host range of ornamentals, vegetables, and field crops is unique among plant-infecting viruses. Belongs to tospoviruses in the Mediterranean area, affect vegetable crops, especially tomato, pepper and lettuce (Turina et al., 2012, Adv Virus Res 84; 403-437).

(3) Tomato yellow leaf curl virus (TYLCV) which is transmitted by whitefly, mostly affects tomato plants. Geminiviruses (DNA viruses) in the genus Begomovirus (including sweepoviruses and legumoviruses)—most devastating pathogens affecting a variety of cultivated crops, including cassava, sweet potato, beans, tomato, cotton and grain legumes (Rey et al. 2012, Viruses 4; 1753-1791). Members include TYLCV above and tomato leaf curl virus (ToLCV).

(4) Cucumber mosaic virus (CMV)—CMV has a wide range of hosts and attacks a great variety of vegetables, ornamentals, and other plants (as many as 191 host species in 40 families). Among the most important vegetables affected by cucumber mosaic are peppers (*Capsicum annuum* L.), cucurbits, tomatoes (*Lycopersicon esculentum* Mill.), and bananas (*Musa L.* spp.).

Other vegetable hosts include: cucumber, muskmelon, squash, tomato, spinach, celery, peppers, water cress, beet, sweet potato, turnip, chayote, gherkin, watermelon, pumpkin, citron, gourd, lima bean, broad bean, onion, groundcherry, eggplant, potato, rhubarb, carrot, dill, fennel, parsnip, parsley, loofah, and artichoke (Chabbouh and Chemf, 1990, FAO Plant Prot. Bull. 38:52-53.).

Ornamental hosts include: China aster, chrysanthemum, delphinium, salvia, geranium, gilia, gladiolus, heliotrope, hyacinth, larkspur, lily, marigold, morning glory, nasturtium, periwinkle, petunia, phlox, snapdragon, tulip, and zinnia (Chupp and Sherf, 1960; Agrios, 1978).

(5) Potato virus Y (PVY)—one of the most important plant viruses affecting potato production.

(6) Cauliflower mosaic virus (CaMV, DNA virus (Rothnie et al., 1994)).

(7) African cassava mosaic virus (ACMV).

(8) Plum pox virus (PPV) is the most devastating viral disease of stone fruit from the genus *Prunus*.

(9) Brome mosaic virus (BMV)—commonly infects *Bromus inermis* and other grasses, can be found almost anywhere wheat is grown.

(10) Potato virus X (PVX) There are no insect or fungal vectors for this virus. This virus causes mild or no symptoms in most potato varieties, but when Potato virus Y is present, synergy between these two viruses causes severe symptoms in potatoes.

Additional Viruses:

Citrus tristeza virus (CTV)—causes the most economically damaging disease to Citrus, including sour orange (*Citrus aurantium*), and any Citrus species grafted onto sour orange root stock, sweet orange (*C. sinensis*), grapefruit (*C. paradisi*), lime and Seville orange (*C. aurantifolia*), and mandarin (*C. reticulata*). CTV is also known to infect *Aeglopsis chevalieri, Afraegle paniculata, Pamburus missionis*, and *Passiflora gracilis*. CTV is distributed worldwide and can be found wherever citrus trees grow.

Barley yellow dwarf virus (BYDV)—most widely distributed viral disease of cereals. It affects the economically important crop species barley, oats, wheat, maize, triticale and rice.

Potato leafroll virus (PLRV) infects potatoes and other members of the family Solanaceae.

Tomato bushy stunt virus (TBSV), RNA virus, a member of the genus Tombusvirus and mostly affects tomatoes and eggplant.

Additional Reviews:

Hamilton et al., 1981, J Gen Virol 54; 223-241—mentions TMV, PVX, PVY, CMV, CaMV.

Additional Scientific Papers:

Makkouk et al., 2012, Adv Virus Res 84; 367-402—Viruses affecting peas and beans with narrow (Faba bean necrotic yellow virus (FBNYN)) and wide (alfalfa mosaic virus (AMV) and CMV) host range.

Insect pests causing plant disease include those from the families of, for example, Apidae, Curculionidae, Scarabaeidae, Tephritidae, Tortricidae, amongst others.

The target gene of the phytopathogenic organism encodes a product essential to the viability and/or infectivity of the pathogen, therefore its down-regulation (by the naked dsRNA) results in a reduced capability of the pathogen to survive and infect host cells. Hence, such down-regulation results in a "deleterious effect" on the maintenance viability and/or infectivity of the phytopathogen, in that it prevents or reduces the pathogen's ability to feed off and survive on nutrients derived from host cells. By virtue of this reduction in the phytopathogen's viability and/or infectivity, resistance and/or enhanced tolerance to infection by a pathogen is facilitated in the cells of the plant. Genes in the pathogen may be targeted at the mature (adult), immature (juvenile) or embryo stages.

Examples of genes essential to the viability and/or infectivity of the pathogen are provided herein. Such genes may include genes involved in development and reproduction, e.g. transcription factors (see, e.g. Xue et al., 1993; Finney et al., 1988), cell cycle regulators such as wee-1 and ncc-1 proteins (see, e.g. Wilson et al., 1999; Boxem et al., 1999) and embryo-lethal mutants (see, e.g. Schnabel et al., 1991); proteins required for modeling such as collagen, ChR3 and LRP-1 (see, e.g. Yochem et al., 1999; Kostrouchova et al., 1998; Ray et al., 1989); genes encoding proteins involved in the motility/nervous system, e.g. acetycholinesterase (see, e.g. Piotee et al., 1999; Talesa et al., 1995; Arpagaus et al., 1998), ryanodine receptor such as unc-68 (see, e.g. Maryon et al., 1998; Maryon et al., 1996) and glutamate-gated chloride channels or the avermeetin receptor (see, e.g., Cully et al., 1994; Vassilatis et al., 1997; Dent et al., 1997); hydrolytic enzymes required for deriving nutrition from the host, e.g. serine proteinases such as HGSP-1 and HGSP-III (see, e.g. Lilley et al., 1997); parasitic genes encoding proteins required for invasion and establishment of the feeding site, e.g. cellulases (see, e.g. de Boer et al., 1999; Rosso et al., 1999) and genes encoding proteins that direct production of stylar or amphidial secretions such as sec-1 protein (see, e.g. Ray et al., 1994; Ding et al., 1998); genes encoding proteins required for sex or female determination, e.g. tra-1, tra-2 and egl-1, a suppressor of ced9 (see, e.g. Hodgkin, 1980; Hodgkin, 1977; Hodgkin, 1999; Gumienny et al., 1999; Zarkower et al., 1992); and genes encoding proteins required for maintenance of normal metabolic function and homeostasis, e.g. sterol metabolism, embryo lethal mutants (see, e.g. Schnabel et al., 1991) and trans-spliced leader sequences (see, e.g. Ferguson et al, 1996), pos-1, cytoplasmic Zn finger protein; pie-1, cytoplasmic Zn finger protein; mei-1, ATPase; dif-1, mitochondrial energy transfer protein; rba-2, chromatin assembly factor; skn-1, transcription factor; plk-1, kinase; gpb-1, G-protein B subunit; par-1, kinase; bir-1, inhibitor of apoptosis; mex-3, RNA-binding protein, unc-37, G-protein B subunit; hlh-2, transcription factor; par-2, dnc-1, dynactin; par-6, dhc-1, dynein heavy chain; and pal-1, homeobox. Such genes have been cloned from parasitic nematodes such as *Meliodogyne* and *Heterodera* species or can be identified by one of skill in the art using sequence information from cloned *C. elegans* orthologs (the genome of *C. elegans* has been sequenced and is available, see The *C. elegans* Sequencing Consortium (1998)).

Several embodiments relate to a method of conferring pathogen resistance on a plant, the method comprising contacting a seed with an exogenous dsRNA molecule comprising a sequence that is essentially identical or essentially complementary to at least 18 contiguous nucleotides of a gene of a phytopathogenic organism, and growing a plant from the seed. As used herein, a "pathogen resistance" trait is a characteristic of a plant that causes the plant host to be resistant to attack from a pathogen that typically is capable of inflicting damage or loss to the plant. Not wishing to be bound by a particular theory, once the phytopathogen is provided with the plant material produced from a seed comprising the naked dsRNA, expression of the gene within the target pathogen is suppressed, and the suppression of expression of the gene in the target pathogen results in the plant being resistant to the pathogen.

In the embodiments described herein, the target gene can encode an essential protein or transcribe an non-coding RNA which, the predicted function is for example selected from the group consisting of ion regulation and transport, enzyme synthesis, maintenance of cell membrane potential, amino acid biosynthesis, amino acid degradation, development and differentiation, infection, penetration, development of appressoria or haustoria, mycelial growth, melanin synthesis, toxin synthesis, siderophore synthesis, sporulation, fruiting body synthesis, cell division, energy metabolism, respiration, and apoptosis, among others.

According to a specific embodiment, the phytopathogenic organism is selected from the group consisting of a fungus, a nematode, a virus, a bacteria and an insect.

To substantiate the anti-pest activity, the present teachings also contemplate observing death or growth inhibition and the degree of host symptomotology following said providing.

To improve the anti-phytopathogen activity, embodiments of the present invention further provide a composition that contains two or more different agents each toxic to the same plant pathogenic microorganism, at least one of which comprises a dsRNA described herein. In certain embodiments, the second agent can be an agent selected from the group consisting of inhibitors of metabolic enzymes involved in amino acid or carbohydrate synthesis; inhibitors of cell division; cell wall synthesis inhibitors; inhibitors of DNA or RNA synthesis, gyrase inhibitors, tubulin assembly inhibitors, inhibitors of ATP synthesis; oxidative phosphorylation uncouplers; inhibitors of protein synthesis; MAP kinase inhibitors; lipid synthesis or oxidation inhibitors; sterol synthesis inhibitors; and melanin synthesis inhibitors.

In some embodiments, a seed comprising an exogenous dsRNA as described herein is treated with a non-polynucleotide pesticide. It is believed that the combination of a plant exhibiting bioactivity against a target pest as a result of treating the seed from which the plant is grown with an exogenous dsRNA coupled with treatment of the seed with certain chemical or protein pesticides provides unexpected synergistic advantages to seeds having such treatment, including unexpectedly superior efficacy for protection against damage to the resulting plant by the target pest. The seeds of the present embodiments are believed to have the property of decreasing the cost of pesticide use, because less of the pesticide can be used to obtain a required amount of protection than if the innovative composition and method is not used. Moreover, because less pesticide is used it is believed that the subject method is therefore safer to the operator and to the environment, and is potentially less expensive than conventional methods.

When it is said that some effects are "synergistic," it is meant to include the synergistic effects of the combination on the pesticidal activity (or efficacy) of the combination of the bioactivity of a plant grown from a dsRNA treated seed and the pesticide. However, it is not intended that such synergistic effects be limited to the pesticidal activity, but that they should also include such unexpected advantages as increased scope of activity, advantageous activity profile as related to type and amount of damage reduction, decreased cost of pesticide and application, decreased pesticide distribution in the environment, decreased pesticide exposure of personnel who produce, handle and plant seeds, and other advantages known to those skilled in the art.

In addition, plants generated according to the teachings of the present embodiments or parts thereof can exhibit altered nutritional or therapeutic efficacy and as such can be employed in the food or feed and drug industries. Likewise, the plants generated according to the teachings of the present embodiments or parts thereof can exhibit altered oil or cellulose content and as such can be implemented in the construction or oil industry.

The seeds of the present invention can be packed in a seed containing device which comprises a plurality of seeds at least some of which (e.g., 5%, 10% or more) containing an exogenous naked dsRNA, wherein the seed is devoid of a heterologous promoter for driving expression of the dsRNA.

The seed containing device can be a bag, a plastic bag, a paper bag, a soft shell container or a hard shell container.

Several embodiments described herein relate to a solution for treating seeds comprising a non-transcribable polynucleotide trigger, for example dsRNA, molecule comprising a sequence that is essentially complementary or essentially identical to at least 18 contiguous nucleotides of a target gene. In some embodiments, the solution may further comprise buffer, for example, EDTA. As used herein "solution" refers to homogeneous mixtures and non-homogeneous mixtures such as suspensions, colloids, micelles, and emulsions. In some embodiments, the solution may be provided in a kit. In some embodiments, the kit may further comprises one or more of seeds, containers, priming solution, and seed growth medium.

Reagents of the present invention can be packed in a kit including the non-transcribable polynucleotide trigger, for example dsRNA, molecule, instructions for introducing the non-transcribable polynucleotide trigger, for example dsRNA, molecule into the seeds and optionally a priming solution.

Compositions of some embodiments of the invention may, if desired, be presented in a pack or dispenser device, which may contain one or more dosage forms containing the active ingredient. The pack may, for example, comprise metal or plastic foil, such as a blister pack. The pack or dispenser device may be accompanied by instructions for introduction to the seed.

According to one embodiment, the non-transcribable polynucleotide trigger, for example dsRNA, molecule and priming solution are comprised in separate containers.

As used herein the term "about" refers to ±10%.

The terms "comprises," "comprising," "includes," "including," "having" and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a," "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the agronomic, chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following Examples. The following Examples are presented for the purposes of illustration and should not be construed as limitations.

EXAMPLES

Reference is now made to the following Examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y.

(1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1: Protocols for dsRNA Production and Seed Treatment

Generating the dsRNA/siRNA Sequences

The dsRNA sequences were custom-created for each gene using in vitro transcription of PCR products. Part of the mRNA, including either the ORF, 3' UTR or 5' UTR for which dsRNA to be produced was PCR-amplified using gene-specific primers, which contain the sequence of the T7 promoter on either side. This product was used as a template for dsRNA production using commercial kits such as the MaxiScript dsRNA kit (Life Technologies) or T7 High Yield RNA Synthesis kit (NEB). Next, the sample is treated with DNase Turbo at 37° C. for 15-30 min followed by phenol treatment and nucleic acid precipitation. Next, one of two different reactions is carried out: (1) dsRNA is ready to use, or (2) processing of the dsRNA with Dicer (Shortcut RNase III (NEB)) to create small interfering RNAs (siRNA).

Either dsRNA or a combination of dsRNA and siRNA were used for seed treatments as described below General Seed Treatment Protocol for Gene Silencing Using a dsRNA/siRNA Mixture Uncoated organic corn seeds were from variety "popcorn," uncoated organic whole grain rice seeds, organic soybean and wheat seeds were purchased from Nitsat Haduvdevan (Israel). Fresh tomato seeds were retrieved from M82 tomato fruits, which are propagated in-house. Uncoated or fresh plant seeds were washed with double distilled water (DDW) prior to treatment for four hours. Next, seeds were dried at 30° C. for 10-16 hours. Following the drying step, seeds were treated with a solution containing the dsRNA formulation, which is made of dsRNA at a final concentration of 40-150 μg/ml in 0.1 mM EDTA. Treatment was performed by gently shaking the seeds in the solution for 24 hours in a dark growth chamber at 15° C. Finally, seeds were washed twice briefly and planted on soil or dried for 0-30 hours and germinated at 25° C. in a dark growth chamber and planted in soil or planted directly in soil. Control seeds were treated in a similar way, with a formulation that lacked the dsRNA or with non-specific dsRNA.

Example 2: Stability of the dsRNA in Seedlings of Rice, Tomato and Sorghum

As an example for an exogenous gene that is not present/expressed in plants, the ORFs encoding the replicase and coat protein of CGMMV (accession number AF417242) were used to as targets for dsRNA treatment of plant seeds using the protocol described in Example 1. Rice, tomato and sorghum seeds were washed for 4 hours at 20° C., tomato and sorghum were dried at 30° C. and rice at 20° C. for overnight. Seeds were immediately treated at 15° C. with 132.7 μg/ml dsRNA (final concentration) for 39 hours for rice, 93.8 μg/ml dsRNA (final concentration) for 48 hours for tomato, and 75 μg/ml dsRNA (final concentration) for 40 hours for sorghum.

Briefly, the virus-derived ORFs were amplified by PCR with specifically designed forward and reverse primers that contain the T7 sequence (5'-TAATACGACTCACTATAGGG-3', SEQ ID NO: 1) at their 5' (see Table 1, below). PCR products were purified from agarose gel and since they carry T7 promoters at both ends they were used as templates for T7-dependent in-vitro transcription, resulting in dsRNA product of the CGMMV genes. PCR on a housekeeping gene, tubulin, was used as a positive control (forward primer 5'-GGTGCTCTGAACGTGGATG-3' (SEQ ID NO: 2), and reverse primer 5'-CATCATCGCCATCCTCATTCTC-3'(SEQ ID NO: 3)).

TABLE 1

PCR primers served as Templates for in vitro Transcription and detection of CGMMV and CGMMV dsRNA products.

| Virus Name | Product Name | Product Sequence/SEQ ID NO: | Forward primer/ SEQ ID NO: | Reverse primer/ SEQ ID NO: |
|---|---|---|---|---|
| 1) CGMMV (NCBI Accession number AF417242) | CGMVV dsRNA product 1 | TAATACGACTCACTATAGGGGGTAAGCG GCATTCTAAACCTCCAAATCGGAGGTTG GACTCTGCTTCTGAAGAGTCCAGTTCTGT TTCTTTTGAAGATGGCTTACAATCCGATC ACACCTAGCAAACTTATTGCGTTTAGTG CTTCTTATGTTCCCGTCAGGACTTTACTT AATTTTCTAGTTGCTTCACAAGGTACCGC TTTCCAGACTCAAGCGGGAAGAGATTCT TTCCGCGAGTCCCTGTCTGCGTTACCCTC GTCTGTCGTAGATATTAATTCTAGATTCC CAGATGCGGGTTTTTACGCTTTCCTCAAC | TAATACGACT CACTATAGGG GGTAAGCGGC ATTCTAAACC/ (SEQ ID NO: 5) CTTCTTATGTT CCCGTCAGG/ (SEQ ID NO: 7) | Set 1: TAATACGACTCA CTATAGGGGAAG ACCCTCGAAACT AAGC/ (SEQ ID NO: 4) Set 2: ACTCAGCAGTCG TAGGATTG/ (SEQ ID NO: 6) |

TABLE 1 -continued

PCR primers served as Templates for in vitro Transcription and detection of CGMMV and CGMMV dsRNA products.

| Virus Name | Product Name | Product Sequence/SEQ ID NO: | Forward primer/ SEQ ID NO: | Reverse primer/ SEQ ID NO: |
|---|---|---|---|---|
| | | GGTCCTGTGTTGAGGCCTATCTTCGTTTC GCTTCTCAGCTCCACGGATACGCGTAAT AGGGTCATTGAGGTTGTAGATCCTAGCA ATCCTACGACTGCTGAGTCGCTTAACGC CGTAAAGCGTACTGATGACGCGTCTACG GCCGCTAGGGCTGAGATAGATAATTTAA TAGAGTCTATTTCTAAGGGTTTTGATGTT TACGATAGGGCTTCATTTGAAGCCGCGT TTTCGGTAGTCTGGTCAGAGGCTACCAC CTCGAAAGCTTAGTTTCGAGGGTCTTCC CCTATAGTGAGTCGTATTA/(SEQ ID NO: 8) | | |
| | CGMVV dsRNA product 2 | TAATACGACTCACTATAGGGGCTTTACC GCCACTAAGAACTCTGTACACTCCCTTG CGGGTGGTCTGAGGCTTCTTGAATTGGA ATATATGATGATGCAAGTGCCCTACGGC TCACCTTGTTATGACATCGGCGGTAACT ATACGCAGCACTTGTTCAAAGGTAGATC ATATGTGCATTGCTGCAATCCGTGCCTA GATCTTAAAGATGTTGCGAGGAATGTGA TGTACAACGATATGATCACGCAACATGT ACAGAGGCACAAGGGATCTGGCGGGTG CAGACCTCTTCCAACTTTCCAGATAGAT GCATTCAGGAGGTACGATAGTTCTCCCT GTGCGGTCACCTGTTCAGACGTTTTCCA AGAGTGTTCCTATGATTTTGGGAGTGGT AGGGATAATCATGCAGTCTCGTTGCATT CAATCTACGATATCCCTTATTCTTCGATC GGACCTGCTCTTCATAGGAAAAATGTGC GAGTTTGTTATGCAGCCTTTCATTTCTCG GAGGCATTGCTTTTAGGTTCGCCTGTAG GTAATTTAAATAGTATTGGGGCTCAGTT TAGGGTCGATGGTGATGCCCTATAGTGA GTCGTATTA/(SEQ ID NO:11) | TAATACGACT CACTATAGGG GCTTTACCGC CACTAAGAAC/ (SEQ ID NO: 10) | Set 3: TAATACGACTCA CTATAGGGCATC ACCATCGACCCT AAAC/ (SEQ ID NO: 9) | dsRNA homologous to green mottle mosaic virus is stable in rice seedlings. Rice seeds were treated at 15° C. with 132.7 µg/ml dsRNA (final concentration) for 39 hours and dsRNA was detected. At one week post germination, dsRNA was detectable in 9 out of 10 seedlings. Detection of tubulin cDNA served as a positive control for the cDNA quality. At two weeks post germination, dsRNA is detectable in 10 out of 10 seedlings. At 3 weeks post germination, dsRNA homologous to green mottle mosaic virus is detected in 5 out of 5 samples in rice seedlings Tomato seeds were treated at 15° C. with 93.8 µg/ml dsRNA (final concentration) for 48 hours and sorghum seeds treated at 5 µg/ml dsRNA (final concentration) for 40 hours. CGMMV dsRNA was detected by RT-PCR in 5 out of 13 tomato seedlings tested at 10 day post-germination and 3 out of four sorghum seedlings 4 weeks after germination.

The exogenous dsRNA was found to be stable for at least three weeks in rice seedlings and at least 10 days in tomato seedlings and four weeks in *Sorghum* plants.

Example 3: The dsRNA is not Integrated into the Genome of Rice

Rice seeds were treated with an exogenous dsRNA as in Example 2. Plants were germinated and grown for five weeks, DNA was extracted and PCR reactions were performed to demonstrate that the dsRNA did not integrate into the rice's genome. Two sets of primers that gave a positive reaction when checked on the RNA level were used, set 1 (see Table 2) of primers were the set of primers used to amplify the template (all the dsRNA sequence). Set 2 (see Table 3) are the primers that were used in the PCR above. A rice endogenous housekeeping gene (tubulin) was used as a positive control for the PCR reaction (see Table 2).

Three different DNA PCR reactions were carried out on dsRNA treated and untreated plants. No amplified DNA corresponding to CGMMV was detected in any treated or untreated plant.

TABLE 2

Tubulin Primers Used for PCR Amplification.

| Primer Name and Direction | Primer Sequence/ (SEQ ID NO:) | Primer Length |
|---|---|---|
| osa_TubA1_736F | GGTGCTCTGAACGTGGATG (SEQ ID NO: 12) | 19 |
| osa_TubA1_1342R | CATCATCGCCATCCTCATTCTC (SEQ ID NO: 13) | 22 |

Example 4: Exogenous dsRNA Molecules are Highly Stable in Solution and do not Get Incorporated into the Genome of Treated Plants Corn seeds were treated using the protocol described in Example 1, seeds were washed for 4 h at 20° C., dried at 30° C. overnight and immediately treated with 40 µg/ml dsRNA (final concentration) directed against the β-glucuronidase (GUS) reporter gene for 60 hours at 15° C., dried and were germinated. Leaves and roots were harvested from control and dsGUS-treated plants 7 and 15 days following germination. RNA was extracted from the harvested tissues and RT-PCR with specific GUS primers was run (Table 3). In addition, a corn endogenous housekeeping gene (ubiquitin) was used as a positive control for the PCR reaction. The GUS dsRNA molecules were found to be extremely stable in the treated seeds, and can be detected in corn plants 7 and 15 days post germination of the seeds.

GUS dsRNA can is detected in corn seedlings by RT-PCR at 7 and 15 days after germination according to an aspect of the present disclosure. At one week, GUS dsRNA is detected in shoots of nine of eleven corn seedlings tested. GUS dsRNA is not detected in untreated plants. At 1 week post-germination, GUS dsRNA is detected in five of five treated corn seedlings' roots 1 week post germination. At 15 days post germination, GUS dsRNA is detected in corn seedlings' roots.

GUS dsRNA molecules do not get incorporated in the genome of treated corn plants one week after germination as determined by agarose gel electrophoresis of DNA PCR reactions on GUS sequence.

seeds). To eliminate the possibility of non-specific autofluorescence, dsRNA-treated seeds are compared to control untreated seeds. Penetration of fluorescent siRNA molecules into plant seeds was observed at 24 hours after seed treatment with siRNA at 2 µM final concentration in *Arabidopsis* seeds, rice seeds, and tomato seeds.

Penetration of fluorescent siRNA molecules into rice seeds was observed at 24 hours following treatment with siGLO dsRNA.

In order to evaluate the distribution efficiency of the fluorescent siRNA inside the seeds, different plant seeds were cut into slices and imaged with a fluorescent microscope 48 hours after treatment. Each treated seed was imaged alongside a control untreated seed. Light and fluorescent images were taken where applicable for rice, tomato, cucumber, bean, sorghum and wheat seed samples.

Penetration of fluorescent siRNA molecules into rice seeds was observed at 48 hours following treatment with siGLO dsRNA. siGLO-treated and control rice seeds were sliced to view the interior distribution of the fluorescent dsRNA using a fluorescent microscope and fluorescent

TABLE 3

Primers for PCR Amplification of GUS and Ubiquitin Genes and GUS dsRNA product.

| Primer Length | Primer Sequence/SEQ ID NO: | Primer Name |
|---|---|---|
| GUS_T7_For | TAATACGACTCACTATAGGGAGATCGACGGCCTGTGGGCATTC/ (SEQ ID NO: 15) | |
| GUS_T7_Rev | TAATACGACTCACTATAGGGAGCATTCCCGGCGGGATAGTCTG/ (SEQ ID NO: 16) | 43 |
| GUS208For | CAGCGCGAAGTCTTTATACC/(SEQ ID NO: 17) | 43 |
| GUS289Rev | CTTTGCCGTAATGAGTGACC/(SEQ ID NO: 18) | 20 |
| zmaUBQ-947F | CCATAACCCTGGAGGTTGAG/(SEQ ID NO: 19) | 20 |
| zmaUBQ1043R | ATCAGACGCTGCTGGTCTGG/(SEQ ID NO: 20) | 20 |
| GUS dsRNA product | TAATACGACTCACTATAGGGAGATCGACGGCCTGTGGGCATTC AGTCTGGATCGCGAAAACTGTGGAATTGATCAGCGTTGGTGG GAAAGCGCGTTACAAGAAAGCGGGCTATTGCTGTGCCAGGC AGTTTTAACGATCAGTTCGCCGATGCAGATATTCGTAATTATG CGGGCAACGTCTGGTATCAGCGCGAAGTCTTTATACCGAAAG GTTGGGCAGGCCAGCGTATCGTGCTGCGTTTCGATGCGGTCAC TCATTACGGCAAAGTGTGGGTCAATAATCAGGAAGTGATGGA GCATCAGGGCGGCTATACGCCATTTGAAGCCGATGTCACGCC GTATGTTATTGCCGGGAAAAGTGTACGTATCACCGTTTGTGTG AACAACGAACTGAACTGGCAGACTATCCCGCCGGGAATGCTC CCTATAGTGAGTCGTATTA/(SEQ ID NO: 21) | |

Example 5: Fluorescence Microscopy of siRNA Sequences in Various Plant Seeds

Plant seeds as per the protocol described in Example 1. Seeds were washed for 4 h at 20° C., dried at 25° C. and were immediately treated with a fluorescent siRNA (siGLO, 2 µM final concentration, Thermo Scientific) at 15° C. for 24 h. The quality of the siGLO before application to a plant seed was verified by gel electrophoresis analysis Bands c corresponding to the expected size of 20-24 bp of the fluorescent siRNA molecules was detected.

Fluorescent pictures of the seeds were taken 24-48 hours post treatment using an Olympus microscope at the lowest objective magnification (5× for bigger seeds such as rice and tomato seeds, and 10× for smaller seeds such as *Arabidopsis* siRNA molecules detected in the treated seed. Fluorescent siGLO RNA is detected in the endosperm and the embryo.

Penetration of fluorescent siRNA molecules into tomato seeds was observed at 48 hours following treatment with siGLO dsRNA. siGLO-treated and control tomato seeds were sliced to view the interior distribution of the fluorescent dsRNA using a fluorescent microscope. Fluorescent siGLO RNA is detected in the endosperm and the embryo.

Penetration of fluorescent siRNA molecules into cucumber seeds was observed at 48 hours following treatment with siGLO dsRNA. siGLO-treated and control cucumber seeds were sliced to view the interior distribution of the florescent dsRNA using a fluorescent microscope. Fluorescent siGLO RNA is detected in the endosperm and the embryo.

Penetration of fluorescent siRNA molecules is detected in sliced seeds of various plant species, including bean, tomato, sorghum and wheat, 48 hours following treatment with siGLO dsRNA. siGLO-treated and control seeds were sliced to view the interior distribution of the fluorescent dsRNA using a fluorescent microscope. Light images were also taken for each seed and are shown alongside the fluorescent image of the seed for reference.

FIG. 1 presents fluorescent images of siGLO-treatment of rice seeds over a 24 hour period. The effect of incubation time with siGLO dsRNA on fluorescence intensity, indicating quantity and quality of dsRNA penetration, was tested. Control seeds that were left untreated (1), were imaged along with seeds treated with siGLO dsRNA for four different incubation times; 10 min (2), 3.5 hours (3), 5.5 hours (4), and 24 hours (5).

It is clear that the siRNA is distributed at various levels between the embryo and the endosperm. Accordingly, dsRNA molecules enter the embryo directly. Though not to be limited by any particular theory, the dsRNA molecules are carried by the water-based solution used for the seed treatment. The dsRNA molecules enter the endosperm as part of the endosperm's water-absorption process. These molecules then are transferred to the embryo as it develops as part of the endosperm to embryo nutrient flow during germination and seed development.

These present findings suggest the RNA molecules used to treat the seeds both penetrate the embryo and function in the embryo as it develops and also penetrate the endosperm and feed the embryo following germination.

Example 6: Time Course Experiment with siGLO Treatment

A time course experiment was performed on rice seeds to monitor the kinetics of siGLO penetration into the seeds following the seed treatment (FIG. 1). The results indicate that the siRNA efficiently penetrates the plant seeds using the protocol described in Example 1.

Example 7: Seed Treatment Against *Spodoptera littoralis* Genes

*Spodoptera littoralis* (or *Prodenia littoralis*), also known as the African Cotton Leafworm or Egyptian Cotton Leafworm is a moth found widely in Africa and Mediterranean Europe. It is a common pest on vegetables, fruits, flowers and other crops.

RNA was extracted for dsRNA production from *Spodoptera littoralis* larvae, and a cDNA library was prepared from 0.5 μg total RNA. Several genes (ATPase, NADPH Cytochrome P450 oxidoreductase (herein referred to as NADPH), inhibitor of apoptosis (IAP) and Chitin Synthase) were selected to test the effect of feeding *S. littoralis* with plants grown from seeds treated with dsRNA directed against these genes (see Table 4). Corn seeds were washed for 4 h, dried at 30° C. and immediately were treated with dsRNA molecules at a final concentration of 40 μg/ml (for IAP and ATPase), 80 μg/ml (for NADPH, 40 μg/ml for each dsRNA sequence, see Table 4), or a mix solution (80 μg/ml final) containing all three genes (20 μg/ml for each of the four dsRNA sequences), for 24 hours. Fresh tomato seeds were not washed and immediately treated with dsRNA molecules at a final concentration of 66 μg/ml (for IAP), 133 μg/ml (for NADPH), or a mix solution (80 μg/ml final) containing dsRNA targeting these two genes, for 48 hours. Treated seeds were germinated and grown into plants. Control seeds which were not treated with dsRNA directed against *S. littoralis* genes but were incubated with a similar solution, either not containing dsRNA or containing dsRNA directed against an unrelated gene, such as GUS, were germinated and grown alongside the treated plants. The leaves of treated and control plants were placed in petri dishes and used as sole food source for *S. littoralis* (typically, about 5 caterpillars per plate). Total body weight of the caterpillars was recorded at the beginning of each experiment, and was tracked throughout. New leaves were supplemented as needed and their weight was recorded as well. Body weight gain of the caterpillars was calculated and used as an indicator to their well-being and survivability.

TABLE 4

Sequences of *Spodoptera littoralis* Genes for Down regulation and Primers used for dsRNA Molecules Generation.

| Gene Name | Organism | SEQ ID NO |
|---|---|---|
| NADPH | *Spodoptera littoralis* NADPH cytochrome P450 oxidoreductase mRNA, complete cds (JX310073.1) | 21 |
| ATPase | *Spodoptera littoralis* H(+)-ATPase B subunit mRNA, partial cds (AY169409.1) | 22 |
| IAP | *Spodoptera littoralis* mRNA for inhibitor of apoptosis (iap gene) (AM709785.1) | 23 |
| Chitin synthase | *Spodoptera exigua* chitin synthase A mRNA, complete cds (DQ062153) | 24 |
| NADPH dsRNA#1 | *Spodoptera littoralis* | 25 |
| NADPH dsRNA#2 | *Spodoptera littoralis* | 26 |
| NADPH dsRNA#1 frwd | *Spodoptera littoralis* | 27 |
| NADPH dsRNA#1 rev | *Spodoptera littoralis* | 28 |
| NADPH dsRNA#2 frwd | *Spodoptera littoralis* | 29 |
| NADPH dsRNA#2 rev | *Spodoptera littoralis* | 30 |
| ATPase dsRNA#1 | *Spodoptera littoralis* | 31 |
| ATPase dsRNA#1 frwd | *Spodoptera littoralis* | 32 |
| ATPase dsRNA#1 rev | *Spodoptera littoralis* | 33 |
| IAP dsRNA#1 | *Spodoptera littoralis* | 34 |
| IAP dsRNA#1 frwd | *Spodoptera littoralis* | 35 |
| IAP dsRNA#1 rev | *Spodoptera littoralis* | 36 |
| Chitin synthase dsRNA#1 | *Spodoptera exigua* | 37 |
| Chitin synthase dsRNA#2 | *Spodoptera exigua* | 38 |
| Chitin synthase dsRNA#1 frwd | *Spodoptera exigua* | 39 |
| Chitin synthase dsRNA#2 frwd | *Spodoptera exigua* | 40 |
| Chitin synthase dsRNA#2 rev | *Spodoptera exigua* | 41 |
| Chitin synthase dsRNA#1 rev | *Spodoptera exigua* | 42 |

Experiment 1

*Spodoptera littoralis* leafworms were placed in petri dishes with corn leaves from germinated control or dsRNA-treated seeds and were monitored daily for consumption of leaves and for body weight gain. Data for *S. littoralis* body weight gain after 24 hours, 48 hours and 5 days are shown in Table 5 respectively. A negative effect on body weight gain of the worms feeding on any dsRNA-treated leaves compared to worms feeding on control untreated leaves is noted. Body weight gain of *S. littoralis* fed on the control leaves was normalized to a value of '1'.

Experiment 2

In this experiment, dsRNA molecules for silencing of the *S. littoralis* NADPH or IAP genes were used to treat corn seeds. Leaves from seedlings grown from these seeds, as well as control leaves, were used as a food source for 5 *Spodoptera littoralis* leafworms in a single petri dish (two plates for each treatment). Control leaves were treated with dsRNA directed against the GUS gene. Body weight gain was recorded for control and treated groups 48 hours from beginning of the experiment (Table 5). The strongest effect on body weight gain was seen in worms feeding on NADPH-dsRNA treated leaves. Body weight gain of *S. littoralis* fed on the control leaves was normalized to a value of '1'.

Experiment 3

In this experiment, dsRNA molecules for silencing of the *S. littoralis* NADPH or IAP genes were used to treat tomato seeds. An additional treatment was also included, where seeds were treated with a mix solution containing the dsRNA molecules targeted against both genes. Leaves from seedlings grown from these seeds, as well as control leaves, were used as a food source for 5 *Spodoptera littoralis* leafworms in a single petri dish. Body weight gain was recorded for control and treated groups 72 hours after treatment is presented in Table 5. Body weight gain of *S. littoralis* fed on the control leaves was normalized to a value of '1'.

Experiment 4

In this experiment, dsRNA molecules for silencing of the *S. littoralis* NADPH, IAP or ATPase genes were used to treat corn seeds. An additional treatment was also included, where seeds were treated with a mix solution containing the dsRNA molecules targeted against all three genes. Leaves from seedlings grown from these seeds, as well as control leaves, were used as a food source for 5 *Spodoptera littoralis* leafworms in a single petri dish. On day 4, the treated corn leaves were replaced with untreated lettuce leaves as the only food source. Body weight gain was recorded for control and treated groups for up to 8 days. The body weight of all worms at 24 hours was used as a reference point and body weight gain of *S. littoralis* fed on the control leaves was normalized to a value of '1'. Data of relative body weight gain of worms feeding on control or treated corn leaves is presented in Table 5.

TABLE 5

*Spodoptera littoralis* body weight gain after twenty four hours on dsRNA treated leaves

| Expt. | Time | control | NADPH | IAP | Mix | ATPase | gus |
|---|---|---|---|---|---|---|---|
|  | 24 hours | 1.0 | 0.64 | 0.38 | n/a | 0.8 | n/a |
| 1 | 48 hours | 1.0 | 0.69 | 0.57 | n/a | 0.7 | n/a |
| 1 | 5 days | 1.0 | 0.36 | 0.84 | na/ | 0.94 | n/a |
| 2 | 48 hours | 1.0 | 0.55 | 0.9 |  |  | 1.0 |
| 3 | 48 hours | 1 | 0.55 | 0.9 |  |  |  |
| 3 | 72 hours | 1 | 0.95 | 0.91 | 0.90 |  |  |
| 4 | 5 days[1] | 1.0 | 0.76 | 0.73 | 0.99 | 1.11 |  |
| 4 | 7 days[2] | 1.0 | 0.88 | 0.87 | 0.89 | 0.91 |  |
| 4 | 8 days[3] | 1.0 | 0.9 | 0.78 | 0.97 | 1.12 |  |

[1] four days of treated corn and 1 day of lettuce;
[2] four days of treated corn and 3 days of lettuce;
[3] four days of treated corn and 4 days of lettuce Example 8: Silencing the PDS-1 Gene in Rice by a dsRNA/siRNA Mixture Rice seeds were washed in wash solution for 4 h at 20° C., dried at 25° C. and immediately treated with a mixture of dsRNA/siRNA at a total concentration of 5 µg/ml at 15° C. Seeds were germinated at room temperature for several days and seed development was monitored. Seeds treated with the PDS and dsRNA/siRNA mixture exhibited stunted and delayed development, as seen by smaller seedlings and reduced rooting. For efficiency considerations and in order to increase the likelihood of an observed effect, two products of the PDS-1 gene are combined (see Table 6).

TABLE 6

Two PDS-1 Gene Products to be Silenced by dsRNA/siRNA Mixture.

| Sequence name | Organism | NCBI Accession Number | SEQ ID NO |
|---|---|---|---|
| Phytoene Desaturase PDS1 dsRNA1 | *Zea mays* | BT084155.1 | 43 |
| Phytoene desaturase PDS1 dsRNA2 | *Zea mays* | BT084155.1 | 44 |

Figure 2A:
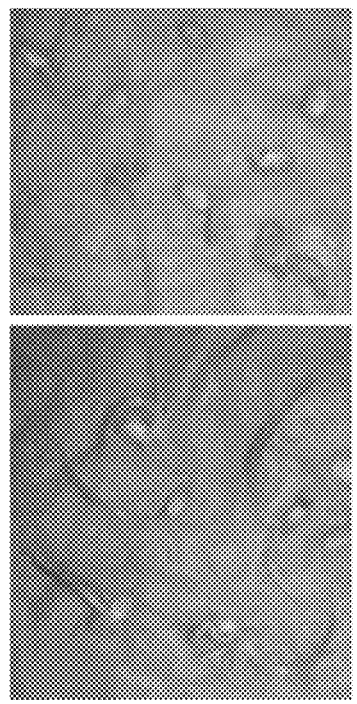

The experiment was performed in three biological repeats and the results are presented in FIGS. 2A-B.

Example 9: Chlorophyll Bleaching and Growth Inhibition Following PDS Silencing

Rice seeds were treated as described in Example 8 and their subsequent development and seedling growth were monitored. Thirty days post PDS-1 silencing treatment the overall phenotype of the two plant groups, control and PDS-silenced, was recorded. PDS silencing has been reported to cause chlorophyll bleaching and growth inhibition (Peretz et al., 2007, Plant Physiol 145: 1251-1263), which correlates with the phenotype of the PDS-silenced plants of the invention. Treated rice plants after thirty days appeared smaller in size and paler in color, respectively, compared to control plants.

Example 10: Detection of the Two PDS-1 Gene Products by Real-Time PCR

Following treatment with the dsRNA/siRNA mixture (ratio 1:1) as described in Example 8, expression levels of PDS-1 gene products are determined by real-time PCR using specifically designed primers:

```
                                    SEQ ID NO: 45
    Forward: GATTGCTGGAGCAGGATTAG;

SEQ ID NO: 46
    Reverse: CCCTTGCCTCAAGCAATATG,.
```

For normalization purposes, UBQ5 expression was also determined using primers:

```
                                    SEQ ID NO: 47
    forward-ACCACTTCGACCGCCACTACT,;

SEQ ID NO: 48
    reverse-ACGCCTAAGCCTGCTGGTT,.
```

Figure 3A:
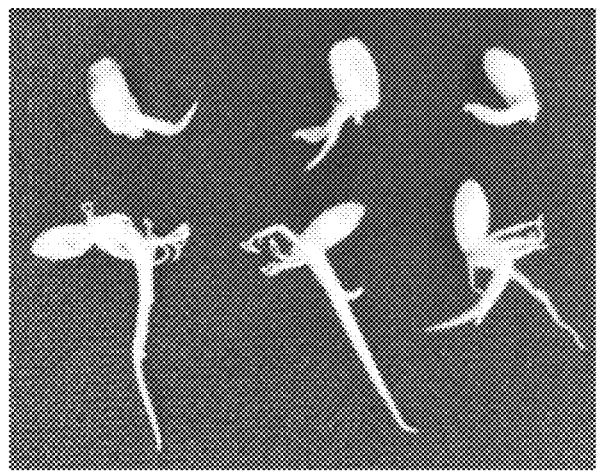
FIGS. 3A-C show PDS-1 expression levels as determined by Real-Time PCR.
Figure 3B:
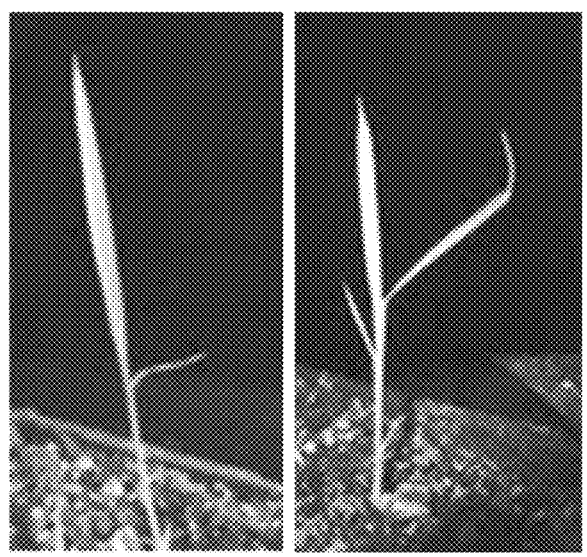
Figure 3C:
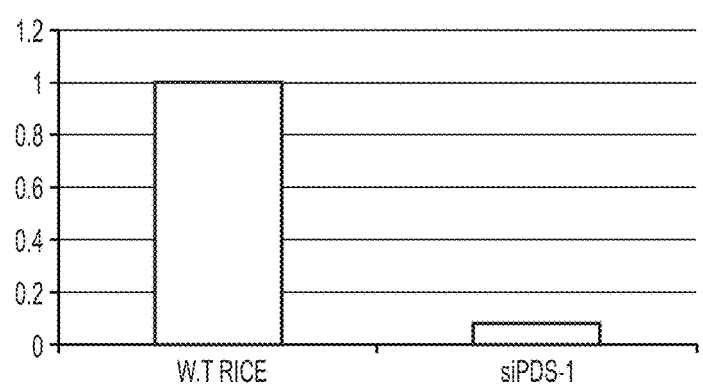

The results are shown in FIGS. 3A-C.

Example 11: HAP2E Target Gene Silencing

Rice seeds were treated using the protocol described in Example 1. Seeds were washed for 4 h at room temperature, dried overnight at 25° C. and immediately treated with a Hap2e dsRNA concentration of 152 µg/ml, for 41 hours at 15° C. (for Hap2e dsRNA sequences see Table 7). Control and Hap2e dsRNA-treated rice seeds that were germinated 5 days post treatment did not exhibit any differences in their root development. RNA was extracted from shoots of germinated seeds, 5 and 7 days post germination, and RT-PCR was run. After testing 3 different sets of primers (see Table 7), located in various regions of the dsRNA molecules (Table 8, showing the fold change relative to the control), the best primer set (primer set 3) was used to evaluate the endogenous Hap2e expression levels in dsRNA-treated plants versus control (untreated) plants. Down-regulation of Hap2e mRNA expression in the treated plants, at a level of over 50% silencing compared to control plants, was achieved with an efficiency of 31.25% (Table 9).

Other rice seeds were treated in same conditions with a Hap2e dsRNA concentration of 145.7 μg/ml, for 42 hours. RT-PCR using random primers+Oligo dT on RNA extracted from seedlings 18 days post germination also exhibited down-regulation of Hap2e mRNA in dsRNA-treated plants (Table 10), with 50% efficiency of reaching down-regulation of over 25% compared to control.

TABLE 7

Primers used for RT-PCR of Hap2e dsRNA Molecules.

| Primer Set | Primer Set Location | Primer Name and Direction | Primer Sequence | SEQ ID No.: |
|---|---|---|---|---|
| 1 | In dsRNA | osaHAP2E501F3 | ACCGGCATCAGCTCAGTCTC | 49 |
|   |   | osaHAP2E589R3 | TGCTGTTCTCTGGGCACAGG | 50 |
| 2 | Junction | osaHAP2E11F5 | TCCCCTCAGATATTAACAAC | 51 |
|   |   | osaHAP2E108R5 | AGGAGGAAAGGCAGCTTCTGTG | 52 |
| 3 | Out of dsRNA | osaHAP2E122F7 | GTGACTCGTCACCAACAAAG | 53 |
|   |   | osaHAP2E202R7 | TGTGTTGTCCGTTGAGACTG | 54 |

TABLE 8

Treatment of Rice seeds with Hap2e dsRNA (target of mir 169) Primer evaluation.

|  | control | EM47766 | EM47767 | EM47769 | EM47772 | EM47773 |
|---|---|---|---|---|---|---|
| Primer set 1 | 1.0 | 0.87 | 0.7 | — | 0.81 | 0.62 |
| Primer set 2 | 1.0 | 0.99 | 0.82 | — | 0.89 | 0.44 |
| Primer set 3 | 1.0 | 0.76 | 0.73 | — | 0.78 | 0.4 |

Fold change relative to untreated control (control = 1.0)

TABLE 9

Treatment of Rice seeds with Hap2e dsRNA (target of mir 169) at 7 days.

|  | control | EM47796 | EM47798 | EM47799 | EM47803 | EM47804 | EM47769 |
|---|---|---|---|---|---|---|---|
| Relative Fold change | 1.0 | 0.41 | 0.77 | 0.52 | 0.47 | 0.83 | 0.0 |

Fold change relative to untreated control (control = 1.0)

TABLE 10

Treatment of Rice seeds with Hap2e dsRNA (target of mir 169) at 18 days.

| control | EM 49050 | EM 49051 | EM 49052 | EM 49053 | EM 49054 | EM 49056 | EM 49047 | EM 49060 | EM 49061 | EM 49063 | EM 49064 |
|---|---|---|---|---|---|---|---|---|---|---|---|
| 1.0 | 0.33 | 0.41 | 0.93 | 0.54 | 0.65 | 0.54 | 0.73 | 0.73 | 0.90 | 0.64 | 0.96 |

Fold change relative to untreated control (control = 1.0)

Example 12: NFY Target Gene Silencing in Corn Seeds

Corn seeds were treated using the protocol described in Example 1, Seeds were washed for 4 h at room temperature, dried overnight at 30° C. and immediately treated with a NFY dsRNA concentration of 56 μg/ml, for 40 hours at 15° C. (for NFY dsRNA sequence see Table 11). RT-PCR on RNA extracted from control and NFY dsRNA-treated corn seeds 10 days after germination was performed to determine the expression level of NFY target gene (see Table 11). Down-regulation of the gene was successfully achieved as exhibited in Table 12.

TABLE 11

Primers used for RT-PCR of NFYA dsRNA Molecules in Corn Seeds 310 Days after Germination.

| Primer Name and Direction | Primer Sequence | SEQ ID No.: |
|---|---|---|
| zma-NFYA3_345 F3 | TCGGAAGCCGTACCTTCGTG | 55 |
| zma-NFYA3_442R3 | CCTGGAGCTGCTGCTTTGTG | 56 |
| zma-NFYA3_457F4 | TACCAGGCGTCGAGTGGTTC | 57 |
| zma-NFY-A3_542R4 | GAAGAGGGCGTGCAAATGGG | 58 |

TABLE 12

Treatment of corn seeds with NFY dsRNA (target of mir169).

| control | EM 48006 | EM 48007 | EM 48009 | EM 48010 | EM 48011 | EM 48012 | EM 48013 | EM 48014 |
|---|---|---|---|---|---|---|---|---|
| 1.0 | 0.51 | 0.62 | 0.67 | 0.33 | 0.50 | 0.76 | 0.85 | 0.11 |

Fold change relative to untreated control (control = 1.0)

Example 10: NFY Target Gene Silencing in Tomato Seeds

Tomato seeds were treated using the protocol described in Example 1. Un washed seeds were treated with a NFY dsRNA concentration of 200 μg/ml, for 24 hours at 15° C., seeds were washed twice briefly and immediately planted in soil without drying. RT-PCR on RNA extracted from control and NFY dsRNA-treated tomato seeds 3 weeks after germination was performed to determine the expression level of NFY target gene (see Table 13). Down-regulation of the gene was successfully achieved as exhibited in Table 14.

Figure 4A:
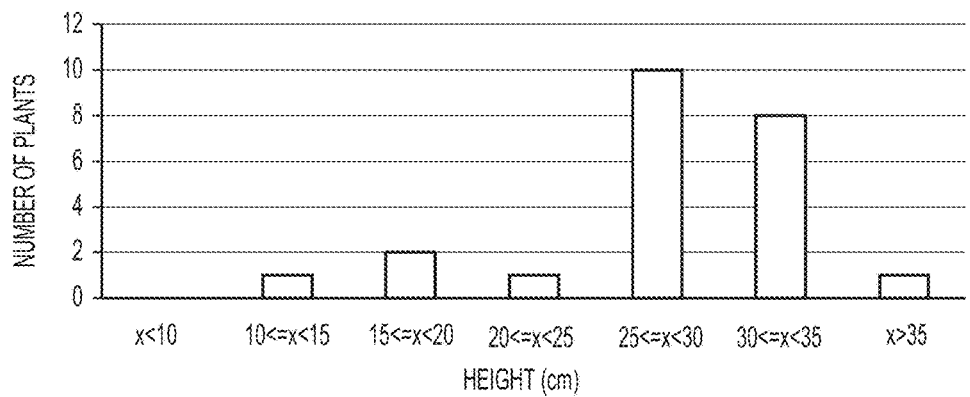
FIGS. 4A-B show height distribution of control and NFY dsRNA-treated tomato plants 55 days post inoculation.
Figure 4B:
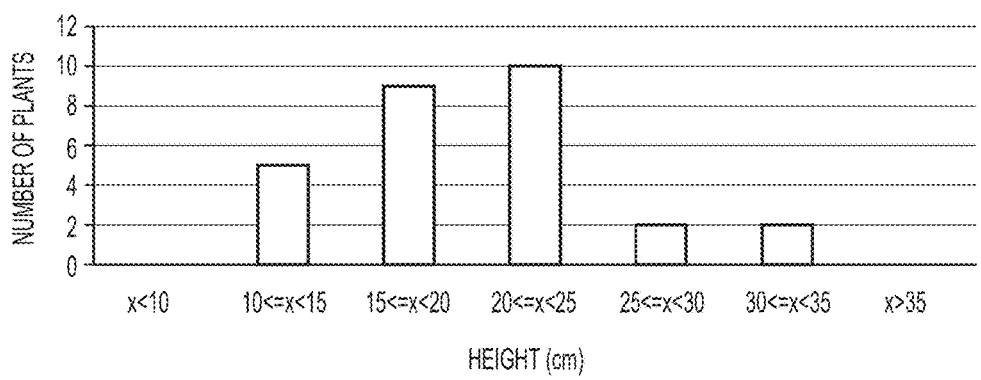

Tomato plants 55 days post treatment with NFY dsRNA molecules were compared to same age control plants. Major phenotypic differences were evident upon comparison, most notably was a shift in height, where treated plants appeared significantly shorter than untreated control plants (FIG. 4).

TABLE 13

Primers used for RT-PCR of NFYA dsRNA Molecules in Tomato and NFY dsRNA product.

| Sequence Name | Sequence | SEQ ID No.: |
|---|---|---|
| slyNFYA125F3 | CTATTGCGTGTGCTCCAAAC | 59 |
| slyNFYA212R3 | ACATGAGGAGGAACCAAAGG | 60 |
| NFY dsRNA product 1 | CTAATACGACTCACTATAGGGAGAGGCTCAAGAACCAG TTTATGTTAATGCTAAGCAGTATCGAAGGATCCTGCAGC GAAGACAGTCACGTGCTAAAGCAGAACTTGAAAAGAAG CAAATAAAGGGTAGAAAGCCATATCTTCACGAGTCTCG ACATCAGCATGCACTGAGGAGGGTAAGGGCCTCGGGTG GACGTTTTGCCAAAAAGACAGATGCTTCTAAGGGTACT GGTTCTGTGAGTTCATCGGGTTCTGAACCTTTGCAGTTC AATGCTGCTGATATTCAAAAGAGGAATGAAAATGGAAG GTTGGCCGAGCTTCAGCAGTCTTATTCAAATGGTAGCAG TTATGGCAATCAAAGTAGCTTTCAAGAATCCAAGGATG AGTACCAGTTTGCTAAAAGCAGGGAAGGAGGTTTTTTT GTCAAGTAATTGGAGATACGTTCATGTGTAAACTAGCTC TTGCCCTCTCCCTATAGTGAGTCGTATTAG | 61 |
| NFY dsRNA product 2 | CTAATACGACTCACTATAGGGAGAGCAGTTATGGCAAT CAAAGTAGCTTTCAAGAATCCAAGGATGAGTACCAGTT TGCTAAAAGCAGGGAAGGAGGTTTTTTTGTCAAGTAATT GGAGATACGTTCATGTGTAAACTAGCTCTTGCCCTGCAA CGAGGGTAGAGTATGAGCAAGAGGAGTTTACAGGGATT GTTTCATTTCTTGGCTTTTCAAGATAGGCGGCAATTCAT TCTTGGCTTTTTACTTTAGTGTTAAAGGGAGCAACAGAG GTGACGAGGGTATCAGTGTTGCAGCATTTGCTTGGAGAT TACATCTTCCCTTATGTACAGAGATGGATGAACTTAGAA CTAGGATTAGAAAGTTTTTCAGTAAGTTTATGTTTGGCC AGTTACTGTAGTTTTAGTTTAGGAGACCATGTAAAAAGG TTGTTAGTTTTGCAAAAGGATCTTTTTTCTTTCCCTAATT GGTGCATTCTCCCTATAGTGAGTCGTATTAG | 62 |

TABLE 14

Treatment of Tomato seeds with NFY dsRNA (target of mir169) at 3 weeks.

| Plant | EM 49778 | EM 49812 | EM 49816 | EM 49818 | EM 49819 | EM 49826 | EM 49827 | EM 49829 |
|---|---|---|---|---|---|---|---|---|
| Relative fold change | 1.0 | 0.8 | 0.9 | 0.5 | 0.6 | 0.9 | 0.8 | 0.6 |
| Plant | EM 49832 | EM 49833 | EM 49834 | EM 49835 | EM 49836 | EM 49837 | EM 49838 | EM 49839 |
| Relative fold change | 0.7 | 0.8 | 0.9 | 0.5 | 0.9 | 0.5 | 0.5 | 0.8 |

Fold change relative to untreated control (control = 1.0)

Example 11: NAC Target Gene Silencing in Corn Seeds

Corn seeds were treated using the protocol described in Example 1, seeds were washed for 4 h at room temperature, dried overnight at 30° C. and immediately treated with a NAC dsRNA concentration of 90 µg/ml, for 40 hours at 15° C. and immediately germinated (for NAC dsRNA sequence see Table 15). RT-PCR on RNA extracted from control and NAC dsRNA-treated corn seeds 10 days after germination was performed to determine the expression level of NAC target gene (see Table 15). Down-regulation of the gene was successfully achieved as exhibited in Table 16.

TABLE 15

Primers used for RT-PCR of NAC dsRNA Molecules in Corn.

| Primer Name and Direction | Primer Sequence | SEQ ID No.: |
|---|---|---|
| zmaNAC5_267F3 | CGAGTCGGGATACTGGAAGG | 63 |
| zmaNAC5_342R3 | CTTCTTCATGCCGACGAGGG | 64 |
| zmaNAC5_187F4 | ACGATGGGCGAGAAGGAGTG | 65 |
| zmaNAC5_250R4 | TCAGTCCCGTCGGGTACTTG | 66 |

TABLE 16

Treatment of Corn Seeds with NAC dsRNA (target of mir164) at 10 days post germination.

| Plant | Control | 1 | 2 | 3 | 4 | 5 | 6 | 7 |
|---|---|---|---|---|---|---|---|---|
| Relative fold change | 1.0 | 0.22 | 0.14 | 0.22 | 0.20 | 0.43 | 0.16 | 0.55 |
| Plant | 8 | 9 | 10 | 11 | 12 | 13 | 14 | |
| Relative fold change | 0.00 | 0.09 | 0.13 | 0.21 | 0.26 | 0.26 | 0.18 | |

Fold change relative to untreated control (control = 1.0)

Example 12: ARF-8 Target Gene Silencing in Rice Seeds

Rice seeds were treated using the protocol described in Example 1, seeds were washed for 4 h, dried overnight at 20° C. and immediately treated with a ARF-8 dsRNA concentration of 66.2 µg/ml, for 42 hours at 15° C. RT-PCR on RNA extracted from control and ARF-8 dsRNA-treated rice seeds 18 days after germination was performed to determine the expression level of ARF-8 target gene (see Table 17). Down-regulation of the gene was successfully achieved as exhibited in Table 18 and Table 19.

TABLE 17

Primers used for RT-PCR of ARF-8 dsRNA Molecules in Corn and ARF-8 dsRNA product.

| Sequence Name | Sequence | SEQ ID No.: |
|---|---|---|
| osaARF8_140F3 | AGGGTCACATCCCGAACTAC | 67 |
| osaARF8_233R3 | ACCTCGTCAGTCTCCACATC | 68 |
| osaARF8_1674F4 | GTTGGATTCGAGCTTCCTTC | 69 |
| osaARF8_1757R4 | TGCTGCTGCTCACTAGCTAC | 70 |
| ARF8 dsRNA product | CTAATACGACTCACTATAGGGAGACAGTCCGTTGGCCTAGTTCCTATTGGAGATCTGTGAAGGTTGGTTGGGATGAATCAACTGCAGGGGAAAGACCACCAAGAGTTTCTTTATGGGAAATTGAACCATTGACAACCTTTCCAATGTATCCATCTCTGTTCCCACTGAGAGTTAAGCATCCTTGGTATTCAGGAGTTGCTTCCCTGCATGATGACAGCAATGCTTTAATGTGGCTGAGAGGAGTTGCTGGTGAGGGAGGTTTTCAGTCTCTGAACTTTCAGTCACCTGGTATTGGCTCCTGGGGACAACAGAGGCTCCATCCATCCTTACTGAGCAGCGATCACGATCAGTACCAAGCAGTAGTTGCTGCTGCTGCTTCCCAATCTGGTGGTTACTTAAAACAGCAATTCTTGCACCTTCAGCAACCTATGCAGTCCCCTCAAGAACACTGCAACCTCAACCCTCTCCCTATAGTGAGTCGTATTAG | 71 |

TABLE 18

Treatment of Rice Seeds with ARF-8 dsRNA (target of mir167) at 18 days post germination.

| Plant | Control | EM 48977 | EM 48983 | EM 48984 | EM 48986 | EM 48987 | EM 48989 |
|---|---|---|---|---|---|---|---|
| Fold change | 1.0 | 0.67 | 0.28 | 0.86 | 0.74 | 0.59 | 0.47 |

Fold change relative to untreated control (control = 1.0)

TABLE 19

Treatment of Rice Seeds with ARF-8 dsRNA (target of mir167) at 18 days post germination.

| Plant | Control | EM 49194 | EM 49196 | EM 49198 | EM 49200 | EM 49201 | EM 493203 | EM 49204 | EM 49206 | EM 49209 |
|---|---|---|---|---|---|---|---|---|---|---|
| Fold change | 1.0 | 0.44 | 0.88 | 0.45 | 0.22 | 0.26 | 0.12 | 0.06 | 0.31 | 0.92 |

Fold change relative to untreated control (control = 1.0)

Example 13: SPL17 Target Gene Silencing in Rice Seeds

Rice seeds were treated using the protocol described in Example 1, seeds were washed for 4 h, dried overnight at 20° C. and immediately treated with a SPL17 dsRNA concentration of 200 µg/ml, for 41 hours at 15° C. (for SPL17 dsRNA sequence see Table 20). Control and SPL17 dsRNA-treated rice seeds that were germinated 5 days post treatment did not exhibit any visual differences. RNA was extracted from 5 days old shoots of these germinated seeds and RT-PCR was run to determine SPL17 expression levels in control and treated plant groups. Two different sets of primers (see Table 20), located in various regions of the dsRNA molecules, were tested (Table 21). When RT-PCR was run on RNA extracted from 14-week old plants, down-regulation of SPL17 mRNA expression in the treated plants was achieved with high efficiency compared to control plants, (Table 22).

TABLE 20

Primers used for RT-PCR of SPL17 dsRNA Molecules in Rice Seeds 5 Days after Germination.

| Primer Set and Location | Sequence Name | Primer Sequence | SEQ ID No.: |
|---|---|---|---|
| 1-in dsRNA | osaSPL17_119F3 | CTCAGCCATGGGATACTACC | 72 |
|  | osaSPL17_189R3 | GCTGGCCGTTGACGACATTG | 73 |
| 2-out of dsRNA | osaSPL17_55F4 | ACCTCAGGTGGATGTCTC | 74 |
|  | osaSPL17_151R4 | TGCTGGTGCTTTGGGTAG | 75 |

TABLE 21

Treatment of Rice Seeds with SPL17 dsRNA (target of mir156) at 5 days post germination.

| Plant | Control | EM 47708 | EM 47709 | EM 47710 | EM 47711 | EM 47712 |
|---|---|---|---|---|---|---|
| Primer set 1 | 1 | 1.42 | 3.14 | 11.97 | 2.33 | 9.01 |
| Primer set 2 | 1 | .76 | .92 | 1 | .69 | .84 |

Fold change relative to untreated control (control = 1.0)

TABLE 22

Treatment of Rice Seeds with SPL17 dsRNA (target of mir156) at 14 week post germination.

| Plant | Control | EM 49502 | EM 49503 | EM 49511 | EM 49513 | EM 49515 | EM 49517 | EM 49519 |
|---|---|---|---|---|---|---|---|---|
| Fold change | 1.0 | 0.085 | 0.141 | 0.27 | 0.337 | 0.275 | 0.129 | 0.321 |

Fold change relative to untreated control (control = 1.0)

Example 15: Silencing of MicroRNA Target Genes with Complementary dsRNA/siRNA The high specificity and efficiency of posttranscriptional gene silencing by target gene-specific dsRNA has become a preferred method to generate preferred phenotype eukaryotic organisms, wherein expression of one or more genes is reduced or inactivated. Specific dsRNA sequences designed to silence corn (*Zea mays*) and rice (*Oryza sative*) microRNA target genes. Specifically, microRNAs shown to associate with improved abiotic stress tolerance will be used. Table 23 below provides several examples for target gene sequences that are produced using PCR amplification to test the gene silencing capabilities of their respective dsRNA/siRNA mixture. These dsRNA molecules will then be used to knock down the endogenous level of the selected target genes.

TABLE 23

Target Gene Sequences and Primers for PCR.

| Sequence name | Organism | SEQ ID NO |
|---|---|---|
| miR169/NFY-A3 | *Zea mays* | 76 |
| miR169/NFY-A3 frwd | artificial Sequence | 77 |
| miR169/NFY-A3 rev | artificial Sequence | 78 |
| miR169/NFY-A3 frwd | artificial Sequence | 79 |
| miR169/NFY-A3 rev | artificial Sequence | 80 |
| HAP2 | *Oryza sativa* | 81 |
| HAP2 frwd | artificial Sequence | 82 |
| HAP2 rev | artificial Sequence | 83 |
| HAP2 frwd | artificial Sequence | 84 |
| HAP2 rev | artificial Sequence | 85 |

TABLE 23-continued

Target Gene Sequences and Primers for PCR.

| Sequence name | Organism | SEQ ID NO |
|---|---|---|
| miR156/SPL17 | *Oryza sativa* | 86 |
| miR156/SPL17 frwd | artificial Sequence | 87 |
| miR156/SPL17 rev | artificial Sequence | 88 |
| miR156/SPL17 frwd | artificial Sequence | 89 |
| miR156/SPL17 rev | artificial Sequence | 90 |

TABLE 23-continued

Target Gene Sequences and Primers for PCR.

| Sequence name | Organism | SEQ ID NO |
|---|---|---|
| miR156/SBP-A3 HQ858696.1 | Zea mays | 91 |
| miR156/SBP-A3 frwd | artificial Sequence | 92 |
| miR156/SBP-A3 rev | artificial Sequence | 93 |
| miR156/SBP-A3 frwd | artificial Sequence | 94 |
| miR156/SBP-A3 rev | artificial Sequence | 95 |
| miR164/NAC NM_001064881.1 | Oryza sativa | 96 |
| miR164/NAC frwd | artificial Sequence | 97 |
| mir164/NAC rev | artificial Sequence | 98 |
| miR164/NAC frwd | artificial Sequence | 99 |
| mir164/NAC rev | artificial Sequence | 100 |
| NAC5 NM_001154298.1 | Zea mays | 101 |
| NAC5 frwd | artificial Sequence | 102 |
| NAC5 rev | artificial Sequence | 103 |
| NAC5 frwd | artificial Sequence | 104 |
| NAC5 rev | artificial Sequence | 105 |

Example 16: ARF-8 Gene Silencing in Tomato Seeds

Tomato seeds were treated using the protocol described in Example 1, unwashed seeds were treated with a ARF-8 dsRNA concentration of 200 μg/ml, for 24 hours at 15° C. and immediately planted in soil. Expression levels of the gene were examined using RT-PCR, 3 and 8 weeks after treatment (see Table 25). Changes in expression were achieved in dsRNA-treated plants 3 weeks after treatment (Table 24).

TABLE 24

Treatment of Tomato Seeds with ARF-8 dsRNA (target of mir167) at 3 weeks and 8 weeks post germination.

| Plant | Control | EM 49933 | EM 49950 | EM 49951 | EM 49952 |
|---|---|---|---|---|---|
| 3 weeks | 1.0 | 0.6 | 0.6 | 0.5 | 0.8 |

| Plant | EM 49953 | EM 49954 | EM 49955 | EM 49957 |
|---|---|---|---|---|
| 3 weeks | 0.8 | 0.5 | 0.6 | 0.9 |

| Plant | Control | EM 50374 | EM 50377 | EM 50378 | EM 50379 |
|---|---|---|---|---|---|
| 8 weeks | 1.0 | 0.97 | 0.68 | 0.98 | 0.68 |

| Plant | EM 50381 | EM 50383 | EM 50398 | EM 50399 | EM 50402 |
|---|---|---|---|---|---|
| 8 weeks | 0.60 | 0.69 | 0.47 | 0.99 | 0.47 |

Fold change relative to untreated control (control = 1.0)

Figures 5A, 5B:
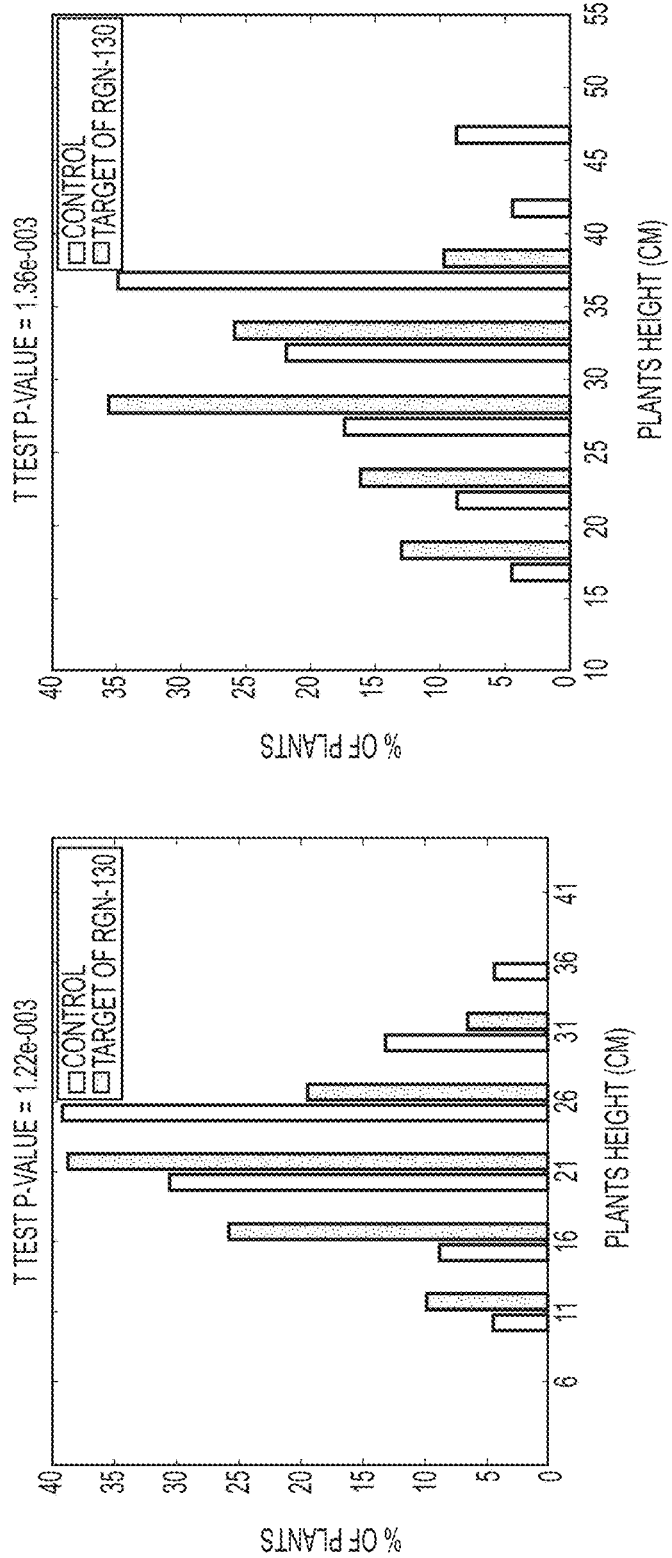
FIGS. 5A-D show the specific distribution of height in control (blue bars) and ARF8 dsRNA-treated (maroon bars) tomato plants 55 (FIG. 5A), 62 (FIG. 5B) and 72 days (FIG. 5C) following treatment.
Figure 5D:
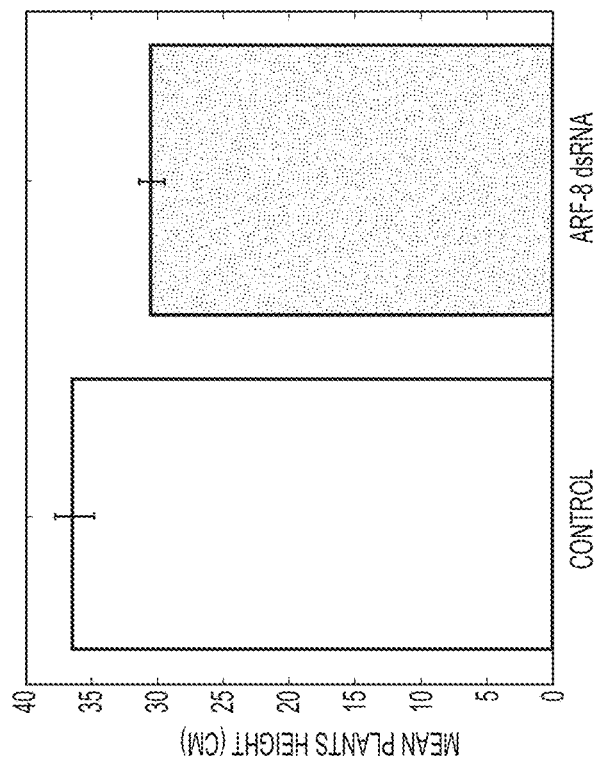
Figure 5C:
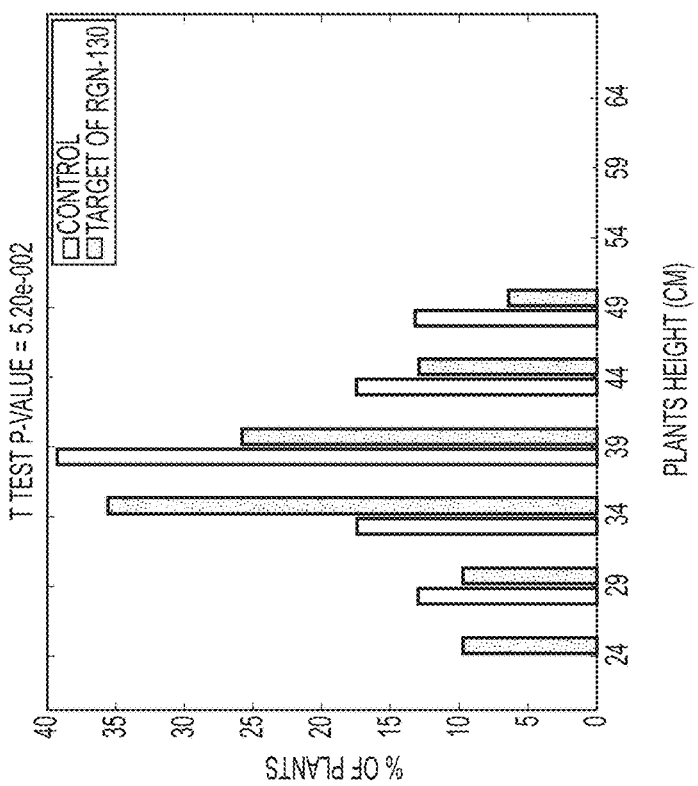

Plants that were treated with dsRNA molecules specific for the ARF8 gene showed a phenotypic difference compared to control plants. This phenotypic difference was observed at different time points (55, 62 and 72 days) and was demonstrated by a decrease in height (FIGS. 5A-C). While the average height of control plants was ~36 cm, the dsRNA treated plants were ~30 cm tall on average (FIG. 5D). In addition to their decreased height (delayed vertical development), dsRNA-treated plants appeared more branched (increased horizontal development) compared to control plants. Thus, plants treated with dsRNA specific for ARF8 appeared shorter and more branched relative to their control counterparts 55 and 72 days after treatment.

TABLE 25

Primers used for RT-PCR of ARF-8 dsRNA Molecules in Tomato and ARF-8 dsRNA product.

| Sequence Name | Sequence | SEQ ID No.: |
|---|---|---|
| slyARF_8_1816F4 | CCTCAACAGTCCTGGATGTC | 106 |
| slyARF_8_1896R4 | CCCGTAAGTTGGAAGTGATG | 107 |
| ARF 8 dsRNA product 1 | CTAATACGACTCACTATAGGGAGAGCTTCTCCTCCCTA CAACTGTGTCTAACGTCGCTACTACATCAATTGATGCT GATATATCCTCTATGCCACTAGGGACTTCTGGATTTCC GAATCCCTTGTATAGTTATGTGCAAGATTCTACTGACT TGTTGCATAATGTAGGGCAAGCTGATGCACAAACTGT GCCCCGTACATTTGTCAAGGTTTACAAATCAGCGTCCC TTGGGAGGTCATTGGACATCACTCGGTTCAACAGCTAT CATGAGCTGCGACAGGAATTAGGGCAGATGTTCGGTA TCGAAGGGTTGCTTGAAGACCCTCAAAGATCAGGCTG GCAGCTTGTATTTGTTGACAGGGAGAATGATGTCCTTC TCCTTGGAGACGATCCGTGGGAGGAATTTGTCAATAA TGTTTGGTACATCAAAATTCTTTCACCCGAGGATGTGC AGAAACTGGGGAAAGAGGAGGTTGGATCCCTCTCCCT ATAGTGAGTCGTATTAG | 108 |
| ARF 8 dsRNA product 2 | CTAATACGACTCACTATAGGGAGATGGGAGATTGAGC CTTTGACTACTTTTCCGATGTATCCATCTCTTTTTCCTC TAAGGCTAAAGAGGCCTTTCTATCAAGGAACCTCATCT TATCAGGATAGTAACAATGAAGCTATTAATCGAATGT CATGGTTAAGAGGGAATGCTGGTGAGCTAGGACATCA TTCAATGAATCTTCAGTCTTTTGGCATGCTTCCTTGGAT GCAACAGAGAGTCGATTCAACAATTCTCCCAAATGAT ATTAATCAGCACTATCAAGCTATGCTGGCTACTGGC TTGCAAAGTTTTGGGAGTGGAGATTTACTGAAACAGC AATTAATGCAGTTTCAGCAGCCTGTCCAATATCTGCAA CATGCAAGTACTGAGAATTCAATTTTGCATCAGCAGC AGCAGCAGCAGCAGCAAATAATGCAGCAAGCAGTTCA TCAGCATATGCTGCCTGCTCAAACCCAAATGCTGTCAG | 109 |

TABLE 25 -continued

Primers used for RT-PCR of ARF-8 dsRNA Molecules in Tomato and ARF-8 dsRNA product.

| Sequence Name | Sequence | SEQ ID No.: |
|---|---|---|
| | AGAACCTTCAAAGGCAATCCCAGCATCAATCCATCTC CCTATAGTGAGTCGTATTAG | |

Example 17: FW2.2 Gene Silencing in Tomato Seeds

Figure 6A:
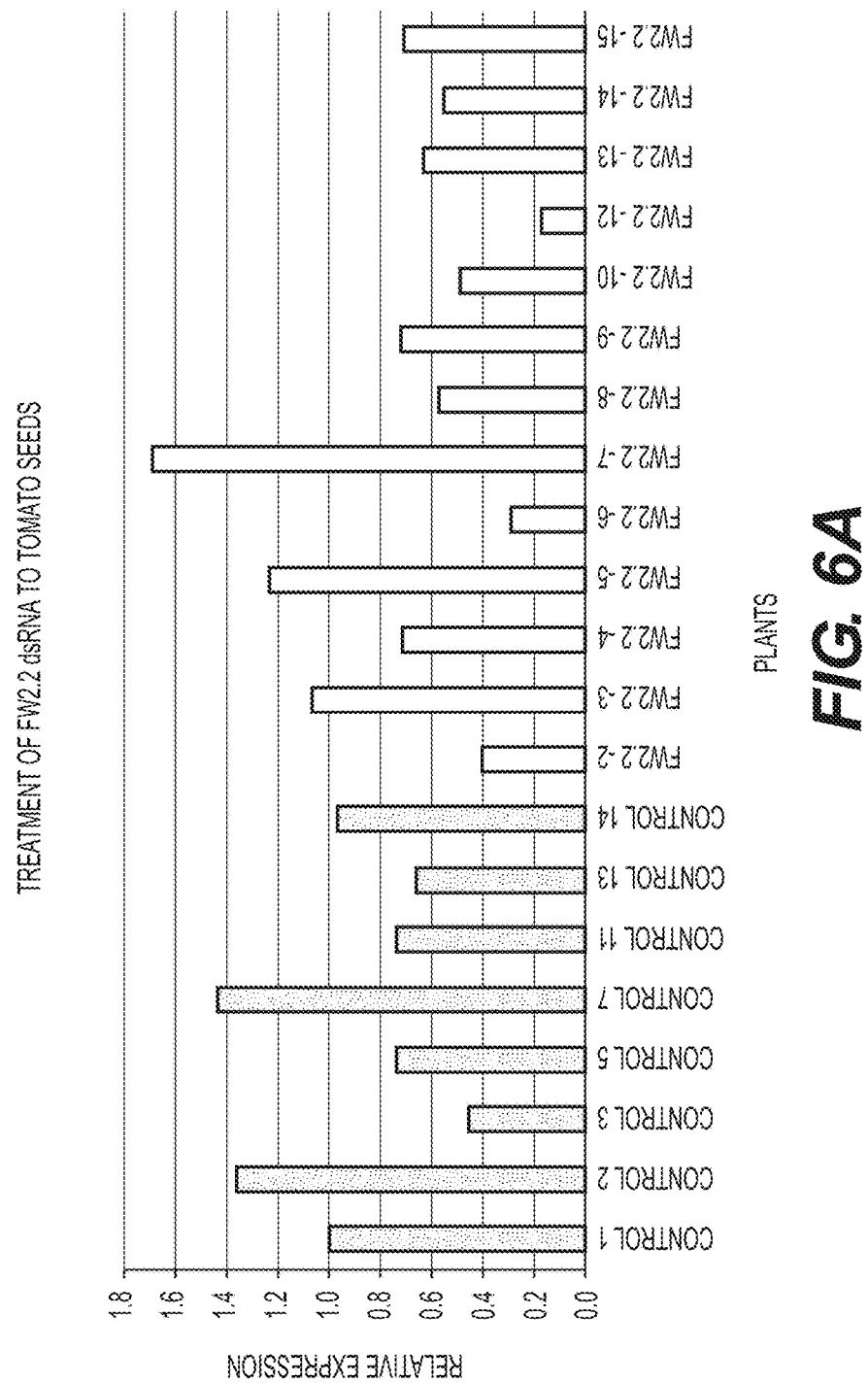
FIGS. 6A-B show the results of RT-PCR on RNA extracted from leaves of control and FW2.2 dsRNA treated tomato plants 9 weeks post germination.
Figure 6B:
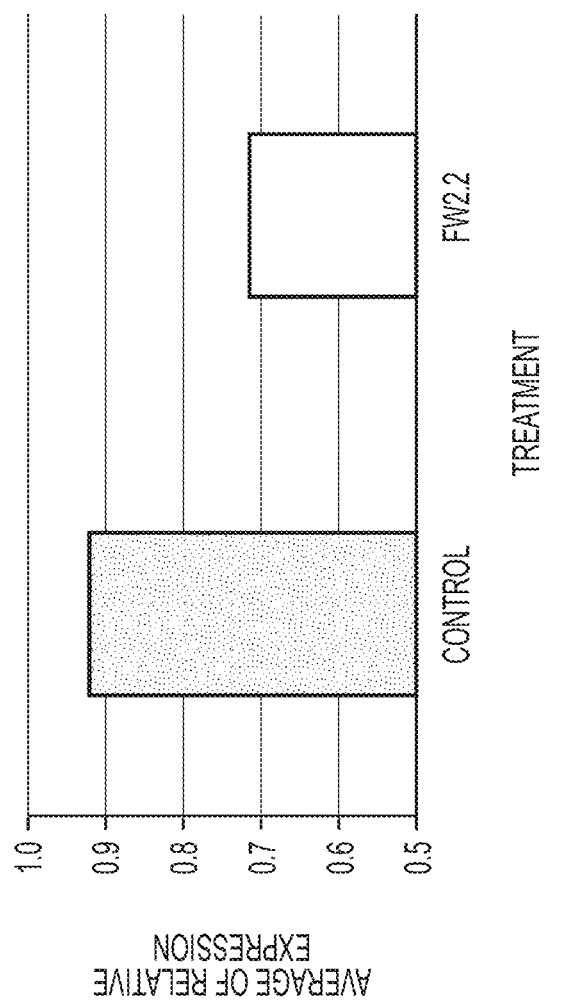

Tomato seeds were treated using the protocol described in Example 1, unwashed seeds were treated with a FW2.2 dsRNA concentration of 100 µg/ml, for 24 hours at 15° C. and immediately planted in soil. Expression levels of the gene were examined using RT-PCR, 9 weeks following germination (primers are listed in Table 26). An approximate 2-fold reduction in the expression level of FW2.2 in dsRNA treated plants compared to control plants was detected (FIG. 6).

Even so, plants that were treated with dsRNA molecules specific for the FW2.2 gene showed no phenotypic differences compared to control plants, ruling out a toxic effect as an alternative explanation for the phenotypic effects seen in Example 15. The plants presented similar height and appearance 72 days after treatment.

TABLE 26

Primers used for RT-PCR of FW2.2 dsRNA Molecules in Tomato and FW2.2 dsRNA product.

| Sequence Name | Sequence | SEQ ID No.: |
|---|---|---|
| slyFW2_316F2 | GAGGCACCTTGTGTTGATTG | 110 |
| slyFW2_406R2 | CAAAGCCACGGTTCTTAAGC | 111 |
| FW2.2 dsRNA product | CTAATACGACTCACTATAGGGAGATCCAGGTCCAATGAAA CAACCTTATGTTCCTCCTCACTATGTATCTGCCCCCGGCAC CACCACGGCGCGGTGGTCGACTGGTCTTTGTCATTGTTTTG ATGACCCTGCTAACTGTTTAGTTACTAGTGTTTGCCCTTGTA TCACCTTTGGACAGATTTCTGAAATACTAAACAAAGGAAC AACTTCATGTGGGAGTAGAGGTGCATTATATTGTTTGCTGG GATTGACAGGATTGCCTAGCCTATATTCCTGCTTCTACAGG TCTAAAATGAGGGGGCAATATGATCTGGAAGAGGCACCTT GTGTTGATTGTCTTGTACATGTATTCTGTGAACCTTGTGCTC TTTGCCAAGAATACAGAGAGCTTAAGAACCGTGGCTTTGA TATGGGAATAGGGTGGCAAGCTAATATGGATAGACAAAGC CGAGGAGTTACCATGCCCCCTTATCATGCAGGCATGACCTC TCCCTATAGTGAGTCGTATTAG | 112 |

Figure 7A:
FIGS. 7A-B show longer and more developed root system in rice seedlings grown from rice seeds treated against the Della gene (FIG. 7B) compared to control plants (FIG. 7A).
Figure 7B:
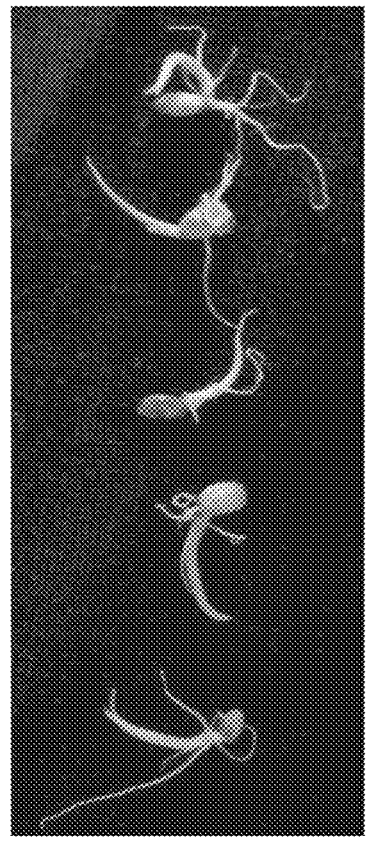

Example 17: Della Gene Down-Regulation in Rice Results in More Developed Roots of Germinated Seeds Rice seeds were treated using the protocol described in Example 1, seeds were washed for 4 h, dried for 24 h at room temperature and immediately treated with a DELLA dsRNA concentration of 66 µg/ml, for 36 hours at 15° C. Rice seeds were treated with dsRNA directed against the Della gene (see Table 28), which is a known plant growth repressor. Arabidopsis seedlings with mutant Della gene are larger with a longer root system (Josse, E. M., Gan, Y., Bou-Torrent, J., Stewart, K. L., Gilday, A. D., Jeffree, C. E., Vaistij, F. E., Martinez-García, J. F., Nagy, F., Graham, I. A., and Halliday, K. J. (2011). A DELLA in disguise: SPATULA restrains the growth of the developing Arabidopsis seedling. Plant Cell 23: 1337-1351.). FIG. 7 shows mimicking of the Arabidopsis phenotypes using dsRNA seed treatment, with treated seedlings being larger with longer roots than control seedlings.

Figures 8A, 8B:
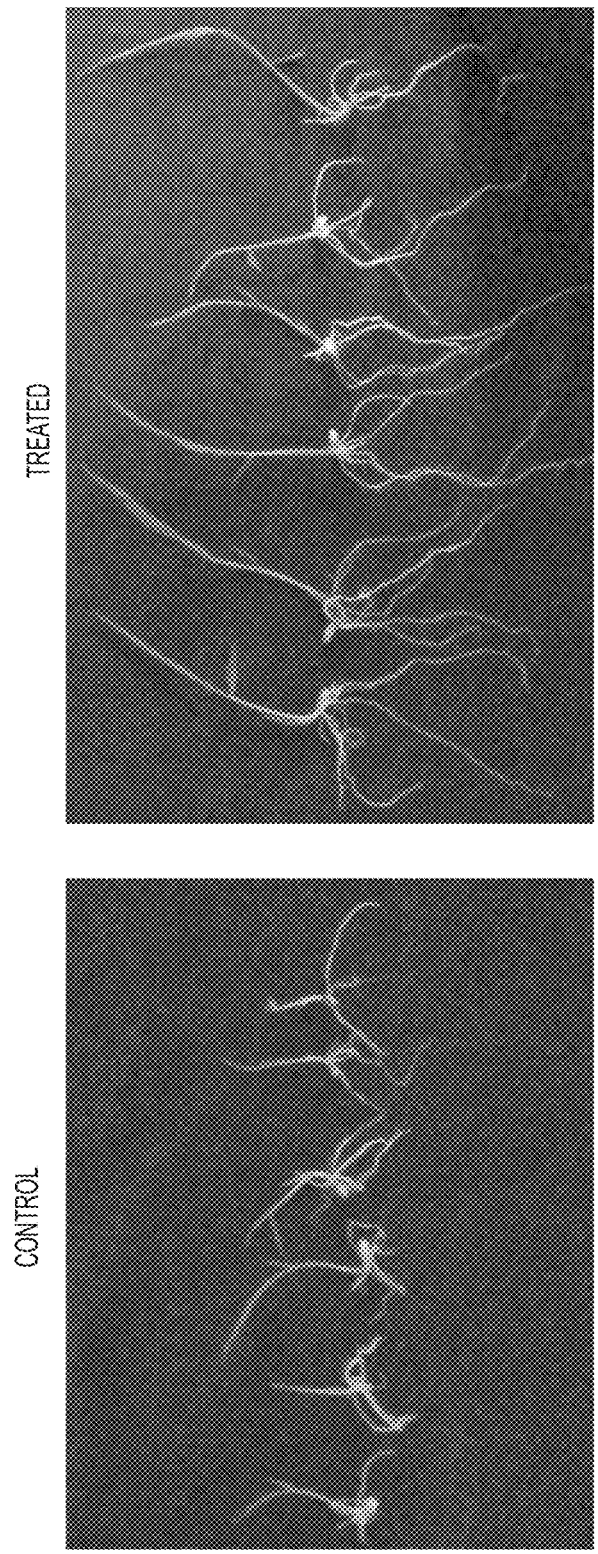
FIGS. 8A-B show longer and more developed root and shoot systems in rice seedlings grown from rice seeds treated against the NRR gene (FIG. 8B) compared to control plants (FIG. 8A) when the seedlings were grown on nitrogen free growth medium.

Example 18: NRR Gene Down-Regulation in Rice Results in More Developed Roots and Shoots of Germinated Seeds Rice seeds were treated using the protocol described in Example 1, seeds were washed for 4 h, dried for 24 h at room temperature and immediately treated with a NRR dsRNA concentration of approximately 4 µg/ml, for 36 hours at 15° C. Rice seeds were treated with dsRNA directed against the NRR gene, which was found to regulate root growth in response to macronutrients in rice (Zhang et al., 2012, Mol Plant 5(1):63-72). Transgenic rice seedlings, with reduced NRR levels using RNAi were shown to have longer roots when grown under nitrogen limiting conditions. FIG. 8 shows mimicking of this phenotype using dsRNA seed treatment, with resulting treated seedlings being larger and with longer roots than control seedlings.

TABLE 27

Products of NRR dsRNA Molecules in rice.

| Sequence Name | Sequence | SEQ ID No.: |
|---|---|---|
| NRR dsRNA product 1 | CTAATACGACTCACTATAGGGAGAAGCTCCTGAACCC ATCATTGAAGAACCAGTGCTTAGCCTTGATCCAGTTG CAGCAGCCATTTCGATGATGTCTGGCAGTGAGAACGT AATGGATGAAACTATAGAGGTTGCAGATATCAGCGAC ATTCAGAATGACTCTCTTTTAAGCGAAGTATTATACG AGTGCGAGAAGGAACTCATGGAGAAGTCCGCAATCGA AGAGACTATTTCTGAACTGCTGGACGTCAAGATTCCT ATGCTGCAAGTGGAAGAGTTCCCTAGGGAAACCCAAG TACAACTACCGGCCATGGAGAAGGAGAAGCCATCAGT TCCTGAATGTTGTTCACTCCAGAAAAGTGTCAGTTCT GGGTGCCTCAACTCAGCTGATTGGATCAATGGACCAG CCAGGCCAAACTTCCTGGACTTCCAAGGATTGGACTT TGAGACAGCGTTTGGGTTGAGGAGGGCATACAGCGAA GGAGACATTCTCCCTATAGTGAGTCGTATTAG | 113 |
| NRR dsRNA product 2 | CTAATACGACTCACTATAGGGAGACATGGAGAAGTCC GCAATCGAAGAGACTATTTCTGAACTGCTGGACGTCA AGATTCCTATGCTGCAAGTGGAAGAGTTCCCTAGGGA AACCCAAGTACAACTACCGGCCATGGAGAAGGAGAAG CCATCAGTTCCTGAATGTTGTTCACTCCAGAAAAGTG TCAGTTCTGGGTGCCTCAACTCAGCTGATTGGATCAA TGGACCAGCCAGGCCAAACTTCCTGGACTTCCAAGGA | 114 |

TABLE 27-continued

Products of NRR dsRNA Molecules in rice.

| Sequence Name | Sequence | SEQ ID No.: |
|---|---|---|
| | TTGGACTTTGAGACAGCGTTTGGGTTGAGGAGGGCAT ACAGCGAAGGAGACATTCAGAATCTTGGAGCTAGCAC CCCTCGACCCGGGAACTCAGGAAACGCTCAATTAGCA TCTTGCGAGAGGCTTGTAACCATCAGTGACCTGAAAT CTGAAGAAAGGAAGCAGAAGCTATCTAGGTACAGAAA GAAGAAGGTGAAGAGAAACTTTGGCAGAAAGATCAAG TATGCTTGCAGGAAGGCTCTCTCCCTATAGTGAGTCG TATTAG | |

Example 19: Simultaneous Silencing of Three Endogenous Genes

In the present Example, the effect of silencing three genes simultaneously is tested. Rice seeds were treated using the protocol described in Example 1, seeds were washed for 4 hours, dried overnight at room temperature and immediately treated with a solution containing a mixture (152.7 µg/ml final concentration) of dsRNA against three genes: Hap2e (59.9 µg/ml, see Table 28), Della (44 µg/ml see Table 28 below) and SQS (48.4 µg/ml see Table 28 below) for 42 h at 15° C. RNA was extracted from shoots of germinated seeds, 18 days post germination, and RT-PCR for each of the three genes was run (see Table 28 below). As can be seen in Table 29, down-regulation of all three genes was highly effective, with treated plants exhibiting decrease in expression of each individual gene at various amounts, ranging from a minimum of 10% decrease to total silencing of the gene (equals 100% down-regulation).

TABLE 28

Primers Used for RT-PCR Analysis for Expression Level of Hap2e, Della and SQS Genes and dsRNA products.

| Sequence Name | Sequence | SEQ ID No.: |
|---|---|---|
| osaHAP2E122F7 | GTGACTCGTCACCAACAAAG | 115 |
| osaHAP2E202R7 | TGTGTTGTCCGTTGAGACTG | 116 |
| osaDella1410F5 | CAGTTCGCGCACACCATTCG | 117 |
| osaDella1494R5 | GCAGCATGAACGGCTCCAAG | 118 |
| osaSQS465F3 | TCCGCAATGCCGTGTGCATC | 119 |
| osaSQS543R3 | GCGGCAGGAATGCTAGTGTC | 120 |
| Della dsRNA product | CTAATACGACTCACTATAGGGAGAGCCCACTTCTACGA GTCCTGCCCCTACCTCAAGTTCGCCCACTTCACCGCAAA TCAAGCCATCCTCGAGGCTTTCGCCGGCTGCCACCGCGT CCACGTCGTCGACTTCGGCATCAAGCAGGGGATGCAAT GGCCAGCTCTCCTCCAGGCCCTCGCCCTTCGTCCCGGCG GCCCCCCATCGTTCCGCCTCACCGGCGTCGGCCCCCGC AGCCGGACGAGACCGACGCCTTGCAGCAGGTGGGTTGG AAGCTTGCCCAGTTCGCGCACACCATTCGCGTCGACTTC CAGTACCGGGGACTCGTCGCCGCCACTCTCGCGGACTT GGAGCCGTTCATGCTGCAGCCGGAGGGCGAGGCGGACG CGAACGAGGAGCCTGAGGTGATCGCCGTCAACTCGGTG TTCGAGCTGCACCGGCTGCTCGCGCAGCCCGGCGCGCT GGAGAAGGTCCTGGGCACGGTGCACGCGGTGCGGCCAA GGATCGTCACCGTGGTAGAGTCTCCCTATAGTGAGTCGT ATTAG | 121 |

TABLE 28-continued

Primers Used for RT-PCR Analysis for Expression Level of Hap2e, Della and SQS Genes and dsRNA products.

| Sequence Name | Sequence | SEQ ID No.: |
| --- | --- | --- |
| SQS dsRNA product 1 | CTAATACGACTCACTATAGGGAGAATATCTACAACCGC GACTGGCATTATTCATGTGGAACAAAAGACTACAAATT ACTGATGGATAAGTTTCGCCTTGTCTCCACGGCTTTCTT GGAGCTTGGTCAAGGTTATCAAGAGGCAATTGAAGAAA TCACTAGGCTAATGGGAGCAGGAATGGCAAAATTTATC TGCAAGGAGGTTGAAACTGTTGATGACTACAATGAGTA CTGTCACTATG TAGCAGGGCTAGTGGGGTATGGGCTTTCCAGGCTCTTTC ATGCTGGTGGGACGGAAGATCTGGCTTCAGATTCACTTT CAAATTCAATGGGCTTGTTTCTGCAGAAAATCAATATAA TTAGGGATTATTTGGAGGACATAAACGAGATACCAAAG TCACGTATGTTCTGGCCTCGAGAAATATGGAGTAAATAT GTCAATAAACTCGAGGATTTGAAATACGAGGAAAATTC AGAAAAGGCAGTTCAGTGTTTGAATGATATGGTGACTA ACGCTCTGTCTCATCTCCCTATAGTGAGTCGTATTAG | 122 |
| SQS dsRNA product 2 | CTAATACGACTCACTATAGGGAGACGCTCTGTCTCATGC TGAAGACTGCCTCCAATACATGTCAGCATTGAAGGATC ATGCCATTTTCCGTTTTTGTGCAATACCTCAGATAATGG CAATTGGGACATGTGCTATTTGCTACAATAATGTGAATG TCTTTAGAGGAGTTGTTAAGATGAGGCGTGGGCTCACT GCACGAGTAATTGATGAGACAAACACAATGTCAGATGT CTATACTGCTTTCTATGAGTTCTCTTCGCTGATAGAATC GAAGATTGATAATAATGATCCAAATGCTTCCCTAACGC GGAAACGTGTTGATGCGATAAAGAGAACCTGCAAGTCA TCTTGCTCACTAAAGAGAAGGGGATACGATTTGGAGAA GTCAAAGTACAACTCCATGCTGATAATGGTTGTACTTCT GTTGGTGGCTCTCCCTATAGTGAGTCGTATTA | 123 |

TABLE 29

Simultaneous Knockdown of Expression in Rice seeds at 18 days post germination.

| RNA | Control | EM 49174 | EM 49175 | EM 49177 | EM 49178 | EM 49179 | EM 49180 |
| --- | --- | --- | --- | --- | --- | --- | --- |
| Hap2e | 1.0 | 0.19 | 0.20 | 0.53 | 0.88 | 0.28 | 0.14 |
| Della | 1.0 | 0.14 | 0.10 | 0.47 | 1.00 | 0.42 | 0.10 |
| SQS | 1.0 | 0.15 | 0.01 | 0.23 | 0.71 | 0.42 | 0.27 |

| RNA | EM 49181 | EM 49183 | EM 49184 | EM 49185 | EM 49186 | EM 49187 | EM 49188 |
| --- | --- | --- | --- | --- | --- | --- | --- |
| Hap2e | 0.06 | 0.27 | 0.92 | 0.24 | 0.27 | 0.29 | 0.37 |
| Della | 0.01 | 0.14 | 0.60 | 0.27 | 0.29 | 0.37 | 0.16 |
| SQS | 0.56 | 0.08 | 0.87 | 0.49 | 0.09 | 0.13 | 0.10 |

Fold change relative to untreated control (control = 1.0)

Example 20: Generation of dsRNA Molecules for Silencing a Target Gene of a Phytopathogen dsRNAs encoding *S. littoralis* genes were analyzed against the corn and tomato genomes (FIGS. 9 and 10 respectively) using BLAST searches with the following parameters: Expect threshold—10; Word size—11; Match/Mismatch score 2, −3; Gap costs: Existence: 5 Extension: 2; Max matches in a query range: 0. BLAST searches were performed against the databases of corn (*Zea mays*—taxid: 4577) and tomato (*Solanum lycopersicum* taxid:4081) sequences that meet the teachings of the present invention are presented.

Example 21: Seed Treatment Against *Spodoptera littoralis* NADPH Gene

Corn seeds (var. 01DKD2) were treated with dsRNA molecules (SEQ ID No. 26) having a nucleotide sequence that is essentially identical or essentially complementary to at least 18 contiguous nucleotides of the *S. littoralis* NADPH gene according to the protocol described in Example 1. A final concentration of 80 μg/ml dsRNA diluted with 0.1 mM EDTA was used. Treatment was performed by gently shaking the seeds in the solution for 3.5 hours in a dark growth chamber at 15° C. After treatment, seeds were planted in soil and grown at about 25° C. with 16 hours photoperiod. The plants were watered with tap water as necessary. Seeds that were treated with GFP dsRNA (SEQ ID No. 124), or with a similar solution not containing dsRNA (EDTA control), were germinated and grown alongside the treated plants as a control.

28 days after seed treatment, the leaves of treated and control plants were placed in petri dishes and used as sole food source for *S. littoralis*. For each plant, 15 larvae were used (5 larvae per plate, three plates per plant). Five plants from each seed treatment (NADPH, GFP and EDTA) were tested. New leaves were supplemented as needed. Body weight of each larva was recorded 12 days after the beginning of feeding and was used as an indicator of their well-being and survivability. A significant (one-way ANOVA, p-value=$8.36 \times 10^{-5}$) negative effect on the body weight of the larvae fed on NADPH dsRNA-treated plants compared to larvae fed on control plants was observed. See Table 30. The average weight of larvae fed on NADPH-treated plants was 23% and 20% lower than the average weight of larvae fed on GFP and EDTA-treated plants, respectively.

TABLE 30

*Spodoptera littoralis* average weight (mg) after 12 days of feeding on treated plants.

| | Sample | | | | | | |
|---|---|---|---|---|---|---|---|
| | 1 | 2 | 3 | 4 | 5 | Average | std. dev. |
| EDTA | 40.8 | 46.7 | 45.3 | 38.9 | 47.1 | 43.8 | 3.7 |
| GFP | 42.9 | 41 | 47.3 | 48.9 | 49.2 | 45.9 | 3.7 |
| sI-NADPH #1 | 38.5 | 26.8 | 32.5 | 35.2 | 43.2 | 35.2 | 6.2 |

73 days after seed treatment, the leaves of treated and control plants were used again as sole food source for *S. littoralis*. Five plants from each group were included in the feeding experiment. The leaves of each plant were placed in five petri dishes containing five larvae each, summing to 25 larvae per plant and 125 larvae per group. Seven days into the experiment, an unusual large number of larvae were found dead in the EDTA control group. Due to the large number of deaths in the control group, the effect of feeding plant tissue collected 73 days after dsRNA seed treatment on *S. littoralis* well-being and survivability was not analyzed further.

The expression levels of NADPH in subsets of larvae fed on plants grown from seeds treated with dsRNA molecules targeting NADPH or GFP (28 days after seed treatment) were determined.

TABLE 31

Larvae from which RNA was extracted.

| | Leaf source | | |
|---|---|---|---|
| Treatment | Plant number | Repeat | Weight (mg) |
| NADPH | 2 | 2 | 22 |
| | | | 29 |
| | | | 15 |
| | | | 35 |
| | | | 18 |
| | 3 | 3 | 36 |
| | | | 28 |
| | | | 32 |
| | | | 30 |
| | | | 39 |
| | | 2 | 29 |
| | | | 28 |

TABLE 31-continued

Larvae from which RNA was extracted.

| | Leaf source | | |
|---|---|---|---|
| Treatment | Plant number | Repeat | Weight (mg) |
| GFP | 1 | 2 | 37 |
| | | | 49 |
| | | | 33 |
| | | | 27 |
| | | | 37 |
| | 2 | 3 | 28 |
| | | | 40 |
| | | | 26 |
| | | | 39 |
| | | | 31 |
| | | 2 | 34 |
| | | | 39 |

Total RNA was extracted from the larvae and cDNA was prepared using oligo-dT primers and the expression level of *S. littoralis* NADPH mRNA was determined in treated and control larvae by real-time PCR (RT-PCR) with SYBR Green (Quanta BioSciences), using the house-keeping genes Actin and EF1α as normalizers. The sequences of the primers used in the RT-PCR analysis are shown in Table 32.

TABLE 32

Primers Used for RT-PCR Analysis for Expression Level of NADPH.

| Primer Name and Direction | Primer Sequence | SEQ ID No. |
|---|---|---|
| NADPH_F | ATGGCTGTTGACGTAAGG | 125 |
| NADPH_R | TGCAGCTTCAGCTTCTGTG | 126 |
| EF1α_F | ACCGTCGTACTGGTAAATCC | 127 |
| EF1α_R | TGGCGGCATCTCCAGATTTG | 128 |
| Actin_F | CTGGTCGTACCACCGGTAT | 129 |
| Actin_R | GCAGAGCGTAACCTTCGTAG | 130 |

No significant change in NADPH expression levels (Wilcoxon rank-sum test, p-value>0.05) was observed by RT-PCR analysis in larvae fed on plants grown from seeds treated with dsRNA molecules targeting NADPH or GFP (28 days after seed treatment).

Example 22: Seed Treatment Against *Spodoptera littoralis* ATPase Gene

Corn seeds were treated according to the protocol described in Example 1 with dsRNA molecules having a nucleotide sequence that is essentially identical or essentially complementary to at least 18 contiguous nucleotides of the *S. littoralis* ATPase gene (SEQ ID No. 31). Briefly, seeds were washed with double distilled water (DDW) prior to treatment for four hours. Next, seeds were dried at 30° C. over-night. Following the drying step, a final concentration of 53 μg/ml dsRNA diluted with 0.1 mM EDTA was used. Treatment was performed by gently shaking the seeds in the solution for 26 hours in a dark growth chamber at 15° C. After treatment, seeds were germinated on wet paper for seven days and then planted in soil and grown at about 25° C. with 16 hours photoperiod. The plants were watered with tap water as necessary. Seeds that were treated with a similar solution not containing dsRNA were germinated and grown alongside the treated plants as a control (EDTA control).

Figure 11A:
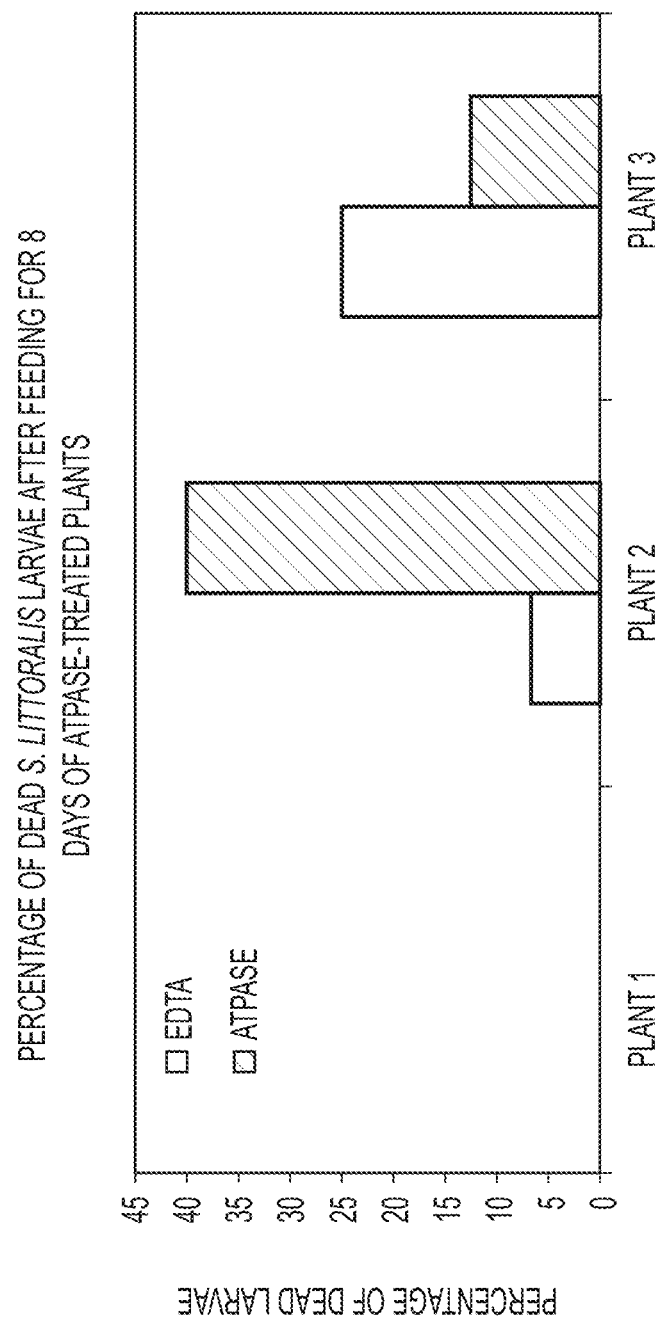
FIGS. 11A-D are bar graphs showing mortality and average weight of live *S. littoralis* larvae.
Figure 11B:
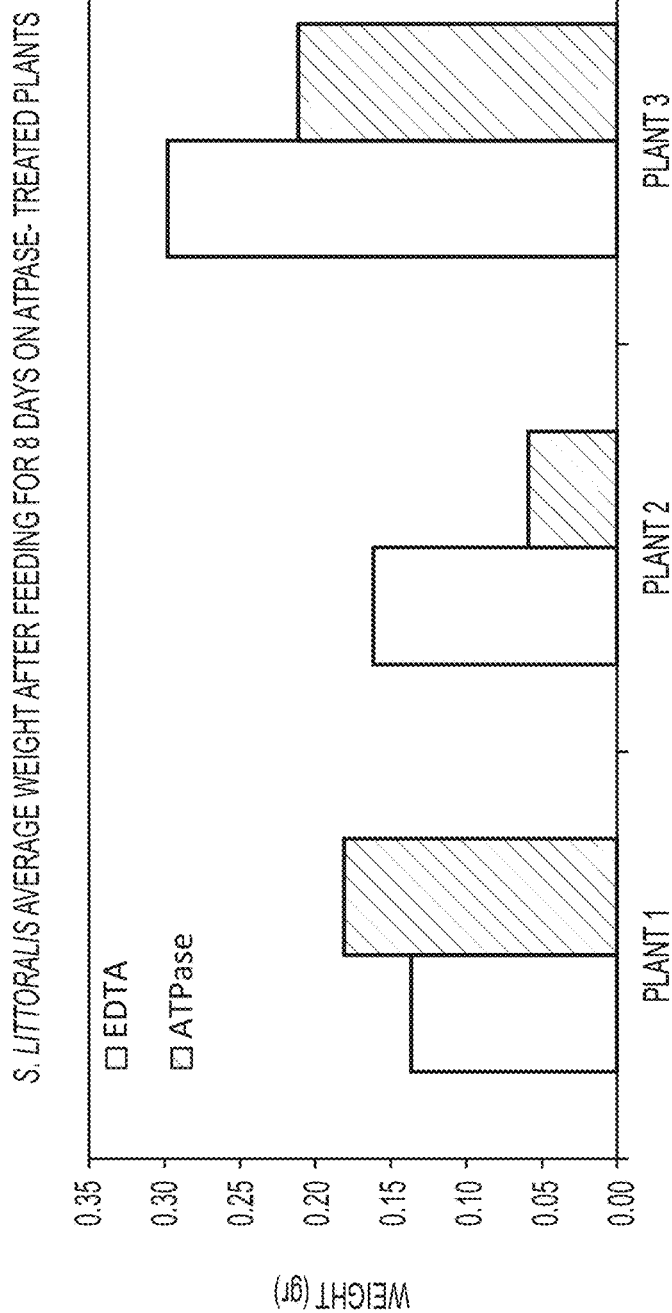

43 days after seed treatment, the leaves of treated and control plants were used as sole food source for *S. littoralis*. Plant number 1 served as a food source for 20 larvae placed in 130×170 mm box. Plant number 2 served as a food source for 15 larvae placed in 124×95 mm box. Plant number 3 served as a food source for 8 larvae placed in petri dish. The surface of all boxes and plates was covered with vermiculite, and new leaves were supplemented as needed. Mortality and body weight of the larvae were tracked throughout the experiment. FIG. 11A shows mortality and FIG. 11B shows the average weight of live *S. littoralis* larvae eight days after the beginning of feeding. While the larvae fed on plants 1 and 3 grown from ATPase dsRNA treated seeds gained comparable weight and showed similar mortality to that of the control group, the larvae fed on plant number 2 grown from an ATPase dsRNA treated seed were almost 3-fold smaller compared to the control group, which had a higher death rate.

Figure 11C:
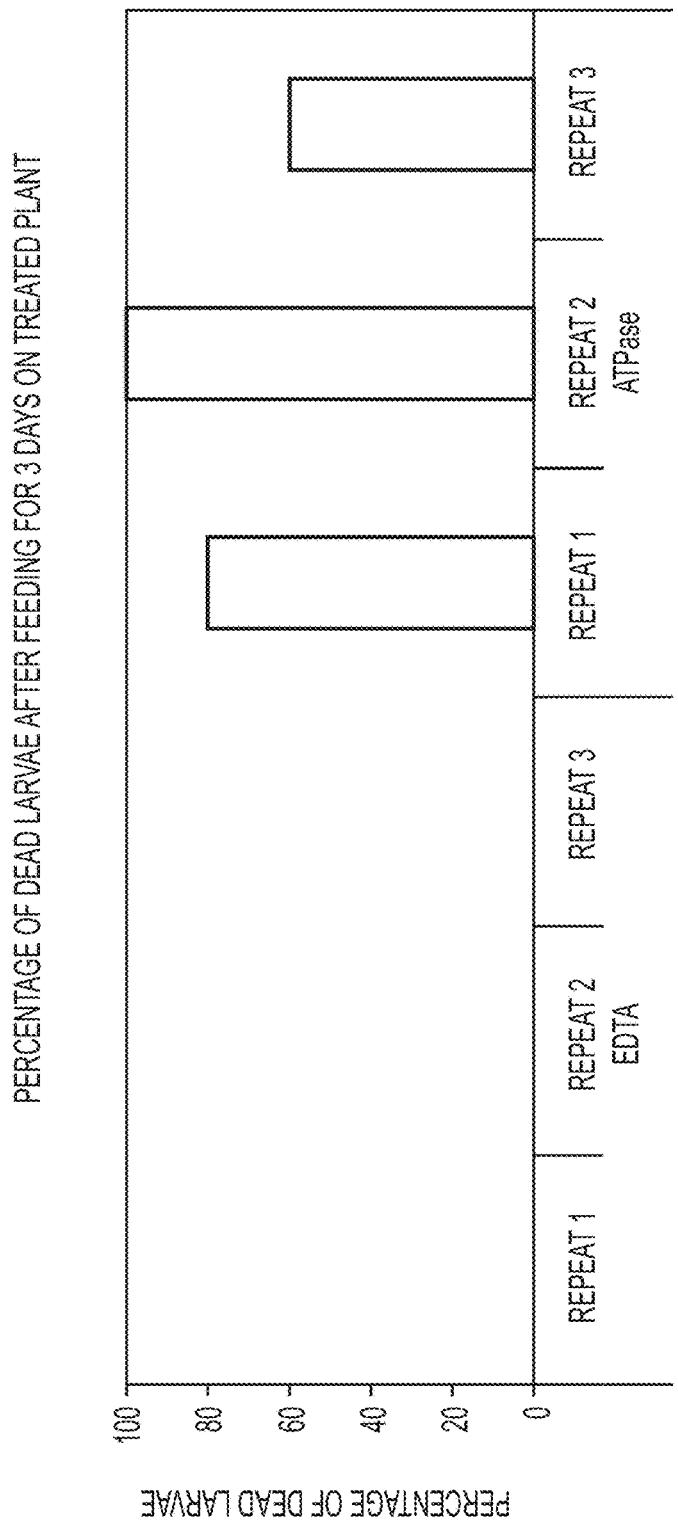

To test the persistence of the effects of dsRNA seed treatment, the leaves of plant number 2 were collected 85 days after seed treatment and used as sole food source for *S. littoralis*. A total of 15 larvae, in three petri dishes containing five larvae each, were used. FIG. 11C shows the percentage of dead larvae three days after the beginning of experiment. In the ATPase dsRNA-treated group 12 out of 15 larvae were dead, while no dead larvae were found in the control group.

Figure 11D:
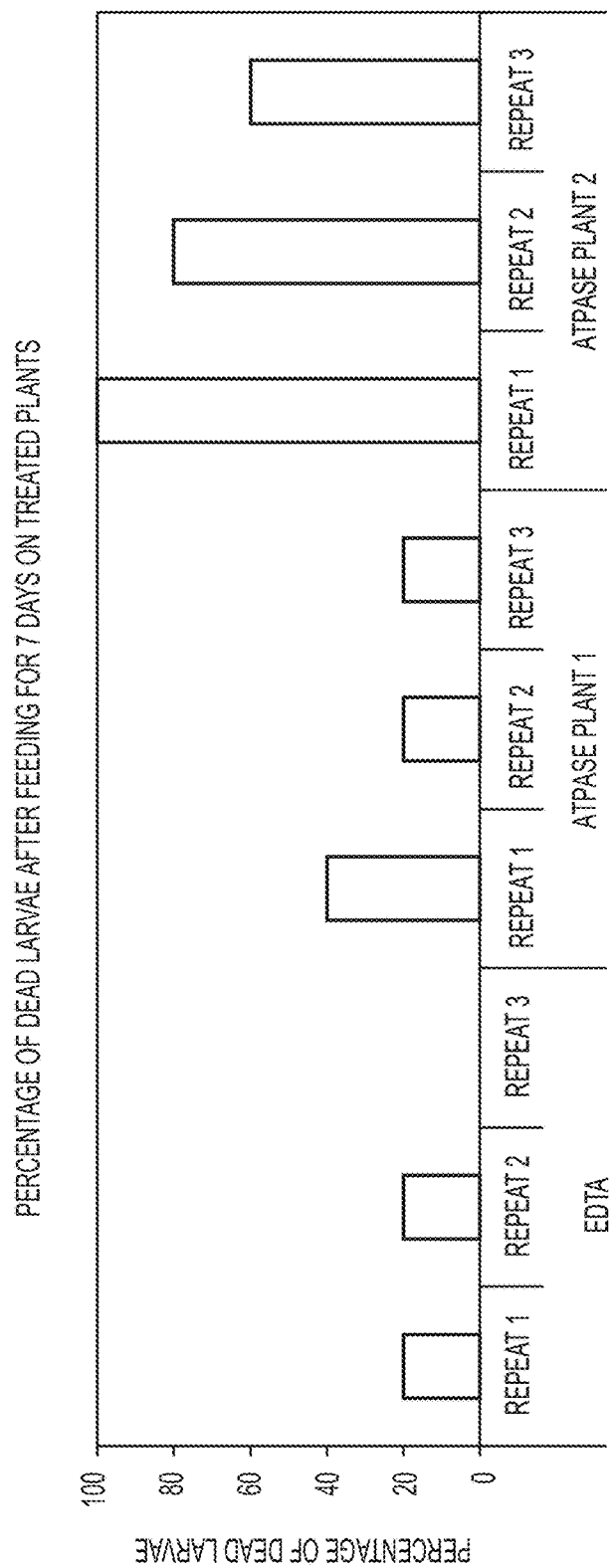

The persistence of the effects of dsRNA seed treatment were further tested by collecting the leaves of plants number 1 and 2 at 91 days after seed treatment, and using the leaves as the sole food source for *S. littoralis*. A total of 15 larvae, in three petri dishes containing five larvae each, were fed on each plant. Four days into the experiment, both groups were fed also on plant number 3. FIG. 11D shows the percentage of dead larvae seven days after the beginning of feeding, compared to the control group.

Example 23: Seed Treatment Against *Spodoptera littoralis* ATPase, IAP and NADPH Genes The plants described in this Example were treated with dsRNA molecules having a nucleotide sequence that is essentially identical or essentially complementary to at least 18 contiguous nucleotides of the *S. littoralis* ATPase, IAP or NADPH gene, and are the same plants described in Example 7.

67 days after seed treatment, leaves of the treated and control plants described in Example 7 were used as sole food source for *S. littoralis*. One plant from each treatment served as a food source for 10 larvae placed in a petri dish. The surface of the plates was covered with vermiculite. FIG. 12 shows the percentage of dead larvae after seven days of feeding.

Example 24: Seed Treatment Against *Spodoptera littoralis* EF1α Gene

Corn seeds were treated with dsRNA molecules having a nucleotide sequence that is essentially identical or essentially complementary to at least 18 contiguous nucleotides of the *S. littoralis* EF1α gene (Table 33) according to the protocol described in Example 1. Briefly, corn seeds were washed with double distilled water (DDW) prior to treatment for four hours. Next, the seeds were dried at 30° C. overnight. Following the drying step, a final concentration of 132 µg/ml dsRNA diluted with 0.1 mM EDTA was used. Treatment was performed by gently shaking the seeds in the solution for 26 hours in a dark growth chamber at 15° C. After treatment, seeds were germinated on wet paper for seven days and then planted in soil and grown at about 25° C. with 16 hours photoperiod. The plants were watered with tap water as necessary. Seeds that were treated with a similar solution not containing dsRNA were germinated and grown alongside the treated plants as a control (EDTA control).

TABLE 33 dsRNAs derived from the *S. littoralis* EF1α gene.

| Sequence Name | Sequence | SEQ ID No.: |
|---|---|---|
| EF1α dsRNA #1 | CTAATACGACTCACTATAGGGAGAATGCCCTGGTTCAAGGGATGGAACGT<br>TGAGCGCAAGGAAGGCAAGGCTGAAGGTAAATGCCTCATTGAGGCCCTC<br>GACGCCATCCTGCCCCCTGCTCGCCCCACAGACAAGCCCCTGCGTCTTCC<br>CCTCCAGGACGTATACAAAATCGGTGGTATTGGTACGGTGCCCGTAGGCA<br>GAGTTGAAACTGGTATCCTCAAGCCTGGTACCATCGTCGTCTTCGCCCCC<br>GCCAACATCACCACTGAAGTCAAGTCTGTGGAGATGCACCACGAAGCTCT<br>CCAAGAGGCCGTACCCGGTGACAACGTTGGTTTCAACGTAAAGAACGTTT<br>CCGTCAAGGAGTTGCGTCGTGGTTACGTCGCTGGTGACTCCAAGAACAAC<br>CCACCCAAGGGCGCCGCCGATTTCACAGCACAGGTCATCGTGCTCAACCA<br>CCCTGGTCAAATCTCAAACGGATACACACCTGTGCTGGATTGCCACACAG<br>CCCACATTGCCTGCAAGTTCGCTGTCTCCCTATAGTGAGTCGTATTAG | 131 |
| EF1α dsRNA #2 | CTAATACGACTCACTATAGGGAGAGGCCCAGGAAATGGGTAAGGGTTCC<br>TTCAAATACGCCTGGGTATTGGACAAACTGAAGGCTGAGCGTGAACGTG<br>GTATCACCATTGATATTGCTCTGTGGAAGTTCGAAACCGCTAAATACTAT<br>GTCACCATTATTGACGCTCCCGGACACAGAGATTTCATCAAGAACATGAT<br>CACTGGAACCTCCCAGGCCGATTGCGCCGTACTCATTGTCGCCGCTGGTA<br>CCGGTGAATTCGAGGCTGGTATCTCGAAGAACGGACAGACCCGTGAGCA<br>CGCTCTGCTCGCTTTCACACTCGGTGTCAAGCAGCTGATTGTGGGCGTCA<br>ACAAAATGGACTCCACTGAGCCCCATACAGCGAATCCCGTTTCGAGGAA<br>ATCAAGAAGGAAGTGTCCTCCTACATCAAGAAGATCGGTTACAACCCAG<br>CTGCTGTCGCTTTCGTACCCATTTCTGGCTGGCACGGAGTCTC-<br>CCTATAGT<br>GAGTCGTATTAG | 132 |

Figure 13A:
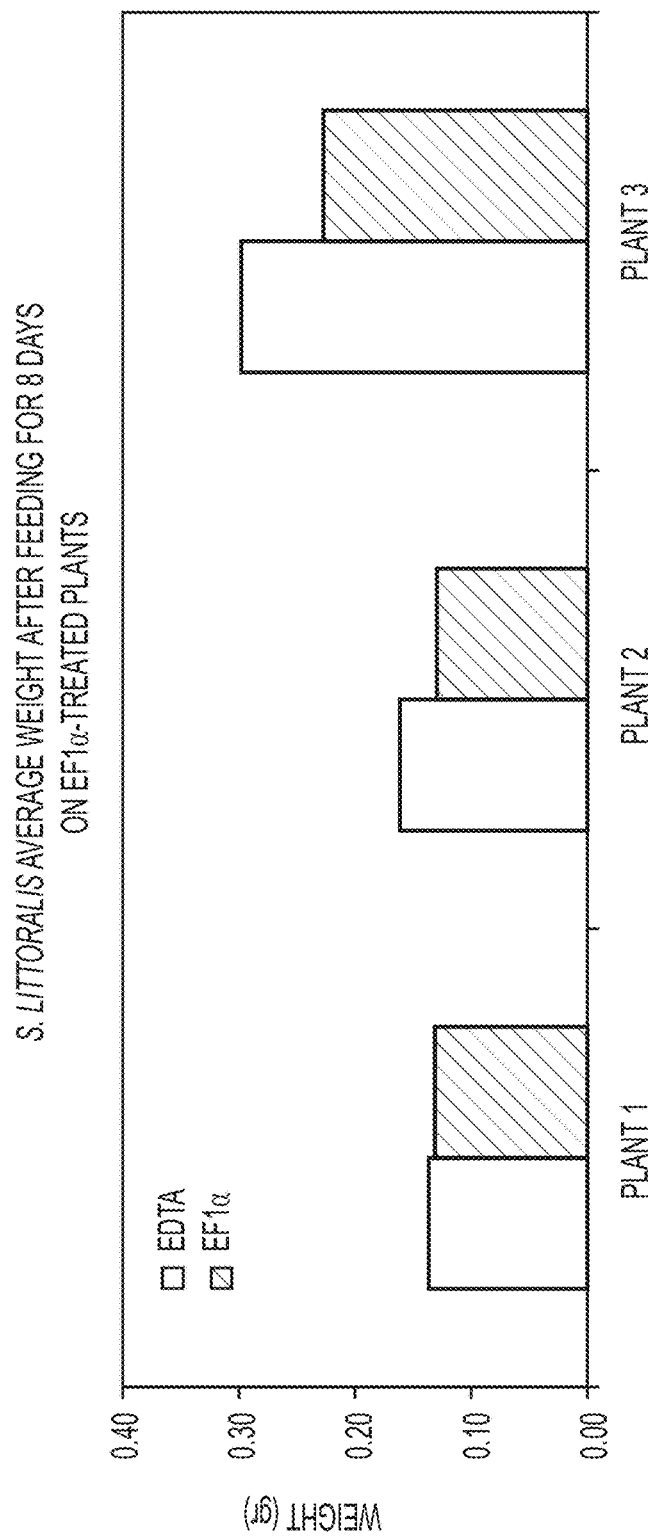
FIGS. 13A-B.

43 days after seed treatment, the leaves of treated and control plants were used as sole food source for *S. littoralis*. Plant number 1 served as a food source for 20 larvae placed in 130×170 mm box. Plant number 2 served as a food source for 15 larvae placed in 124×95 mm box. Plant number 3 served as a food source for 8 larvae placed in petri dish. The surface of all boxes and plates was covered with vermiculite, and new leaves were supplemented as needed. Mortality and body weight of the larvae were tracked throughout the experiment. Eight days after the beginning of the feeding experiment, eight larvae out of 43 were found dead in the EF1α treated group, and three out of 43 larvae were dead in the control group. FIG. 13A shows the average weight of live *S. littoralis* larvae eight days after the beginning of feeding.

Figure 13B:
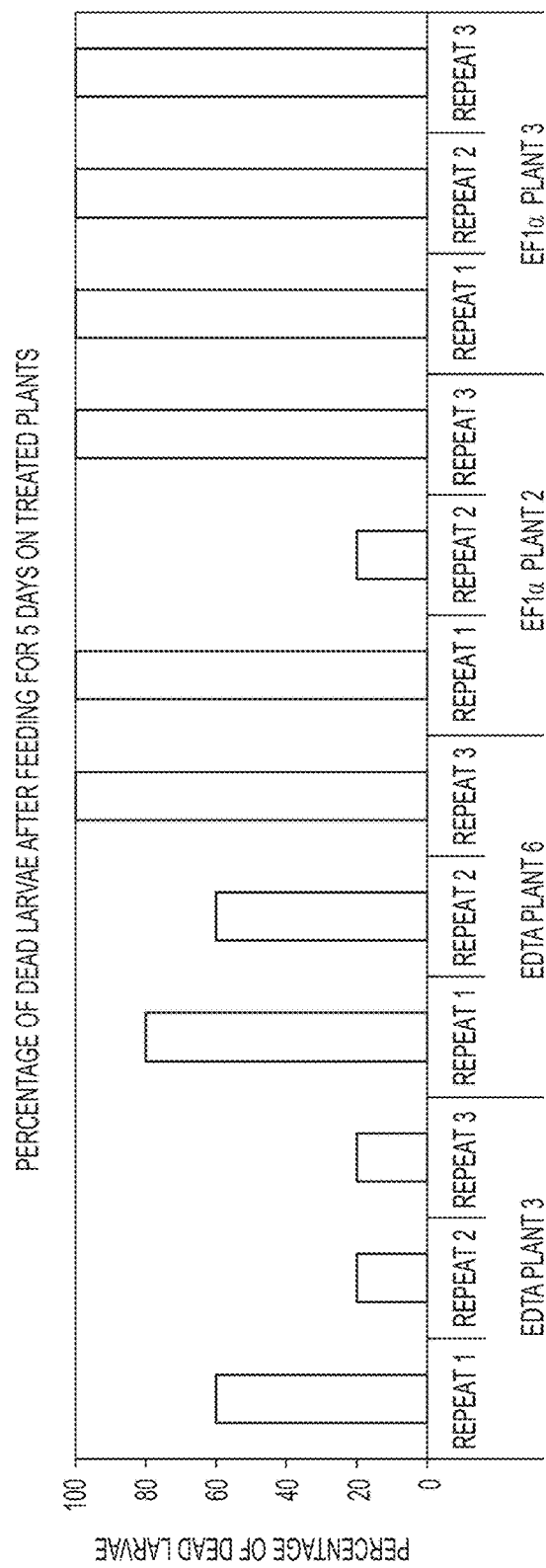

87 days after seed treatment, the leaves of plants number 2 and 3 were used for a second time as sole food source for *S. littoralis*. A total of 15 larvae, in three petri dishes containing five larvae each, were fed on each EF1α-treated plant, and on two control plants (plants number 3 and 6). FIG. 13B shows the percentage of dead larvae five days after the beginning of experiment.

Example 25: Seed Treatment Against *Spodoptera littoralis* Beta Actin Gene

Corn seeds were treated with dsRNA molecules having a nucleotide sequence that is essentially identical or essentially complementary to at least 18 contiguous nucleotides of the *S. littoralis* Beta actin gene (Table 34) according to the protocol described in Example 1. Seeds were washed with double distilled water (DDW) prior to treatment for four hours. Next, seeds were dried at 30° C. overnight. Following the drying step, a final concentration of 76 μg/ml dsRNA diluted with 0.1 mM EDTA was used. Treatment was performed by gently shaking the seeds in the solution for 26 hours in a dark growth chamber at 15° C. After treatment, seeds were germinated on wet paper for seven days and then planted in soil and grown at about 25° C. with 16 hours photoperiod. The plants were watered with tap water as necessary. Seeds that were treated with a similar solution not containing dsRNA were germinated and grown alongside the treated plants as a control (EDTA control).

TABLE 34 dsRNA derived from the *S. littoralis* Beta actin gene.

| Sequence Name | Sequence | SEQ ID No.: |
|---|---|---|
| Beta actin dsRNA #1 | CTAATACGACTCACTATAGGGAGAATGGCTCC GGCATGTGCAAGGCCGGTTTCGCCGGCGACGA CGCGCCCCGCGCCGTCTTCCCATCCATCGTAGG TCGCCCTCGTCACCAGGGTGTGATGGTTGGTAT GGGTCAGAAGGACTCCTACGTAGGCGATGAGG CCCAGAGCAAGAGAGGTATCCTCACCCTGAAG TACCCCATCGAGCACGGTATCATCACCAACTG GGACGACATGGAGAAGATCTGGCACCACACCT TCTACAACGAGCTGCGCGTCGCCCCTGAGGAA CACCCAGTCCTCCTGACTGAGGCTCCCCTCAAC CCTAAGGCCAACAGGGAGAAGATGACCCAGA TCATGTTTGAGACCTTCAACTCCCCCGCCATGT ACGTCGCCATCCAGGCTGTGCTCTCTCTGTACG CCTCTGGTCGTACCACCGGTATCGTCCTGGACT CCGGTGATGGTGTCTCCCACACCGTTCTCCCTA TAGTGAGTCGTATTAG | 133 |

Figure 14:
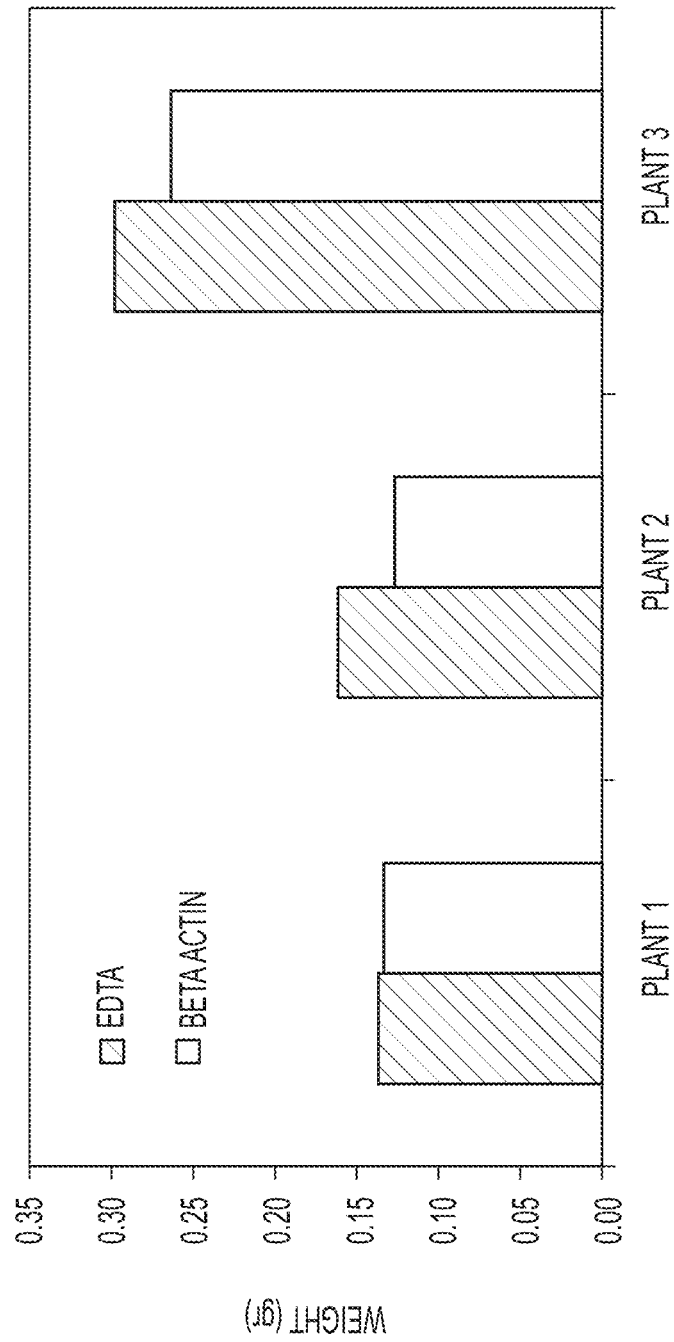
FIG. 14 is a bar graph showing average weight of live *S. littoralis* larvae eight days after feeding on 43-day-old Beta-actin dsRNA trigger-treated and control (EDTA) corn plants.

43 days after seed treatment, the leaves of treated and control plants were used as sole food source for *S. littoralis*. Plant number 1 served as a food source for 20 larvae placed in 130×170 mm box. Plant number 2 served as a food source for 15 larvae placed in 124×95 mm box. Plant number 3 served as a food source for 8 larvae placed in petri dish. The surface of all boxes and plates was covered with vermiculite, and new leaves were supplemented as needed. Mortality and body weight of the caterpillars were tracked throughout the experiment. Eight days after the beginning of the feeding experiment, three larvae out of 43 were found dead in both the Beta-actin treated group and the control group. FIG. 14 shows average weight of live *S. littoralis* larvae eight days after the beginning of feeding.

Example 26: Seed Treatment Against *Spodoptera littoralis* NADPH Gene

Corn seeds were treated with dsRNA molecules (SEQ ID No. 26) having a nucleotide sequence that is essentially identical or essentially complementary to at least 18 contiguous nucleotides of the *S. littoralis* NADPH gene according to the protocol described in Example 1. Briefly, seeds were washed with double distilled water (DDW) prior to treatment for four hours. Next, seeds were dried at 30° C. overnight. Following the drying step, a final concentration of 154 μg/ml dsRNA diluted with 0.1 mM EDTA was used. Treatment was performed by gently shaking the seeds in the solution for 26 hours in a dark growth chamber at 15° C. After treatment, seeds were germinated on wet paper for seven days and then planted in soil and grown at about 25° C. with 16 hours photoperiod. The plants were watered with tap water as necessary. Seeds that were treated with a similar solution not containing dsRNA were germinated and grown alongside the treated plants as a control (EDTA control).

Figure 15A:
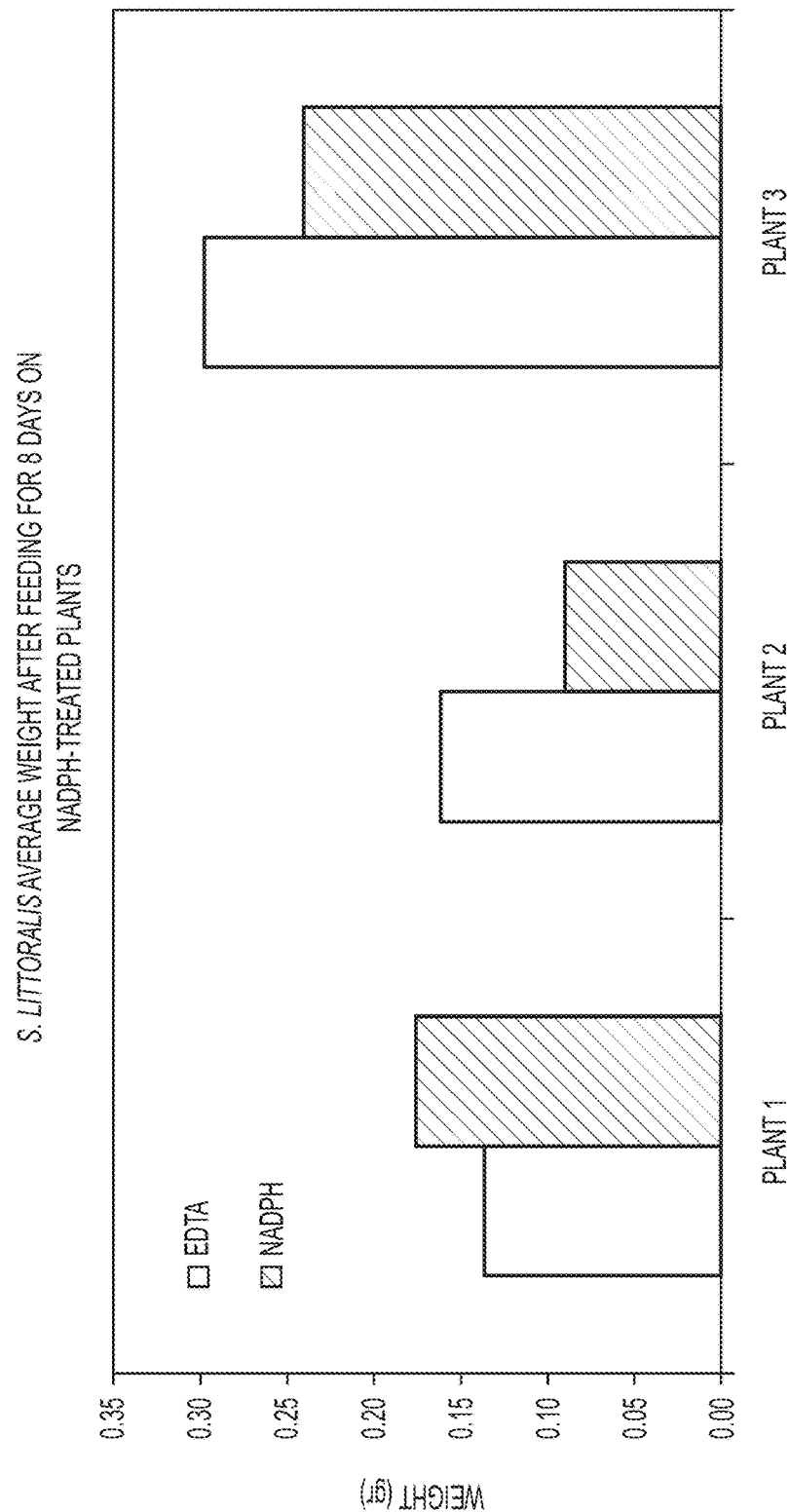
FIGS. 15A-B.

43 days after seed treatment, the leaves of treated and control plants were used as sole food source for *S. littoralis*. Plant number 1 served as a food source for 20 larvae placed in 130×170 mm box. Plant number 2 served as a food source for 15 larvae placed in 124×95 mm box. Plant number 3 served as a food source for 8 larvae placed in petri dish. The surface of all boxes and plates was covered with vermiculite, and new leaves were supplemented as needed. Mortality and body weight of the larvae were tracked throughout the experiment. Eight days after the beginning of the feeding experiment, three larvae out of 43 were found dead in both the NADPH treated group and the control group. FIG. 15A shows average weight of live *S. littoralis* larvae eight days after the beginning of feeding.

Figure 15B:
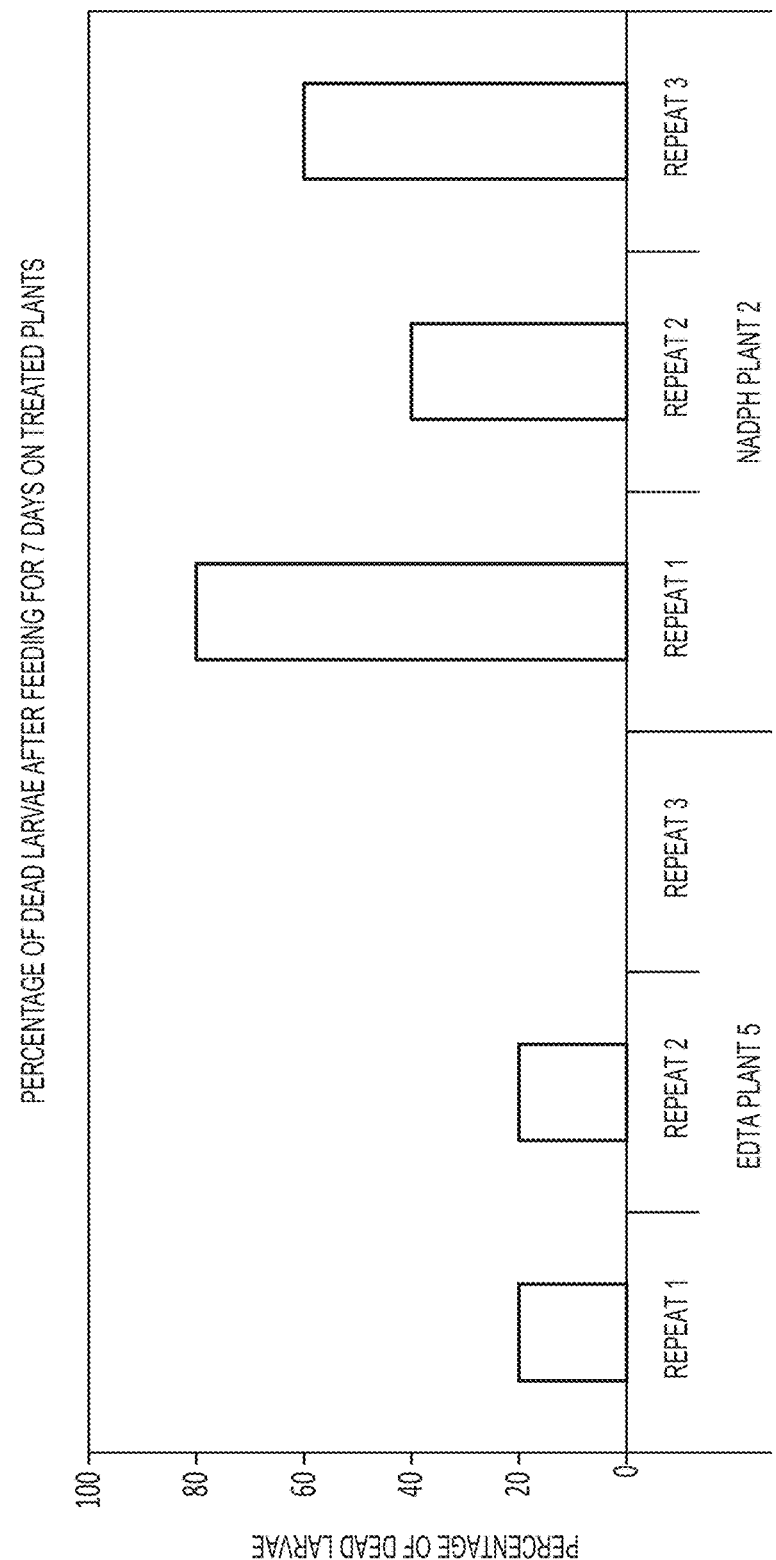

91 days after seed treatment, the leaves of plant number 2 were used for a second time as sole food source for *S. littoralis*. A total of 15 larvae, in three petri dishes containing five larvae each, were fed on the NADPH-treated plant. Additional 15 larvae, in three petri dishes containing five larvae each, were fed on control plant. FIG. 15B shows the percentage of dead larvae seven days after the beginning of experiment. In the NADPH-treated group 9 out of 15 larvae were dead, while in the control group 2 out of 15 larvae were dead.

Example 27: Seed Treatment Against *Spodoptera littoralis* IAP, ATPase and NADPH Genes Corn seeds were treated according to the protocol described in Example 1 with dsRNA molecules (SEQ ID No. 34) having a nucleotide sequence that is essentially identical or essentially complementary to at least 18 contiguous nucleotides of the *S. littoralis* IAP gene or with a solution containing a mix of dsRNAs (SEQ ID Nos. 34, 25, 26, and 31) having a nucleotide sequence that is essentially identical or essentially complementary to at least 18 contiguous nucleotides of the *S. littoralis* IAP, NADPH and ATPase genes. These two solutions were first used for the seed treatment described in Example 7, and then re-used in the experiment described here. Seeds were washed with double distilled water (DDW) prior to treatment for four hours. Next, seeds were dried at 30° C. overnight. Treatment was performed by gently shaking the seeds in the solution for 24 hours in a dark growth chamber at 15° C. After treatment, the seeds were dried overnight at 30° C., planted in soil and grown at about 25° C. with 16 hours photoperiod. The plants were watered with tap water as necessary. Seeds that were treated with a similar solution (EDTA) not containing dsRNA were germinated and grown alongside the treated plants as a control.

Figure 16A:
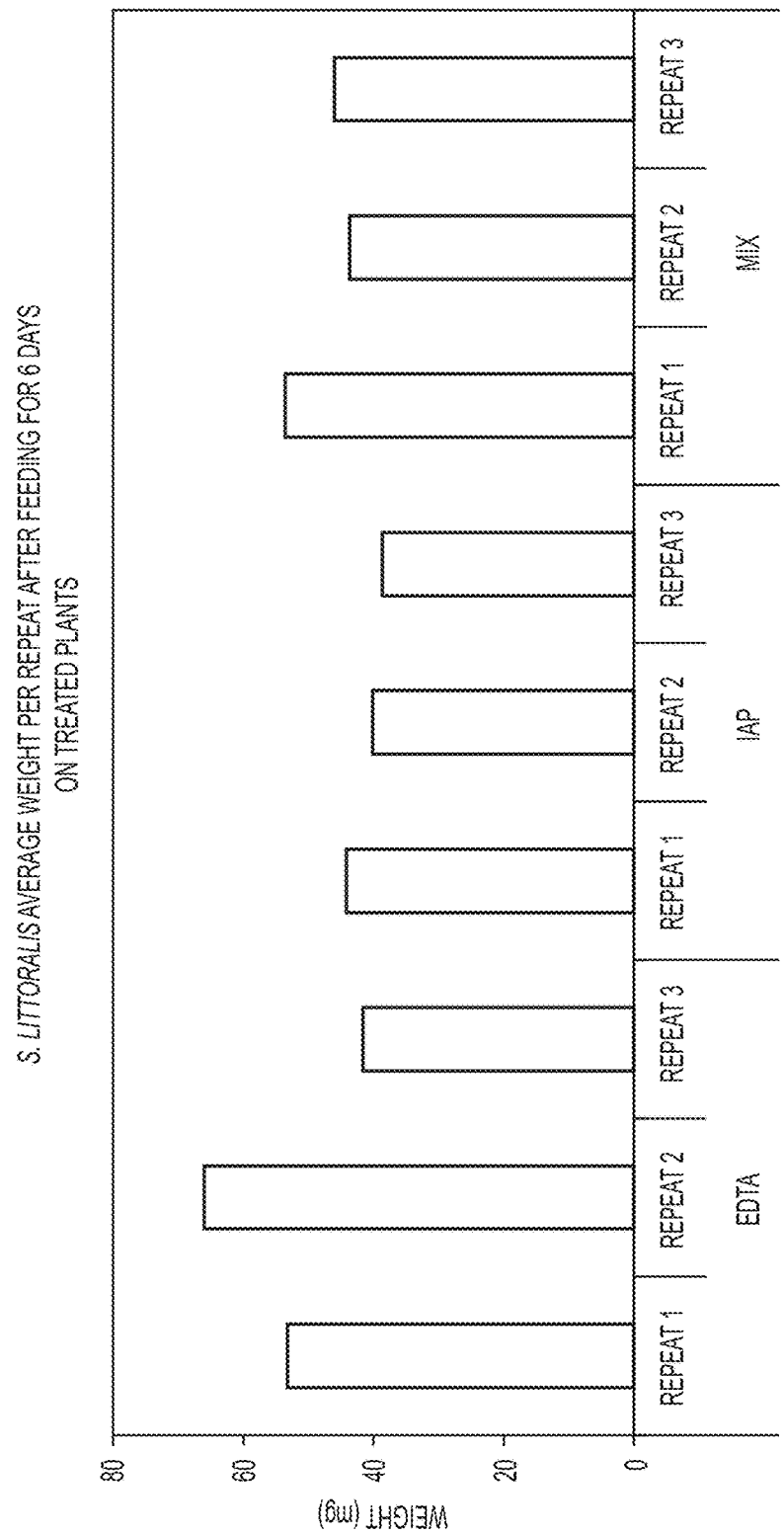
FIGS. 16A-B are bar graphs showing average weight of live *S. littoralis* larvae six days after feeding on 27-day-old dsRNA trigger-treated (IAP or MIX (IAP, NADPH and ATPase)) compared to control (EDTA) plants.
Figure 16B:
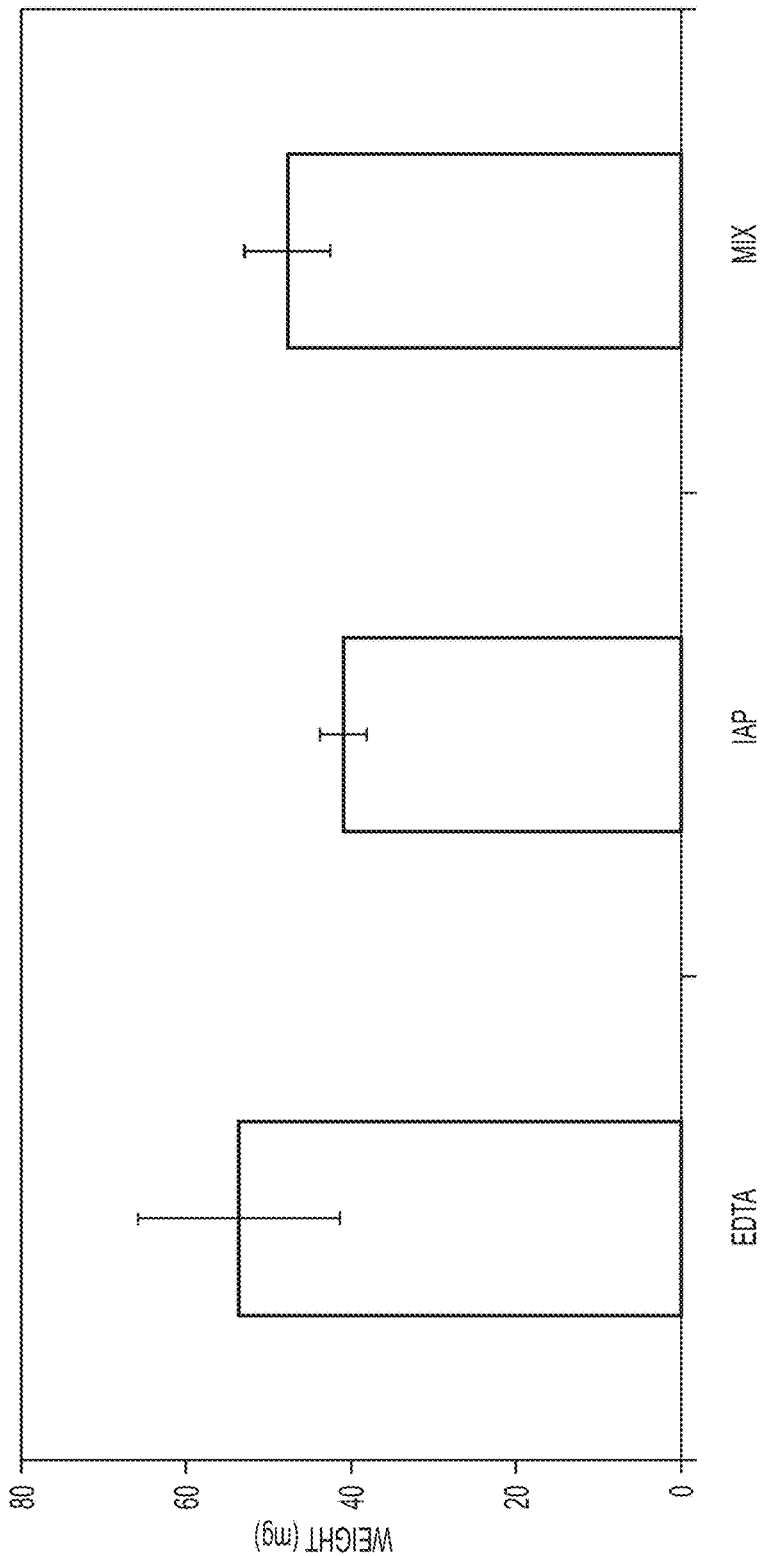

27 days after seed treatment, the leaves of the treated and control plants were used as sole food source for *S. littoralis*. A total of 24 larvae, in three petri dishes containing eight larvae each, were used for each treatment. One repeat from the IAP treatment contained nine larvae. Each repeat was fed from one plant, and three days into the experiment a second plant from the same treatment was added to the plate. Mortality and body weight of the caterpillars were tracked throughout the experiment. FIGS. 16A-B shows average weight of live *S. littoralis* larvae six days after the beginning of the feeding experiment.

Example 28: Seed Treatment Against *Spodoptera littoralis* EF1α Gene

Corn seeds were treated according to the protocol described in Example 1 with two dsRNA molecules having a nucleotide sequence that is essentially identical or essentially complementary to at least 18 contiguous nucleotides of the *S. littoralis* EF1α gene (Table 33). Briefly, seeds were washed with double distilled water (DDW) prior to treatment for four hours. Next, seeds were dried at 30° C. overnight. Two dsRNA sequences (SEQ ID No. 131 and SEQ ID No. 132) were used separately in two different seed treatments; each at a final concentration of 67 µg/ml dsRNA diluted with 0.1 mM EDTA. Treatment was performed by gently shaking the seeds in the solution for 24 hours in a dark growth chamber at 15° C. After treatment, seeds were dried at 30° C. overnight and then planted in soil and grown at about 25° C. with 16 hours photoperiod. The plants were watered with tap water as necessary. Seeds that were treated with dsRNA molecules having a nucleotide sequence that is essentially identical or essentially complementary to at least 18 contiguous nucleotides of the corn DWF1 gene (Table 35) (44 µg/ml for DWF1#1 (SEQ ID No. 134) and 51 µg/ml for DWF1#2 (SEQ ID No. 135)) were germinated and grown alongside the treated plants as two separated controls.

TABLE 35

Control dsRNAs derived from the corn DWF gene.

| Sequence Name | Sequence | SEQ ID No.: |
|---|---|---|
| DWF1 dsRNA #1 | CTAATACGACTCACTATAGGGAGTGTCAACATGGGTCA GATAACCAGAGCTACCTGCCCAATGAACCTTGCCCTTG CGGTCGTCGCCGAGCTCGACGACCTCACTGTTGGTGGG CTGATCAACGGTTACGGCATCGAGGGGAGCTCTCACCT CTATGGCCTTTTCTCCGACACGGTTGTCGCGATGGAGG TTGTTCTCGCAGATGGCCGGGTCGTCAGAGCCACCAAG | 134 |

TABLE 35-continued

Control dsRNAs derived from the corn DWF gene.

| Sequence Name | Sequence | SEQ ID No.: |
|---|---|---|
| | GACAACGAGTACTCTGACCTTTTCTATGGAATTCCCTG GTCCCAGGGAACACTGGGGTTCCTTGTCTCTGCAGAGA TCAAGCTGATCCCCATCAAGGAGTACATGAAGCTCACC TACACTCCAGTCAAGGGGGGTCTAAAGGAGATCGCGCA GGCCTACGCGGATTCTTTCGCTCCGAGGGACGGTGACC CGGCAAAGGTCCCTGACTTTGTTGAAGGGATGGTGTAC ACAGAGAGCGAGGGTGTCATGATGACGGGCGTGTACGC TTCGAAAGAAGAGGCGAAGAAGAAGGGCAACAAGATCA ACTGCGTGGGGTGGTGGTTTAAGCCCTGGTTCTACCTC TCCCTATAGTGAGTCGTATTAG | |
| DWF1 dsRNA #2 | CTAATACGACTCACTATAGGGAGAGCGAGTTTGTGGAG TACATCCCGACGAGGGAGTACTACCACCGGCACACCCG GTGCCTGTACTGGGAGGGGAAGCTGATCCTGCCCTTCG GCGACCAGTTCTGGTTCAGGTTCCTGCTGGGCTGGCTG ATGCCACCGAAGGTGTCCCTGCTGAAGGCGACCCAGGG CGAGGCTATCAGGAACTACTACCACGACAACCATGTGA TCCAGGACATGCTGGTGCCGCTGTACAAGGTTGGGGAT GCGCTGGAGTTCGTGCACCGCGAGATGGAGGTGTATCC TCTGTGGCTGTGCCCTCACCGGCTGTACAAGCTGCCGG TGAAGACGATGGTGTACCCGGAGCCTGGGTTCGAGCAC CAGCACAGGCAGGGCGACGCGAGCTACGCACAGATGTT CACGGACGTGGGCGTGTACTACGCCCCCGGGGCGGTGC TGAGGGGGGAGGAGTTCAACGGCGCGGAGGCTGTGCAC AGGCTGGAGCAGTGGCTGATCGAGAACCACAGCTACCA GCCGCAGTACGCGGTGTCGGAGCTGAACGAGAAGGACT CCTGTCTCCCTATAGTGAGTCGTATTAG | 135 |

35 days after seed treatment, the leaves of the treated and control plants were used as sole food source for *S. littoralis*. Two plants from each treatment and from the DWF1#1 control were included in the feeding experiment. The leaves of each plant were placed in two petri dishes containing 10 larvae each, summing to 40 larvae fed on each seed treatment. Mortality and body weight of the larvae were tracked throughout the experiment. Nine days after the beginning of the feeding experiment, four larvae out of 40 were found dead in the EF1α #2 treated group and in the control group. Six larvae out of 40 were found dead in the EF1α#1 treated group. FIG. 17A shows average weight of live *S. littoralis* larvae nine days after the beginning of the feeding experiment.

Figure 17B:
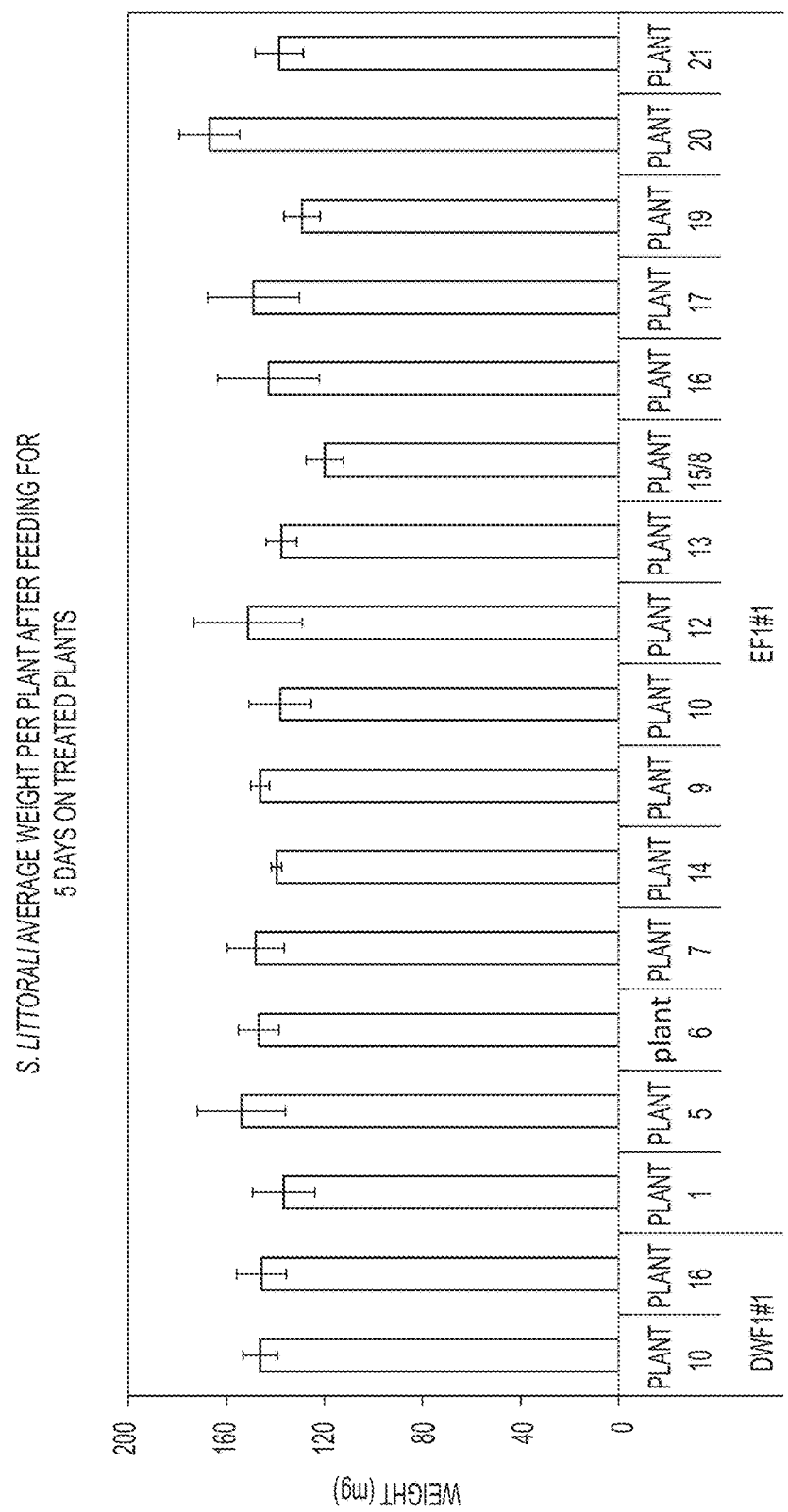

36 days after seed treatment, other plants from the same EF1α#1 and DWF1#1 seed treatment were used as sole food source for *S. littoralis*. Fifteen plants from the treatment were included in the feeding experiment. The leaves of each plant were placed in three petri dishes containing 5 larvae each, summing to 15 larvae per plant and 225 larvae total. Two days into the experiment, plant number 15 was replaced by plant number 8. Two plants from the control group were included in the feeding experiment. The leaves of each control plant were placed in three petri dishes containing 5 larvae each, summing to 15 larvae per plant and 30 larvae total. Body weight of the larvae was tracked throughout the experiment. FIG. 17B shows average weight of *S. littoralis* larvae after five days of feeding.

71 days after seed treatment, the leaves of the EF1α #2 treated and DWF1#2 control plants were used as sole food source for *S. littoralis*. Ten plants from the treatment were included in the feeding experiment, from which two plants were tested for the second time (see FIG. 17A) and eight plants were tested for the first time. The leaves of each plant were placed in three petri dishes containing five larvae each, summing to 15 larvae per plant and 150 larvae total. Two plants from the control group, that were not tested previously, were included in the feeding experiment. The leaves of each control plant were placed in three petri dishes containing five larvae each, summing to 15 larvae per plant and 30 larvae total. Eight days into the experiment, an unusually large number of larvae were found dead in both treatment and control groups. Therefore, this time point was not analyzed further.

Example 29: Seed Treatment Against *Spodoptera littoralis* ATPase Gene

Corn seeds were treated with dsRNA molecules (SEQ ID No. 31) having a nucleotide sequence that is essentially identical or essentially complementary to at least 18 contiguous nucleotides of the *S. littoralis* ATPase gene according to the protocol described in Example 1. Briefly, seeds were washed with double distilled water (DDW) prior to treatment for four hours. Next, seeds were dried at 30° C. overnight. Following the drying step, a final concentration of 145 µg/ml dsRNA diluted with 0.1 mM EDTA was used. The dsRNA solution contained a mixture of un-treated dsRNA molecules and phenol-treated dsRNA molecules as described in Example 1. Treatment was performed by gently shaking the seeds in the solution for 24 hours in a dark growth chamber at 15° C. After treatment, seeds were dried at 30° C. overnight and then planted in soil and grown at about 25° C. with 16 hours photoperiod. The plants were watered with tap water as necessary. Seeds that were treated with 67 µg/ml dsRNA (SEQ ID No. 20) derived from GUS sequence were germinated and grown alongside the treated plants as a control.

Figure 18A:
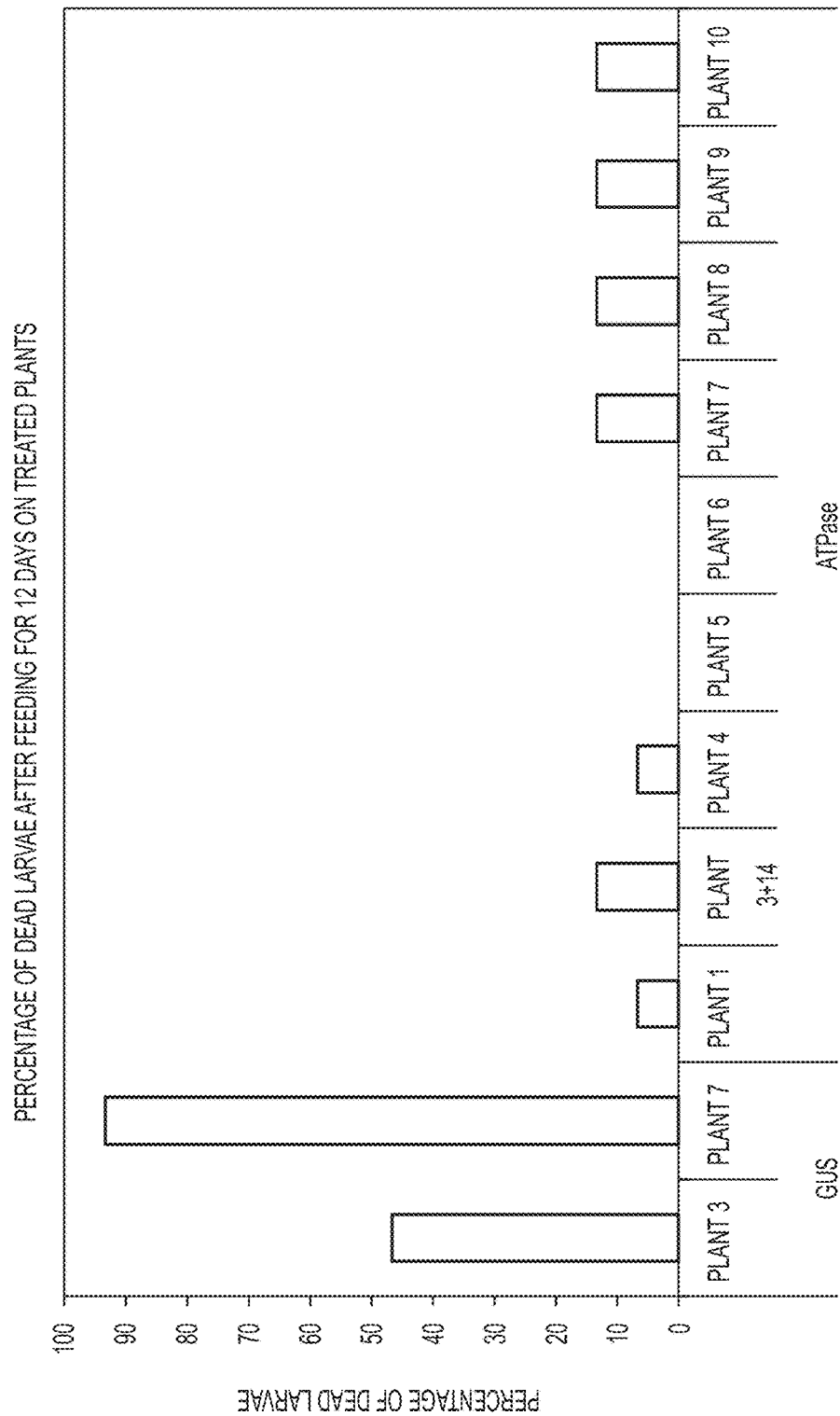
FIGS. 18A-B.

56 days after seed treatment, the leaves of treated and control plants were used as sole food source for *S. littoralis*. Ten plants from the treatment were included in the feeding experiment. The leaves of each plant were placed in three petri dishes containing five larvae each, except for plants number 3 and 14 that were placed together in the same plates. A total of 15 larvae per plant and 135 larvae total were tested. Two plants from the control group were included in the feeding experiment. The leaves of each control plant were placed in three petri dishes containing five larvae each, summing to 15 larvae per plant and 30 larvae total. After twelve days of feeding, 12 out of 135 larvae were found dead in the ATPase treated group and 21 out of 30 larvae were found dead in the control group. FIG. 18A shows the percentage of dead larvae 12 days after the beginning of experiment.

Figure 18B:
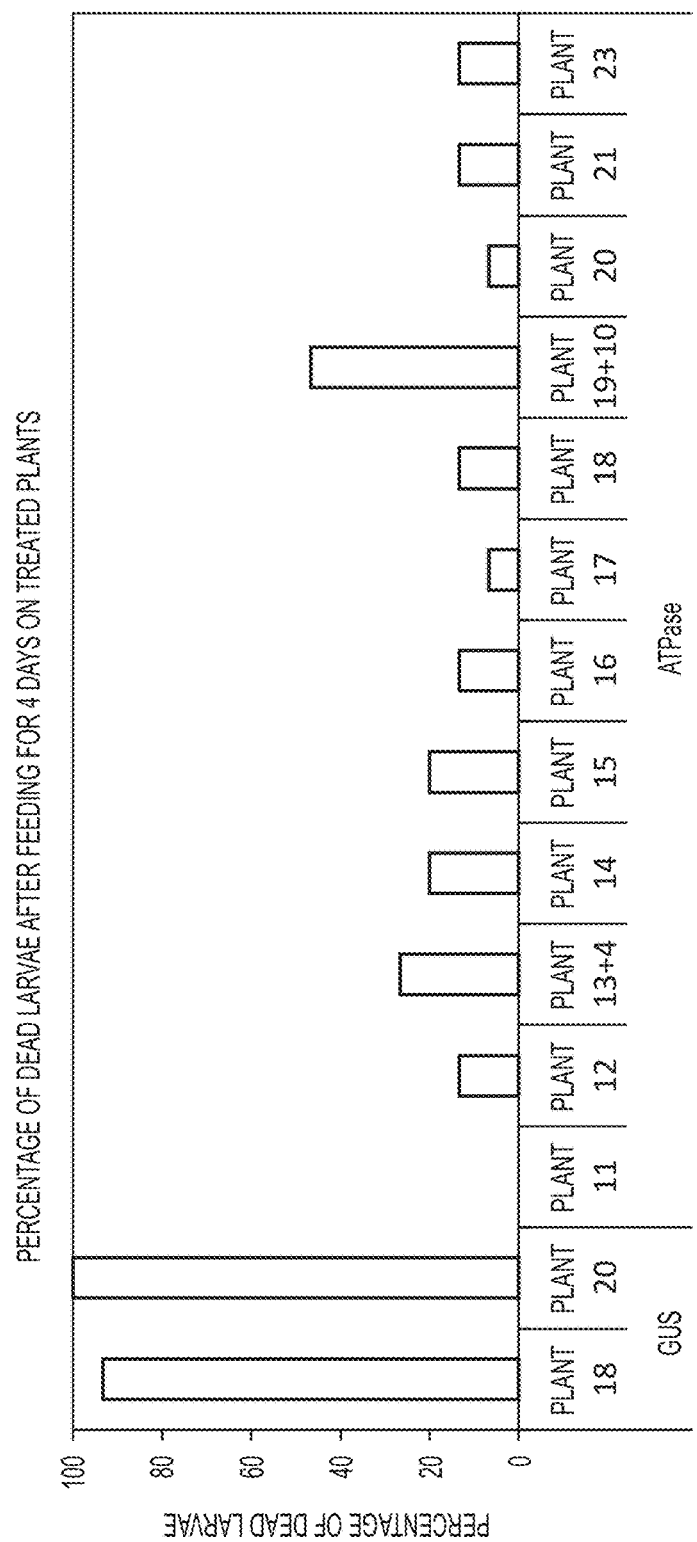

57 days after seed treatment, other plants from the same treated and control groups were used as sole food source for *S. littoralis*. Fourteen plants from the treatment were included in the feeding experiment. The leaves of each plant were placed in three petri dishes containing five larvae each, except for plants number 13 and 4, which were placed together in the same plates, and plants number 10 and 19, which were placed together in the same plates (plants 4 and 10 were analyzed for the second time, see FIG. 18A). A total of 15 larvae per plant and 180 larvae overall were tested. Two plants from the control group were included in the feeding experiment. The leaves of each control plant were placed in three petri dishes containing five larvae each, summing to 15 larvae per plant and 30 larvae total. Four days after feeding begun, 29 larvae out of 180 were found dead in the ATPase treated group and 29 larvae out of 30 were found dead in the control group. FIG. 18B shows the percentage of dead larvae four days after the beginning of experiment.

Example 30: Seed Treatment Against *Spodoptera littoralis* EF1α Gene

Corn seeds (var. Vivani) were treated with dsRNA molecules (SEQ ID Nos. 131 and 132) having a nucleotide sequence that is essentially identical or essentially complementary to at least 18 contiguous nucleotides of the *S. littoralis* EF1α gene according to the protocol described in Example 1. A mixture of 25 µg/ml from each of the two dsRNAs was used. The dsRNA was diluted either with 0.1 mM EDTA alone, or additionally mixed with 40 µg/ml of PEG-modified carbon nanotubes (CNTP). Treatment was performed by gently shaking the seeds in the solution for 4 hours in a dark growth chamber at 15° C. After treatment, seeds were planted in soil and grown at about 25° C. with 16 hours photoperiod. The plants were watered with tap water as necessary. Seeds that were treated with 50 µg/ml dsRNA derived from GFP sequence (SEQ ID No. 124), or with a similar solution not containing dsRNA, with or without 40 µg/ml of PEG-modified carbon nanotubes, were germinated and grown alongside the treated plants as a control.

Figure 19A:
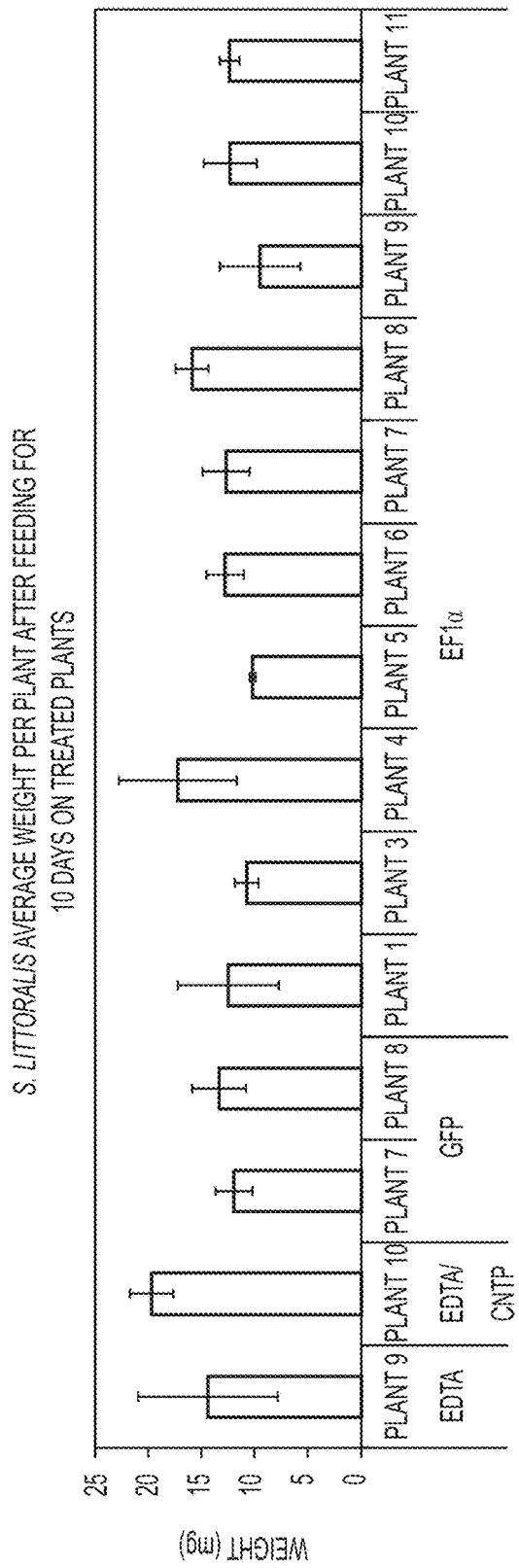
FIGS. 19A-B.

24 days after seed treatment, leaves of treated and control plants were used as sole food source for *S. littoralis*. Ten plants from the EF1α treatment group, two plants from the GFP control, one plant from the EDTA control and one plant from the EDTA/CNTP control were included in the feeding experiment. The leaves of each plant were placed in three petri dishes containing five larvae each, summing to 15 larvae per plant, 150 larvae for EF1α treatment, 30 larvae for GFP control and 15 for both of the EDTA controls. FIG. 19A shows average weight of *S. littoralis* larvae after ten days of feeding.

Figure 19B:
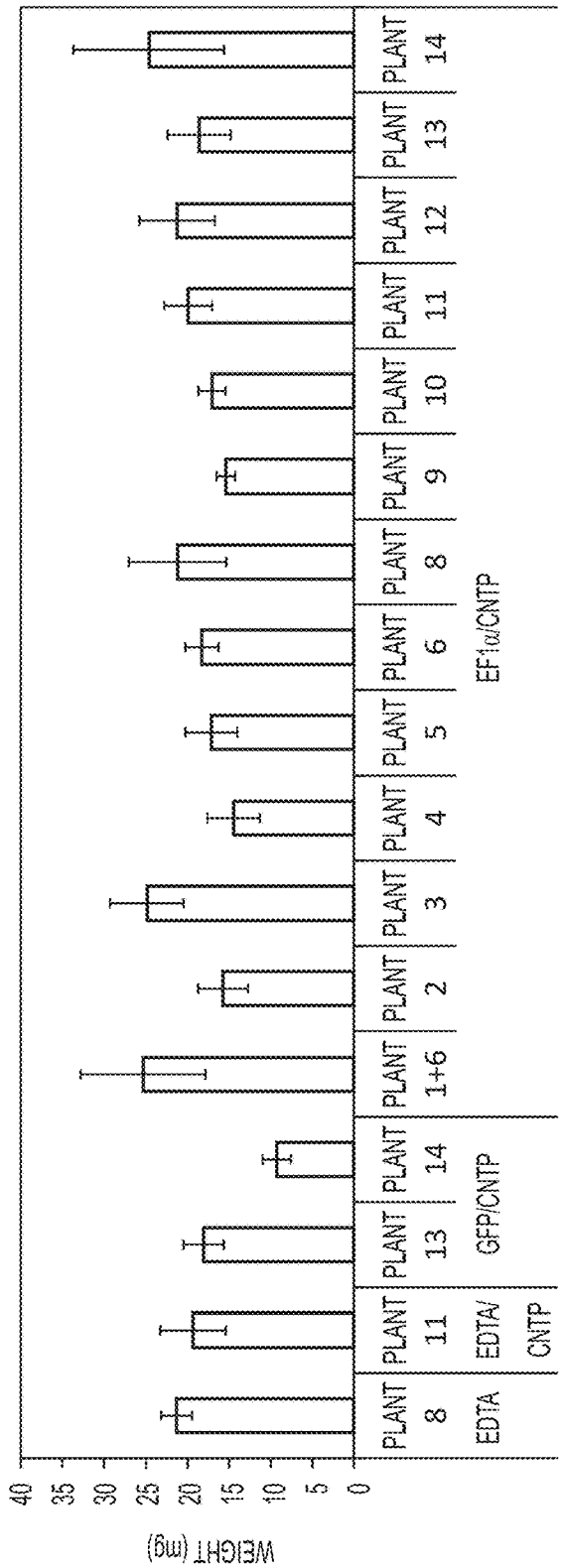

25 days after seed treatment, leaves of treated and control plants were used as sole food source for *S. littoralis*. Thirteen plants from the EF1α/CNTP treatment group, two plants from the GFP/CNTP control, one plant from the EDTA/CNTP control and one plant from the EDTA control were included in the feeding experiment. The leaves of each plant were placed in three petri dishes containing five larvae each, summing to 15 larvae per plant, except for plant 9 in the EF1α/CNTP group, where only two plates were analyzed. A total of 190 larvae for EF1α/CNTP treatment, 30 larvae for GFP/CNTP control and 15 larvae for both of the EDTA controls were tested. Seven days into the feeding experiment, plant 1 from the EF1α/CNTP group was replaced by plant 6 from the same group. FIG. 19B shows average weight of *S. littoralis* larvae after ten days of feeding. To determine the expression levels of EF1α in the larvae ten days after feeding on treated plants, each repeat (plate) of five larvae was pooled together, and total RNA was extracted. cDNA was prepared using oligo-dT primers (SEQ ID Nos. 136-143) and the expression level of *S. littoralis* EF1α mRNA was determined in treated and control larvae by real-time PCR with SYBR Green (Quanta BioSciences), using Actin and ATPase as normalizers. No significant change in EF1α expression levels (Wilcoxon rank-sum test, p-value>0.05) was observed.

61 days after seed treatment, leaves of treated and control plants were used again as sole food source for *S. littoralis*. Thirteen plants from the EF1α/CNTP treatment group and three plants from the GFP/CNTP control were included in the feeding experiment. Some of the plants from the EF1α/CNTP group were tested for the first time and some were tested for the second time (see FIG. 19B). The three plants from the GFP/CNTP control were tested for the first time. The leaves of each plant were placed in three petri dishes containing five larvae each, summing to 15 larvae per plant, except for plant 8 in the EF1α/CNTP group, where only two plates were analyzed. A total of 190 larvae for EF1α/CNTP treatment and 45 larvae for GFP/CNTP control were tested. Twelve days into the experiment, an unusually large number of larvae were found dead in both treatment and control groups. Therefore, this time point was not further analyzed.

Example 31: Seed Treatment Against *Spodoptera littoralis* EF1α Gene

Corn seeds (var. 01DKD2) were treated with dsRNA molecules (SEQ ID Nos. 131 and 132) having a nucleotide sequence that is essentially identical or essentially complementary to at least 18 contiguous nucleotides of the *S. littoralis* EF1α gene according to the protocol described in Example 1. A mixture of 25 μg/ml from each of the two dsRNAs was used. The dsRNA was diluted either with 0.1 mM EDTA alone, or additionally mixed with 40 μg/ml of PEG-modified carbon nanotubes (CNTP). Treatment was performed by gently shaking the seeds in the solution for 4 hours in a dark growth chamber at 15° C. After treatment, seeds were planted in soil and grown at about 25° C. with 16 hours photoperiod. The plants were watered with tap water as necessary. Seeds that were treated with 50 μg/ml dsRNA (SEQ ID No. 20) derived from GUS sequence, with or without 40 μg/ml of PEG-modified carbon nanotubes, were germinated and grown alongside the treated plants as a control.

Figure 20A:
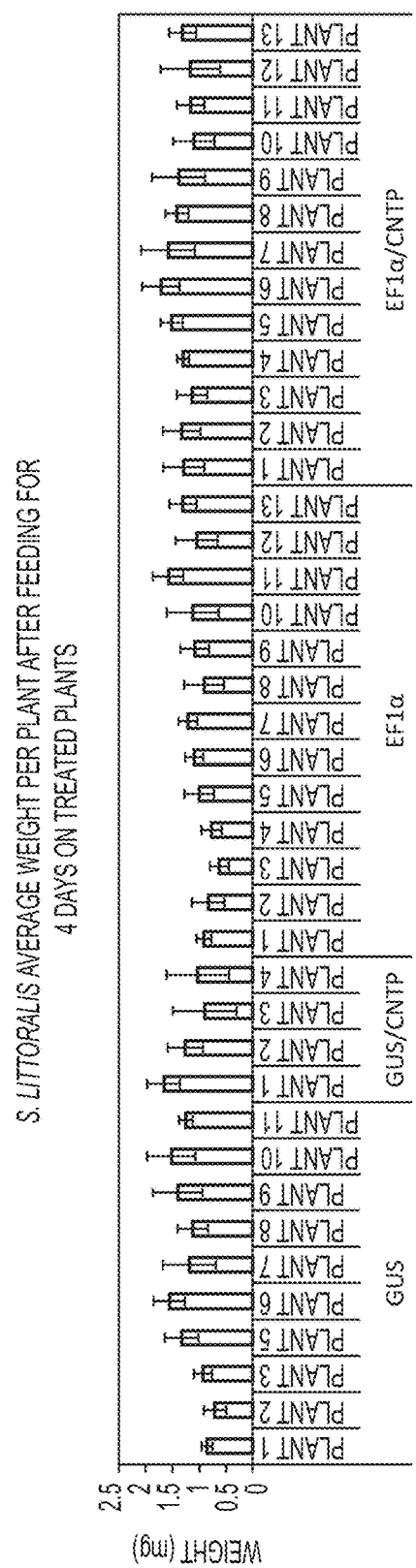
FIGS. 20A-B are bar graphs showing average *S. littoralis* larvae weight 4 days after feeding on eight-day-old dsRNA trigger-treated (EF1α and EF1α/CNTP) and control (GUS and GUS/CNTP) corn plants.
Figure 20B:
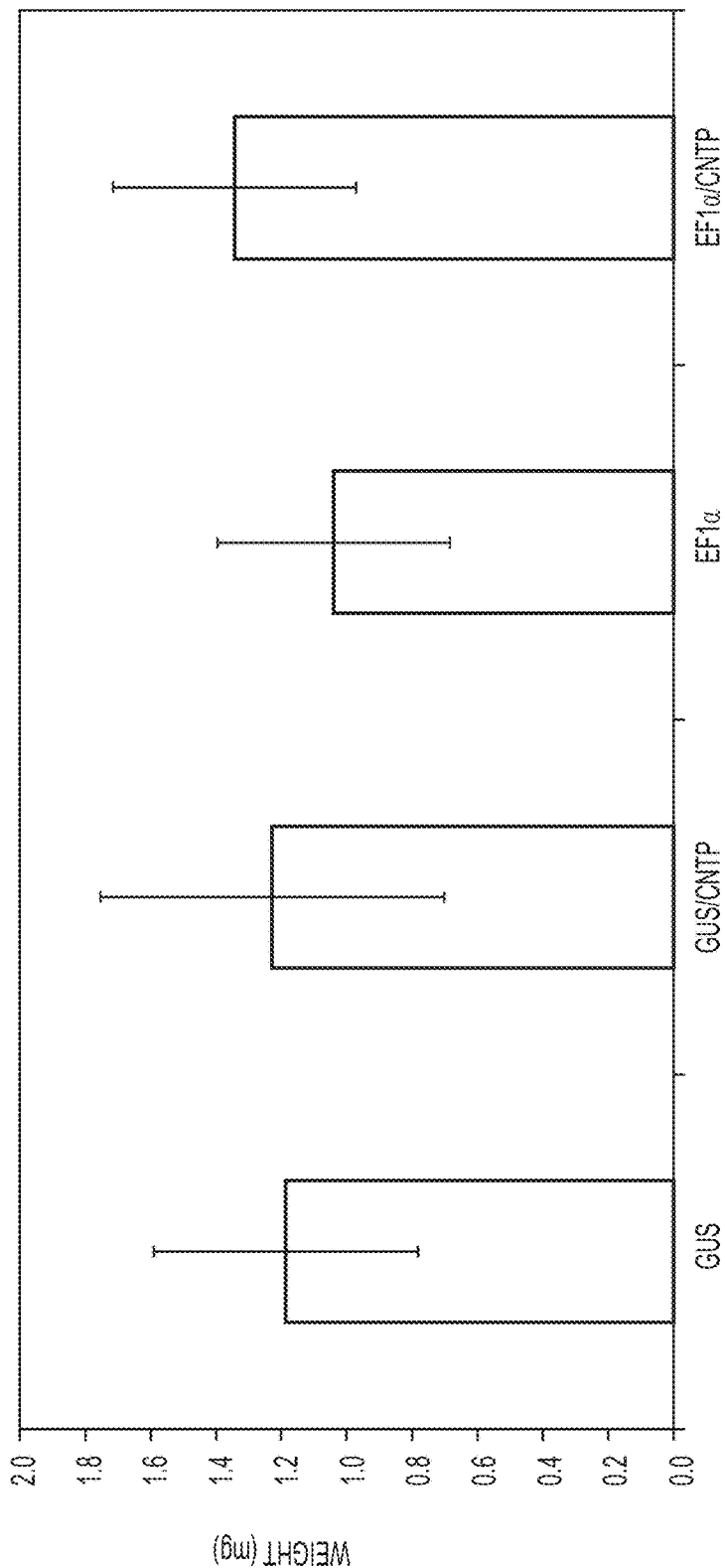

Eight days after seed treatment, the leaves of treated and control plants were used as sole food source for *S. littoralis*. Thirteen plants from the EF1α treatment, thirteen plants from the EF1α/CNTP treatment, ten plants from the GUS control and four plants from the GUS/CNTP control were included in the feeding experiment. The leaves of each plant were placed in two petri dishes covered with 1% agar. Each plate contained three larvae, summing to six larvae per plant, 78 larvae for both the EF1α and EF1α/CNTP treatments, 60 larvae for the GFP control and 24 for the GUS/CNTP control. Body weight of the larvae was recorded four days after feeding. FIGS. 20A-B shows average weight of *S. littoralis* larvae in control and treatment groups.

Example 32: Seed Treatment Against *Spodoptera littoralis* IAP, ATPase and NADPH Genes Tomato plants grown from the tomato seeds described in Example 7, which were treated with dsRNA molecules (SEQ ID Nos. 34, 35, 25 and 26) having a nucleotide sequence that is essentially identical or essentially complementary to at least 18 contiguous nucleotides of the *S. littoralis* IAP gene, ATPase gene or NADPH gene were examined further for control of *S. littoralis*.

Figure 21:
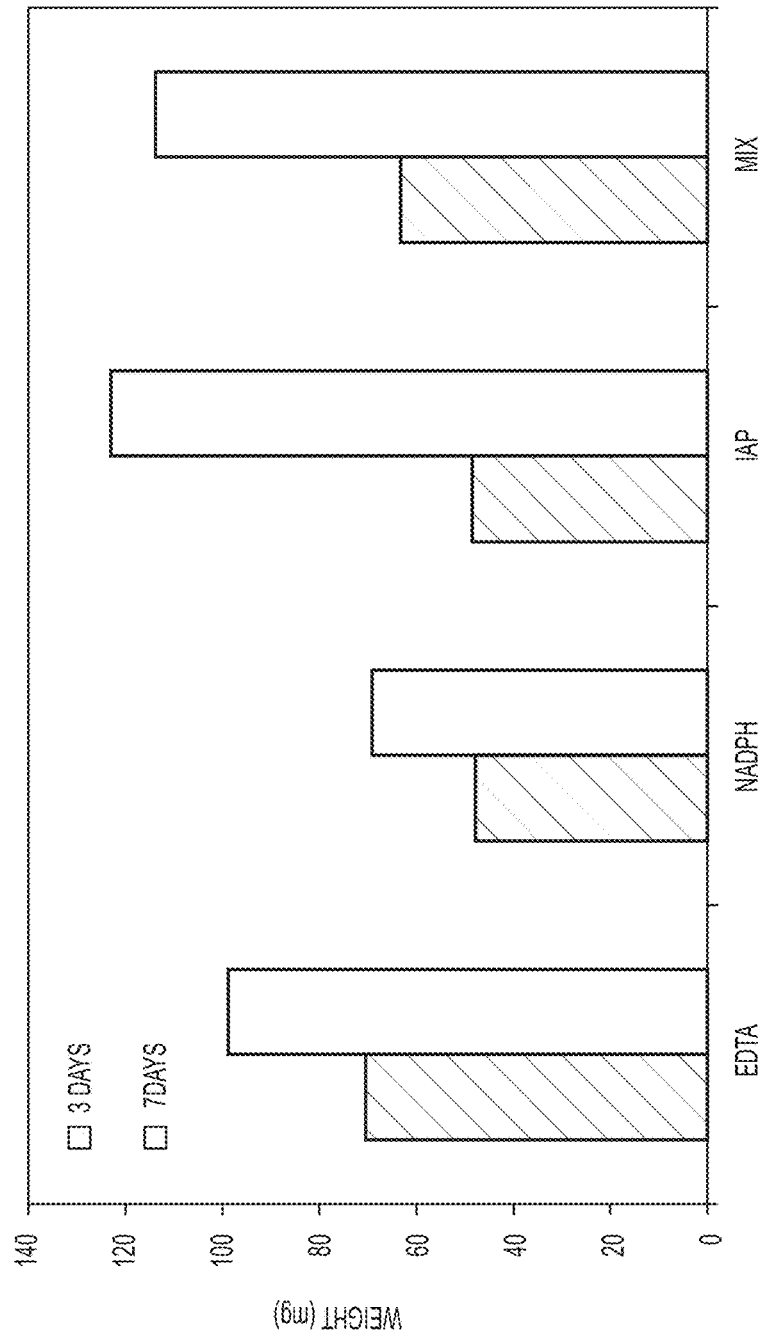
FIG. 21 is a bar graph showing average weight of live *S. littoralis* larvae three and seven days after feeding on 48-day-old dsRNA trigger-treated (NADPH, IAP, and MIX (IAP, ATPase and NADPH)) and control (EDTA) tomato plants.

48 days after seed treatment, the leaves of treated and control plants were used as sole food source for *S. littoralis*. One plant from each treatment served as a food source for seven larvae placed in a petri dish. The surface of all plates was covered with vermiculite. Mortality and body weight of the larvae were tracked throughout the experiment. Three days into the experiment, one larva was found dead in the IAP treated group, and two larvae were found dead in the MIX treated group. No further death occurred in the following days up to day 7. FIG. 21 shows the average weight of live *S. littoralis* larvae after three and seven days of feeding.

Example 33: Seed Treatment Against *Spodoptera littoralis* Beta Actin, ATPase and NADPH Genes Tomato seeds were treated with dsRNA molecules (SEQ ID Nos. 133, 31, 25, and 26) having a nucleotide sequence that is essentially identical or essentially complementary to at least 18 contiguous nucleotides of the *S. littoralis* Beta actin gene (see Table 34), ATPase gene or NADPH gene according to the protocol described in Example 1. A final concentration of 96 μg/ml dsRNA for Beta actin, 73 μg/ml dsRNA for ATPase and 164 μg/ml dsRNA for NADPH, diluted with 0.1 mM EDTA was used. Treatment was performed by gently shaking the seeds in the solution for 26 hours in a dark growth chamber at 15° C. After treatment, seeds were germinated in soil and grown at about 25° C. with 16 hours photoperiod. The plants were watered with tap water as necessary. Seeds that were treated with a similar solution (EDTA) not containing dsRNA were germinated and grown alongside the treated plants as a control.

Figure 22:
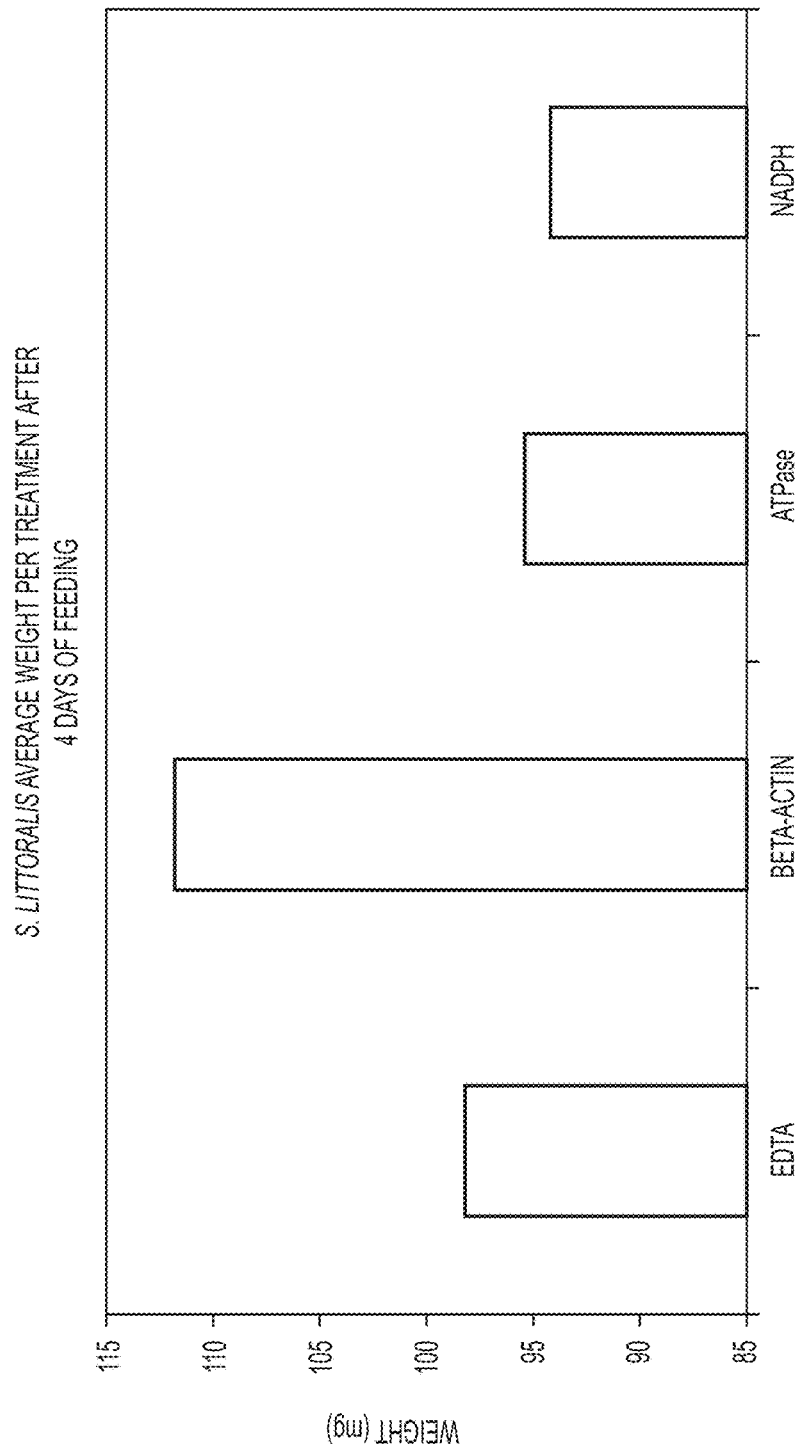
FIG. 22 is a bar graph showing average weight of live *S. littoralis* larvae after feeding for four days on 42-day-old dsRNA trigger-treated (Beta-actin, ATPase and NADPH) and control (EDTA) tomato plants.

42 days after seed treatment, the leaves of treated and control plants were used as sole food source for *S. littoralis*. Plants number 1 and 2 from the Beta actin and ATPase treatments and plants number 21 and 23 from the NADPH treatment were used. The plants from each treatment served as a food source for five larvae placed in a petri dish. The surface of all plates was covered with vermiculite. Body weight of the larvae was tracked throughout the experiment. FIG. 22 shows average weight of *S. littoralis* larvae after four days of feeding.

Example 34: Seed Treatment Against *Spodoptera littoralis* ATPase Gene

The tomato plants described in this Example originate from the seed treatment with ATPase dsRNA described in Example 33 above.

Figure 23A:
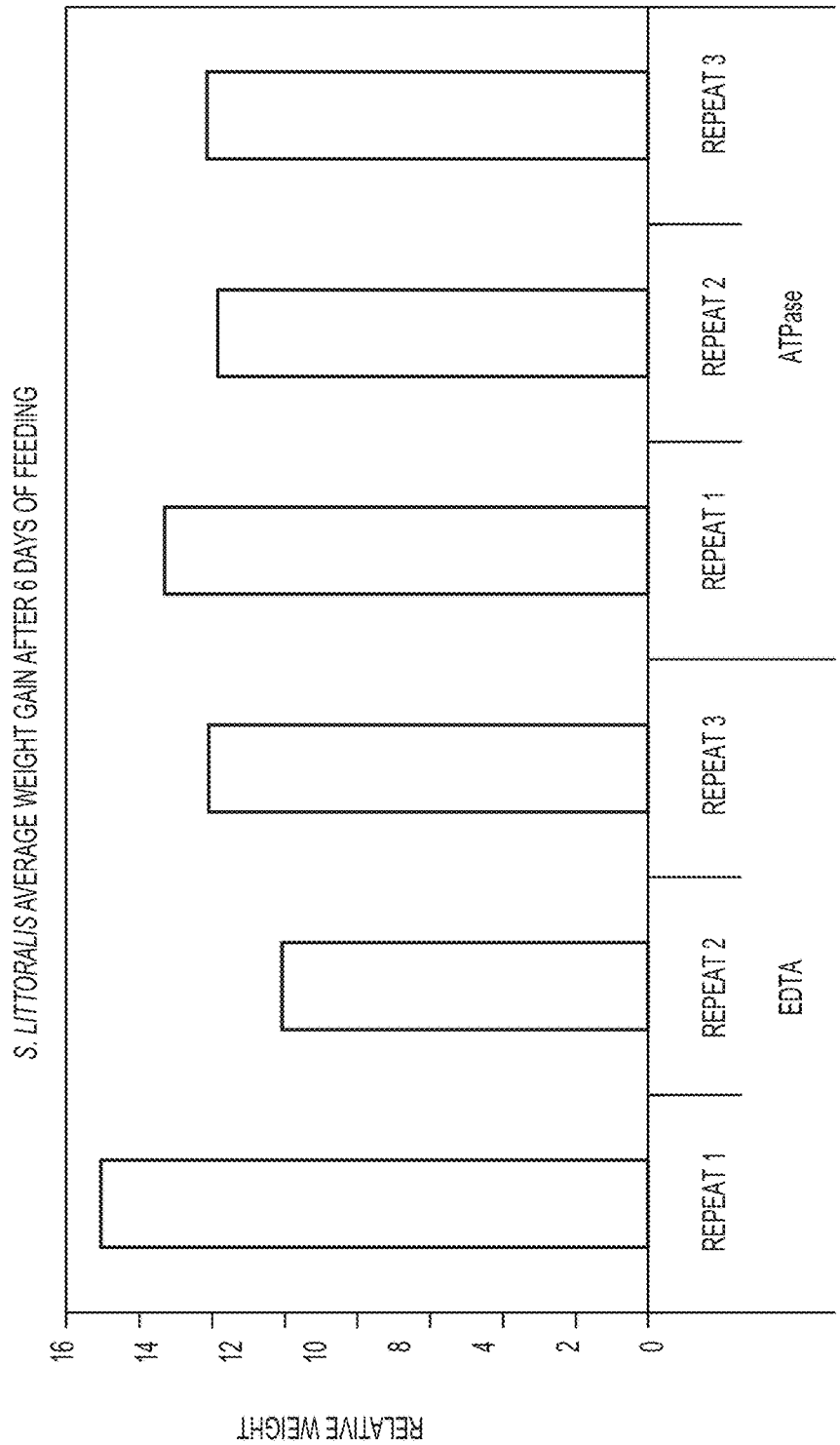
FIGS. 23A-B.

85 days after seed treatment, the leaves of treated and control plants described in Example 33 were used again as sole food source for *S. littoralis*. One plant from the ATPase treatment and one plant from the control were used. Leaves from these plants were placed in three petri dishes contain five larvae each. Three days into the experiment, another plant from the treatment and another plant from the control were added to their respective plates. Body weight of the larvae was tracked throughout the experiment. Since at the onset of the feeding experiment the larvae fed from the control group were 30% smaller when the larvae fed from the treatment, the weight of the larvae relative to their initial weight was recorded. FIG. 23A shows relative weight of *S. littoralis* larvae after six days of feeding.

Figure 23B:
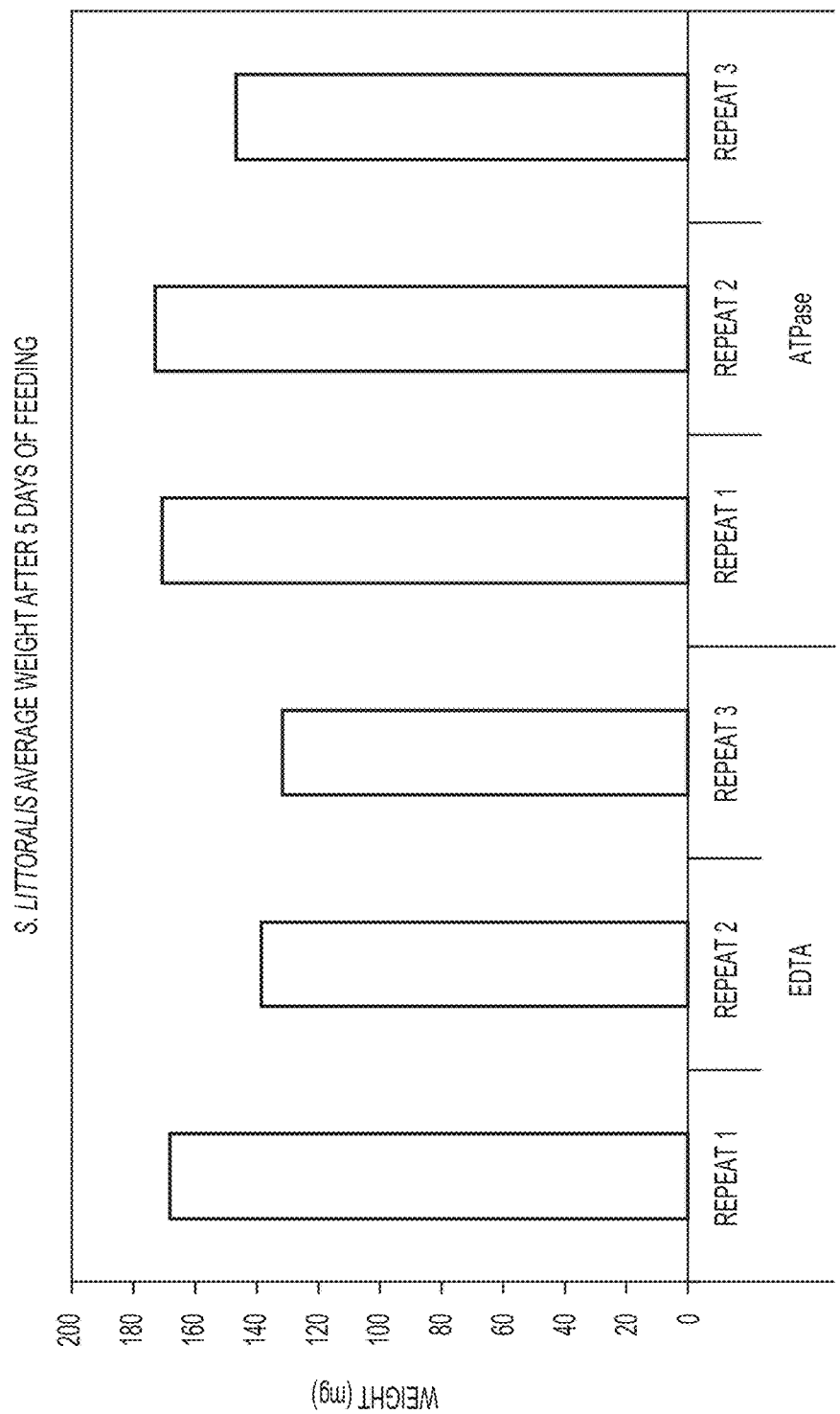

88 days after seed treatment, other plants from the same seed treatment were used as sole food source for *S. littoralis*. Three plants from the ATPase treatment and two plants from the control were used. Leaves from these plants were placed in three petri dishes contain five larvae each. Mortality and body weight of the larvae were tracked throughout the experiment. After feeding for five days, 4 out of 15 and 1 out of 15 worms were found dead in the ATPase and control group, respectively. FIG. 23B shows average weight of live *S. littoralis* larvae after five days of feeding.

Example 35: Seed Treatment Against *Spodoptera littoralis* NADPH Gene

The tomato plants described in this Example originate from the seed treatment with NADPH dsRNA described in Example 33 above.

Figure 24A:
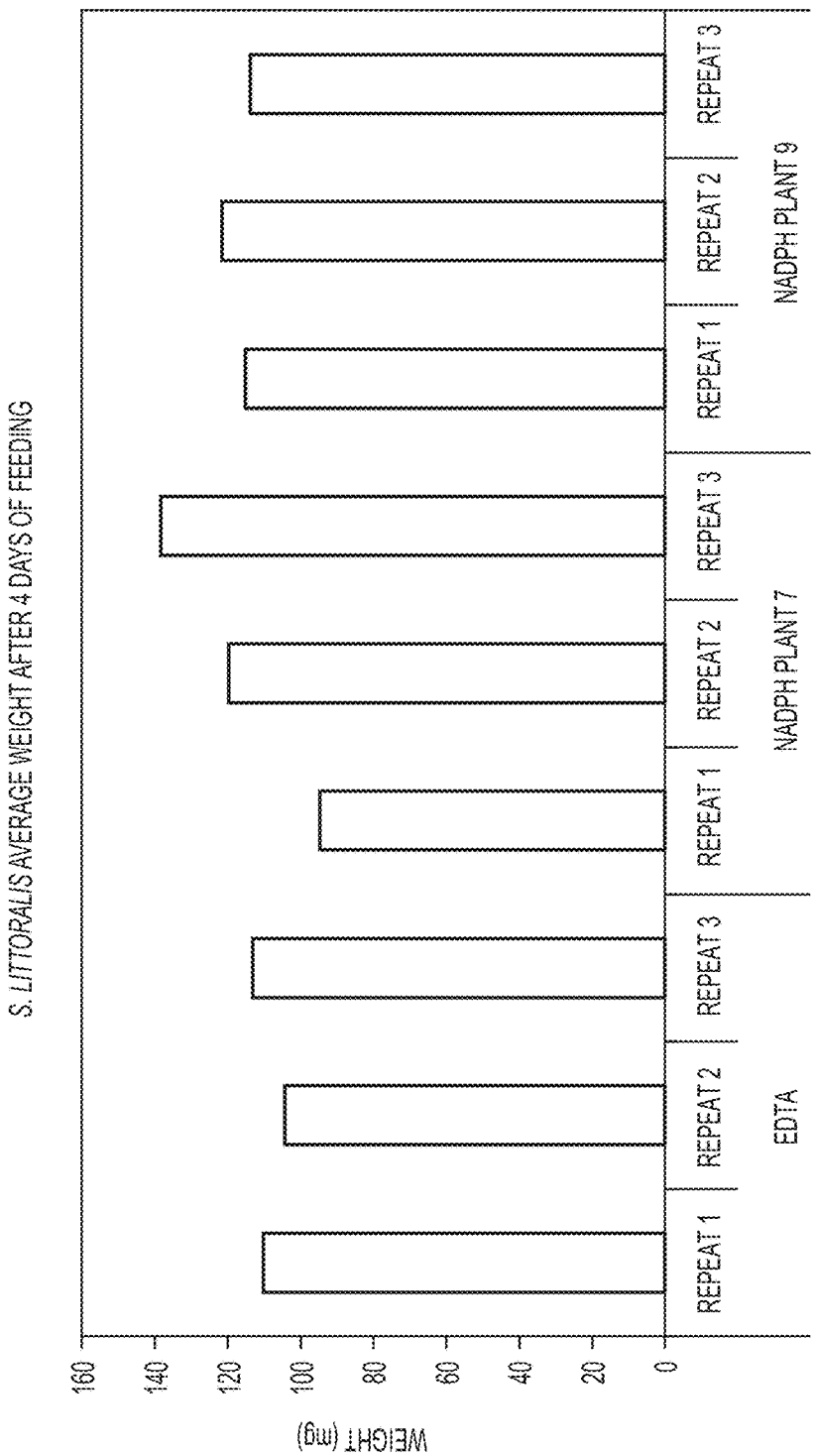
FIGS. 24A-B.
Figure 24B:
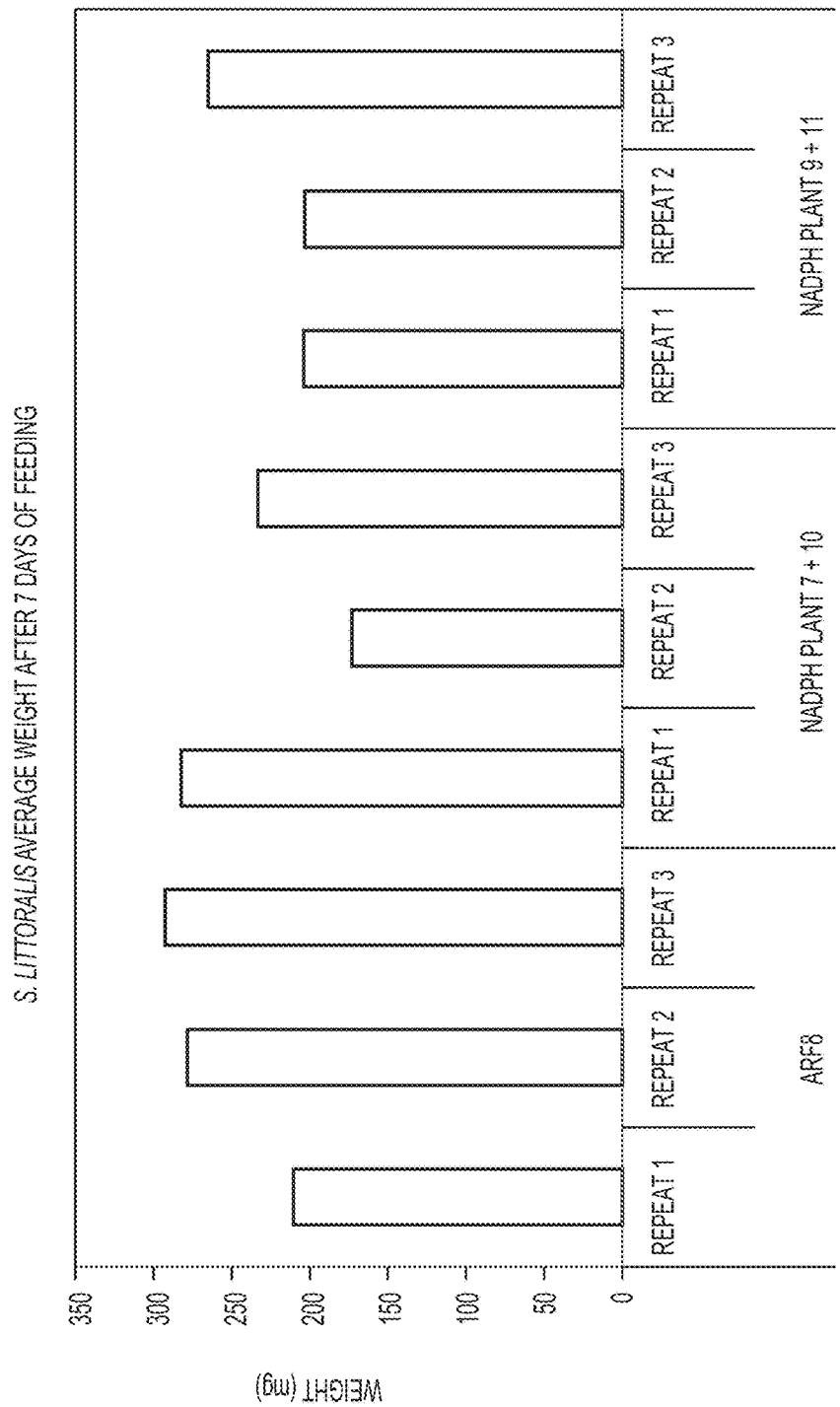

95 days after seed treatment, leaves of treated and control plants were used as sole food source for *S. littoralis*. Two plants from the NADPH treatment (not tested previously) and a pool of plants from the control were used. Leaves from these plants were placed in three petri dishes contain five larvae each. Body weight of the caterpillars was tracked throughout the experiment. FIG. 24A shows average weight of *S. littoralis* larvae after four days of feeding. On the fourth day, the control plants were replaced by plants that were germinated from seeds treated against the tomato gene AFR8. These seeds were treated with a mixture of two dsRNA sequences (SEQ ID Nos. 25 and 26) at a final concentration of 200 µg/ml (100 µg/ml from each dsRNA) for 24 hours. On the sixth day, another plant was added to each of the two NADPH treated plants. FIG. 24B shows average weight of *S. littoralis* larvae seven days after the feeding experiment begun.

Example 36: Seed Treatment Against Non-*Spodoptera littoralis* Genes

The corn plants described in this Example originate from the seed treatments described in Example 28 (DWF1 dsRNA#2, SEQ ID NO 135) and in Example 29 (GUS, SEQ ID NO 20).

69 days after seed treatment, the leaves of the germinated plants were used as sole food source for *S. littoralis*. Two plants from the DWF1 dsRNA#2 treatment and five plants from the GUS treatment were included in the feeding experiment. The leaves of each plant were placed in three petri dishes containing five larvae each, summing to 15 larvae per plant, 30 larvae for the DWF1 dsRNA#2 treatment and 75 larvae for the GUS treatment. Ten days into the experiment, an unusually large number of larvae were found dead in both treatments. Due to the large number of death in both treatment groups, this experimental time point was not further analyzed.

70 days after seed treatment, other plants from the same treatments were used as sole food source for *S. littoralis*. Two plants from the DWF1 dsRNA#2 treatment and 16 plants from the GUS treatment were included in the feeding experiment. The leaves of each plant were placed in three petri dishes containing five larvae each, summing to 15 larvae per plant, 30 larvae for the DWF1 dsRNA #2 treatment and 240 larvae for the GUS treatment. Nine days into the experiment, an unusually large number of larvae were found dead in both treatments. Due to the large number of death in both treatment groups, this experimental time point was not further analyzed.

Example 37: Seed Treatment Against *Spodoptera littoralis* ATPase, EF1α and NADPH Genes Corn seeds (var. Vivani) were treated with dsRNA molecules (SEQ ID Nos. 131, 132, 31, 25 and 26) having a nucleotide sequence that is essentially identical or essentially complementary to at least 18 contiguous nucleotides of the *S. littoralis* EF1α gene, ATPase gene or NADPH gene according to the protocol described in Example 1, without pre-treatment wash. The two EF1α dsRNAs were used separately. A final concentration of 160 µg/ml dsRNA, diluted with 0.1 mM EDTA, was used. Treatment was performed by gently shaking the seeds in the solution for 2 hours in a dark growth chamber at 15° C. After treatment, seeds were washed briefly with DDW, planted in soil and grown at about 25° C. with 16 hours photoperiod. The plants were watered with tap water as necessary. Seeds that were treated with 160 µg/ml dsRNA (SEQ ID No. 124) derived from GFP sequence, or with a similar solution not containing dsRNA (EDTA) were germinated and grown alongside the treated plants as a control.

Figure 25A:
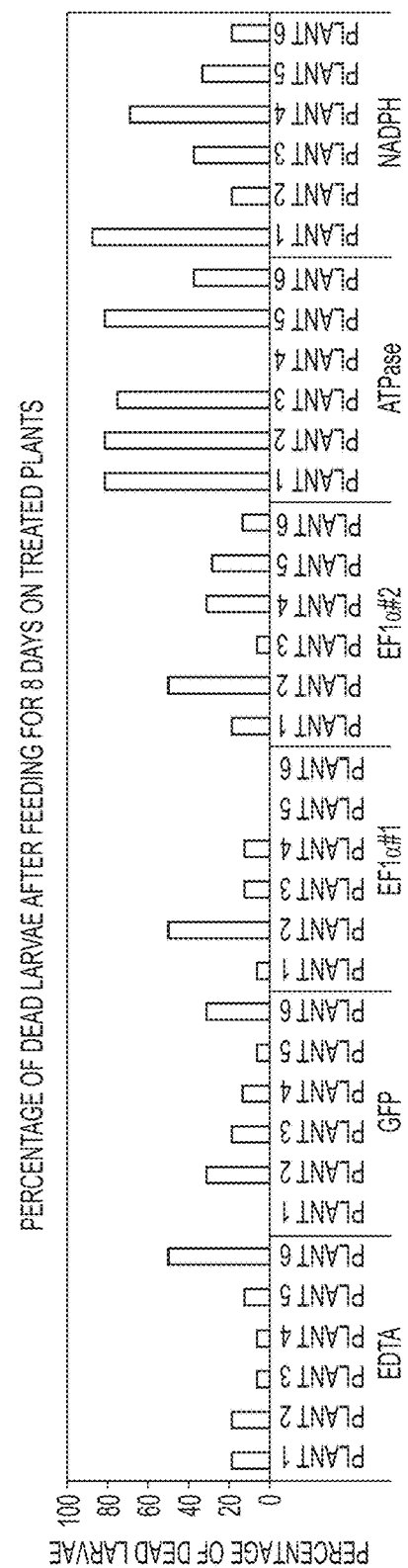
FIGS. 25A-F.
Figure 25B:
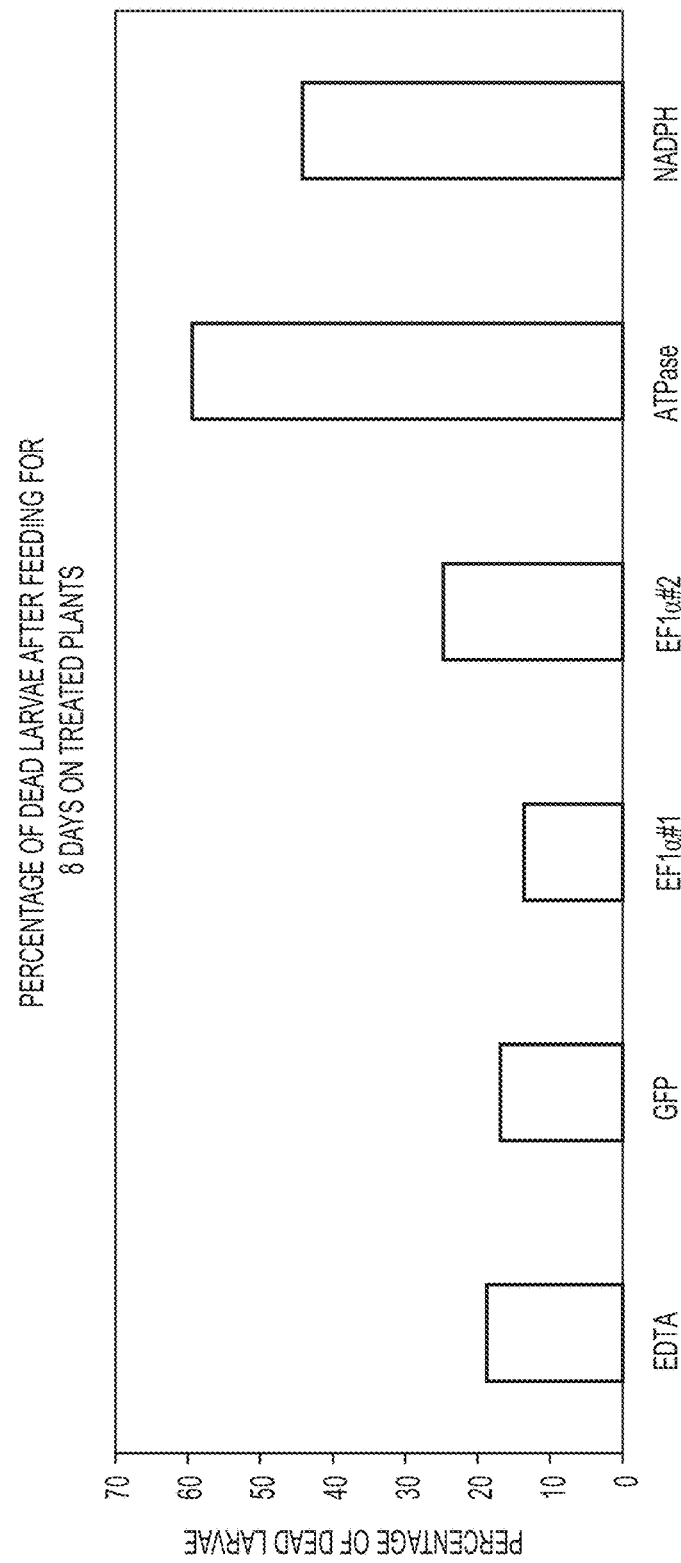
Figure 25C:
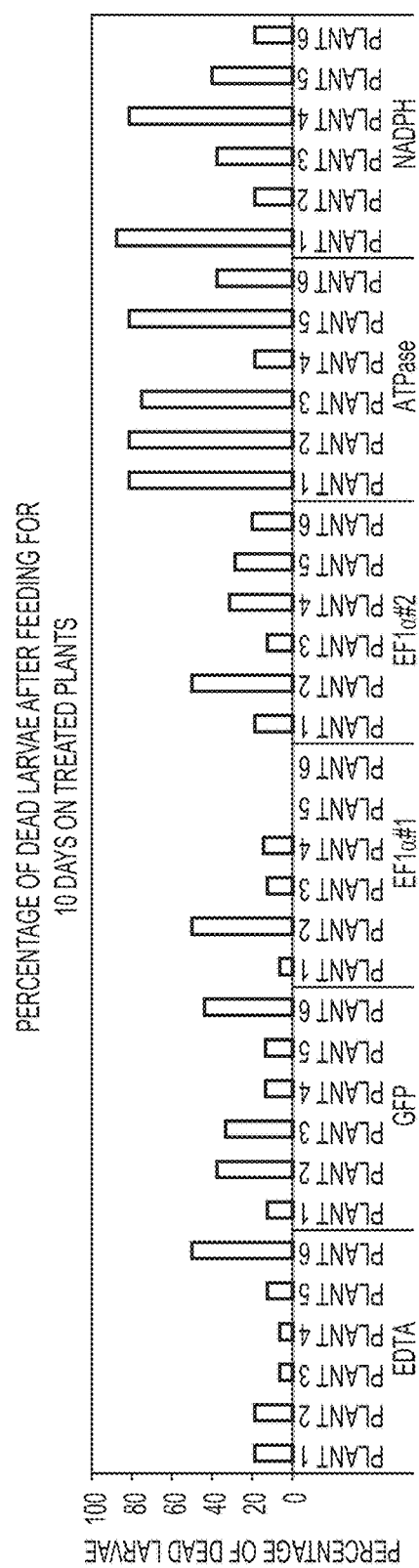
Figure 25D:
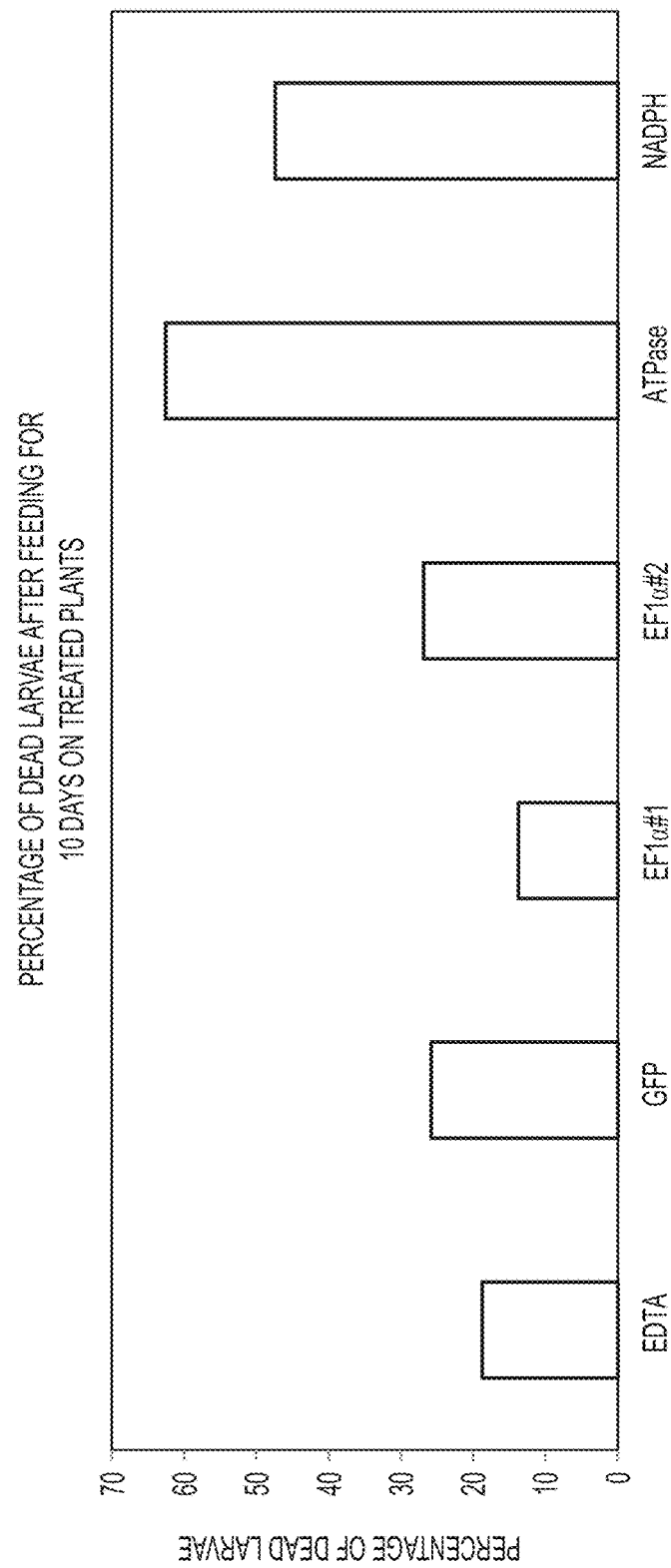
Figure 25E:
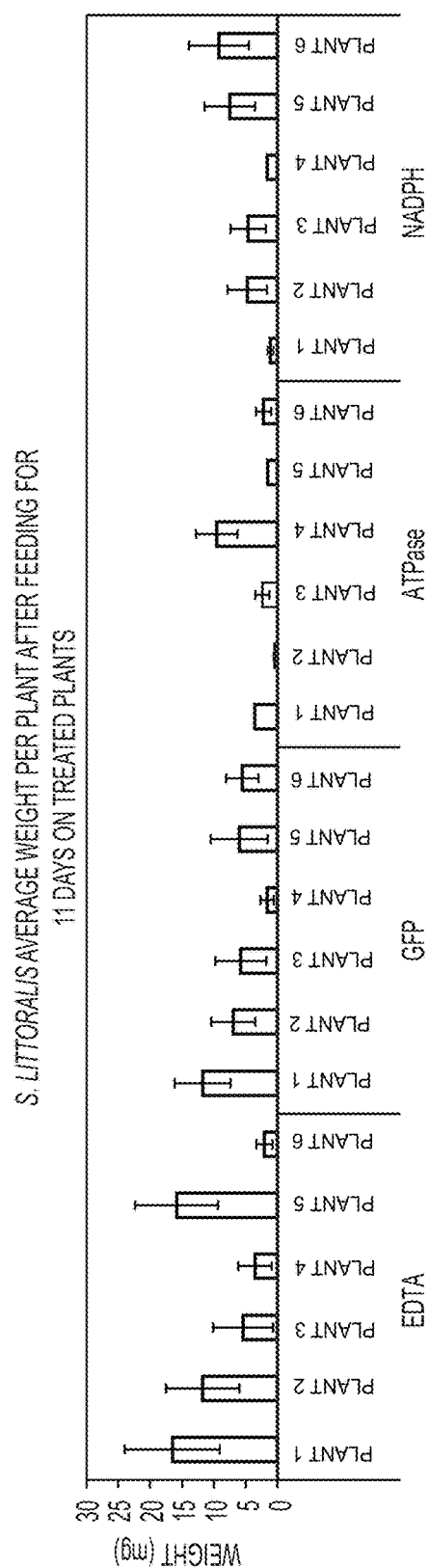

31 days after seed treatment, the leaves of germinated plants were used as sole food source for *S. littoralis*. The larvae taken for this experiment were up to five hours old (i.e. up to five hours after hatching). Six plants from each treatment were included in the feeding experiment. The leaves of each plant were placed in 16 wells of 24-well plate containing one larva each, summing to 16 larvae per plant and 96 larvae per treatment. The surface of the wells were covered with 1% agarose. Eight days after feeding had begun, 57 larvae were found dead in the ATPase treated group and 42 larvae were found dead in the NADPH treated group. The number of dead larvae in other groups ranged between 13 and 23. The average number of dead larvae in the six ATPase treated plants was significantly higher than the average number of dead larvae in the six GFP control plants, with a p-value of 0.03 (t-test). Similarly, the average number of dead larvae in the NADPH treated plants was higher compared to the average number of dead larvae in the GFP control plants (t-test, p-value=0.07). FIGS. 25A and B shows the percentage of dead larvae eight days after the beginning of feeding. FIGS. 25C and D shows the percentage of dead larvae ten days after the beginning of feeding. FIG. 25E shows average weight of live *S. littoralis* larvae 11 days after the feeding experiment had begun.

Figure 25F:
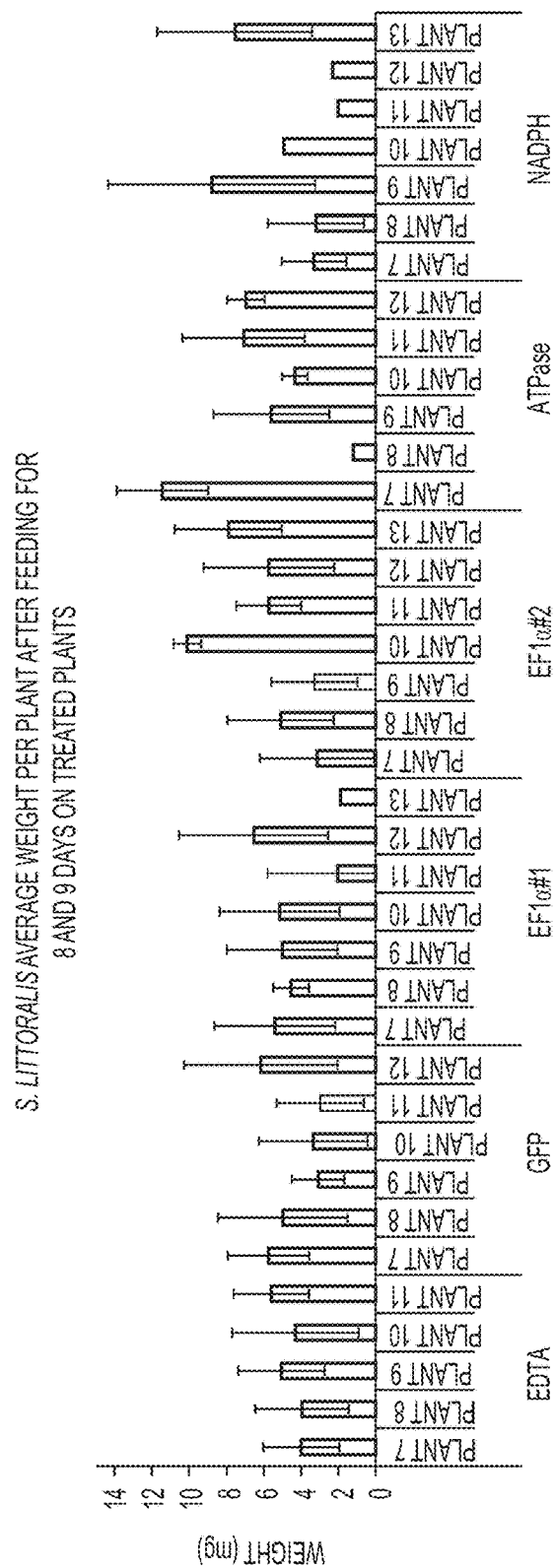

32 days after seed treatment, other plants from the same seed treatment were used as sole food source for *S. littoralis*. The larvae taken for this experiment were up to 24 hours old. Five to seven plants from each treatment were included in the feeding experiment. The leaves of each plant were placed in 16 wells of 24-well plate containing one larva each, summing to 16 larvae per plant, 80 larvae for EDTA, 96 larvae for GFP and ATPase and 112 larvae for NADPH and for the two EF1α treatments. The surface of the wells were covered with 1% agarose. Body weight of the larvae was recorded eight and nine days after the start of feeding; some of the larvae, feeding on a subset of the plants, were recorded in the eighth day and the remaining larvae were recorded in the ninth day. FIG. 25F shows the average weight of live *S. littoralis* larvae per plant.

Example 38: Seed Treatments Targeting Coleopteran Pests

This Example illustrates non-limiting embodiments of a method of providing a plant having improved resistance to an coleopteran pest, including the step of growing a plant from a seed that has been contacted with a exogenous non-transcribable dsRNA, wherein said plant exhibits improved resistance to said coleopteran pest, relative to a plant grown from a seed not contacted with said dsRNA. More specifically this Example illustrates a method of providing a maize plant having improved resistance to a corn rootworm (*Diabrotica* sp.), including the step of growing a maize plant from a maize seed that has been contacted with at least one dsRNA designed to silence a target gene endogenous to a corn rootworm, wherein the maize plant germinated from the maize seed exhibits improved resistance to the corn rootworm, relative to a maize plant grown from a maize seed not contacted with the dsRNA.

Figure 26A:
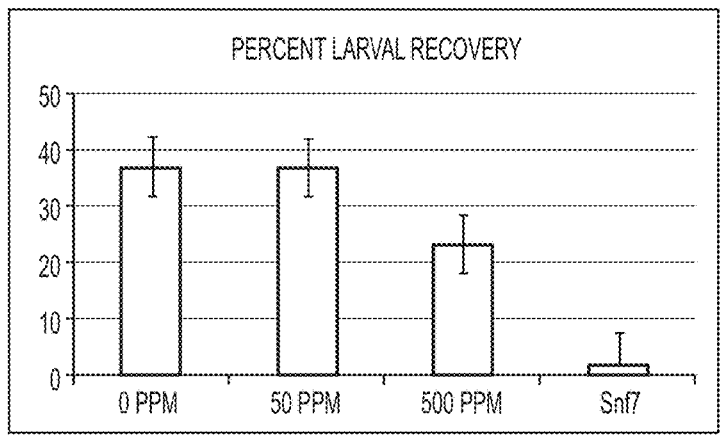
FIGS. 26A-C are bar graphs showing larval recovery and weight of Western corn rootworm (WCR) fed on corn plants grown from seeds treated with 0 ppm (Null control), 50 ppm or 500 ppm MON104454 or transgenic maize plants expressing an RNA suppression construct targeting WCR Snf7 (positive control).
Figure 26B:
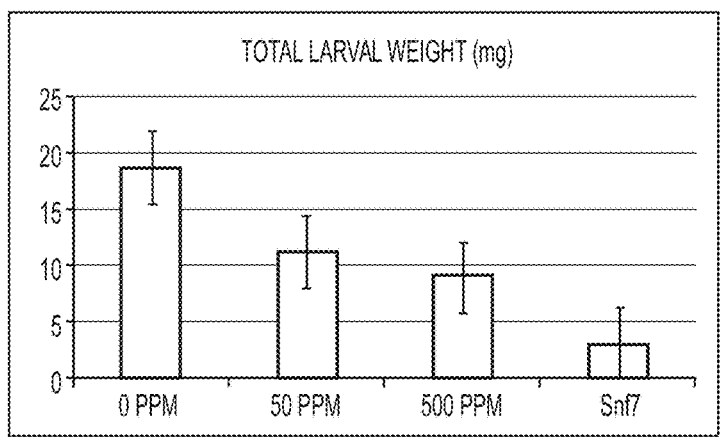
Figure 26C:
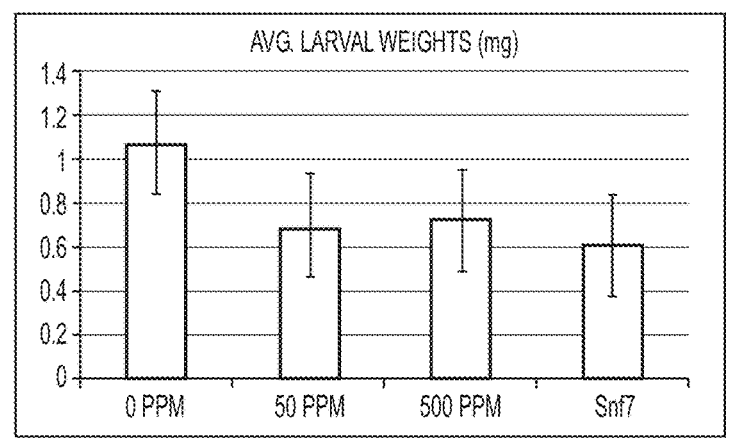

A 228 bp dsRNA trigger with the sense strand sequence of GGCTGATAGCACTTAAGGAGCTTCCTAATCAC- GAAAGAATTCTGCAGGATTTAGTTA TGGACATACT- GAGAGTACTCTCTGCTCCTGACTTAGAAGTCCG- CAAGAAGACTTTAA
GTCTAGCCCTTGAATTAGTCTCTTCACGGAACATA- GAAGAAATGGTATTAGTATTAA CAAAGGAAGT- GAGTAAAACGGTAGACAGTGAACATGAGGATACA- GGAAAGTACAG GC (MON104454, SEQ ID No.:144) was tested in a corn rootworm infestation assay in maize plants grown from maize seeds contacted prior to germination with the dsRNA trigger. Maize seeds (70 seeds, variety LH244) were placed in a 50-milliliter Falcon tube with 35 milliliters of a solution of the dsRNA trigger in buffer (0.1 millimolar EDTA, diluted from a 0.5 molar pH 8 stock) or 35 milliliters of buffer alone as a null control, and incubated in the dark at 15° C. with gentle agitation for 8 hours. Seeds of a transgenic maize plant that expresses an RNA suppression construct targeting DvSnf7 and that has resistance to corn rootworm were used in a transgenic positive control and were similarly incubated prior to germination in 35 milliliters of buffer alone. DvSnf7 is the Snf7 ortholog from *Diabrotica virgifera virgifera* (Western corn rootworm, WCR) and is a component of the ESCRT-III complex (endosomal sorting complex required for transport); see Bolognesi et al. (2012) PLoS ONE 7(10): e47534, doi: 10.1371/journal.pone.0047534. The following day, the seeds were washed 3 times (1 minute/wash with gentle agitation) in enough water to fill the Falcon tube. The washed seeds were planted at a depth of 0.5 inch in 6" closed-bottom polyethylene pots filled with Metromix 200 soil. Greater than 85% of the seeds germinated in all treatments. At the V2/V3 stage (approximately 2 weeks after planting), 50 neonate *Diabrotica virgifera virgifera* larvae were added to each pot (12-15 replicates performed). As a transgenic positive control, maize plants expressing a recombinant Snf7 transgene and similarly challenged with *Diabrotica virgifera virgifera* larvae were used. After ~4 weeks, the larvae were isolated using a Berlese funnel, counted, and weighed. Larval recovery and weight were calculated. The results are shown in FIG. 26. Larval recovery per plant did not differ significantly between larvae fed on maize plants grown from seed treated with the dsRNA trigger at 50 ppm (micrograms/milliliter) and larvae fed on control plants (FIG. 26A), but total larval weight (FIG. 26B) and average larval weight (FIG. 26C) were significantly reduced in the larvae fed on maize plants grown from seed treated with the dsRNA trigger at 50 ppm (micrograms/milliliter), compared to larvae fed on control plants. The plants grown from seed treated with the dsRNA trigger at 500 ppm exhibited stunted plant growth and root growth, which may have affected the observed results; nonetheless, larval recovery per plant was significantly decreased (FIG. 26A), and total larval weight (FIG. 26B) and average larval weight (FIG. 26C) were significantly reduced in the larvae fed on maize plants grown from seed treated with the dsRNA trigger at 500 ppm (micrograms/milliliter), compared to larvae fed on control plants. Quantigene assays did not detect a significant amount of MON104454 RNA in either leaf or root tissue of the maize plants grown from seed treated with the dsRNA trigger at 500 ppm.

Figure 27A:
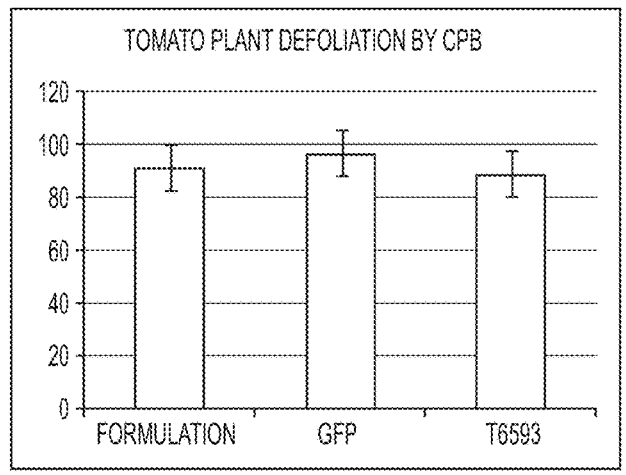
FIGS. 27A-C are bar graphs showing the results of a Colorado potato beetle (CPB) infestation assay on tomato plants grown from seeds treated with T6593, buffer ("formulation") or a GFP dsRNA trigger.
Figure 27B:
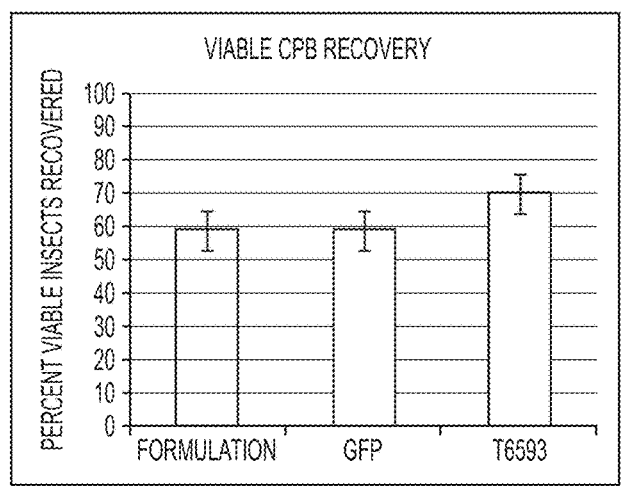
Figure 27C:
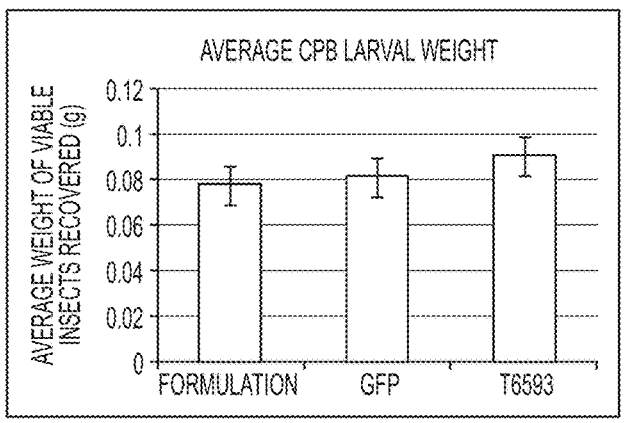
Figure 28A:
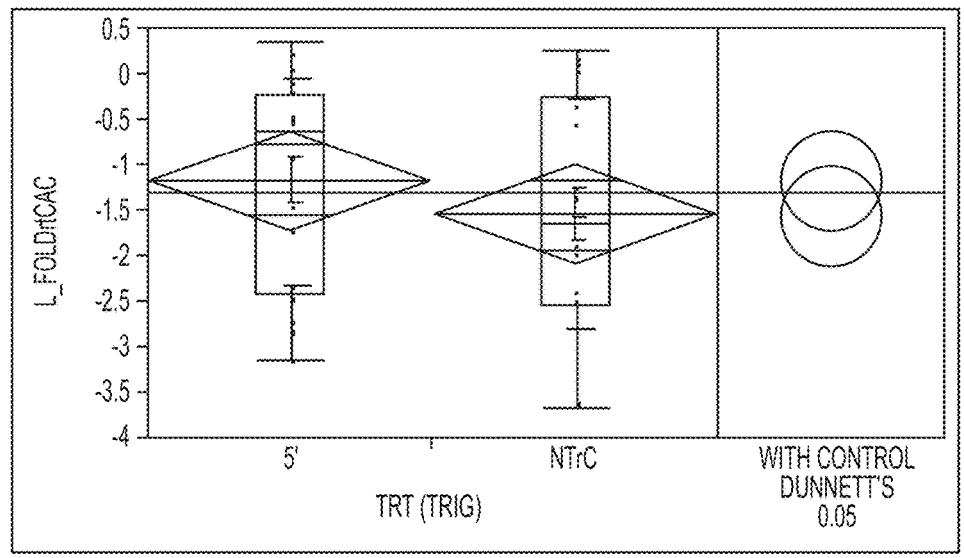
FIGS. 28A-B.
Figure 28B:
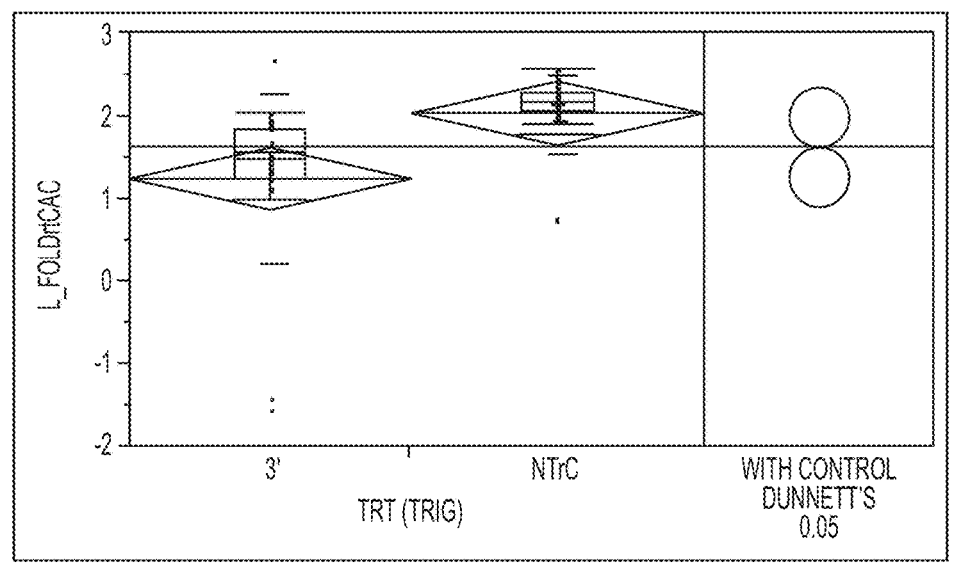

A similar experiment was carried out in tomato plants grown from seeds treated prior to germination by incubating overnight in 100 ppm (micrograms/milliliter) of a 279 bp blunt-ended dsRNA trigger with the sense strand sequence of TACCTGTGGCTCTCACAGGCAGCGAAGATGG-TACCGTTAGAGTTTGGCATACGAATA CACACA-GATTAGAGAATTGTTTGAATTATGGGTTCGAGA-GAGTGTGGACCATTTGTT
GCTTGAAGGGTTCGAATAATGTTTCTCTGGGGTAT-GACGAGGGCAGTATATTAGTGA AAGTTGGAAGA-GAAGAACCGGCAGTTAGTATGGATGCCAGTGGCG-GTAAAATAATT
TGGGCAAGGCACTCGGATTACAACAAGCTAATTT-GAAGGCGCTGCCAGAAGG (T6593, SEQ ID No.:145) and subjected to a *Leptinotarsa decemlineata* (Colorado potato beetle, CPB) infestation assay. Control plants were treated with either buffer ("formulation") or a dsRNA trigger for green fluorescent protein (GFP). Germination rate was >90% and no obvious effects on plant growth were observed for the treated plants, compared to the control plants. No significant effect on either the tomato plant defoliation rate (FIG. 27A) or on recovery of viable larvae (FIG. 27B) or average larval weight (FIG. 27C) were observed for the plants treated with either T6593 dsRNA or GFP dsRNA, compared to the control plants. Quantigene assays did not detect a significant amount of T6593 RNA in analyzed tissues (young leaf, old leaf, cotyledon, root) of the tomato plants grown from seed treated with the T6593 dsRNA trigger at 500 ppm.

Example 39: Seed Treatments Targeting Essential Coleopteran Genes

This Example illustrates non-limiting embodiments of a method of providing a plant having improved resistance to an coleopteran pest, including the step of growing a plant from a seed that has been contacted with a exogenous non-transcribable dsRNA, wherein said plant exhibits improved resistance to said coleopteran pest, relative to a plant grown from a seed not contacted with said dsRNA. More specifically this Example illustrates a method of providing a maize plant having improved resistance to a corn rootworm (*Diabrotica* sp.), including the step of growing a maize plant from a maize seed that has been contacted with at least one polynucleotide trigger designed to silence a target gene endogenous to a corn rootworm, wherein the maize plant germinated from the maize seed exhibits improved resistance to the corn rootworm, relative to a maize plant grown from a maize seed not contacted with the polynucleotide trigger.

Double-stranded RNA (dsRNA) triggers for the target genes identified in Table 36 are produced. Suitable triggers are of 21-1,000 base pairs in length, in some embodiments, 21-50, 50-100, 100-200, 200-500, 500-700, or 700-1,000 base pairs in length. The triggers provided in Table 36 are between 173-504 base pairs in length, but both shorter or longer triggers are useful in the methods disclosed herein. All of the dsRNA triggers provided in Table 36 were determined to cause significant larval stunting and mortality at 10 ppm and at 0.1 ppm in a diet bioassay with *Diabrotica virgifera virgifera* (Western corn rootworm, WCR) as described in the working examples in US Patent Application Publication 2009/0307803, which are incorporated by reference herein, where the dsRNA trigger is delivered as an overlayer on the surface of a solid insect diet in a 96-well plate.

TABLE 36 dsRNA triggers.

| Trigger ID | Trigger Length (bp) | Target Gene | SEQ ID NO. OF TARGET GENE |
|---|---|---|---|
| T33514 | 501 | Croquemort | 146 |
| T33515 | 502 | predicted: similar to ENSANGP00000020392 | 147 |
| T33516 | 500 | Cathepsin L-like proteinase | 148 |
| T33519 | 501 | Uncharacterized conserved protein | 149 |
| T30147 | 502 | Eukaryotic translation initiation factor 3 subunit, putative | 150 |
| T30502 | 501 | Cleavage and polyadenylation specificity factor subunit 6 | 151 |
| T32275 | 502 | Cleavage and polyadenylation specificity factor subunit 6 | 152 |
| T32328 | 504 | Cleavage and polyadenylation specificity factor subunit 6 | 153 |
| T30501 | 501 | Lissencephaly-1 homolog | 154 |
| T30145 | 502 | Wd-repeat protein | 155 |
| T33520 | 501 | Sodium-dependent phosphate transporter | 156 |
| T30139 | 502 | T-complex protein 1 subunit delta | 157 |
| T30137 | 502 | Putative uncharacterized protein | 158 |
| T32250 | 502 | Solute carrier family 2, facilitated glucose transporter member 6 | 159 |
| T30133 | 501 | 26S proteasome non-ATPase regulatory subunit, putative | 160 |
| T30471 | 501 | WD repeat-containing protein 75 | 161 |
| T30132 | 501 | THO complex subunit 5-like protein | 162 |
| T30469 | 502 | Another transcription unit protein | 163 |
| T30467 | 502 | CG8315 | 164 |
| T30466 | 374 | Putative uncharacterized protein | 165 |
| T33522 | 500 | E3 ubiquitin-protein ligase UBR2 | 166 |
| T30463 | 502 | TMEM9 domain family member B | 167 |
| T30462 | 501 | Eukaryotic translation initiation factor 2 subunit 1 | 168 |
| T32319 | 500 | Eukaryotic translation initiation factor 2 subunit 1 | 169 |
| T30126 | 502 | Pre-mRNA-processing factor 6 | 170 |
| T32320 | 496 | Delta-aminolevulinic acid dehydratase | 171 |
| T30456 | 502 | StAR-related lipid transfer protein 7 | 172 |
| T32316 | 496 | 26S proteasome non-ATPase regulatory subunit, putative | 173 |
| T30117 | 502 | Putative uncharacterized protein | 174 |
| T30112 | 502 | General transcription factor IIF subunit 2 | 175 |
| T30423 | 501 | Proliferating cell nuclear antigen | 176 |
| T32201 | 502 | Proliferating cell nuclear antigen | 177 |
| T30420 | 501 | Cactin | 178 |
| T30417 | 501 | Vesicle-trafficking protein SEC22b | 179 |
| T30106 | 482 | Putative uncharacterized protein | 180 |
| T33528 | 501 | Anon-15Ab | 181 |
| T30411 | 502 | ATP-dependent RNA helicase SUV3, mitochondrial | 182 |
| T33531 | 501 | ATP-binding cassette transporter | 183 |
| T30371 | 490 | Nuclear pore complex protein Nup107 | 184 |

** (+) significant stunting or mortality compared with water-treated control; (−) no significant stunting or mortality compared with water-treated control; NT = either (1) trigger was not tested, or (2) both of the following occurred: the sample did not provide significant stunting/mortality and the positive control did not provide significant stunting/mortality in that test. Positive control used in this assay was dsRNA with the sequence previously disclosed as SEQ ID NO. 880 in U.S. Pat. No. 7,943,819.

Blunt-ended double-stranded RNA (dsRNA) triggers for each of the trigger sequences provided in Table 36 are synthesized and tested in a corn rootworm infestation assay in maize plants grown from maize seeds contacted prior to germination with the individual dsRNA trigger as described above in Example 38 using *Diabrotica virgifera virgifera* larvae, wherein mortality or stunting of the larvae due to contact with or ingestion of the polynucleotide triggers is assayed. Triggers that are found to be effective in causing larval stunting or mortality or both are further tested.

It is anticipated that methods using a combination of certain polynucleotide triggers according to the present embodiments (e.g., the dsRNA triggers described herein) with one or more non-polynucleotide pesticidal agents will result in a synergetic improvement in prevention or control of insect infestations, when compared to the effect obtained with the polynucleotide triggers alone or the non-polynucleotide pesticidal agent alone. In one embodiment, maize plants having improved resistance to corn rootworm infestation are grown from seed having in their genome a recombinant DNA sequence encoding a non-polynucleotide pesticidal agent, wherein the seed are contacted prior to germination with an effective amount of a polynucleotide trigger. Bioassays such as the corn rootworm infestation assay described herein are useful for defining dose-responses for larval mortality or growth inhibition using combinations of the polynucleotide triggers of the present embodiments and one or more non-polynucleotide pesticidal agents (e.g., a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphearicus* insecticidal protein). One of skill in the art can test combinations of polynucleotide triggers and non-polynucleotide pesticidal agents in routine bioassays to identify combinations of bioactives that are synergistic and desirable for use in protecting plants from insect infestations.

Example 40: Seed Treatment with dsRNA Polynucleotides Targeting Tomato Golden Mottle Virus (ToGMoV)

Figure 29A:
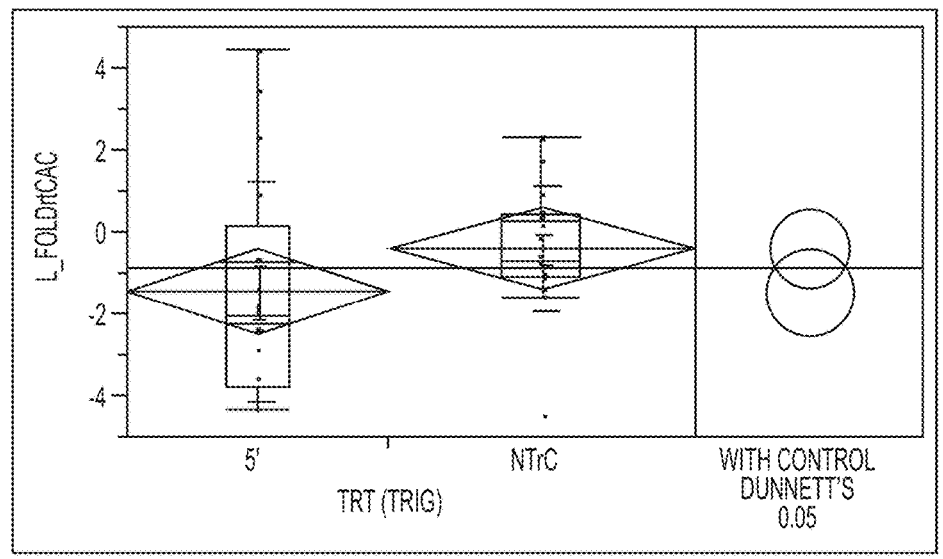
FIGS. 29A-B.
Figure 29B:
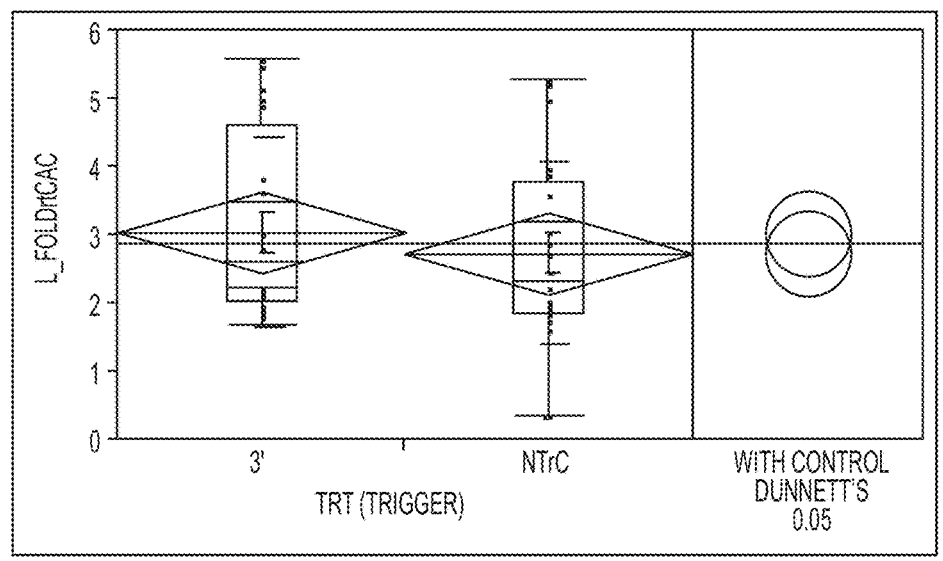

The following Example illustrates a method of providing a plant with improved resistance to a viral pathogen, including the step of growing a plant from a seed imbibed with an exogenous non-transcribable dsRNA polynucleotide comprising a sequence that is essentially identical or essentially complementary to at least 18 contiguous nucleotides of a viral pathogen gene. In this experiment, each treatment was applied to forty seeds.

dsRNA polynucleotide triggers comprising a sequence homologous to either a 5' or 3' sequence of the AC1 (replicase-associated protein) gene of Tomato golden mottle virus (ToGMoV) as described in Table 37 were diluted to 100 µg/ml in 0.1 mM EDTA pH 8.0, in a final volume of 0.6 ml. For each dsRNA polynucleotide trigger, forty tomato seeds (*Solanum lycopersicum* var. HP375) were placed in 2 ml Eppendorf tubes and allowed to incubate in the dsRNA polynucleotide solution. An additional set of forty tomato seeds was incubated in a solution containing a dsRNA polynucleotide targeting the *E. coli* β-glucuronidase (GUS) gene sequence as a negative control. Incubation was performed in the dark at 15° C. with gentle agitation for 24 hours.

TABLE 37

Sequences of ToGMoV used in seed treatment experiments.

| SEQ ID NO | Target Gene | Species |
|---|---|---|
| 185 | ToGMoV AC1/Rep1 (5') | Tomato Golden Mottle Virus |
| 186 | ToGMoV AC1/Rep1 (3') | Tomato Golden Mottle Virus |

The following day the seeds were washed three times (1 minute/wash with gentle agitation) in enough water to fill the Eppendorf tube. The washed seeds were planted at a depth of 0.5 inch in 6" polyethylene pots filled with Metromix 200 soil and incubated under standard growth chamber conditions: 25° C. day, 22° C. night; 12 hour day; light intensity ~15000 lux. Approximately 2 weeks after planting, the emerging cotyledons were inoculated with ToGMoV via agroinoculation.

Agroinfection of tomato plants was performed essentially as described in Grimsley N, Hohn T, Davies J W, Hohn B (1987) *Agrobacterium*-mediated delivery of infectious Maize streak virus into maize plants. Nature 325:177-179. Briefly, agroinfectious clones of the DNA-A and DNA-B components of ToGMoV were grown in Luria-Broth media supplemented with the selective antibiotic spectinomycin (resistance to which was conferred by the binary vector). Cultures were grown to an OD600 of 0.4-0.5 at 28° C. in a shaking incubator. Agroinfection was conducted 2 times on each plant. Agroinfected plants were maintained under growth chamber conditions and monitored for signs of viral infection alongside uninoculated plants growing in the same growth chamber.

Fourteen days after virus inoculation, plant leaves, approximately 226 $mm^2$, equivalent to 2 standard leaf punches, were harvested and prepared for Quantigene analysis. As can be seen in FIG. 28A, plants treated with the Tomato golden mottle virus (ToGMoV) 5' AC1 (SEQ ID NO. 185) dsRNA triggers accumulated virus (as measured by RNA levels of the AC1 gene) at a level not significantly different from the control group. Conversely, plants treated with the Tomato golden mottle virus (ToGMoV) 3' AC1 (SEQ ID NO 186) dsRNA triggers showed a statistically significant decrease in accumulation of ToGMoV virus levels relative to the GUS-treated control group, significant at an alpha of 0.05. See FIG. 28B.

Example 41: Seed Treatment with dsRNA Polynucleotides Targeting Cucumber Mosaic Virus (CMV)

The following Example illustrates a method of providing a plant with improved resistance to a viral pathogen, including the step of growing a plant from a seed imbibed with an exogenous non-transcribable dsRNA polynucleotide comprising a sequence that is essentially identical or essentially complementary to at least 18 contiguous nucleotides of a Cucumber Mosaic Virus (CMV) gene. In this experiment, each treatment was applied to forty seeds.

dsRNA polynucleotide triggers comprising a sequence homologous to either a 5' or 3' sequence of the 3b Nucleocapsid (NC) gene of CMV as described in Table 38 were diluted to 100 μg/ml in 0.1 mM EDTA pH 8.0, in a final volume of 0.6 ml. For each dsRNA polynucleotide trigger, forty tomato seeds (*Solanum lycopersicum* var. HP375) were placed in 2 ml Eppendorf tubes and allowed to incubate in the dsRNA polynucleotide solution. An additional set of forty tomato seeds were incubated in the presence of a dsRNA polynucleotide targeting the *E. coli* β-glucuronidase (GUS) gene sequence as a negative control. Incubation was performed in the dark at 15° C. with gentle agitation for 24 hours.

TABLE 38

Sequences of CMV used in seed treatment experiments.

| SEQ ID NO | Target Gene | Species |
|---|---|---|
| 187 | 3b-Nucleocapsid (NC) | Cucumber Mosaic Virus |
| 188 | 3b-Nucleocapsid (NC) | Cucumber Mosaic Virus |

The following day, the seeds were washed three times (1 minute/wash with gentle agitation) in enough water to fill the Eppendorf tube. The washed seeds were then planted at a depth of 0.5 inch in 6" polyethylene pots filled with Metromix 200 soil and incubated under standard greenhouse conditions: 28° C. day, 21° C. night; 16 hour day cycle. Approximately 2 weeks after planting, the emerging cotyledons were inoculated with CMV via rub infection using a standard protocol known in the literature (Roger Hull: Mechanical Inoculation of Plant Viruses; Current Protocols in Microbiology, 2005, 13:16 B6.1-16B6.4). Briefly, one gram of symptomatic leaf tissue from known CMV-infected plants was ground in a sterile mortar and pestle in 25 ml of ice-cold 0.1M phosphate buffer (pH 7.8). This inoculation buffer was gently rubbed onto cotyledons of plants dusted with carborundum powder. After inoculation, plants remained under greenhouse conditions and were monitored for signs of infection.

Fourteen days after virus inoculation, plant leaves, approximately 226 $mm^2$, equivalent to 2 standard leaf punches, were harvested and prepared for Quantigene analysis. As can be seen in FIG. 29A, plants treated with the Cucumber Mosaic Virus (CMV) 5' 3b dsRNA polynucleotide trigger (SEQ ID NO. 187) accumulated virus (as measured by RNA levels of the 3b-NC gene) at a level not significantly different from the control group, albeit with a slight downward trend. A similar result was observed in plants treated with the Cucumber Mosaic Virus (CMV) 5' 3b dsRNA polynucleotide trigger (SEQ ID NO. 188). See FIG. 29B.

Example 42: Seed Treatment with dsRNA Polynucleotides Targeting Tomato Spotted Wilt Virus (TSWV)

The following Example illustrates a method of providing a plant with improved resistance to a viral pathogen, including the step of growing a plant from a seed imbibed with an exogenous non-transcribable dsRNA polynucleotide comprising a sequence that is essentially identical or essentially complementary to at least 18 contiguous nucleotides of a Tomato Spotted Wilt Virus (TSWV) gene.

A dsRNA polynucleotide trigger comprising a sequence homologous to a 3' sequence of the Nucleocapsid (N) gene of TSWV (SEQ ID NO. 190) was diluted to 100 µg/ml in 0.1 mM EDTA pH 8.0, in a final volume of 0.6 ml. Forty tomato seeds (*Solanum lycopersicum* var. HP375) were placed in a 2 mL Eppendorf tube and allowed to incubate in the dsRNA polynucleotide solution. An additional set of forty tomato seeds was incubated in the presence of a dsRNA polynucleotide targeting the *E. coli* β-glucuronidase (GUS) gene sequence as a negative control. Incubation was performed in the dark at 15° C. with gentle agitation for 24 hours. The following day, the seeds were washed three times (1 minute/wash with gentle agitation) in enough water to fill the Eppendorf tube. The washed seeds were planted at a depth of 0.5 inch in 6" polyethylene pots filled with Metromix 200 soil and incubated under standard greenhouse conditions: 28° C. day, 21° C. night; 16 hour day cycle.

Approximately 2 weeks after planting, the emerging cotyledons were inoculated with TSWV via rub infection using a standard protocol described in the literature (Roger Hull: Mechanical Inoculation of Plant Viruses; Current Protocols in Microbiology, 2005, 13:16B6.1-16B6.4). Briefly, one gram of symptomatic leaf tissue from known TSWV-infected plants was ground in a sterile mortar and pestle in 25 ml of ice-cold 0.1M phosphate buffer (pH 7.8). This inoculation buffer was gently rubbed onto cotyledons of plants dusted with carborundum powder. After inoculation, the plants remained under greenhouse conditions and were monitored for signs of infection.

Figure 30:
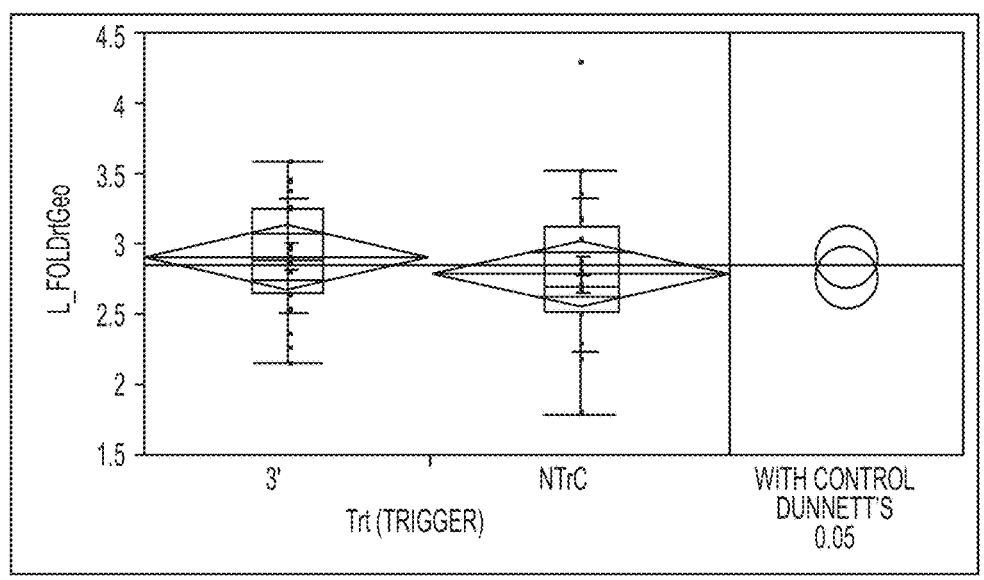
FIG. 30 shows the results of the Quantigene analysis on plants treated with Tomato Spotted Wilt Virus (TSWV) 3' N dsRNA polynucleotide sequence (3') compared to the GUS treated control (NTrC).

Fourteen days after virus inoculation, plant leaves, approximately 226 mm$^2$, equivalent to 2 standard leaf punches, were harvested and prepared for Quantigene analysis. As can be seen in FIG. 30, plants treated with the Tomato Spotted Wilt Virus (TSWV) 3' N dsRNA polynucleotide (SEQ ID NO. 190) accumulated virus (as measured by RNA levels of the 3b-NC gene) at a level not significantly different from the control group.

Example 43: Seed Treatment with dsRNA Polynucleotides Targeting Tomato Spotted Wilt Virus (TSWV)

The following Example illustrates a method of providing a plant with improved resistance to a viral pathogen, including the step of growing a plant from a seed imbibed with an exogenous non-transcribable dsRNA polynucleotide comprising a sequence that is essentially identical or essentially complementary to at least 18 contiguous nucleotides of a Tomato Spotted Wilt Virus (TSWV) gene.

A dsRNA polynucleotide trigger comprising a sequence homologous to a 5' sequence of the Nucleocapsid (N) gene of TSWV (SEQ ID NO. 189) is diluted to 100 µg/ml in 0.1 mM EDTA pH 8.0, in a final volume of 0.6 ml. Forty tomato seeds (*Solanum lycopersicum* var. HP375) are placed in a 2 mL Eppendorf tube containing the dsRNA polynucleotide solution. An additional set of forty tomato seeds is incubated in the presence of a dsRNA polynucleotide targeting the *E. coli* β-glucuronidase (GUS, SEQ ID No. 20) gene sequence as a negative control. Incubation is performed in the dark at 15° C. with gentle agitation for 24 hours. The next day, the seeds are washed three times (1 minute/wash with gentle agitation) in enough water to fill the Eppendorf tube. The washed seeds are planted at a depth of 0.5 inch in 6" polyethylene pots filled with Metromix 200 soil and incubated under standard greenhouse conditions: 28° C. day, 21° C. night; 16 hour day cycle.

Approximately 2 weeks after planting, the emerging cotyledons are inoculated with TSWV via rub infection using a standard protocol described in the literature (Roger Hull: Mechanical Inoculation of Plant Viruses; Current Protocols in Microbiology, 2005, 13:16B6.1-16B6.4). Briefly, one gram of symptomatic leaf tissue from known TSWV-infected plants is ground in a sterile mortar and pestle in 25 ml of ice-cold 0.1M phosphate buffer (pH 7.8). This inoculation buffer is gently rubbed onto cotyledons of plants dusted with carborundum powder. After inoculation, the plants remain under greenhouse conditions and are monitored for signs of infection.

Fourteen days after virus inoculation, plant leaves, approximately 226 mm$^2$, equivalent to 2 standard leaf punches, are harvested and prepared for Quantigene analysis. Plants treated with TSWV 5' N dsRNA polynucleotide (SEQ ID NO. 189) are expected to accumulate virus (as measured by RNA levels of the 3b-NC gene) at a level lower than that of the control group.

Example 44: Generation of dsRNA Molecules for Silencing EF1α Gene of *S. littoralis* dsRNA polynucleotide triggers derived from the *S. littoralis* EF1α gene were analyzed against the corn genome (*Zea mays*—taxid:4577, FIG. 31) using the same BLAST parameters as described in Example 7. dsRNAs targeting *S. littoralis* EF1α and having homology to a corn gene are selected.

Example 45: Altered Corn EF1α Expression Following Seed Treatment with *S. littoralis* dsRNA Corn seeds (var. Vivani) were treated according to the protocol described in Example 1 with exogenous non-transcribable dsRNA trigger molecules (SEQ ID Nos. 131 and 132) derived from the *S. littoralis* EF1α gene sequence, with no pre- and post-treatment washes. A mixture of 25 μg/ml from each dsRNA was used. The dsRNA was diluted either with 0.1 mM EDTA, or mixed with 40 μg/ml of PEG-modified carbon nanotubes. Treatment was performed by gently shaking the seeds in the solution for 4 hours in a dark growth chamber at 15° C. After treatment, seeds were planted in soil and grown at about 25° C. with 16 hours photoperiod. The plants were watered with tap water as necessary. Seeds treated with 50 μg/ml dsRNA derived from GFP sequence were germinated and grown alongside the EF1α dsRNA treated plants as a control.

Total RNA was extracted from leaves of germinated seeds, 20 days post treatment. cDNA was prepared using oligo-dT primers and the expression level of corn EF1α mRNA was determined in treated and control plants by real-time PCR with SYBR Green (Quanta BioSciences).

The house-keeping genes GPM120 and NFE101 were used as endogenous control genes to normalize for input amounts. Primers were designed so as to not amplify the dsRNA trigger and thus detect only corn-derived EF1α mRNA.

TABLE 39

Primers Used for RT-PCR Analysis for Expression Level of EF1α.

| Target Gene | Forward/Reverse | Primer Sequence | SEQ ID No. |
|---|---|---|---|
| EF1α | Forward | GCAACCACTCCCAAATACTC | 191 |
| EF1α | Reverse | CAGGGTTGTACCCAACTTTC | 192 |
| GPM120 | Forward | AGGCTTTCGCTGCGTGTT | 193 |
| GPM120 | Reverse | TGGCCCATCCAAACTCAGA | 194 |
| NFE101 | Forward | GCTCAAGTTCTTCGGATGAC | 195 |
| NFE101 | Reverse | ACTTCTTCCAGCAGACTAGC | 196 |

Figure 32A:
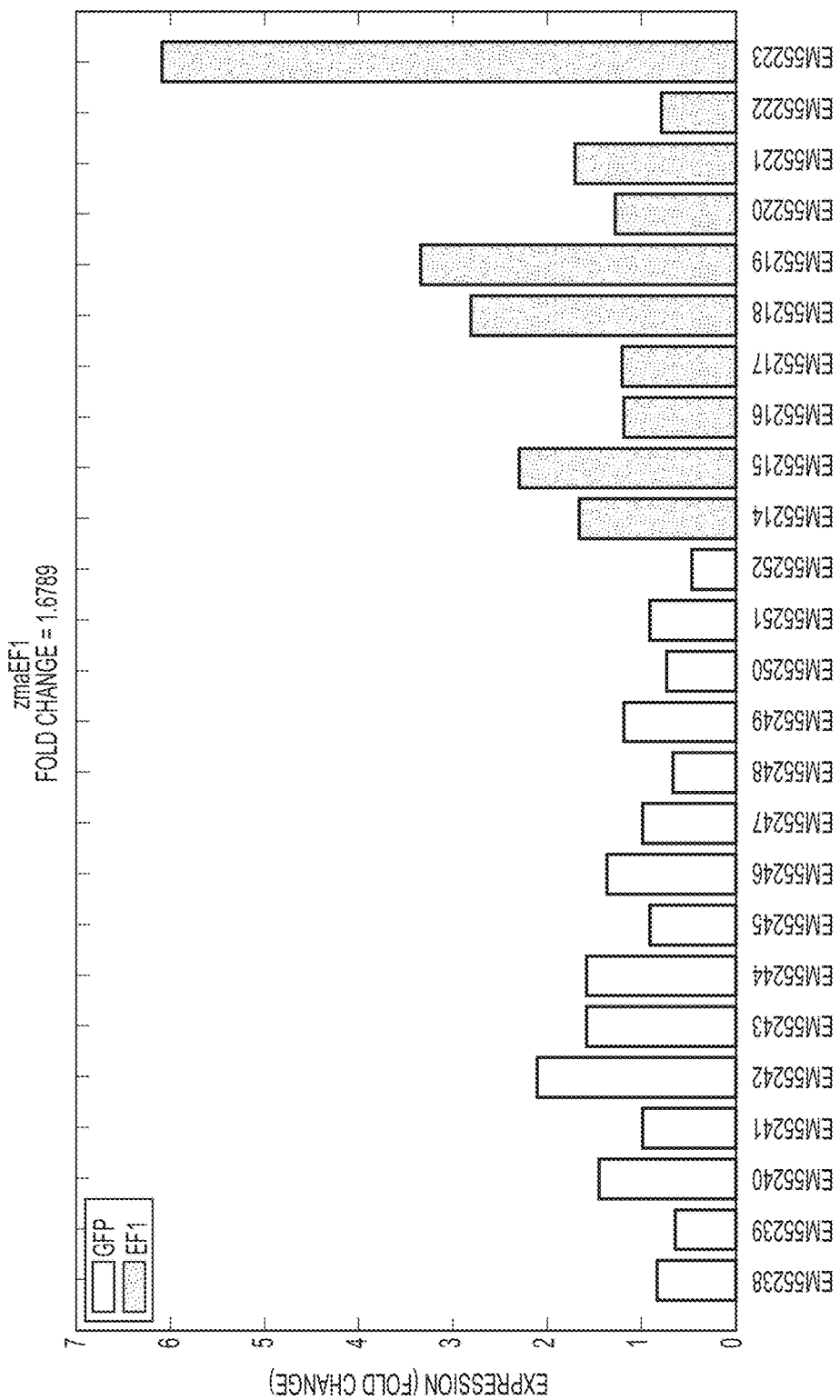
FIGS. 32A-C are bar graphs showing real-time PCR analyses of corn EF1α mRNA expression in 20-day-old and 48-day-old corn plants germinated from seeds treated with 50 µg/ml dsRNA for 4 hours.
Figure 32B:
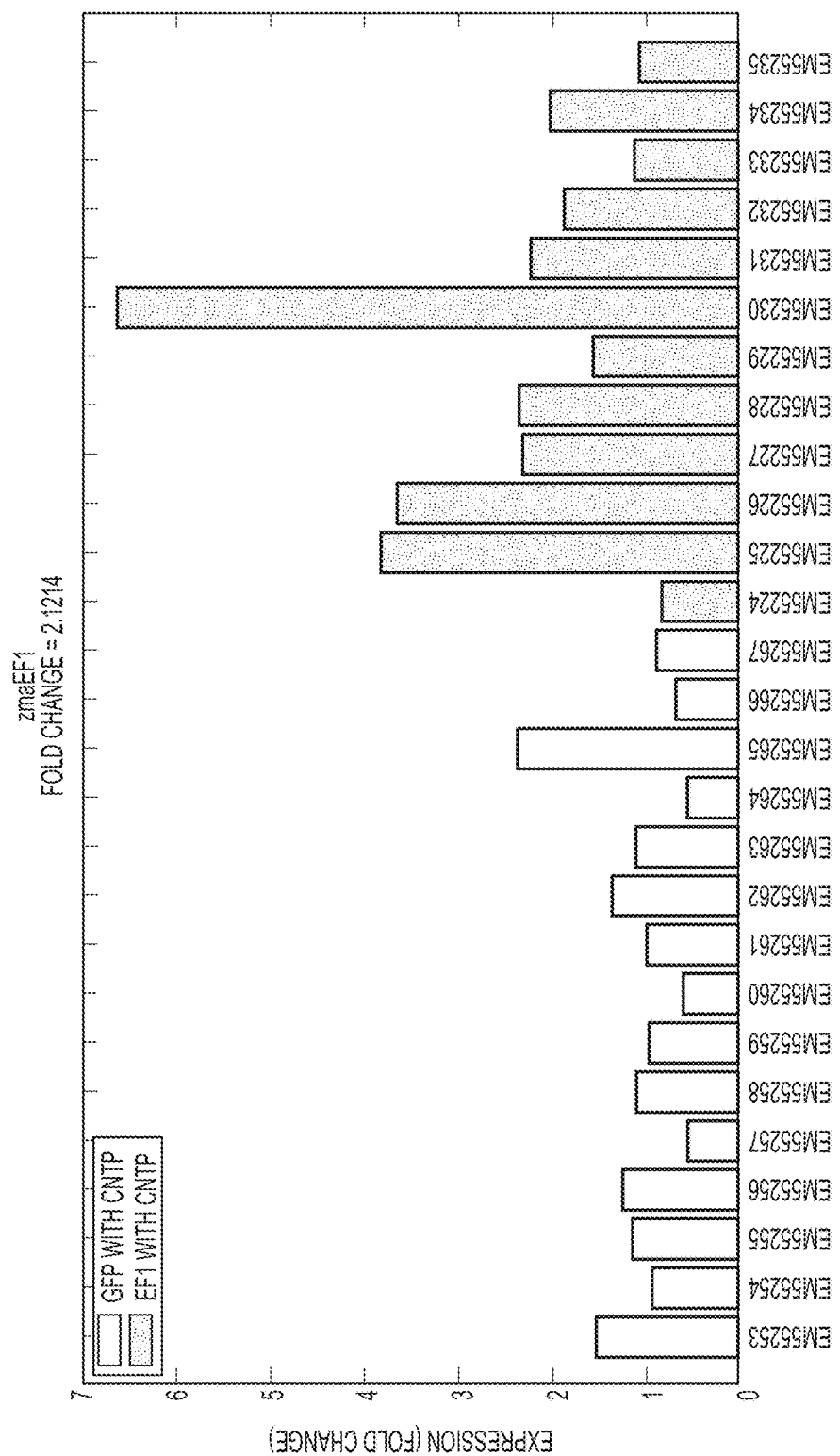
Figure 32C:
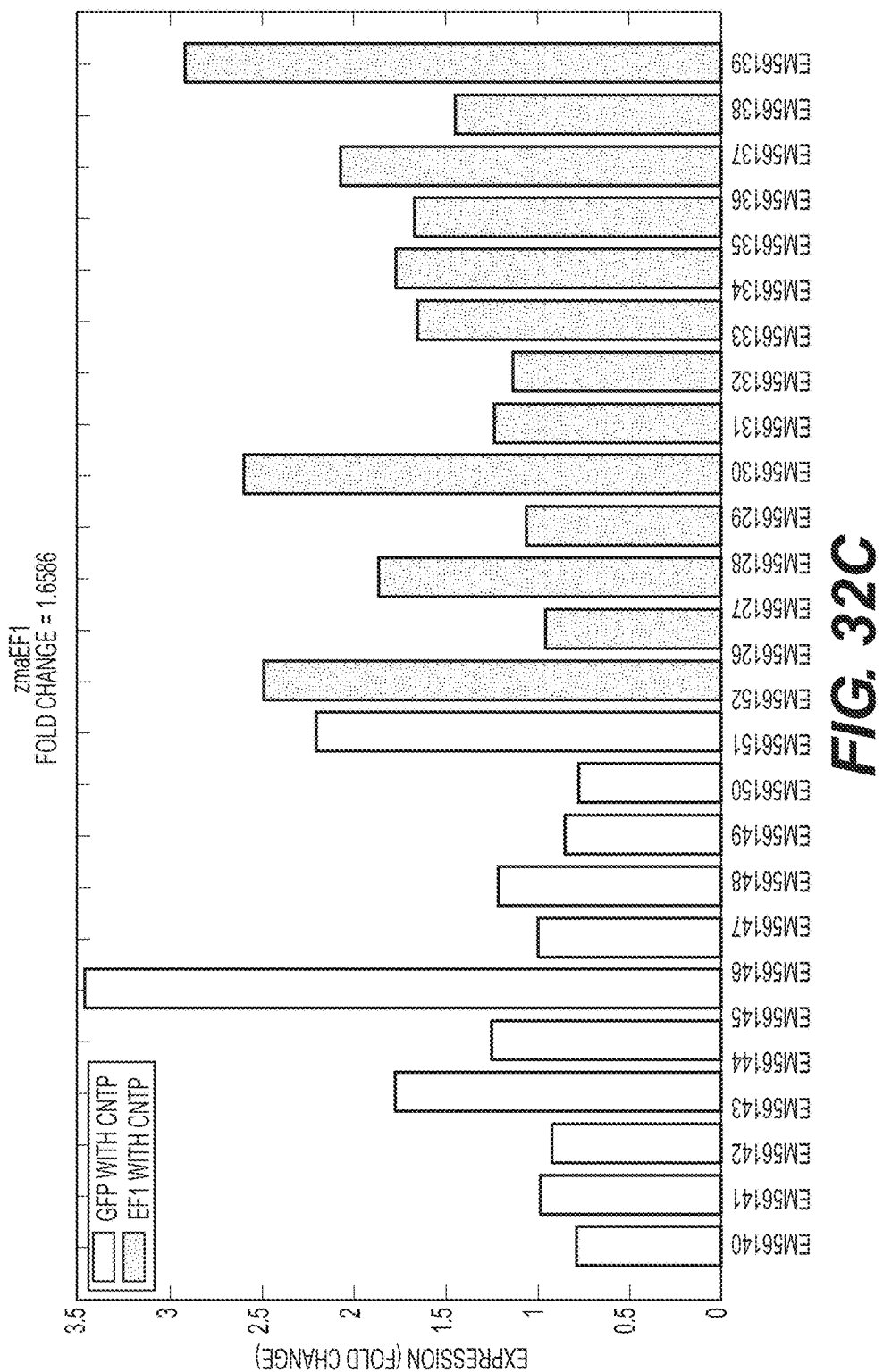
Figure 33:
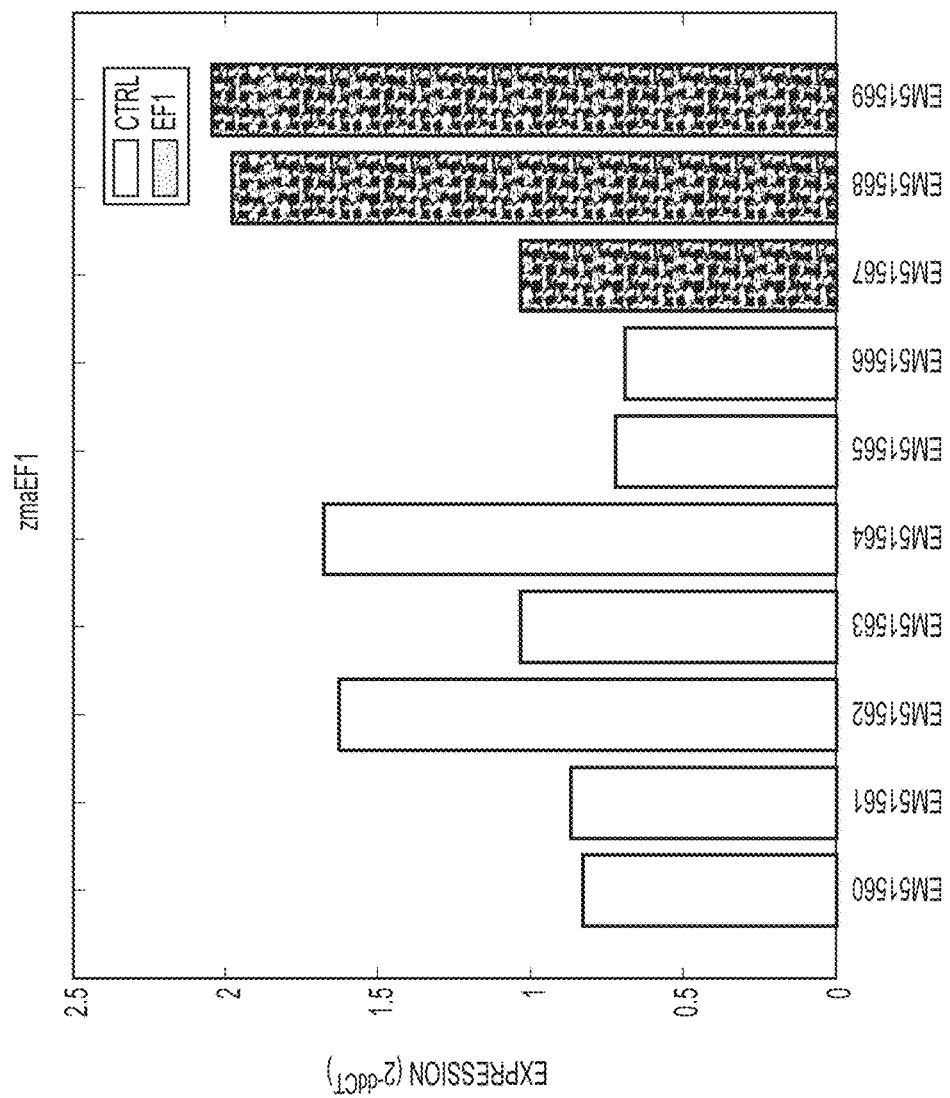
FIG. 33 is a bar graph showing real-time PCR analysis of corn EF1α mRNA expression in nine-week-old corn plants germinated from seeds treated with 132 µg/ml dsRNA derived from S. littoralis sequence. Expression values per individual plants were normalized to the median expression of all control plants. The difference in expression relative to control group had a p-value of 0.12.

This analysis showed a significant (Wilcoxon rank-sum test, p-value<0.05) up-regulation of corn EF1α mRNA. The median expression level of EF1α in plants treated with *S. littoralis* dsRNA was 2.12 and 1.68-fold higher than in control plants treated with GFP dsRNA, with or without PEG-modified carbon nanotubes, respectively. See FIGS. 32A and B.

The plants treated with dsRNA/CNTP were analyzed again for EF1α expression level 48 days post treatment. This analysis showed an up-regulation of corn EF1α mRNA. The median expression level of EF1α in plants treated with *S. littoralis* dsRNA was 1.66-fold higher than in control plants treated with GFP dsRNA. See FIG. 32C.

Example 46: Corn EF1α, Beta Actin, ATPase and NADPH Expression Following Seed Treatment with *S. littoralis* dsRNAs Corn seeds were treated with exogenous non-transcribable dsRNA trigger molecules derived from *S. littoralis* genes according to the protocol described in Example 1. Seeds were washed with double distilled water (DDW) prior to treatment for four hours. Next, seeds were dried at 30° C. overnight. Following the drying step, a final concentration of 132 μg/ml dsRNA for EF1α (a mixture of dsRNA#1 (SEQ ID No. 131) and dsRNA#2 (SEQ ID No. 132) at about equal concentrations), 53 μg/ml dsRNA for ATPase (SEQ ID No. 31), 76 μg/ml dsRNA for Beta actin (SEQ ID No. 133) and 154 μg/ml dsRNA for NADPH (SEQ ID Nos. 25 and 26), all diluted with 0.1 mM EDTA, was used. Treatment was performed by gently shaking the seeds in the solution for 26 hours in a dark growth chamber at 15° C. After treatment seeds were washed briefly with DDW and placed on wet paper for germination without a drying step. Seven days after germination the seedlings were planted in soil and grown at about 25° C. with 16 hours photoperiod. The plants were watered with tap water as necessary. Seeds that were treated with a similar solution (EDTA) not containing dsRNA were germinated and grown alongside the treated plants as a control.

Nine weeks after treatment, total RNA was extracted from leaves of germinated seeds. cDNA was prepared using oligo-dT and random primers and the expression level of corn EF1α, Beta actin, ATPase and NADPH was determined in treated and control plants. The numbers of plants analyzed were 3, 4, 3, 3 and 7 for EF1α, Beta actin, ATPase, NADPH and control respectively. The house-keeping gene FKBP was used as endogenous control gene to normalize for input amounts. Primers were designed so as to not amplify the dsRNA triggers and thus detect only corn-derived mRNAs.

TABLE 40

Primers Used for RT-PCR Analysis for Expression Level of EF1α, BETA ACTIN, ATPase AND NADPH.

| Target Gene | Forward/ Reverse | Primer Sequence | SEQ ID No. |
|---|---|---|---|
| EF1α | Forward | GCAACCACTCCCAAATACTC | 197 |
| EF1α | Reverse | CAGGGTTGTACCCAACTTTC | 198 |
| Beta actin | Forward | TCTGGCATCACACCTTCTAC | 199 |
| Beta actin | Reverse | TTCTCACGGTTAGCCTTTGG | 200 |
| ATPase | Forward 1 | TGTCCTGCCATCTCTATCTC | 201 |
| ATPase | Reverse 1 | ACATCCGAATGGTCTCTACG | 202 |
| ATPase | Forward 2 | CACAACCGTGCAGTTTACAG | 203 |
| ATPase | Reverse 2 | AAATGCGCCCAAGCATATCG | 204 |
| NADPH | Forward | CAGAGGACGAGGAATATGAG | 205 |
| NADPH | Reverse | CTAGCAGCATTGTCAGTAGG | 206 |
| FKBP | Forward | CGGTGTTCGACAGCAGCTAC | 207 |
| FKBP | Reverse | CTTCGCCGCCAACAATACCC | 208 |

Due to the small group size, this analysis showed no significant difference in the expression of these genes (Wilcoxon rank-sum test, p-value>0.05), but the expression of EF1α showed an up-regulation trend. The median expression level of EF1α in plants treated with *S. littoralis EF1α* dsRNA was 2.28-fold higher than in control plants (FIG. 33).

Example 47: Corn EF1α and ATPase Expression Following Seed Treatment with *S. littoralis* dsRNAs Corn seeds were treated with exogenous non-transcribable dsRNA trigger molecules derived from the *S. littoralis* EF1α and ATPase genes according to the protocol described in Example 1. Seeds were washed with double distilled water (DDW) prior to treatment for four hours and dried at 30° C. overnight. Two EF1α dsRNA sequences (dsRNA#1 (SEQ ID No. 131) and #2 (SEQ ID No. 132)) were used separately in two different seed treatments; each at a final concentration of 67 μg/ml dsRNA. ATPase dsRNA (SEQ ID No. 31) was used at a final concentration of 145 μg/ml. All dsRNAs were diluted with 0.1 mM EDTA. Treatment was performed by gently shaking the seeds in the solution for 24 hours in a dark growth chamber at 15° C. After treatment, seeds were dried at 30° C. overnight and then planted in soil and grown at about 25° C. with 16 hours photoperiod. The plants were watered with tap water as necessary. Seeds that were treated with 67 μg/ml dsRNA (SEQ ID No. 20) derived from GUS sequence were germinated and grown alongside the treated plants as a control.

Seven days after treatment, total RNA was extracted from leaves of germinated seeds and the expression level of corn EF1α and ATPase was determined in treated and control plants as described in Example 2 above. The house-keeping gene GPM120 was used as endogenous control gene to normalize for input amounts. Primers were designed so as to not amplify the dsRNA triggers and thus detect only corn-derived mRNA.

TABLE 41

Primers Used for RT-PCR Analysis for Expression Level of EF1α and ATPase.

| Target Gene | Forward/Reverse | Primer Sequence | SEQ ID No. |
|---|---|---|---|
| EF1α | Forward | GCAACCACTCCCAAATACTC | 191 |
| EF1α | Reverse | CAGGGTTGTACCCAACTTTC | 192 |
| ATPase | Forward | GCGCAAGTTTTTCGTAGATGAC | 209 |
| ATPase | Reverse | ACCATAGTCCACAGATGACAC | 210 |
| GMP120 | Forward | GCTGCGTGTTGTGCGTTCTG | 211 |
| GMP120 | Reverse | TCGTCGCGTGCTGTCTGTTC | 212 |

No significant difference in the expression of these genes was observed.

Example 48: Corn NADPH Expression Following Seed Treatment with S. littoralis dsRNA Corn seeds (var. 01DKD2) were treated according to the protocol described in Example 45 with exogenous non-transcribable dsRNA trigger molecules (SEQ ID No. 26) derived from the S. littoralis NADPH gene. A final concentration of 80 μg/ml dsRNA diluted with 0.1 mM EDTA was used. Treatment was performed by gently shaking the seeds in the solution for 3.5 hours in a dark growth chamber at 15° C. After treatment, seeds were planted in soil and grown at about 25° C. with 16 hours photoperiod. The plants were watered with tap water as necessary. Seeds that were treated with GFP dsRNA, or with a similar solution not containing dsRNA, were germinated and grown alongside the treated plants as a control.

20 days after treatment, total RNA was extracted from leaves of germinated seeds and the expression level of corn NADPH was determined in treated and control plants as described in Example 45 above. The house-keeping genes GPM120 and NFE101 were used as endogenous control genes to normalize for input amounts. Primers were designed so as to not amplify the dsRNA trigger and thus detect only corn-derived mRNA.

TABLE 42

Primers Used for RT-PCR Analysis for Expression Level of NADPH.

| Target Gene | Forward/Reverse | Primer Sequence | SEQ ID No. |
|---|---|---|---|
| NADPH | Forward | CAGAGGACGAGGAATATGAG | 205 |
| NADPH | Reverse | CTAGCAGCATTGTCAGTAGG | 206 |
| GPM120 | Forward | AGGCTTTCGCTGCGTGTT | 213 |
| GMP120 | Reverse | TGGCCCATCCAAACTCAGA | 214 |

TABLE 42-continued

Primers Used for RT-PCR Analysis for Expression Level of NADPH.

| Target Gene | Forward/Reverse | Primer Sequence | SEQ ID No. |
|---|---|---|---|
| NFE101 | Forward | GCTCAAGTTCTTCGGATGAC | 215 |
| NFE101 | Reverse | ACTTCTTCCAGCAGACTAGC | 216 |

No significant difference in the expression of NADPH was observed.

Example 49: Corn EF1α Expression Following Seed Treatment with S. littoralis dsRNAs Corn seeds (var. 01DKD2) were treated according to the protocol described in Example 45 with exogenous non-transcribable dsRNA trigger molecules (SEQ ID No. 131) derived from the S. littoralis EF1α gene. A mixture of 25 μg/ml from each of the two dsRNAs was used. The dsRNA was diluted either with 0.1 mM EDTA alone, or additionally mixed with 40 μg/ml of PEG-modified carbon nanotubes (CNTP). Treatment was performed by gently shaking the seeds in the solution for 4 hours in a dark growth chamber at 15° C. After treatment, seeds were planted in soil and grown at about 25° C. with 16 hours photoperiod. The plants were watered with tap water as necessary. Seeds that were treated with 50 μg/ml dsRNA derived from GUS sequence, with or without 40 μg/ml of PEG-modified carbon nanotubes, were germinated and grown alongside the treated plants as a control.

20 days after treatment, total RNA was extracted from leaves of germinated seeds and the expression level of corn EF1α was determined in treated and control plants as described in Example 45. The house-keeping genes GPM120, NFE101 and Expressed were used as endogenous control genes to normalize for input amounts. Primers were designed so as to not amplify the dsRNA trigger and thus detect only corn-derived mRNA.

TABLE 43

Primers Used for RT-PCR Analysis for Expression Level of EF1α.

| Target Gene | Forward/Reverse | Primer Sequence | SEQ ID No. |
|---|---|---|---|
| EF1α | Forward | GCAACCACTCCCAAATACTC | 198 |
| EF1α | Reverse | CAGGGTTGTACCCAACTTTC | 199 |
| GPM120 | Forward | AGGCTTTCGCTGCGTGTT | 193 |
| GMP120 | Reverse | TGGCCCATCCAAACTCAGA | 194 |
| NFE101 | Forward | GCTCAAGTTCTTCGGATGAC | 215 |
| Expressed | Forward | GGATGCTACTCGCCAGACA | 217 |
| Expressed | Reverse | GTGGTCAGCCTGCTTCAAC | 218 |

No significant difference in the expression of EF1α was observed.

Example 50: Corn EF1α Expression Following Seed Treatment with S. littoralis dsRNAs Corn seeds (var. Vivani) were treated according to the protocol described in Example 1, with exogenous non-transcribable dsRNA trigger molecules (SEQ ID Nos. 131 and 132) derived from the S. littoralis EF1α gene, without pre-treatment wash. A mixture of 25 μg/ml from each of the two dsRNAs was used. The dsRNA was diluted either with 0.1 mM EDTA alone, or additionally mixed with 40 µg/ml of PEG-modified carbon nanotubes (CNTP). Treatment was performed by gently shaking the seeds in the solution for 4 hours in a dark growth chamber at 15° C. After treatment seeds were washed briefly with DDW and directly germinated in soil without a drying step. Plants were grown at about 25° C. with 16 hours photoperiod and watered with tap water as necessary. Seeds that were treated with a similar solution not containing dsRNA, or with 50 µg/ml dsRNA derived from GFP sequence, with or without 40 µg/ml of PEG-modified carbon nanotubes, were germinated and grown alongside the treated plants as a control.

14 days after treatment, total RNA was extracted from leaves of germinated seeds and the expression level of corn EF1α was determined in treated and control plants as described in Example 45 above. The house-keeping genes NFE101 and Expressed were used as endogenous control genes to normalize for input amounts. Primers were designed so as to not amplify the dsRNA trigger and thus detect only corn-derived mRNA.

TABLE 44

Primers Used for RT-PCR Analysis for Expression Level of EF1α.

| Target Gene | Forward/Reverse | Primer Sequence | SEQ ID No. |
|---|---|---|---|
| EF1α | Forward | GCAACCACTCCCAAATACTC | 197 |
| EF1α | Reverse | CAGGGTTGTACCCAACTTTC | 198 |
| NFE101 | Forward | GCTCAAGTTCTTCGGATGAC | 215 |
| Expressed | Forward | GGATGCTACTCGCCAGACA | 217 |
| Expressed | Reverse | GTGGTCAGCCTGCTTCAAC | 218 |

No significant difference in the expression of EF1α was observed.

Example 51: Corn EF1α Expression Following Seed Treatment with S. littoralis dsRNAs Corn seeds (var. Vivani) were treated according to the protocol described in Example 1, with exogenous non-transcribable dsRNA trigger molecules (SEQ ID Nos. 131 and 132) derived from the S. littoralis EF1α gene, without pre-treatment wash. The two dsRNAs were used separately, each at a final concentration of 160 µg/ml. The dsRNAs were diluted either with IDT buffer alone (30 mM HEPES, pH 7.5, 100 mM Potassium Acetate), or additionally mixed with 40 µg/ml of PEG-modified carbon nanotubes (CNTP). Treatment was performed by gently shaking the seeds in the solution for 7 hours in a dark growth chamber at 25° C. After treatment, seeds were washed briefly with DDW and directly germinated in soil without a drying step. Plants were grown at about 25° C. with 16 hours photoperiod and watered with tap water as necessary. Seeds that were treated with a similar solution not containing dsRNA, or with 160 µg/ml dsRNA derived from GFP sequence, with or without 40 µg/ml of PEG-modified carbon nanotubes, were germinated and grown alongside the treated plants as a control.

Six days after treatment, total RNA was extracted from leaves of germinated seeds and the expression level of corn EF1α was determined in treated and control plants as described in Example 45 above. The house-keeping genes GPM120 and Expressed were used as endogenous control genes to normalize for input amounts. Primers were designed so as to not amplify the dsRNA trigger and thus detect only corn-derived mRNA.

TABLE 45

Primers Used for RT-PCR Analysis for Expression Level of EF1α.

| Target Gene | Forward/Reverse | Primer Sequence | SEQ ID No. |
|---|---|---|---|
| EF1α | Forward 1 | GCAACCACTCCCAAATACTC | 197 |
| EF1α | Reverse 1 | CAGGGTTGTACCCAACTTTC | 198 |
| EF1α | Forward 2 | CCCAGGTCATCATCATGAAC | 191 |
| EF1α | Reverse 2 | GAGCTCAGCAAACTTGACAG | 192 |
| GPM120 | Forward | GCTGCGTGTTGTGCGTTCTG | 211 |
| Expressed | Forward | GGATGCTACTCGCCAGACA | 217 |
| Expressed | Reverse | GTGGTCAGCCTGCTTCAAC | 218 |

Figure 34A:
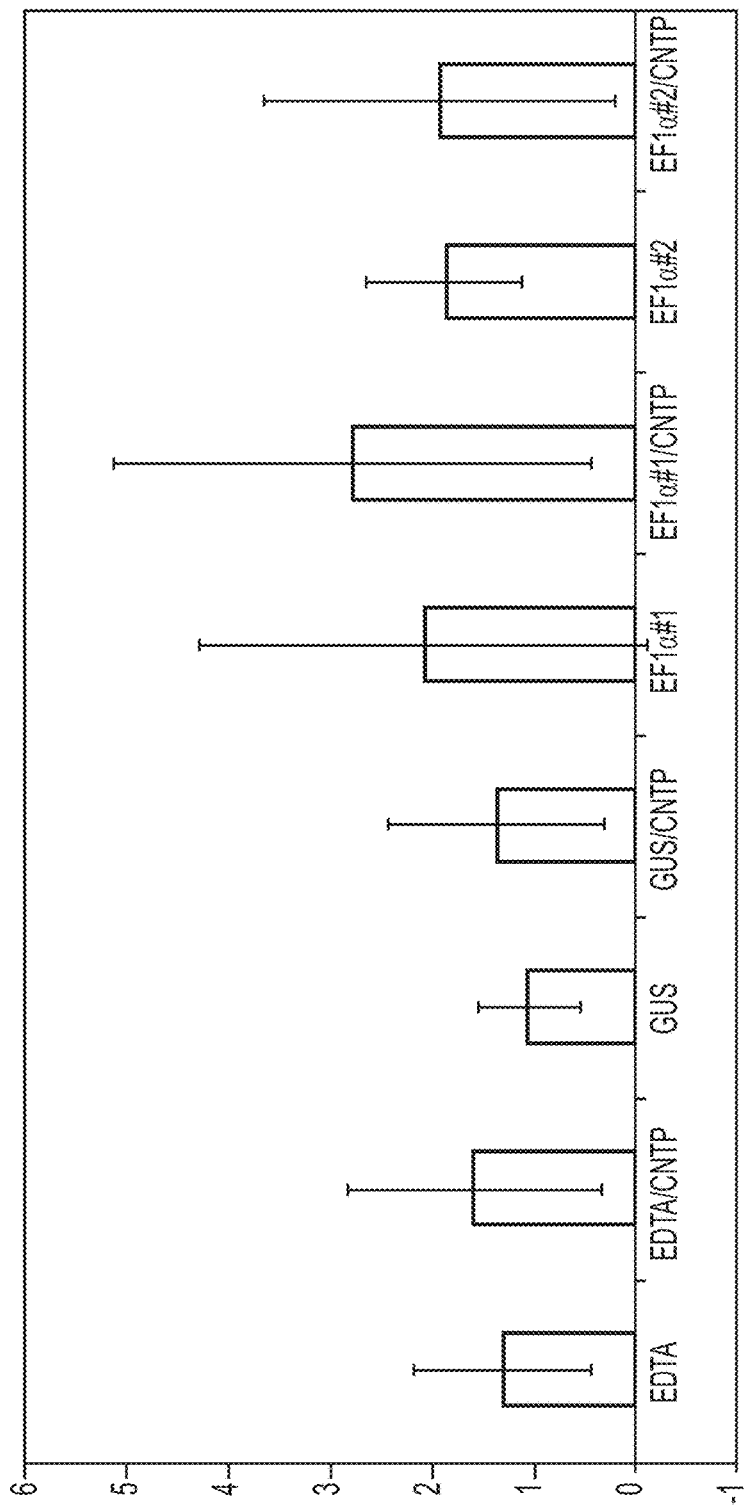
FIGS. 34A-B are bar graphs showing real-time PCR analyses of corn EF1α mRNA expression in six-day-old corn plants germinated from seeds treated with 160 µg/ml dsRNA for 7 hours.
Figure 34B:
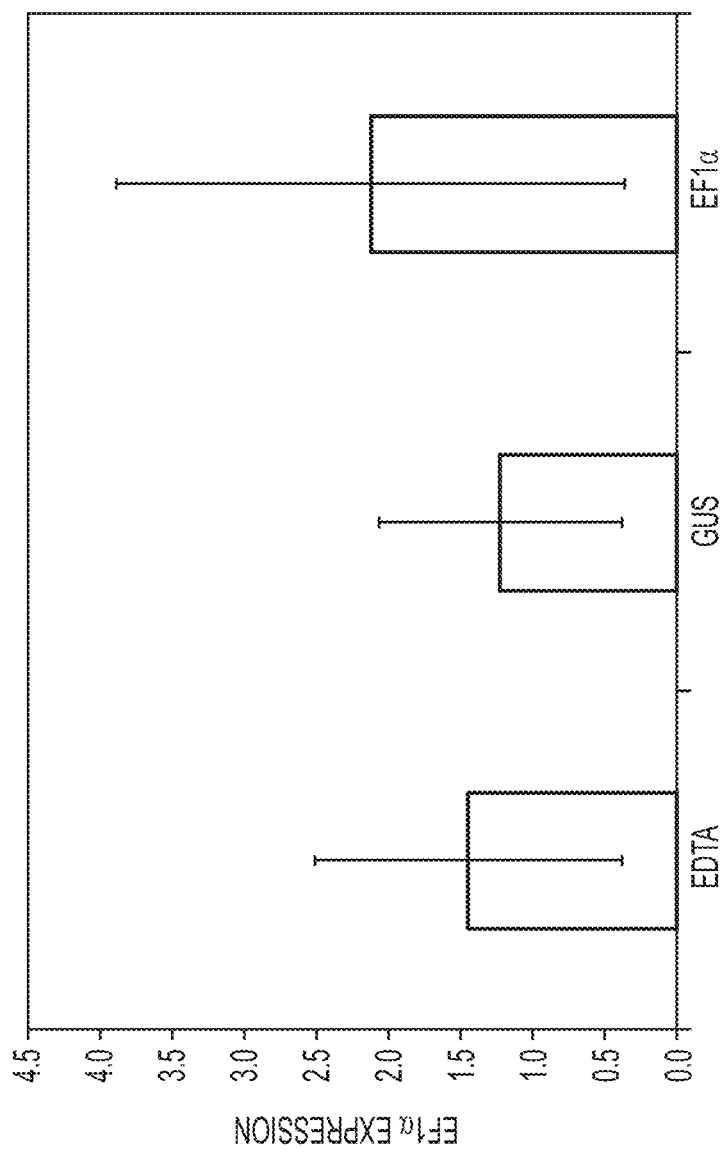

The results of this analysis are shown in FIG. 34. A significant up-regulation of corn EF1α mRNA was observed in plants following treatment with EF1α dsRNA #1 (t-test, p-value=0.004). The average expression level of EF1α in plants treated with this dsRNA was 1.8 higher than in control plants treated with GUS dsRNA. When grouping all the plants treated with EF1α dsRNAs (both dsRNA #1 and #2, with and without CNTP) and comparing to all plants treated with GUS dsRNA (with and without CNTP) a significant up-regulation of corn EF1α mRNA was observed. See FIG. 34B. The average expression level of EF1α in plants treated with EF1α dsRNAs was 1.73 higher than in control plants treated with GUS dsRNA (t-test, p-value=0.005).

Example 52: Corn ATPase and NADPH Expression Following Seed Treatment with S. littoralis dsRNAs Corn seeds (var. Vivani) were treated according to the protocol described in Example 1 with exogenous non-transcribable dsRNA trigger molecules (SEQ ID Nos. 31 and 26) derived from the S. littoralis ATPase and NADPH genes, without pre-treatment wash. A final concentration of 160 µg/ml dsRNA, diluted with 0.1 mM EDTA, was used. Treatment was performed by gently shaking the seeds in the solution for 2 hours in a dark growth chamber at 15° C. After treatment, seeds were washed briefly with DDW, planted in soil and grown at about 25° C. with 16 hours photoperiod. The plants were watered with tap water as necessary. Seeds that were treated with 160 µg/ml dsRNA (SEQ ID No. 124) derived from GFP sequence, or with a similar solution not containing dsRNA (EDTA) were germinated and grown alongside the treated plants as a control.

27 days after treatment, total RNA was extracted from leaves of germinated seeds and the expression levels of corn ATPase and NADPH were determined in treated and control plants as described in Example 45 above. The house-keeping gene, Expressed, was used as endogenous control genes to normalize for input amounts. Primers were designed so as to not amplify the dsRNA trigger and thus detect only corn-derived mRNA.

TABLE 46

Primers Used for RT-PCR Analysis for Expression Level of ATPase and NADPH.

| Target Gene | Forward/Reverse | Primer Sequence | SEQ ID No. |
|---|---|---|---|
| ATPase | Forward | GCGCAAGTTTTTCGTAGATGAC | 219 |
| ATPase | Reverse | ACCATAGTCCACAGATGACAC | 220 |
| NADPH | Forward | CAGAGGACGAGGAATATGAG | 205 |
| NADPH | Reverse | CTAGCAGCATTGTCAGTAGG | 206 |
| Expressed | Forward | GGATGCTACTCGCCAGACA | 217 |
| Expressed | Reverse | GTGGTCAGCCTGCTTCAAC | 218 |

Figure 35A:
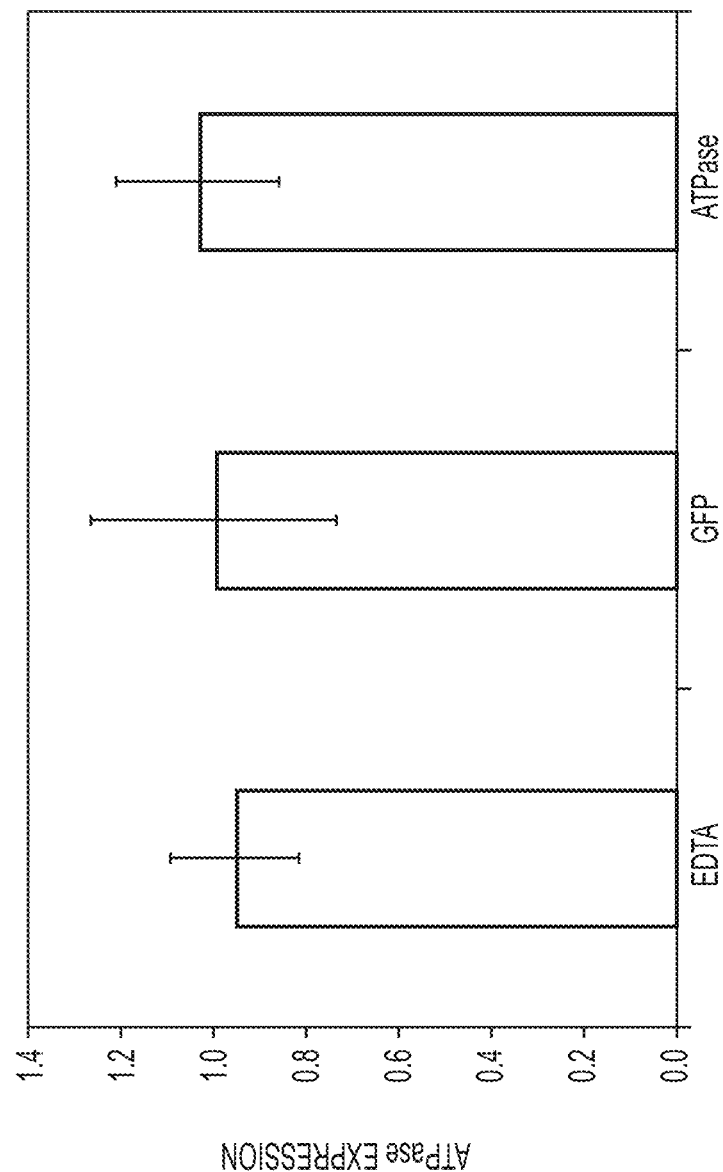
Figure 35C:
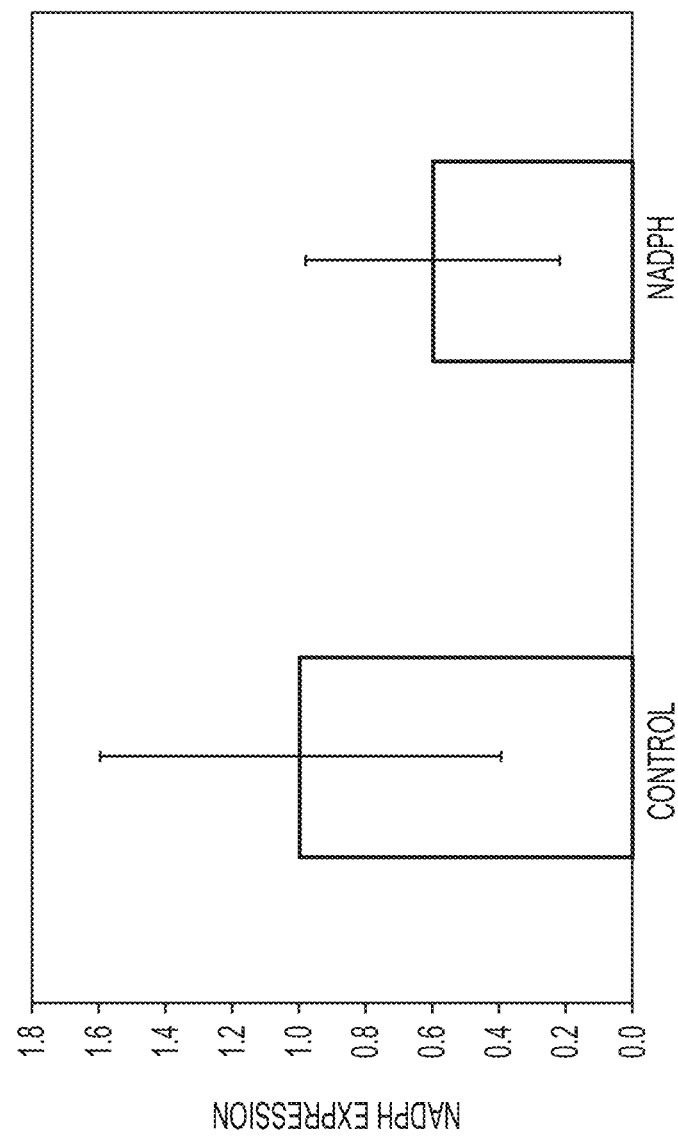

The results of this analysis are shown in FIGS. 35A (ATPase expression) and 35B and C (NADPH expression). No difference in corn ATPase expression levels was detected following treatment with S. littoralis ATPase dsRNA. However, a trend of down-regulation of corn NADPH mRNA was observed in plants following treatment with NADPH dsRNA triggers. The average expression level of NADPH in plants treated with this dsRNA trigger was 1.37 fold lower than in control plants treated with GFP dsRNA trigger (t-test, p-value=0.11). When grouping all control plants (those treated with GFP dsRNA and those treated with EDTA) and comparing to plants treated with NADPH dsRNA trigger, a significant down-regulation of corn NADPH mRNA was observed, with an average decrease of 1.67 fold in NADPH expression levels following treatment with NADPH dsRNAs (t-test, p-value=0.02).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of providing a maize, soybean, rice, wheat, tomato, or cucumber plant having improved resistance to an insect pest selected from the group consisting of a Spodoptera spp., Diabrotica virgifera virgifera, and Leptinotarsa decemlineata, comprising:
   growing said plant from a seed,
   wherein said seed has been soaked in a solution comprising a concentration of 0.005-1.5 µg/µL exogenous non-transcribable double-stranded RNA (dsRNA) molecule comprising a nucleic acid sequence that is identical or complementary to at least 21 contiguous nucleotides of an essential gene of said insect pest or to the sequence of an RNA transcribed from said essential gene, wherein said seed is shaken in said solution for up to 24 hours,
   wherein said plant exhibits improved resistance to said insect pest relative to a control plant, and
   wherein said control plant is grown from a seed not contacted with said exogenous dsRNA molecule.

2. The method of claim 1, wherein said insect pest is Spodoptera littoralis.

3. The method of claim 1, wherein said insect pest gene is selected from the group consisting of V-ATPase, NADPH Cytochrome P450 Oxidoreductase, Inhibitor of Apoptosis (IAP), Chitin Synthase, EF1α, and β-actin.

4. The method of claim 1, wherein said exogenous non-transcribable dsRNA molecule further comprises a nucleic acid sequence that is at least 80% identical to at least 25 consecutive bases of a nucleic acid sequence of an endogenous maize, soybean, rice, wheat, tomato, or cucumber gene.

5. The method of claim 1, wherein said seed is further treated with an agent selected from the group consisting of a pesticide, a fungicide, an insecticide, a fertilizer, a coating agent, and a coloring agent.

6. A method for generating a maize, soybean, rice, wheat, tomato, or cucumber plant having insect resistance-comprising:
  a) soaking an ungerminated seed in a solution comprising a non-transcribable double-stranded RNA (dsRNA) molecule at a concentration of 0.005-1.5 µg/µL,
  b) shaking said ungerminated seed in said solution for up to 24 hours,
  wherein said non-transcribable dsRNA molecule is introduced into said ungerminated seed,
  wherein said non-transcribable dsRNA molecule comprises at least one polynucleotide strand comprising at least one segment comprising a first nucleic acid sequence identical or complementary to at least 21 contiguous nucleotides of an essential insect pest gene in either anti-sense or sense orientation,
  wherein said insect pest is selected from the group consisting of a *Spodoptera* spp., *Diabrotica virgifera virgifera*, and *Leptinotarsa decemlineata*; and
  c) germinating said ungerminated seed to generate said maize, soybean, rice, wheat, tomato, or cucumber plant exhibiting insect resistance after emerging from the seed.

7. The method of claim 6, wherein said plant does not comprise detectable levels of DNA having a nucleic acid sequence of said the nucleic acid molecule after emerging from the seed.

8. The method of claim 6, wherein said insect pest gene is selected from the group consisting of V-ATPase, NADPH Cytochrome P450 Oxidoreductase, Inhibitor of Apoptosis (IAP), Chitin Synthase, EF1α, and β-actin.

9. The method of claim 6, wherein said insect resistance is resistance to *Spodoptera littoralis* infestation.

10. The method of claim 6, wherein said non-transcribable nucleic acid molecule further comprises a second segment having a second nucleic acid sequence that is at least 80% identical to at least 25 consecutive bases to an endogenous maize, soybean, rice, wheat, tomato, or cucumber gene.

11. The method of claim 6, further comprising priming said seed prior to introducing said non-transcribable nucleic acid molecule.

12. The method of claim 11, wherein said priming comprises:
  (i) washing said seed prior to introducing said nucleic acid molecule; and
  (ii) drying said seed following step (i).

* * * * *

SEQUENCE LISTING

```
<160> NUMBER OF SEQ ID NOS: 224

<210> SEQ ID NO 1
<211> LENGTH: 20
<212> TYPE: DNA
<213> ORGANISM: Artificial Sequence
<220> FEATURE:
<223> OTHER INFORMATION: polynucleotide sequence or in vitro generated
      dsRNA

<400> SEQUENCE: 1
taatacgact cactataggg                                                    20

<210> SEQ ID NO 2
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 2
ggtgctctga acgtggatg                                                     19

<210> SEQ ID NO 3
<211> LENGTH: 22
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 3
catcatcgcc atcctcattc tc                                                 22

<210> SEQ ID NO 4
<211> LENGTH: 40
<212> TYPE: DNA
<213> ORGANISM: artificial Sequence
```

```
<220> FEATURE:
<223> OTHER INFORMATION: polynucleotide sequence or in vitro generated
      dsRNA

<400> SEQUENCE: 4
taatacgact cactataggg gaagaccctc gaaactaagc                             40

<210> SEQ ID NO 5
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 5
taatacgact cactataggg ggtaagcggc attctaaacc                             40

<210> SEQ ID NO 6
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 6
actcagcagt cgtaggattg                                                  20

<210> SEQ ID NO 7
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 7
cttcttatgt tcccgtcagg                                                  20

<210> SEQ ID NO 8
<211> LENGTH: 616
<212> TYPE: RNA
<213> ORGANISM: CGMMV

<400> SEQUENCE: 8
uaauacgacu cacuauaggg gguaagcggc auucuaaacc uccaaaucgg agguuggacu       60
cugcuucuga agaguccagu ucuguuucuu uugaagaugg cuuacaaucc gaucacaccu     120
agcaaacuua uugcguuuag ugcuucuuau guucccguca ggacuuuacu uaauuuucua     180
guugcuucac aagguaccgc uuuccagacu caagcgggaa gagauucuuu ccgcgagucc     240
cugucugcgu uacccucguc ugcguagau auuaauucua gauucccaga ugcggguuuu      300
uacgcuuucc ucaacggucc uguugagg ccuaucuucg uuucgcuucu cagcuccacg       360
gauacgcgua auaggggucau ugagguugua gauccuagca auccuacgac ugcugagucg   420
cuuaacgccg uaaagcguac ugaugacgcg ucuacggccg cuagggcuga gauagauaau    480
uuaauagagu cuauuucuaa ggguuuugau guuuacgaua gggcuucauu ugaagccgcg    540
uuuucgguag ucuggucaga ggcuaccacc ucgaaagcuu aguucgagg gucuuccccu      600 auagugaguc guauua                                                     616

<210> SEQ ID NO 9
```

```
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 9
taatacgact cactataggg catcaccatc gaccctaaac                           40

<210> SEQ ID NO 10
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 10
taatacgact cactataggg gctttaccgc cactaagaac                           40

<210> SEQ ID NO 11
<211> LENGTH: 598
<212> TYPE: RNA
<213> ORGANISM: CGMMV

<400> SEQUENCE: 11
uaauacgacu cacuauaggg gcuuuaccgc cacuaagaac ucuguacacu cccuugcggg     60
uggucugagg cuucuugaau uggaauauau gaugaugcaa gugcccuacg gcucaccuug    120
uuaugacauc ggcgguaacu auacgcagca cuuguucaaa gguagaucau augugcauug    180
cugcaauccg ugccuagauc uuaaagaugu gcgaggaau gugauguaca acgauaugau     240
cacgcaacau guacagaggc acaagggauc uggcgggugc agaccucuuc caacuuccca    300
gauagaugca uucaggaggu acgauaguuc ucccugugcg gucaccuguu cagacguuuu    360
ccaagagugu uccuaugauu uugggagugg uagggauaau caugcagucu cguugcauuc    420
aaucuacgau aucccuuauu cuucgaucgg accugcucuu cauaggaaaa augugcgagu    480
uuguuaugca gccuuucauu ucucggaggc auugcuuuua gguucgccug uagguaauuu    540
aaauaguauu ggggcucagu uuagggucga uggugaugcc cuauagugag ucguauua      598

<210> SEQ ID NO 12
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 12
ggtgctctga acgtggatg                                                  19

<210> SEQ ID NO 13
<211> LENGTH: 22
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 13
catcatcgcc atcctcattc tc                                              22
```

```
<210> SEQ ID NO 14
<211> LENGTH: 43
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 14
taatacgact cactataggg agcattcccg gcgggatagt ctg            43

<210> SEQ ID NO 15
<211> LENGTH: 43
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 15
taatacgact cactataggg agcattcccg gcgggatagt ctg            43

<210> SEQ ID NO 16
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 16
cagcgcgaag tctttatacc                                      20

<210> SEQ ID NO 17
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 17
ctttgccgta atgagtgacc                                      20

<210> SEQ ID NO 18
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 18
ccataaccct ggaggttgag                                      20

<210> SEQ ID NO 19
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 19
atcagacgct gctggtctgg                                      20

<210> SEQ ID NO 20
```

```
<211> LENGTH: 443
<212> TYPE: RNA
<213> ORGANISM: Escherichia coli

<400> SEQUENCE: 20
uaauacgacu cacuauaggg agaucgacgg ccugugggca uucagucugg aucgcgaaaa      60
cuguggaauu gaucagcguu gguggaaag cgcguuacaa gaaagccggg cuauugcugu     120
gccaggcagu uuuaacgauc aguucgccga ugcagauauu cguaauuaug cgggcaacgu     180
cugguaucag cgcgaagucu uuauaccgaa agguugggca ggccagcgua ucgugcugcg     240
uuucgaugcg gucacucauu acggcaaagu guggguacau aaucaggaag ugauggagca     300
ucagggcggc uauacgccau uugaagccga ugucacgccg uauguuauug ccgggaaaag     360
uguacguauc accguuugug ugaacaacga acugaacugg cagacuaucc cgccgggaau     420
gcucccuaua gugagucgua uua                                            443

<210> SEQ ID NO 21
<211> LENGTH: 2070
<212> TYPE: DNA
<213> ORGANISM: Spodoptera littoralis

<400> SEQUENCE: 21
atgtcagaca gcgcacagga cgttctacag gatgcggtag ccggcgccgc cgctgctgct      60
gccgatgccg ctgatggatc gctgtttagc acctttgata taattgttct cgttatctta     120
ttgggaggca ccatctggtg gctatacaac tccaaaaagg aaacaaaaa agatgaaatt      180 ctgctgagca atattccat ccaggctgcg ggatccattc aagttactga aaattctttt     240
ataaacaaac taaagtcatc tggaagaagt ttagttgtat tctatgggtc tcaaacgggt     300
actggtgagg agttcgcggg acgtcttgcc aaggagggca tacgatacaa gatgaagggt     360
atggttgctg atcccgaaga atgtgatgtg gaagaactta tgaaactcca agaaataccg     420
aattcattag ctgtgttctg tatggcaaca tatggtgaag gagatcccac agacaactct     480
atggagtttt atgaatggat aaagaacgga gaaccggacc taactggttt aaattatgcc     540
gtgtttggcc ttggcaacaa gacatatgaa cattacaatg cggttgctat atatctagat     600
aaacgtcttg aagaacttgg cgctacaaga gtcttttgaac ttgggcttgg agatgatgac     660
gctaatattg aagatgactt tatcacctgg aaagaaaagt tctggccagc tgtatgtgag     720
aaattcaata ttgagagcac tggtgaagaa gagttgattc gtcagttccg tcttgttact     780
cacggacctg atgacataca acctaacaac atatttactg gagaaattgc cagattacac     840
tccttacaag tccagaggcc accttatgat gccaagaatc cattccttgc tcaaatcaca     900
gttaatagag aattacataa gggtggagat aggtcttgta tccatgtcga attggatatt     960
tcagactcca aaatgcgata tgaagcaggt gatcatgtgg ctgtgtaccc aataaatgac    1020
tctaaccttg tagatcgtct aggacaatta acaggggcca accttgacga gatcttctct    1080
ctcatcaaca ctgaccagga aagcagcaaa aagcatcctt tcccttgccc aacctcctat    1140
cgcactgcat tatcacacta tgttgagatt actgcattgc cccgtactca catattaaga    1200
gagttggttg aatactgtac agatgaagaa gacaaaaaga aattgatgct catggcaact    1260
aattctcaag agggcaaggc catgtaccaa tcatttattg tagaggcttg cagaaatatt    1320
gtgcacatct ggaagatgt accatcttgt aaacctccac tggaccactt gtgtgaactt    1380
ttacctcgcc tacaaccaag atactactcc atctcatcca gtcctaagat gtatccagag    1440
acagtgcata ttactgcagt cgttgttcaa tataaaacac ctacgggtcg cgtcaacaaa    1500
```

| | |
|---|---|
| ggtgttacga caacatggtt agcagataac aaacccgaac ccggcaagcc tcttcctcgt | 1560 |
| gtacccgtat ttatcagaaa atcacaattc cgattacccc tgcaaagtca aaccccata | 1620 |
| ataatggtcg gtcctggtac aggattagct cctttccgtg gattcttgca agagcgtgct | 1680 |
| ttcgcgcgtg cgaatggcaa agaagtggga gacaatgttc tatactttgg atgcagacat | 1740 |
| cgcgaccagg attacattta tcaagaggaa cttgagaaat acgagcaaaa tggtgatgtc | 1800 |
| aaattgaacc tagcattctc tcgtgatcaa aagaaaaag tgtatgtaac acatttacta | 1860 |
| gaaaaagata tggatctctt atgggatgtc atcggtaatc gtaatggaca tttctacatt | 1920 |
| tgcggggacg ctaagaatat ggctgttgac gtaaggaata ttgtcttaaa gactatccaa | 1980 |
| ctaaaaggtg gacgcacaga agctgaagct gcacaattta tcaagaagct tgagtctatg | 2040 |
| aagaaatatt ctgctgacgt atggagttaa | 2070 |

<210> SEQ ID NO 22
<211> LENGTH: 817
<212> TYPE: DNA
<213> ORGANISM: Spodoptera littoralis

<400> SEQUENCE: 22

| | |
|---|---|
| acatctggta tcgacgccaa gaacactctc tgtgagttta ccggcgatat cctgcgtact | 60 |
| cccgtctctg aagatatgtt gggtcgtgta ttcaacggct ccggaaagcc cattgacaag | 120 |
| ggtccccaa tcctcgccga ggacttcttg acatccagg acagcccat caacccatgg | 180 |
| tcccgtatct accccgagga gatgatcag actggtatct ccgctatcga cgtgatgaac | 240 |
| tccattgctc gtggtcagaa gatccccatc ttctctgccg ctggtctgcc ccacaatgaa | 300 |
| attgccgccc agatctgtag acaggccggt cttgttaaga tccccggcaa atcagtgttg | 360 |
| gatgaccacg aggacaactt cgccatcgta ttcgcagcta tgggtgtgaa catggaaacc | 420 |
| gcccggttct tcaaacagga cttcgaagag aacggttcta tggagaacgt gtgcctgttc | 480 |
| ttgaacttgg ccaatgaccc cactattgag agaattatca caccccgtct tgctttgact | 540 |
| gctgccgagt tcttggccta ccagtgcgag aaacacgtgt tggtcatctt gactgacatg | 600 |
| tcctcatacg ccgaggctct gcgtgaggtg tccgccgccc gtgaggaggt accccggacgt | 660 |
| cgtggtttcc caggttacat gtacaccgat ttggccacca tctacgagcg tgccggacgt | 720 |
| gtagagggca ggaatggatc catcacccag atcccccattc tgactatgcc caacgacgac | 780 |
| atcacccatc ctattcctga tttgacggga tatatta | 817 |

<210> SEQ ID NO 23
<211> LENGTH: 1532
<212> TYPE: DNA
<213> ORGANISM: Spodoptera littoralis

<400> SEQUENCE: 23

| | |
|---|---|
| cattgaagcg acagctgcac tgctcgctag ttctcaagta atcattatca ggtgaaagaa | 60 |
| acgaaaatgt tggcttatat ataagttgtg aacagtgaac ctttacaata tattaatatc | 120 |
| attcaagaca tggaaaaaaa caataaatca aagcaaaatg tggaaaatat aaatactcca | 180 |
| actgcttcgg ggtcagctgc tacttcagtg gcatccaatg gccccgcctc aacattaacg | 240 |
| ctattcaaga gcggaccgcg tgaggctaaa attcgacccc tcgcgccatt aatgctcccg | 300 |
| acgcaaagtt acgactcaaa cgccggctct ccggcttcgt caccatccac ccctcgttct | 360 |
| tcatcttctt tctccatcga taaaaccgac aatcacgaca cctttggctt cagtgcggac | 420 |

```
acggctgata tgagaaaaga ggatgaacgt atgaaaacat ttgaaaaatg gcccgtcagt        480
ttcctaaccg gacagcaact tgctcgaaat ggatttttact acctaggccg tggagatgaa       540
gcccgttgcg ccttctgtaa agtggagatt atgaggtggg ttgagggcga tgaccctgcg        600
aaggaccatc agcgttgggc gccacagtgc ccattcgtgc gcaagctcaa cggtagtgcc        660
agcagcgaca cgggtagttc gggccaggac gaatgtgggg cccgcgccac tccctccggt        720
acctctccgc cacgtatggc cggtcccgtg cacccacgat atgcgtctga agccgcacga       780
ctacgtagct ttaaagactg ccacgatgc atgcggcaaa acctgaaga actcgcagag         840 gctggctttt tttacactgg tcagggagac aaaaccaagt gtttttactg cgatggtgga       900
ttaaaagatt gggagaacca tgacgtaccc tgggaacaac atgcacggtg gtttgaccgt      960
tgcgcctacg tgcaattggt gaaggctcga gaatacgttc aaaaggtgat ttctgaggct      1020
tgtgaggtat ccgcatcgga agcagaacgt gatgttgctc cctcacgaac taccagcgag      1080
tccagcgcgc cagttgagac gccggagaac tcagtcgacg actcaaagtt gtgtaaaatc      1140
tgttacgcgg aagagcgtaa cgtgtgcttc gtgccgtgcg ccacgtggt ggcttgcgcc       1200 aagtgcgcgc tggcagccga caagtgcccc atgtgccgca ggacgtttca gaatgcagtg      1260
cgattatatt tctcgtgaga agagccgcca atttgaaggc tcgattctag tcttaaggga      1320
cggccggata gagctgtgtg ctgaaaccac gagctcggaa gccacgtttc cacaggcgga      1380
gtaacctatt aaaacatatt gtttgatagt ttcgatagga actcgctcgc tagtgtagca      1440
aaagacgaaa ttgagagtcc tcaggagtaa gacagatata tttaggtata gtgaattata     1500
aaatacttag ttagcaaaaa aaaaaaaaaa aa                                    1532
```

<210> SEQ ID NO 24
<211> LENGTH: 5207
<212> TYPE: DNA
<213> ORGANISM: Spodoptera exigua

<400> SEQUENCE: 24

```
gagtgagcgc gcggcctacc gaccgaacgc acgcgcaaac catgcgcagc gacgctgtcc        60
cgcgagtgca ctcctcgtta cattgtgaag tgatatacag tataaacacg gattacaaca       120
acgcttatct ccacaacata ctgaactaat attaattaaa aatggcgacg tcaggaggga      180
aacggcggga agagggcagc gataactccg atgatgagct acaccgctc gctaacgata       240 tttatggcgg aagccaaagg acagtacaag aaacgaaagg atgggacgtg ttccgggagt      300
ttccaccgaa gcaggacagt gggtctatgg agactcagaa atgtttggag ttcacagtgc      360
ggttgctgaa ggtgacggca tatctagtcg tcttcattgc ggtcctcggg tccggagtcg      420
tagcaaaggg cagcacgctc tttatgacat cacagctaaa aaaggacagg cggattgcgt      480
attgtaatag gaatttaggt agggataaac aatttatagt aagtcttcca gacgaggaac      540
gagtggcttg gatgtgggct attttggctg cgttcgccat accagaaata ggaacactca      600
ttagatcagt gaggatatgc ttttcaaaa cttctagacg accgactagc acacaattcg      660
ctgtgatttt catagcggag acgttgcata cgataggaat gggtctccta ttcttttttga    720 tcctaccaga actggacgtg gtcaaaggag caatgattac gaactgcctt tgcataattc      780
ctgccgtttt gggcttgctc tcacgcaact ccagagattc gaaacggttc ataaaagtga      840 tgtggacat gcggcaata gttgcgcaag tcactggatt cattgtatgg ccactattag       900
agaataaacc tgtactatgg ttgataccag tcgcatcact atgcatatcc cttgatggt       960 gggaaaacta tgtcacacgt cagagtccga taggtataat caaaagcctt ggcagattaa     1020
```

```
aagatgaatt aaccttcact cgctactaca cgtaccgttt tatatctgtc tggaaaatct   1080
tggtcttcct catgtgcatt ctcttcagca tttggctcga aggtgacgag cctgccatgt   1140
ttttccaact gttcaatgcc ggttttggac cacacagtat cgttgtcgaa gaggtacaaa   1200
ttcaattagg cgggaccgtc attcctgatt tagctaatgt tactttaacc ggagactcag   1260
ttgaggtcgc agctgcttac aaatccgcat tctacgtgat gcttatccaa atatttgcag   1320
cgtatatctg ctacatattt ggaaagttcg cttgtaagat cctcatccaa ggcttcagtt   1380
acgcgttccc catcaatctc gtcattccat ggtggtcaa cttgttgatt gccgcgtgtg    1440
gtatcagaaa tggtgacaat tgctatttcc atgggacagt tcccgattat ctttacttcg   1500
agagtccacc agtgtttacg ctaagcgatt tcatatctcg tcaaatggca tggatatggc   1560
tactatggct attgtcgcaa acatggatca ccatacacat ctggacacca aaagctgaac   1620
gtttggcctc tacggagaag ttattcgtga tgccaatgta caacggttta cttattgatc   1680
agagtatggc cttaaacaga aagaggaatg atcaaagaga tgttaagact gaggacctcg   1740
cagaaataga aaagaaaaa ggcgacgaat actatgaaac tatatcagtt cacacggata    1800
acactgggtc ttctccaaaa gctattaagt catcagatca gatcaccagg atatatgcat   1860
gcgctactat gtggcacgaa actaaagacg agatgatgga gttcttgaag tccattcttc   1920
ggttagacga ggatcagtgc gctcggcgtg tagctcaaaa gtatttacga gtcgttgacc   1980
ctgattacta tgaattcgaa acacatatct tcttagacga cgccttcgaa atatcagatc   2040
acagtgacga tgattctcag gtgaatcgat tcgtaaaact gcttgttgac actatcgatg   2100
aagcggcttc cgaggtacat cagacgaaca ttcgtattcg accacctaag aagtatcccg   2160
cgccttacgg aggacgattg acgtgggtac tgccaggaaa gacgaagatg atttgtcact   2220
tgaaggataa ggcaaagatt cgtcacagga acgttggtc tcaggtgatg tacatgtact    2280
acctactcgg tcaccgacta atggagctgc caatatctgt ggatcgtaaa gaagttatgg   2340
ctgagaacac ctatctgctg accctggacg gagacatcga tttccaacct catgctgtac   2400
gtttgcttat cgatttgatg aagaagaaca agaatctggg agctgcttgc ggtcgtattc   2460
atcccgtagg ctctggccct atggtgtggt atcaaatgtt cgagtatgcc attggtcatt   2520
ggctgcaaaa ggcaactgaa cacatgattg gctgtgtact gtgtagccct ggctgcttct   2580
ccctcttcag aggaaaggct ttgatggacg acaacgtaat gaagaagtat acattgaggt   2640
ctgatgaagc tcggcattac gtacagtacg atcaaggga agatcgatgg ttatgtacgc    2700
tgttacttca acgaggttac cgtgtagagt actcagctgc ctccgacgcc tacactcact   2760
gtcccgaagg ttttaacgag ttctacaacc aacgtcgtcg ttgggtgcct tccaccatcg   2820
ccaacattat ggacttgctt gccgattgca aacacaccat caagattaac gataacatct   2880
ccagtcctta tatcgcatac cagatgatgt tgatgggtgg tacaatcttg ggtcccggaa   2940
ctatattcct tatgttggtg ggtgccttcg tggccgcttt ccgtattgac aactggactt   3000
ctttcgaata taacttgtat cccatttga tcttcatgtt tgtatgtttt acgatgaaat     3060
ccgaaattca attgctcgtg gctcagatat tatcgacggc atacgccatg attatgatgg   3120
cttttatagt cggtaccgcg cttcagttag gcgaggacgg tatcgatct ccttcggcta    3180 tatttttgat atcactttcg agttcgttct tcatagccgc ttgcttgcat ccgcaggagt   3240
tctggtgtat tgtaccggga attatttatc ttttatctat accctctatg tacttgcttt   3300
tgattttata ttcgattata aatcttaacg tagtatcttg gggtactcga gaagtagctg   3360
```

```
ttaagaagac gaagaaggaa atcgaagcag aaaagaaaga agcagaatta gcaaaaaaat    3420
cggcaaaaca gaagtctttg ttaggtttcc ttcaaggagt aaacagcaat gaagaagaag    3480
gatctataga attctcgttc gccggtctat tcaagtgtct gttatgcacg catccaaaag    3540
gaaacgaaga gaaagtgcaa ctcttgcata ttgcatctac tctagagaag ttggaaaaga    3600
aattagaaac tgttgagagg gctgttgatc ctcacggcat tagcagagga cgtaaactgt    3660
cggttggacc aagaggtagc accactggag atcatggttt ggacgctcta gctgaaggac    3720
cagaagagga taacgactca gattctgaaa ctgacacact ttctactgtg ccaagagaaa    3780
agagagatga tctcataaac ccatactgga ttgaggatcc tgagttgaaa aagggtgaag    3840
tagactttt gagtcccgcc gaattatctt tctggaaaga tctcattgac aaatatttat    3900
accctattga tgctaacaag gaggagcagg cccgtatatc caaggatctg aaagaattga    3960
gagactcgtc tgttttttct ttctttatgg tcaatgctct ctttgtattg attgtattct    4020
tgctacaact gaacaaggac aaccttcaca ttaagtggcc cttcggagtt aaaactaaca    4080
taacatacga tgaggttact caagaggtgt taatatcaaa ggaatatctg caactggagc    4140
ctattggttt agtgtttgta ttcttcttcg ccttgatcct ggtgatacag ttctccgcca    4200
tgttgttcca tagatttgga accctttcac acatattagc gtcgcagaaa ctgaactggt    4260
tctgttctaa gaagtccgac gacttgtctc aagacgcact attagataag aatgcaatag    4320
caatagtaaa agacctgcag aaattgaatg gtctggacga cgattatgac aatgactcgg    4380
gctcgggtcc tcataacgtc ggcagaagaa agactattca caatttggag aaggcgagac    4440
agaagaagag gaatataggc acactggatg tggccttcaa gaagagattc ttcaatatga    4500
acgccaacga tggaccaggt acaccagttc taaatcgtaa gatgacgttg agaagggaaa    4560
cgctaaaggc tttagagacg agaaggaatt cagtgatggc ggaaagaaga aaatcccaga    4620
tgcaaacact tggtgccaat aatgaatatg gagtgacagg aatgctcaat aataacttag    4680
gtgtcgggcc gcggcacagg acatctaatg ccaacatatc agtgaaagat gttttcggcg    4740
agccaaacgg aggtcaagtc aaccgaggct acgaaaccac cataggcgac gaagatgaca    4800
caaactcaat gagattacaa cctagacaaa accaagtttc cttccagggt agattctaaa    4860
agagttgcca aactaagtgc ctaggttaaa caaatgtaga tactagaaat atagactgta    4920
aaatttttta caatgaagaa tctcagcaaa tgtttgcggg aatcatgtat tgcttgtgat    4980
atatactttt ttttaggtcg tgacagcaat gtgctgtcat taaataccaa catcggacaa    5040
tttacagctt tattgtaaga taaaacatac gaatttacac tgccacttaa ctttacatta    5100
ttgatctttt tatacttatt taaaataata tcttttgtat taaaagattt ttgtttagt     5160
ttttatgaaa gtagacatcg aattagtgtt gtatgttttt aatgggg                  5207
```

<210> SEQ ID NO 25
<211> LENGTH: 543
<212> TYPE: RNA
<213> ORGANISM: Spodoptera littoralis

<400> SEQUENCE: 25

```
cuaauacgac ucacuauagg gagaacuugg gcuuggagau gaugacgcua auauugaaga     60
ugacuuuauc accuggaaag aaaaguucug gccagcugua ugugagaaau ucaauauuga    120
gagcacuggu gaagaagagu ugauucguca guuccgucuu guuacucacg gaccugauga    180
cauacaaccu aacaacauau uuacuggaga aauugccaga uuacacuccu uacaaguccaa   240
gaggccaccu uaugaugcca agaauccauu ccuugcucaa aucacaguua auagagaauu    300
```

```
acauaagggu ggagauaggu cuuguaucca ugucgaauug gauauuucag acuccaaaau    360
gcgauaugaa gcaggugauc auguggcugu guacccaaua aaugacucua accuuguaga    420
ucgucuagga caauuaacag gggccaaccu ugacgagauc uucucucuca ucaacacuga    480
ccaggaaagc agcaaaaagc auccuuuccc uugcccaacu ucccuauag ugagucguau     540 uag                                                                  543

<210> SEQ ID NO 26
<211> LENGTH: 533
<212> TYPE: RNA
<213> ORGANISM: Spodoptera littoralis

<400> SEQUENCE: 26
cuaauacgac ucacuauagg gagaccaacc uugacgagau cuucucucuc aucaacacug     60
accaggaaag cagcaaaaag cauccuuucc cuugcccaac ucccuaucgc acugcauuau    120
cacacuaugu ugagauuacu gcauugcccc guacucacau auuaagagag uugguugaau    180
acuguacaga ugaagaagac aaaaagaaau ugaugcucau ggcaacuaau ucucaagagg    240
gcaaggccau guaccaauca uuuauuguag aggcuugcag aaauauugug cacaucuugg    300
aagauguacc aucuuguaaa ccuccacugg accacugug ugaacuuuua ccucgccuac     360
aaccaagaua cuacuccauc ucauccaguc cuaagaugua uccagagaca gugcauauua    420
cugcagucgu uguucaauau aaaacaccua cgggucgcgu caacaaaggu guuacgacaa    480
caugguuagc agauaacaaa cccgaacccu uccccuauag ugagucguau uag           533

<210> SEQ ID NO 27
<211> LENGTH: 44
<212> TYPE: DNA
<213> ORGANISM: Spodoptera littoralis

<400> SEQUENCE: 27
ctaatacgac tcactatagg gagaacttgg gcttggagat gatg                      44

<210> SEQ ID NO 28
<211> LENGTH: 44
<212> TYPE: DNA
<213> ORGANISM: Spodoptera littoralis

<400> SEQUENCE: 28
ctaatacgac tcactatagg gagagttggg caagggaaag gatg                      44

<210> SEQ ID NO 29
<211> LENGTH: 44
<212> TYPE: DNA
<213> ORGANISM: Spodoptera littoralis

<400> SEQUENCE: 29
ctaatacgac tcactatagg gagaccaacc ttgacgagat cttc                      44

<210> SEQ ID NO 30
<211> LENGTH: 44
<212> TYPE: DNA
<213> ORGANISM: Spodoptera littoralis

<400> SEQUENCE: 30
ctaatacgac tcactatagg gagagggttc gggtttgtta tctg                      44

<210> SEQ ID NO 31
```

```
<211> LENGTH: 525
<212> TYPE: RNA
<213> ORGANISM: Spodoptera littoralis

<400> SEQUENCE: 31
cuaauacgac ucacuauagg gagaccggaa agcccauuga caagggucccc ccaauccucg      60 ccgaggacuu cuuggacauc cagggacagc ccaucaaccc augguccccgu aucuaccccg    120 aggagaugau ccagacuggu aucuccgcua ucgacgugau gaacuccauu gcucgugguc    180
agaagauccc caucuucucu gccgcugguc ugccccacaa ugaaauugcc gcccagaucu    240
guagacaggc cggucuuguu aagaucccccg gcaaaucagu guuggaugac cacgaggaca    300
acuucgccau cguauucgca gcuaugggug ugaacaugga aaccgcccgg uucuucaaac    360
aggacuucga agagaacggu ucuauggaga acgugugccu guucuugaac uuggccaaug    420
accccacuau ugagagaauu aucacacccc gucuugcuuu gacugcugcc gaguucuugg    480
ccuaccagug cgagaaacac gucucccuau agugagucgu auuag              525

<210> SEQ ID NO 32
<211> LENGTH: 45
<212> TYPE: DNA
<213> ORGANISM: Spodoptera littoralis

<400> SEQUENCE: 32
ctaatacgac tcactatagg gagaccggaa agcccattga caagg              45

<210> SEQ ID NO 33
<211> LENGTH: 45
<212> TYPE: DNA
<213> ORGANISM: Spodoptera littoralis

<400> SEQUENCE: 33
ctaatacgac tcactatagg gagacgtgtt tctcgcactg gtagg              45

<210> SEQ ID NO 34
<211> LENGTH: 524
<212> TYPE: RNA
<213> ORGANISM: Spodoptera littoralis

<400> SEQUENCE: 34
cuaauacgac ucacuauagg gagauucgug cgcaagcuca acgguagugc cagcagcgac      60
acggguaguu cgggccagga cgaauguggg gcccgcgcca cucccuccgg uaccucuccg    120
ccacguaugg ccggucccgu gcacccacga uaugcgucug aagccgcacg acuacguagc    180
uuuaaagacu ggccacgaug caugcggcaa aaaccugaag aacucgcaga ggcuggcuuu    240
uuuuacacug gucagggaga caaaaccaag uguuuuacu gcgaugguggg auuaaaagau    300 ugggagaacc augacguacc cugggaacaa caugcacggu gguugaccg uucgccuac    360 gugcaauugg ugaaggguccg agaauacguu caaaaggugu auucugaggc uugugaggua    420
uccgcaucgg aagcagaacg ugauguugcu cccucacgaa cuaccagcga guccagcgcg    480
ccaguugaga cgccggagaa ucucccuaua gugagucgua uuag              524

<210> SEQ ID NO 35
<211> LENGTH: 44
<212> TYPE: DNA
<213> ORGANISM: Spodoptera littoralis

<400> SEQUENCE: 35
ctaatacgac tcactatagg gagattcgtg cgcaagctca acgg              44
```

```
<210> SEQ ID NO 36
<211> LENGTH: 44
<212> TYPE: DNA
<213> ORGANISM: Spodoptera littoralis

<400> SEQUENCE: 36
ctaatacgac tcactatagg gagattctcc ggcgtctcaa ctgg            44

<210> SEQ ID NO 37
<211> LENGTH: 513
<212> TYPE: RNA
<213> ORGANISM: Spodoptera exigua

<400> SEQUENCE: 37
cuaauacgac ucacuauagg gagauauuca ucccguaggc ucuggcccua uggguguggua      60 ucaaauguuc gaguaugcca uuggucauug gcugcaaaag gcaacugaac acaugauugg     120
cuguguacug uguagcccug gcugcuucuc ccucuucaga ggaaaggcuu ugauggacga     180
caacguaaug aagaaguaua cauugagguc ugaugaagcu cggcauuacg uacaguacga     240
ucaaggggaa gaucgaugguu uauguacgcu guuacuucaa cgagguuacc guguagagua     300
cucagcugcc uccgacgccu acacucacug ucccgaaggu uuuaacgagu ucuacaacca     360
acgucgucgu uggguugccuu ccaccaucgc caacauuaug gacuugcuug ccgauugcaa     420
acacaccauc aagauuaacg auaacaucuc cagaguccuuau aucgcauacc agaugauguu     480 gaugggguggu cucccuauag ugagucguau uag                                513

<210> SEQ ID NO 38
<211> LENGTH: 713
<212> TYPE: RNA
<213> ORGANISM: Spodoptera exigua

<400> SEQUENCE: 38
cuaauacgac ucacuauagg gagacugcaa cuggagccua uugguuuagu guuuguauuc      60
uucuucgccu ugauccuggu gauacaguuc uccgccaugu uguuccauag auuuggaacc     120
cuuucacaca uauuagcguc gacagaacug aacugguucu guucuaagaa guccgacgac     180
uugucucaag acgcacauau uagauaagaau gcaauagcaa uaguaaaaga ccugcagaaa     240 uugaauggguc uggacgacga uuaugacaau gacucgggcu cggguccuca uaacgucggc     300
agaagaaaga cuauucacaa uuuggagaag gcgagacaga agaaggaau uauaggcaca     360 cuggaugugg ccuucaagaa gagauucuuc aauaugaacg ccaacgaugg accagguaca     420
ccaguucuaa aucguaagau gacguugaga agggaaacgc uaaaggcuuu agagacgaga     480
aggaauucag ugauggcgga aagaagaaaa ucccagaugc aaaacacuugg ugccaauaau     540 gaauauggag ugacaggaau gcucaauaau aacuuaggug ucgggccgcg gcacaggaca     600
ucuaaugcca acauaucagu gaaagauguu uucggcgagc caaacggagg ucaagucaac     660
cgaggcuacg aaaccaccau aggcgacgau ucccuauag ugagucguau uag             713

<210> SEQ ID NO 39
<211> LENGTH: 44
<212> TYPE: DNA
<213> ORGANISM: Spodoptera exigua

<400> SEQUENCE: 39
ctaatacgac tcactatagg gagatattca tcccgtaggc tctg            44
```

<210> SEQ ID NO 40
<211> LENGTH: 44
<212> TYPE: DNA
<213> ORGANISM: Spodoptera exigua

<400> SEQUENCE: 40
ctaatacgac tcactatagg gagaccaccc atcaacatca tctg              44

<210> SEQ ID NO 41
<211> LENGTH: 44
<212> TYPE: DNA
<213> ORGANISM: Spodoptera exigua

<400> SEQUENCE: 41
ctaatacgac tcactatagg gagactgcaa ctggagccta ttgg              44

<210> SEQ ID NO 42
<211> LENGTH: 44
<212> TYPE: DNA
<213> ORGANISM: Spodoptera exigua

<400> SEQUENCE: 42
ctaatacgac tcactatagg gagatcgtcg cctatggtgg tttc              44

<210> SEQ ID NO 43
<211> LENGTH: 495
<212> TYPE: RNA
<213> ORGANISM: Zea mays

<400> SEQUENCE: 43
uaauacgacu cacuauaggg agauuggcga gcuuaggauu gaggaucguu uacaguggaa        60
agaacacucu augauauucg ccaugccaaa caagccagga gaauucagcc gguuugauuu       120
cccagaaacu uugccagcac cuauaaaugg gauaugggcc auauugagaa acaaugaaau       180
gcuuaccugg cccgagaagg ugaaguuugc aaucggacuu cugccagcaa ugguggugg        240 ucaaccuuau guugaagcuc aagauggcuu aaccguuuca gaauggauga aaaagcaggg       300
uguuccugau cgggugaacg augagguuuu auugcaaug uccaaggcac ucaauuucau        360
aaauccugau gagcuaucua gcagugcau uugauugcu ugaaccgau ucuucagga           420 gaagcauggu ucuaaaaugg cauucuugga ugguaauccg ccugaaaggc uaucucccua       480
uagugagucg uauua                                                        495

<210> SEQ ID NO 44
<211> LENGTH: 593
<212> TYPE: RNA
<213> ORGANISM: Zea mays

<400> SEQUENCE: 44
uaauacgacu cacuauaggg ugaucgggug aacgaugagg uuuuauugc aaugucaag         60 gcacucaauu ucauaaaucc ugaugagcua ucuaugcagu gcauuugau ugcuugaac         120 cgauucuuc aggagaagca ugguucuaaa auggcauucu uggaugguaa uccgccugaa        180
aggcuaugca ugccuaugu ugaucacauu cggucuaggg guggagaggu ccgccgaauu        240
cucguauuaa aaagauagag cugaauccug auggaacugu aaaacacuuc gcacuuagug       300
auggaacuca gauaacugga gaugcuuaug uuugugcaac accagucgau aucuucaagc       360
uucuuguacc ucaagagugg agugaaauua cuuauucaa gaaacuggag aaguggugg         420 gaguuccugu uaucaauguu cauauaauggu uugacagaaa acugaacaac acauaugacc     480
accuucuuuu cagcaggagu ucacuuuuaa gugucuaugc agacauguca guaaccugca    540
aggaauacua ugacccaaac cguucaaugc uggcccuaua gugagucgua uua    593

<210> SEQ ID NO 45
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 45
gattgctgga gcaggattag    20

<210> SEQ ID NO 46
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 46
cccttgcctc aagcaatatg    20

<210> SEQ ID NO 47
<211> LENGTH: 21
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 47
accacttcga ccgccactac t    21

<210> SEQ ID NO 48
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 48
acgcctaagc ctgctggtt    19

<210> SEQ ID NO 49
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 49
accggcatca gctcagtctc    20

<210> SEQ ID NO 50
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

```
<400> SEQUENCE: 50
tgctgttctc tgggcacagg                                              20

<210> SEQ ID NO 51
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 51
tcccctcaga tattaacaac                                              20

<210> SEQ ID NO 52
<211> LENGTH: 22
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 52
aggaggaaag gcagcttctg tg                                           22

<210> SEQ ID NO 53
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 53
gtgactcgtc accaacaaag                                              20

<210> SEQ ID NO 54
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 54
tgtgttgtcc gttgagactg                                              20

<210> SEQ ID NO 55
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 55
tcggaagccg taccttcgtg                                              20

<210> SEQ ID NO 56
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 56
```

```
cctggagctg ctgctttgtg                                                 20

<210> SEQ ID NO 57
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 57
taccaggcgt cgagtggttc                                                 20

<210> SEQ ID NO 58
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 58
gaagagggcg tgcaaatggg                                                 20

<210> SEQ ID NO 59
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 59
ctattgcgtg tgctccaaac                                                 20

<210> SEQ ID NO 60
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 60
acatgaggag gaaccaaagg                                                 20

<210> SEQ ID NO 61
<211> LENGTH: 490
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 61
cuaauacgac ucacuauagg gagaggcuca agaaccaguu uauguuaaug cuaagcagua      60
ucgaaggauc cugcagcgaa gacagucacg ugcuaaagca gaacuugaaa agaagcaaau    120 aaagguaga aagccauauc uucacgaguc ucgacaucag caugcacuga ggagggugaag    180 ggccucgggu ggacguuuug ccaaaaagac agaugcuucu aagggacug guucugugag     240 uucaucgggu ucugaaccuu ugcaguucaa ugcugcugau auucaaaaga ggaaugaaaa    300
uggaagguug gccgagcuuc agcagucuua uucaaauggu agcaguuaug caaucaaag     360 uagcuuucaa gaauccaagg augaguacca guuugcuaaa agcagggaag gagguuuuuu    420
```

```
ugucaaguaa uuggagauac guucaugugu aaacuagcuc uugcccucuc ccuauaguga      480
gucguauuag                                                            490

<210> SEQ ID NO 62
<211> LENGTH: 497
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 62
cuaauacgac ucacuauagg gagagcaguu auggcaauca aaguagcuuu caagaaucca      60
aggaugagua ccaguuugcu aaaagcaggg aaggagguuu uuugucaag uaauuggaga     120 uacguucaug uguaaacuag cucuugcccu gcaacgaggg uagaguauga gcaagaggag     180
uuuacaggga uuguuucauu ucuuggcuuu ucaagauagg cggcaauuca uucuuggcuu    240
uuuacuuuag uguuaaaggg agcaacagag gugacgaggg uaucagcuguu gcagcauuug   300 cuuggagauu acaucuuccc uuaugucag agauggauga acuuagaacu aggauuagaa    360
aguuuuucag uaaguuuaug uuuggccagu uacuguaguu uuaguuuagg agaccaugua    420
aaaagguugu uaguuuugca aaaggaucuu uuucuuuccc cuaauuggug cauucuccccu   480 auagugaguc guauuag                                                   497

<210> SEQ ID NO 63
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 63
cgagtcggga tactggaagg                                                 20

<210> SEQ ID NO 64
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 64
cttcttcatg ccgacgaggg                                                 20

<210> SEQ ID NO 65
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 65
acgatgggcg agaaggagtg                                                 20

<210> SEQ ID NO 66
<211> LENGTH: 20
<212> TYPE: DNA
<213> ORGANISM: artificial Sequence
<220> FEATURE:
```

```
<223> OTHER INFORMATION: polynucleotide sequence or in vitro generated
      dsRNA

<400> SEQUENCE: 66
tcagtcccgt cgggtacttg                                                    20

<210> SEQ ID NO 67
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 67
agggtcacat cccgaactac                                                    20

<210> SEQ ID NO 68
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 68
acctcgtcag tctccacatc                                                    20

<210> SEQ ID NO 69
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 69
gttggattcg agcttccttc                                                    20

<210> SEQ ID NO 70
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 70
tgctgctgct cactagctac                                                    20

<210> SEQ ID NO 71
<211> LENGTH: 490
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 71
cuaauacgac ucacuauagg gagacagucc guuggccuag uuccuauugg agaucuguga         60
agguugguug ggaugaauca acugcagggg aaagaccacc aagaguuucu uuaugggaaa       120
uugaaccauu gacaaccuuu ccaauguauc caucucuguu cccacugaga guuaagcauc       180
cuugguauuc aggaguugcu ucccugcaug augacagcaa ugcuuuaaug uggcugagag       240
gaguugcugg ugagggaggu uuucagucuc ugaacuuuca gucaccuggu auuggcuccu       300
```

```
gggacaaca gaggcuccau ccauccuuac ugagcagcga ucacgaucag uaccaagcag    360
uaguugcugc ugcugcugcu ucccaaucug gugguuacuu aaaacagcaa uucuugcacc    420
uucagcaacc uaugcagucc ccucaagaac acugcaaccu caacccucuc ccuauaguga    480
gucguauuag                                                            490
```

```
<210> SEQ ID NO 72
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 72
ctcagccatg ggatactacc                                                 20

<210> SEQ ID NO 73
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 73
gctggccgtt gacgacattg                                                 20

<210> SEQ ID NO 74
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 74
acctcaggtg gatgtctc                                                   18

<210> SEQ ID NO 75
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 75
tgctggtgct ttgggtag                                                   18

<210> SEQ ID NO 76
<211> LENGTH: 530
<212> TYPE: DNA
<213> ORGANISM: Zea mays

<400> SEQUENCE: 76
taccatgcga tccttaggag gaggcagaca cgtgctaaac tggaggcgca aaacaagatg    60
gtgaaaggtc ggaagccgta ccttcgtgag tctcgacacc gtcatgccat gaagcgggcc   120
cgtggctcag gagggcggtt cctcaacaca aagcagcagc tccaggagca gaaccagcag   180
taccaggcgt cgagtggttc aatgtgctca aagaccattg gcgacagcgt aatctcccaa   240
agtggcccca tttgcacgcc ctcttctgac gctgcaggtg cttcagcagc cagccaggac   300
```

```
cgcggctgct tgccctcggt tggcttccgc cccacagcca acttcagtga gcaaggtgga    360
ggcggctcga agctggtcgt gaacggcatg cagcagcgtg tttccaccat aaggtgaaga    420
gaagtgggca cgacaccatt cccaggcgcg cactgcctgt ggcaactcat ccttggcttt    480
tgaaactatg aatatgcaat ggacatgtag ctttgagttc ctcagaataa                530

<210> SEQ ID NO 77
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 77
taatacgact cactataggg ccgcatgcca ttgtccatcc                            40

<210> SEQ ID NO 78
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 78
taatacgact cactataggg tgcatgccgt tcacgaccag                            40

<210> SEQ ID NO 79
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 79
taatacgact cactataggg caaatagtcc ggttatgttg                            40

<210> SEQ ID NO 80
<211> LENGTH: 42
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 80
taatacgact cactataggg gctacatgtc cattgcatat tc                         42

<210> SEQ ID NO 81
<211> LENGTH: 936
<212> TYPE: RNA
<213> ORGANISM: Oryza sativa

<400> SEQUENCE: 81
ucaguguuug uccccucaga uauuaacaac aaugauaguu gugggagcg ggaccauggc       60 acuaagucgg uauugucuuu ggggaacaca gaagcugccu uuccuccuuc aaaguucgau    120
uacaaccagc cuuuugcaug uguuucuuau ccauauggua cugauccaua uuauggugga    180
guaucaacag gauacacuuc acaugcauuu guucauccuc aaauuacugg ugcugcaaac    240
ucuaggaugc cauuggcugu ugauccuucu guagaagagc ccauauuugu caaugcaaag    300
caauacaaug cgauccuuag aagaaggcaa acgcgugcaa aauuggaggc ccaaaauaag    360
```

```
gcggugaaag gucggaagcc uuaccuccau gaaucucgac aucaucaugc uaugaagcga    420
gcccguggau caggugguCg guccuuacc aaaaaggagc ugcuggaaca gcagcagcag    480
cagcagcagc agaagccacc accggcauca gcucagucuc aacagguag agccagaacg    540 agcggcggug ccguuguccu uggcaagaac cugugcccag agaacagcac auccugcucg    600
ccaucgacac cgacaggcuc cgagaucucc agcaucucau uggggcgg caugcuggcu    660 caccaagagc acaucagcuu cgcaccgcu gaucgccacc ccacaaugaa ccagaaccac    720 cgugucccg ucaugaggug aaaaccucgg gaucgcggga cacgggcggu ucugguuuac    780
ccucacuggc gcacuccggu gugcccgugg caauucaucc uuggcuuaug aaguaucuac    840
cugauaauag ucugcugca guuuauaugc aaugcaaccu cugucagaua aacucuuaua    900 guuuguuua uuguaagcua ugacugaacg aacugu    936
```

<210> SEQ ID NO 82
<211> LENGTH: 43
<212> TYPE: DNA
<213> ORGANISM: artificial Sequence
<220> FEATURE:
<223> OTHER INFORMATION: polynucleotide sequence or in vitro generated dsRNA

<400> SEQUENCE: 82

```
taatacgact cactataggg ctgcctttcc tccttcaaag ttc    43
```

<210> SEQ ID NO 83
<211> LENGTH: 40
<212> TYPE: DNA
<213> ORGANISM: artificial Sequence
<220> FEATURE:
<223> OTHER INFORMATION: polynucleotide sequence or in vitro generated dsRNA

<400> SEQUENCE: 83

```
taatacgact cactataggg tgctgttctc tgggcacagg    40
```

<210> SEQ ID NO 84
<211> LENGTH: 41
<212> TYPE: DNA
<213> ORGANISM: artificial Sequence
<220> FEATURE:
<223> OTHER INFORMATION: polynucleotide sequence or in vitro generated dsRNA

<400> SEQUENCE: 84

```
taatacgact cactataggg cattggctgt tgatccttct g    41
```

<210> SEQ ID NO 85
<211> LENGTH: 40
<212> TYPE: DNA
<213> ORGANISM: artificial Sequence
<220> FEATURE:
<223> OTHER INFORMATION: polynucleotide sequence or in vitro generated dsRNA

<400> SEQUENCE: 85

```
taatacgact cactataggg ttcgttcagt catagcttac    40
```

<210> SEQ ID NO 86
<211> LENGTH: 512
<212> TYPE: RNA
<213> ORGANISM: Oryza sativa

```
<400> SEQUENCE: 86 cauggugcu cagcggcugg ggcaccaaug cuccaccacc cagccuuuga gcucaccuca      60 ggugauguc ucgcgggagu cgccaccgac uccagcugug cucucucucu ucugucaacu    120
cagccauggg auacuaccca aagcaccagc agccacaacc gguccccgcc aaugucguca    180
acggccagcg ccuucggagg cggcaacaac ccgguguccgc ccucggucau ggcaagcaac    240
uacauggcgg cgagcccgg cuggaacagc uccagccggg gccaugacgg cgccaggaac    300
gugcaccugc cgccaccgca cggggtugug cugaacgagg ucccuccggg cucuguccac    360
cacggccauu ucuccggcga gcucgagcuc gcacugcagg gaggugcccc guccaaccgg    420
ccggaagcca agcauggcuc cggcagcggc gccuucagcc acuccaccaa ugccaugaac    480
uggucucugu agagaccauu gaucaucuuc uu                                  512

<210> SEQ ID NO 87
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 87
taatacgact cactataggg tcacctcagg tggatgtctc                           40

<210> SEQ ID NO 88
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 88
taatacgact cactataggg cattggtgga gtggctgaag                           40

<210> SEQ ID NO 89
<211> LENGTH: 44
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 89
taatacgact cactataggg ccaatgctcc accacccagc cttt                      44

<210> SEQ ID NO 90
<211> LENGTH: 43
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 90
taatacgact cactataggg agttcatggc attggtggag tgg                       43

<210> SEQ ID NO 91
<211> LENGTH: 840
<212> TYPE: RNA
<213> ORGANISM: Zea mays

<400> SEQUENCE: 91
```

-continued

```
auggaaggaa acgguggcgc gggcggcggu agcggaagcg cggcaccgcc cuggaucuc      60 gccaugcacu gggcacccgc cguagugucg uccuacccgc cgcagcccuu ggagcugcag    120
cagcaggagc uuaccugccu caagcugggg aagcggcccg ccugcugcug gcaggggcg     180 ccgggcaacc aagcggcgca gguccacggc aauggcggcg cugguggcgc agcugcgag     240 gguaagagga aggacaaggc gccugccgcg gcggccguga cgaggugcca gguggagggg    300
ugccaccugu cgcuggcgga cgccaaggag uaccaccggc ggcacaaggu gugcgaggcg    360
cacuccaagu cgccccgggu cgucguccuc ggcgccgagc agcgcuucug ccagcagugc    420
agccgguucc acgcgaucuc ggaguucgac gacgcgaagc ggagcugccg acggcgucug    480
gccgggcaca acgagcggcg gcggaagagc aacgccagcg aggccauggc aagaggcguc    540
gcgcacccac acggagugac ggcuuucggc cacggcggcu uccugcccuc gcgcggccuc    600
guccccgcag ggucgucccc ggcggcggcu ggugcucucu cucuucuguc aucggccaga    660
ggcagcgugg cgggcgccag cgggcccugg cuggucacgg cggcgcggga ggacaucccg    720
gcgcgcucca gcgcggcgcu cgacgaccuu aucgccgaga accgcgccgc cgcgcuccuc    780
gcgcggcagu acuucgucuc cgaccgcucg ccggcgccca gacgggauuu cgucgccucu    840
```

<210> SEQ ID NO 92
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 92

```
taatacgact cactataggg cgccgtagtg tcgtcctacc                           40
```

<210> SEQ ID NO 93
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 93

```
taatacgact cactataggg aaagccgtca ctccgtgtgg                           40
```

<210> SEQ ID NO 94
<211> LENGTH: 38
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 94

```
taatacgact cactataggg cgcaggtcca cggcaatg                             38
```

<210> SEQ ID NO 95
<211> LENGTH: 41
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 95

```
taatacgact cactataggg cggtcggaga cgaagtactg c                    41
```

<210> SEQ ID NO 96
<211> LENGTH: 800
<212> TYPE: RNA
<213> ORGANISM: Oryza sativa

<400> SEQUENCE: 96

```
augagcggga ugaauucgcu gagcauggug gaggcgaggc ugccgccggg guucagguuc    60
cacccgcgag acgacgagcu cgugcuggac uaccuggaaa ggaagcuccu cgacggcggc   120
gugggcggcg ccgcggcggc ggcggcggcg gucaccaucu acggcugccc ggugaugguc   180
gacgucgauc ucaacaagug cgagccaugg gaccuuccug agaucgcuug cguugguggc   240
aaggaguggu acuucuauag ccuuagggau aggaaguaug caacuggcca acgaacaaau   300
agagcaaccg aaucgggcua cuggaaggcc acaggaaaag aucgcccaau aagccggaaa   360
ggauugcucg ucgguaugcg aaaaacccug uguucuaca aagguagagc cccuaagggg   420
aagaagaccg aguggguccau gcaugaauuc cgcaaagaag acaagggga uccgaugaag   480
uugccucuca aggaggacug ggucuugugu agagucuucu acaagaguag gacaaccauu   540
gccaagcugc caacgagggg uagcuacaac aauauugaca gugauggccac aacuucacug   600
ccucccccuca cugacaacua cauugcauuu gaucagccug guucaaugca aaaccuagag   660
gguuaugagc aagugcccug cuucuccaau aaucccucuc aacagccauc gucgucgaug   720
aauguuccgu ugacaucggc cauggguuag caagagcaaa acaauauggg uagggcgauc   780
aaggaugugc ugagccaauu                                              800
```

<210> SEQ ID NO 97
<211> LENGTH: 41
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 97

```
taatacgact cactataggg ttcaggttcc acccgcgaga c                    41
```

<210> SEQ ID NO 98
<211> LENGTH: 41
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 98

```
taatacgact cactataggg ccgttggcag cttggcaatg g                    41
```

<210> SEQ ID NO 99
<211> LENGTH: 41
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 99

```
taatacgact cactataggg cgtgctggac tacctggaaa g                    41
```

<210> SEQ ID NO 100

```
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 100
taatacgact cactataggg caaccatggc cgatgtcaac                             40

<210> SEQ ID NO 101
<211> LENGTH: 799
<212> TYPE: DNA
<213> ORGANISM: Zea mays

<400> SEQUENCE: 101
atggagcacg acgtgcacca ccagcaggcc atggagctgc cgccggggtt ccgattccac       60
cccaccgacg aggagctcat cacgcactac ctcgccagga aggccgccga cgcccgcttc      120
gccccgcgcg ccgtcggcga ggccgacctc aacaagtgcg agccatggga cctgccatcc      180
cgggcgacga tgggcgagaa ggagtggtac ttcttctgcg tcaaggaccg caagtacccg      240
acgggactga ggacgaaccg ggccaccgag tcgggatact ggaaggcgac gggcaaggac      300
agggagatct tcaggagcaa ggccctcgtc ggcatgaaga agacgctcgt cttctacacg      360
gggagggcgc ccaggggagg caagaccggc tgggtcatgc acgagtaccg cctccacggc      420
aagcacgcca gcagcagccg cctcatgccg tcgtcggtca gagctggcgc gtcaaaggac      480
gagtgggtgc tgtgcagggt gttcaagaag agcatcgagc cgccgccgtc agtgggcaag      540
aggtcgtcgg tcgcgtgtac ggggatgatg ttggtggagg acgtcgtggg accgccgtcc      600
atgtccatgg aggacgacct cgccgcgtgc gcgctgcctc cgctgatgga cgtgtccggc      660
ggtggcggcg ccaacatggc ggcggcgtcc atcgagctgc tggcgccacc ggcaccacac      720
gtgacctgct tctccaacgc gctggagggc cagttcttcc tgaacccacc ctgcctccac      780
ccctccacgt cgccgctcc                                                   799

<210> SEQ ID NO 102
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 102
taatacgact cactataggg ccaccgacga ggagctcatc                             40

<210> SEQ ID NO 103
<211> LENGTH: 40
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 103
taatacgact cactataggg cgacgtcctc caccaacatc                             40

<210> SEQ ID NO 104
<211> LENGTH: 39
<212> TYPE: DNA
<213> ORGANISM: artificial Sequence
<220> FEATURE:
```

```
<223> OTHER INFORMATION: polynucleotide sequence or in vitro generated
      dsRNA

<400> SEQUENCE: 104
taatacgact cactataggg aggccgacct caacaagtg                               39

<210> SEQ ID NO 105
<211> LENGTH: 42
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 105
taatacgact cactataggg tcaggaagaa ctggccctcc ag                           42

<210> SEQ ID NO 106
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 106
cctcaacagt cctggatgtc                                                   20

<210> SEQ ID NO 107
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 107
cccgtaagtt ggaagtgatg                                                   20

<210> SEQ ID NO 108
<211> LENGTH: 506
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 108
cuaauacgac ucacuauagg gagagcuucu ccucccuaca acugucucua acgucgcuac        60
uacaucaauu gaugcugaua uaccucuau gccacuaggg acuucuggau uuccgaaucc       120
cuuguauagu uaugugcaag auucacuga cuuguugcau aauguagggc aagcugaugc       180
acaaacugug ccccguacau uugucaaggu uuacaaauca gcgucccuug ggaggucauu       240
ggacaucacu cgguucaaca gcaucauga gcugcgacag gaauuagggc agauguucgg       300
uaucgaaggg uugcuugaag acccucaaag aucaggcugg cagcuuguau uuguugacag       360
ggagaaugau guccuucucc uuggagacga uccgugggag gaauuuguca auaauguuug       420
guacaucaaa auucuuucac ccgaggaugu gcagaaacug gggaaagagg agguuggauc       480
ccucucccua uagugagucg uauuag                                           506

<210> SEQ ID NO 109
<211> LENGTH: 544
<212> TYPE: RNA
```

```
<213> ORGANISM: artificial Sequence
<220> FEATURE:
<223> OTHER INFORMATION: polynucleotide sequence or in vitro generated
      dsRNA

<400> SEQUENCE: 109
cuaauacgac ucacuauagg gagaugggag auugagccuu ugacuacuuu uccgauguau    60
ccaucucuuu uuccucuaag gcuaaagagg ccuuucuauc aaggaaccuc aucuuaucag   120
gauaguaaca augaagcuau uaaucgaaug ucaugguuaa gagggaaugc ugguagcua    180
ggacaucauu caaugaaucu ucagucuuuu ggcaugcuuc cuuggaugca acagagaguc   240
gauucaacaa uucucccaaa ugauauuaau cagcacuauc aagcuaugcu ggcuacuggc   300
uugcaaaguu uugggagugg agauuuacug aaacagcaau uaaugcaguu ucagcagccu   360
guccaauauc ugcaacaugc aaguacgag aauucaauuu ugcaucagca gcagcagcag    420
cagcagcaaa uaaugcagca agcaguucau cagcauaugc ugccugcuca aacccaaaug   480
cugucagaga accuucaaag gcaaucccag caucaaucca ucucccuaua gugagucgua   540
uuag                                                               544

<210> SEQ ID NO 110
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 110
gaggcaccuu gugugattg                                                20

<210> SEQ ID NO 111
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 111
caaagccacg gttcttaagc                                               20

<210> SEQ ID NO 112
<211> LENGTH: 511
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 112
cuaauacgac ucacuauagg gagauccagg uccaaugaaa caaccuuaug uuccuccuca    60
cuauguaucu gcccccggca ccaccacggc gcggugucg acuggucuuu gucauuguu    120
ugaugacccu gcuaacuguu uaguuacuag uguuugcccu uguaucaccu uuggacagau   180
uucugaaaua cuaaacaaag gaacaacuuc augugggagu agaggugcau uauauuguuu   240
gcugggauug acaggauugc cuagccuaua uuccugcuuc uacaggucua aaaugagggg   300
gcaauaugau cuggaagagg caccuugugu ugauugucuu guacauguau ucugugaacc   360
uugugcucuu ugccaagaau acagagagcu uaagaaccgu ggcuuugaua ugggaauagg   420
guggcaagcu aauauggaua gacaaagccg aggaguuacc augcccccuu aucaugcagg   480
```

```
caugaccucu cccuauagug agucguauua g                              511
```

<210> SEQ ID NO 113
<211> LENGTH: 513
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 113

```
cuaauacgac ucacuauagg gagaagcucc ugaacccauc auugaagaac cagugcuuag    60
ccuugaucca guugcagcag ccauuucgau gaugucuggc agugagaacg uaauggauga   120
aacuauagag guugcagaua ucagcgacau ucagaaugac ucucuuuuaa gcgaaguauu   180
auacgagugc gagaaggaac ucauggagaa guccgcaauc gaagagacua uuucgaacu    240
gcuggacguc aagauuccua ugcugcaagu ggaagaguuc ccuagggaaa cccaaguaca   300
acuaccggcc auggagaagg agaagccauc aguuccugaa uguugucac uccagaaaag    360
ugucaguucu gggugccuca acucagcuga uuggaucaau ggaccagcca ggccaaacuu   420
ccuggacuuc caaggauugg acuuugagac agcguuggg uugaggaggg cauacagcga    480
aggagacauu ucccuauag ugagucguau uag                                513
```

<210> SEQ ID NO 114
<211> LENGTH: 524
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 114

```
cuaauacgac ucacuauagg gagacaugga gaaguccgca aucgaagaga cuauuucuga    60
acugcuggac gucaagauuc cuaugcugca agugggaagag uucccuaggg aaacccaagu   120
acaacuaccg gccauggaga aggagaagcc aucaguuccu gaauguuguu cacuccagaa   180
aagugucagu ucugggugcc ucaacucagc ugauuggauc aauggaccag ccaggccaaa   240
cuuccuggac uuccaaggau uggacuuuga cagcguuu gggguugagga gggcauacag   300
cgaaggagac auucagaauc uuggagcuag caccccucga cccgggaacu caggaaacgc   360
ucaauuagca ucuugcgaga ggcuuguaac caucagugac cugaaaucug aagaaggaa    420
gcagaagcua ucuagguaca gaaagaagaa ggugaagaga aacuuuggca gaaagaucaa   480
guaugcuugc aggaaggcuc ucucccuaua gugagucgua uuag                    524
```

<210> SEQ ID NO 115
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 115

```
gtgactcgtc accaacaaag                                              20
```

<210> SEQ ID NO 116
<211> LENGTH: 20
<212> TYPE: DNA
<213> ORGANISM: artificial Sequence

```
<220> FEATURE:
<223> OTHER INFORMATION: polynucleotide sequence or in vitro generated
      dsRNA

<400> SEQUENCE: 116
tgtgttgtcc gttgagactg                                                   20

<210> SEQ ID NO 117
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 117
cagttcgcgc acaccattcg                                                   20

<210> SEQ ID NO 118
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 118
gcagcatgaa cggctccaag                                                   20

<210> SEQ ID NO 119
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 119
tccgcaatgc cgtgtgcatc                                                   20

<210> SEQ ID NO 120
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 120
gcggcaggaa tgctagtgtc                                                   20

<210> SEQ ID NO 121
<211> LENGTH: 543
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 121
cuaauacgac ucacuauagg gagagcccac uucuacgagu ccugccccua ccucaaguuc       60
gcccacuuca ccgcaaauca agccauccuc gaggcuuucg ccggcugcca ccgcguccac      120
gucgucgacu ucggcaucaa gcaggggaug caauggccag cucuccucca ggcccucgcc      180
cuucgucccg gcggcccccc aucguuccgc cucaccggcg ucggccccuu gcagccggac      240
```

| | |
|---|---|
| gagaccgacg ccuugcagca ggugggüugg aagcuugccc aguucgcgca caccauucgc | 300 |
| gucgacuucc aguaccgggg acucgucgcc gccacucucg cggacuugga gccguucaug | 360 |
| cugcagccgg agggcgaggc ggacgcgaac gaggagccug aggugaucgc cgucaacucg | 420 |
| guguucgagc ugcaccggcu gcucgcgcag cccggcgcgc uggagaaggu ccugggcacg | 480 |
| gugcacgcgg ugcggccaag gaucgucacc gugguagagu cucccuauag ugagucguau | 540 |
| uag | 543 |

<210> SEQ ID NO 122
<211> LENGTH: 547
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 122

| | |
|---|---|
| cuaauacgac ucacuauagg gagaauaucu acaaccgcga cuggcauuau ucauguggaa | 60 |
| caaaagacua caaauuacug auggauaagu ucgccuugu cuccacggcu uucuuggagc | 120 |
| uuggucaagg uuaucaagag gcaauugaag aaaucacuag gcuaauggga gcaggaaugg | 180 |
| caaaauuuau cugcaaggag guugaaacug uugaugacua caaugaguac ugucacauag | 240 |
| uagcagggcu aguggguau gggcuuucca ggcucuuuca ugcugguggg acggaagauc | 300 |
| uggcuucaga uucacuuuca aauucaaugg gcuuguuucu gcagaaaauc aauauaauua | 360 |
| gggauuauuu ggaggacaua aacgagauac caaagucacg uauguucugg ccucgagaaa | 420 |
| uauggaguaa auaugucaau aaacucgagg auuugaaaua cgaggaaaau ucagaaaagg | 480 |
| caguucagug uuugaaugau auggugacua acgcucuguc ucaucccucu auagugaguc | 540 |
| guauuag | 547 |

<210> SEQ ID NO 123
<211> LENGTH: 455
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 123

| | |
|---|---|
| cuaauacgac ucacuauagg gagacgcucu gucucaugcu gaagacugcc uccaauacau | 60 |
| gucagcauug aaggaucaug ccauuuuccg uuuuugugca auaccucaga uaauggcaau | 120 |
| ugggacaugu gcuauuugcu acaauaaugu gaaugucuuu agaggaguug uuaagaugag | 180 |
| gcgugggcuc acugcacgag uaauugauga dacaaacaca augucagaug ucuauacugc | 240 |
| uuucuaugag uucucuucgc ugauagaauc gaagauugau aauaaugauc caaaugcuuc | 300 |
| ccuaacgcgg aaacguguug augcgauaaa gagaaccugc aagucaucuu gcucacuaaa | 360 |
| gagaagggga uacgauuugg agaagucaaa guacaacucc augcugauaa ugguuguacu | 420 |
| ucuguuggug gcucucccua uagugagucg uauua | 455 |

<210> SEQ ID NO 124
<211> LENGTH: 480
<212> TYPE: RNA
<213> ORGANISM: Aqueoria victoria

<400> SEQUENCE: 124

| | |
|---|---|
| cuaauacgac ucacuauagg gcgagccaac acuugucacu acuuucucuu auggugulca | 60 |

```
augcuuuuca agauacccag aucauaugaa gcggcacgac uucuucaaga gcgccaugcc    120
ugagggauac gugcaggaga ggaccaucuc uuucaaggac gacgggaacu acaagacacg    180
ugcugaaguc aaguuugagg gagacacccu cgucaacagg aucgagcuua agggaauuga    240
uuucaaggag gacggaaaca uccucggcca caaguuggaa uacaacuaca acucccacaa    300
cguauacauc acggcagaca aacaaaagaa uggaaucaaa gcuaacuuca aaauuagaca    360
caacauugaa gauggaagcg uucaacuagc agaccauuau caacaaaaua cuccuauugg    420
cgauggcccu guccuuuuac cagacaacca uuaccuucgc ccuauaguga gucguauuag    480
```

```
<210> SEQ ID NO 125
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 125
atggctgttg acgtaagg                                                  18

<210> SEQ ID NO 126
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 126
tgcagcttca gcttctgtg                                                 19

<210> SEQ ID NO 127
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 127
accgtcgtac tggtaaatcc                                                20

<210> SEQ ID NO 128
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 128
tggcggcatc tccagatttg                                                20

<210> SEQ ID NO 129
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 129
ctggtcgtac caccggtat                                                 19
```

<210> SEQ ID NO 130
<211> LENGTH: 20
<212> TYPE: DNA
<213> ORGANISM: artificial Sequence
<220> FEATURE:
<223> OTHER INFORMATION: polynucleotide sequence or in vitro generated dsRNA

<400> SEQUENCE: 130
gcagagcgta accttcgtag             20

<210> SEQ ID NO 131
<211> LENGTH: 547
<212> TYPE: RNA
<213> ORGANISM: artificial Sequence
<220> FEATURE:
<223> OTHER INFORMATION: polynucleotide sequence or in vitro generated dsRNA

<400> SEQUENCE: 131
cuaauacgac ucacuauagg gagaaugccc ugguucaagg gauggaacgu ugagcgcaag      60
gaaggcaagg cugaagguaa augccucauu gaggcccucg acgccauccu gcccccugcu    120
cgccccacag acaagcccu gcgucuuccc cuccaggacg uauacaaaau cggugguauu     180
gguacggugc ccguaggcag aguugaaacu gguauccuca agccugguac caucgucguc    240
uucgcccccg ccaacaucac cacugaaguc aagucugugg agaugcacca cgaagcucuc    300
caagaggccg uacccgguga caacguuggu uucaacguaa agaacguuuc cgucaaggag    360
uugcgucgug guuacgucgc uggugacucc aagaacaacc cacccaaggg cgccgccgau    420
uucacagcac aggucaucgu gcucaaccac ccuggucaaa ucucaaacgg auacacaccu    480
gugcuggauu gccacacagc ccacauugcc ugcaaguucg cugucucccu auagugaguc    540
guauuag                                                               547

<210> SEQ ID NO 132
<211> LENGTH: 509
<212> TYPE: RNA
<213> ORGANISM: artificial Sequence
<220> FEATURE:
<223> OTHER INFORMATION: polynucleotide sequence or in vitro generated dsRNA

<400> SEQUENCE: 132
cuaauacgac ucacuauagg gagaggccca ggaaaugggu aagggguuccu ucaaauacgc    60 cuggguauug gacaaacuga aggcugagcg ugaacguggu aucaccauug auauugcucu   120
guggaaguuc gaaaccgcua aauacuaugu caccauuauu gacgcucccg gacacagaga   180
uuucaucaag aacaugauca cuggaaccuc ccaggccgau ugcgccguac ucauugucgc   240
cgcugguacc ggugaauucg aggcugguau cucgaagaac ggacagaccc gugagcacgc   300
ucugcucgcu uucacacucg gugucaagca gcugauugug ggcgucaaca aaauggacuc   360
cacugagccc ccauacagcg aaucccguuu cgaggaaauc aagaaggaag uguccuccua   420
caucaagaag aucgguuaca acccagcugc ugucgcuuuc guaccauuu cuggcuggca    480 cggagucucc cuauagugag ucguauuag                                      509

<210> SEQ ID NO 133
<211> LENGTH: 502
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 133

| cuaauacgac ucacuauagg gagaauggcu ccggcaugug caaggccggu uucgccggcg | 60 |
| acgacgcgcc ccgcgccguc uucccaucca ucguaggucg cccucgucac cagggugugu | 120 |
| ugguuggguau gggucagaag gacuccuacg uaggcgauga ggcccagagc aagagaggua | 180 |
| uccucacccu gaaguacccc aucgagcacg guaucaucac caacugggac gacauggaga | 240 |
| agaucuggca ccacaccuuc uacaacgagc ugcgcgucgc cccugaggaa cacccagucc | 300 |
| uccugacuga ggcuccccuc aacccuaagg ccaacaggga gaagaugacc cagaucaugu | 360 |
| uugagaccuu caacuccccc gccauguacg ucgccaucca ggcugugcuc ucucuguacg | 420 |
| ccucuggucg uaccaccggu aucguccugg acuccgguga uggugucucc cacaccguuc | 480 |
| ucccuauagu gagucguauu ag | 502 |

<210> SEQ ID NO 134
<211> LENGTH: 592
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 134

| cuaauacgac ucacuauagg gagugucaac augggucaga uaaccagagc uaccugccca | 60 |
| augaaccuug cccuugcggu cgucgccgag cucgacgacc ucacuguugg ugggcugauc | 120 |
| aacgguuacg gcaucgaggg gagcucucac cucuauggcc uuuucuccga cacgguugu c | 180 |
| gcgauggagg uuguucucgc agauggccgg gucgucagag ccaccaagga caacgaguac | 240 |
| ucugaccuuu ucuauggaau ucccuggucc cagggaacac uggggguuccu ugucucugca | 300 |
| gagaucaagc ugauccccau caaggaguac augaagcuca ccuacacucc agucaagggg | 360 |
| ggucuaaagg agaucgcgca ggccuacgcg gauucuuucg cuccgaggga cggugacccg | 420 |
| gcaaaggucc cugacuuugu ugaagggaug ugguacacag agagcgaggg ugucaugaug | 480 |
| acgggcgugu acgcuucgaa agaagaggcg aagaagaagg gcaacaagau caacugcgug | 540 |
| ggguggguggu uuaagcccug guucuaccuc ucccuauagu gagucguauu ag | 592 |

<210> SEQ ID NO 135
<211> LENGTH: 598
<212> TYPE: RNA
<213> ORGANISM: artificial Sequence
<220> FEATURE:
<223> OTHER INFORMATION: polynucleotide sequence or in vitro generated
      dsRNA

<400> SEQUENCE: 135

| cuaauacgac ucacuauagg gagagcgagu uuguggagua caucccgacg agggaguacu | 60 |
| accaccggca cacccggugc cuguacuggg aggggaagcu gauccugccc uucggcgacc | 120 |
| aguucugguu cagguccug cugggcuggc ugaugccacc gaaggugucc cugcugaagg | 180 |
| cgacccaggg cgaggcuauc aggaacuacu accacgacaa ccaugugauc caggacaugc | 240 |
| uggugccgcu guacaagguu ggggaugcgc uggaguucgu gcaccgcgag auggagugu | 300 |
| auccucugug gcugugcccu caccggcugu acaagcugcc ggugaagacg augguguacc | 360 |
| cggagccugg guucgagcac cagcacaggc agggcgacgc gagcuacgca cagauguuca | 420 | cggacguggg cguguacuac gcccccgggg cggugcugag gggggaggag uucaacggcg    480 cggaggcugu gcacaggcug gagcagugge ugaucgagaa ccacagcuac cagccgcagu    540 acgcgguguc ggagcugaac gagaaggacu ccugucuccc uauagugagu cguauuag     598

<210> SEQ ID NO 136
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 136
atggctgttg acgtaagg                                                  18

<210> SEQ ID NO 137
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 137
tgcagcttca gcttctgtg                                                 19

<210> SEQ ID NO 138
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 138
accgtcgtac tggtaaatcc                                                20

<210> SEQ ID NO 139
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 139
tggcggcatc tccagatttg                                                20

<210> SEQ ID NO 140
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 140
gtcgtggttt cccaggttac                                                20

<210> SEQ ID NO 141
<211> LENGTH: 20
<212> TYPE: DNA
<213> ORGANISM: artificial Sequence
<220> FEATURE:
<223> OTHER INFORMATION: polynucleotide sequence or in vitro generated dsRNA

<400> SEQUENCE: 141
gatccattcc tgccctctac                                                    20

<210> SEQ ID NO 142
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 142
ctggtcgtac caccggtat                                                     19

<210> SEQ ID NO 143
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 143
gcagagcgta accttcgtag                                                    20

<210> SEQ ID NO 144
<211> LENGTH: 228
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 144
ggctgatagc acttaaggag cttcctaatc acgaaagaat tctgcaggat ttagttatgg       60
acatactgag agtactctct gctcctgact tagaagtccg caagaagact ttaagtctag      120
cccttgaatt agtctcttca cggaacatag aagaaatggt attagtatta acaaaggaag      180
tgagtaaaac ggtagacagt gaacatgagg atacaggaaa gtacaggc                    228

<210> SEQ ID NO 145
<211> LENGTH: 279
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 145
tacctgtggc tctcacaggc agcgaagatg gtaccgttag agtttggcat acgaatacac       60
acagattaga gaattgtttg aattatgggt tcgagagagt gtggaccatt tgttgcttga      120
agggttcgaa taatgtttct ctggggtatg acgagggcag tatattagtg aaagttgaa       180 gagaagaacc ggcagttagt atggatgcca gtggcggtaa aataatttgg gcaaggcact      240
cggattacaa caagctaatt tgaaggcgct gccagaagg                              279

<210> SEQ ID NO 146
<211> LENGTH: 501
<212> TYPE: RNA
<213> ORGANISM: Diabrotica virgifera

<400> SEQUENCE: 146

```
gggacaaugu cacaauuaau gauaauucca caauuuccuu uuacaacaga aggacgugga    60
aguuuguacc agaaagaucc gugggagauc uuacugauca aaucacgacu uucaauccua   120
uuguggcauc gauagccagc uuaguuaagg acaaaaacua cauaguacuu auaggaguag   180
acuuuuucuu ggaagaauac aagaucaauu ugacuguuac caagacugua gaagaauuca   240
cuuuugaggg uuacgacgau ccuuugcuua agcuagucca aaaauuaaau auaaccgguu   300
ugaagauacc cuuuaaaaaa uuggguggu uguagacag aaacgacuca gcuccauacg     360
auggaaugug gaacauggac aauggagcua auucaauuga uacucuaggc cuaguuagaa   420
auuggaauua ugaaucucgu ugccuuauu augaagggac guguggagaa guggaaggua    480 cucaaggga acuaugguau c                                             501

<210> SEQ ID NO 147
<211> LENGTH: 502
<212> TYPE: RNA
<213> ORGANISM: Diabrotica virgifera

<400> SEQUENCE: 147
gccaacuaaa agauaauaaa acggcuugcc uggaugauau acgaacagaa caaauaaaga    60
acuuuggacc gaaaccguua aguggcuccu aaaaaugaug aauugcugua uccguacauu   120
acauaucccc aaaaccugga ggaaagcuaa aguggaugca cuauuaaaac cagggaagug   180
uccggcagau acaaagaguu uuagaccugu cucucuucug ugugaccuuu ucaaagugug   240
acacugaacu ugaccgccga aucuauggag acuaaaauua uuccagaaca agcaagaaug   300
aauaaaucau uaaacccuua aucucaucca acauauugau uuugguuuuu aacggaaaaa   360
auaacaggug uaacguuagu agaccuaacu gucgccuaug acacaguuaa ccaucaacgg   420
cugcagcaaa acucuacgaa ucuacaaaga auuccgacu ucaagguua guggaaugu     480 gccuacagaa uggacguaaa gc                                           502

<210> SEQ ID NO 148
<211> LENGTH: 500
<212> TYPE: RNA
<213> ORGANISM: Diabrotica virgifera

<400> SEQUENCE: 148
ggcauuaaau gauaaagaag aaugggugca auuuaagguu aaaaauaaca aaaguuacag    60
aagcuauguu gaagaacaaa cacgauucag aauuuucaa gaaaaucuga gaaaaaucga   120
aaaucacaau gaaaaauaua acaauggaga gucuacuuuu aaguugggug uuaccaaauu   180
ugcagaccua acugaaaaag aauuucugga ccuguuggug cuaucuaaaa augcaaggcc   240
uaauagaacu caugcuacac auuugcuagc cccacuaaga gaucuaccau cagcauuaga   300
uuggagagac aagggagcug uaacugaggu aaaagaucaa ggaaugugug gcucuuguug   360
gaccuuuagu acaacugggu caguagaagg agcucauuuu cuuaaaacug aaaucuggu   420 auccuuaagu gaacaaaauc uaguagauug cgcaaaagac acuugcuaug ggugguggagg   480 uggcuggaug gacaaagcuc                                              500

<210> SEQ ID NO 149
<211> LENGTH: 501
<212> TYPE: RNA
<213> ORGANISM: Diabrotica virgifera

<400> SEQUENCE: 149
```

```
gacacgacga cacagaauuc ucuaaccaaa guauccuuaa cgucauggag aaauucguaa    60
agaccgucaa caaaauggau gaaaccauuu uagugccuug ucguuugaug gaccugaaag   120
ucggagauga gcaagaccca gcuugucaaa auucaaaaac caaaucaucc cacucuguac   180
accaaauucu aaguucuaca gaccuguuug agaucuacaa uauguugaau ggggguaaagg   240 acucgcuguu auggggagga gcucaagagc cuccaaagaa uccuccacca ccuacuaccg   300
caauuguaac aucaguaacu acuccaaucg ucaaggggcca cauccggcga cccucuucag   360
ugagugugac uuccacaaau cgucaucua cucucagcga uacugauucu gagucuggca   420
gcaaugaaau cgauucugga aucgaugaaa cgucccaaga ggaaggaaaa gccgaaagaa   480
ucgcucaaga uuuuaaaaga c                                            501
```

<210> SEQ ID NO 150
<211> LENGTH: 502
<212> TYPE: RNA
<213> ORGANISM: Diabrotica virgifera

<400> SEQUENCE: 150

```
gaccugagug aaagccaaag agaggacaaa ccagagggac ccacuuugca aguuaugccu    60
agugagcaag ucagaaauca acuuauuaac augucuacug uauugaauca agccaucaaa   120
gucauuaauc cuaauaagaa gaagcuugaa cgcgaaaaac uuagagcugu uauggguucag   180 aauuaucacg aaacaaaggu uagagaacac cagaaaauuu uacaaaggca caagauuauu   240
gaggacagaa aggaauauau ugagcguuug aauacaguca gggaagaaga ggagcagaaa   300
agauuggaag aaaaugcaacg gcagcacuua cuggccgaac aaaaacgauu ggaccaagaa   360
agagaagaaa gagagcggaa acgugcucua aaugaaauccc agcagguuaa agacagacac   420
uuaaaggaaa aacuacaaca aaucagacag acuggucaug gucagaagau ucugaagaaa   480
auggaugaag acgauaucaa ac                                           502
```

<210> SEQ ID NO 151
<211> LENGTH: 501
<212> TYPE: RNA
<213> ORGANISM: Diabrotica virgifera

<400> SEQUENCE: 151

```
ggagcaccca auaauauaaa uucuucugga agaagacauc agcuguaugu uggaaaucug    60
acuuggugga caacugauca agauauagaa aaugcagugc augauauagg gguaaccgac   120
uuccaugaag uuaaguuuuu ugaacacaga gcaaauggucc aaccaagggg auucugguguc   180 auaucuuugg gaucugaggg aagcaugaga cucugccugg aacuccuauc uaaaaaagag   240
aucaauggcc aaaauccccu uguuacccuu cccacaaaac aagcucuuag uaacuuugaa   300 agucaagucua aaacacgccc uucuccuacu aauaauucua cucacgucc uccccauccu   360 aauaauaaug uucauucagg uccuaugcag aauuauggag guagaaugcc uaugaacccu   420
uccaugcguc ccaugcccccc agguaugcaa ggugcuccaa gaaugcaggg uccaccugga   480
uuuaauggac caccaaacau c                                            501
```

<210> SEQ ID NO 152
<211> LENGTH: 502
<212> TYPE: RNA
<213> ORGANISM: Diabrotica virgifera

<400> SEQUENCE: 152

```
ggguggccca ccuccagacc accgcgcuga gauuccucag uuaacagagc aagaguuuga    60
```

```
ggauauaaug ucccggaaua gaacaguuuc caguucggcg auugggcggg ccguauccga    120
cgccgcagcu ggagaauuug caagcgccau ugagacuuug guuacugcua uuucacucau    180
caaacaaucc aaaguggcua acgacgaucg uugcaagauc cuuauaaguu cgcugcaaga    240
uacuuugcgu ggugucgaag acaaaagcua cagcuccagc cgcagagacc ggucaagauc    300
cagggacaga ucacauagaa gaacuagaag agaacgaucc ucgucacggu acagagacag    360
aagcagagag agggagcgug aacgcgauag agaucgugau cgugaacgug acagauauua    420
ugauagauac agcgaaagag aaagagaccg agaucguuca agaagcagag aaagaacaga    480
aagggauaga gaacgagauu ac                                            502
```

<210> SEQ ID NO 153
<211> LENGTH: 504
<212> TYPE: RNA
<213> ORGANISM: Diabrotica virgifera

<400> SEQUENCE: 153

```
ggaauggacc uagaccuaau gguccugggc ccaauauggg aaugagaccc auggggccac     60
cucauggaca acaagggccc ccaagaccac caaugcaggg accaccgcag caagguccuc    120
caagaggaau gccgccacaa gguccaccgc agaugcgucc agaauggaau cgaccaccaa    180
ugcaacaagg guacccucaa ggcccgccgc auaugcaagg accuaacaug gguccaagag    240 guccaccccca aaugggacca cccggggcgc ucaacagca aggaccagcu ccgcacguaa    300
auccagcauu cuuucaacaa ggaggaggac caccgcccccc aaugcaacac augccuggac    360
cagggcccgu caugccuccu caaggacccc cgcaagaucc accacgga ccuguuggac    420 cuccacacgg cccaccauug gguccagcga auguuccgcc ucauggacca ccucacggau    480
augguccacc ugcagcgaug ccac                                           504
```

<210> SEQ ID NO 154
<211> LENGTH: 501
<212> TYPE: RNA
<213> ORGANISM: Diabrotica virgifera

<400> SEQUENCE: 154

```
guaauggagu uagagucaaa auugaacgaa gccgaaaaag aauacauaga gggcgcuccc     60
acgcgaaaca aacguacccc uucgaaaugg auaccgcggc cgccugaaaa guucugucuc    120
acaggucauc gagcgccugu gacucgagua aucuuucauc cagucuucag ucucaugguu    180
ucggcaagug aagacgccac caucaaagug ugggacuucg agacuggugu auucgaacgc    240
acccuuaaag gucacacgga uugcguccag gauauagcuu ugaugcauc ggguaaauua    300 cugguauccu guagugccga caugagcauc aaacuauggg auuccaaca gacguuugag    360 ugcgugcgca cuauguuagg ucacgaucac aacguuucga gcguuucguu caugccagcu    420
ggcgauuucg ucauuucguc uaguagggau aagaccauca aaaugggga gguaucgacg    480 ggguauugcg ugaaaacaua c                                              501
```

<210> SEQ ID NO 155
<211> LENGTH: 502
<212> TYPE: RNA
<213> ORGANISM: Diabrotica virgifera

<400> SEQUENCE: 155

```
gcggaauuga ugauagcuua aggcaaauug auguagaagg aaaacacguac aaagcucaaa     60
```

| | |
|---|---|
| gucugaaacu cgguucucaa ccgagaggua uggauauacu uaaauccgaa aacguuauua | 120 |
| uaacugccag guaaaugaa auuacgguag ccaaagauac ccaaaaacuu agcacuuuaa | 180 |
| aagugaauua cgaaccuucc agcguuaguu guuccucgaa uggucacauu gcauuggag | 240 |
| gaacuguaga uaauaaagua cacguguuca aacucgaaaa uaauaauuug gaaccaguua | 300 |
| cagaguugac ccaucucggu ccuguaaugg acguugccua uucaccggac gacaaguauu | 360 |
| uaguagcuug ugauggucau aggaagguag uacuguauga gacagaagaa uauaagcuug | 420 |
| ccaauaacca ggaguggga uuccacaaug ccagagugaa cuguuugcc uggucaccag | 480 |
| acucacuauu gguggcuagu gc | 502 |

<210> SEQ ID NO 156
<211> LENGTH: 501
<212> TYPE: RNA
<213> ORGANISM: Diabrotica virgifera

<400> SEQUENCE: 156

| | |
|---|---|
| gguacgaaug gaaaauaaaa guguaguucu uucuucguuu uucggggcu acauuguuu | 60 |
| gcaaauauuu gcuggacaac uuggucaaac uuauggacu aaaugguugg cuucguuuc | 120 |
| aauggccguc aauucaacag cuuguuucau uaucccauuc auggcugaau ggcugggauc | 180 |
| uucuggaguu auagcauguc gugugguaca aggauuauca cagggaauucu uuuucccuuc | 240 |
| ggugcauaau auuugggaa auggggcccc auuggaagag agagcguuuc uuucgaugau | 300 |
| agcuuuugca ggaccaucau ucgguacaau ugugcacua auugcuagcg gagcaauagc | 360 |
| aucuucuugg gcaggguggc cguaugcauu cuacauauuu ggagggcugg guuauguuug | 420 |
| gaugcuaccg uggcauuccc uugcagcgaa uaccccugcc uuacauccga auauauccaa | 480 |
| agcagaaaaa gauuauauag c | 501 |

<210> SEQ ID NO 157
<211> LENGTH: 502
<212> TYPE: RNA
<213> ORGANISM: Diabrotica virgifera

<400> SEQUENCE: 157

| | |
|---|---|
| guuaaaagug cauccacuuc ccuaaacuca aaaguuguu cccaacacuc aagcuuuug | 60 |
| gguccacuug cugucgaugc aguucuuaaa auuguugaac cugguagaga acaagcuugu | 120 |
| aauuuaucug auaucaaagu uauuaagcaa cuuggaggua caguagaaga uaccgaauua | 180 |
| guagaaggaa uuuguuuccc ucaaagaucu gcaaaugucu cuggaccaaa aaggauugag | 240 |
| aaagcuaaaa uugguuucau ccaguucugu auuucaccuc caaaacaga uauggaccac | 300 |
| aaugucauug uuucugauua cgcugcuaug gauagaguau uaaaagaaga gagagcauau | 360 |
| auuugaauua uugucaagca gauaaagaaa gcuggaugua auguacuuuu gguucaaaaa | 420 |
| ucaauuuuga gggaugcagu uucagaucuu gccuuacacu uuuuggauaa aaucaagugu | 480 |
| augguuauua aggauauuga ac | 502 |

<210> SEQ ID NO 158
<211> LENGTH: 502
<212> TYPE: RNA
<213> ORGANISM: Diabrotica virgifera

<400> SEQUENCE: 158

| | |
|---|---|
| gcgauaaaaa ugauaacaaa acggacaagu uuauuaauuu aagagacgga aaagagagcu | 60 |
| ugaaaaggaa aaagacuuua ucaguguauu cgcuuccuaa uuacgaugaa uugaaguuga | 120 |

```
cguuuccga auuuaaagau gauaauaaag ggccauccuc ucuaaagacg acaaaaaag       180 gucauccuuc agaaauaucu cuaccaguag accacaaaaa gacugcaaca ggcucuacgg      240
gaaaguugga uacguacaua acaagaugcc gaaguuuugg auccauuuuc ccacagcaac      300
ugaagaaauu acguccgcga aaagcaccaa cagauauuga aagcgaugau uccuuuggug      360
guuuagaaga cugggacuua ggacuaauug aacauuauaa uccaaaagau gcaguuuac       420 caagaccaag gaaaccaguu guuaaugaug auuccguauu agcaggccua gaaggcauga     480
ucguaacaga agaagaaaua gc                                               502
```

```
<210> SEQ ID NO 159
<211> LENGTH: 502
<212> TYPE: RNA
<213> ORGANISM: Diabrotica virgifera

<400> SEQUENCE: 159
ggauuuucua ugucuguugu cauagcuuau cuuauaaaua ucuauggcag aaagacauua       60
uguacuaugu cgaguauugg uauggcccuu accaugucag uaguugcgau auacguaaaa     120
uauuaugaaa uauacccaga caaagaaaag uguuagcua cuugccacua auuguguca       180 uguugaacgu ggcauucagu augguuggca ugcuucccgu uccaugggguc augguaggag     240 aaauguuccc cuugaaaguc agacccauaa ugucugggau aguaguaagc uuggcgcaac     300
uauugauauu uauuugugca aagauuuaua uaaauaugaa cgacgcuuua acuuuagcg      360 gaacuuuaau aguauuugua guagcuucaa uuuuagcugc cguuuacuca aagacgauac     420
uaacagaaac uaaaaacaag acgcuggaag aaaucgaagc ucauuuuagg ggaaacaaaa     480
aaguauguac aguugaugau ac                                              502
```

```
<210> SEQ ID NO 160
<211> LENGTH: 501
<212> TYPE: RNA
<213> ORGANISM: Diabrotica virgifera

<400> SEQUENCE: 160
gcagcuaugu ggaugaaacu ccagauaagg agacuaaagu gaaacuuaua gacacauuaa       60
ggcaaguuac agaagguaaa auuuacguag aaguugaaag ggcucgucug acucacaaau     120
uagcuaaaau ccgugaagau gauggugaca uacaacaagc ugcugacauu auucaagaac     180
ugcaggugga aacauaugga ucuauggaga aaagagagaa aguggaauua auacuagagc     240
agaugagguu gugugugugcc aagcaggacu acauuagaac ucagaucauu ccaagaaga    300 ucaauacuaa auucuucgau gaagauggcu cuucagauuu aaaauuaaag uauuacagac     360
ugaugaugga gguggaugaa caugagggcu cauauuuggc aacuuguaaa cauuauaggg     420
cuguucuuaa uaccccaagc auuauggcag acgccgaaga aagacaagcu gcagcgcaag     480
ccguuguucu uuacauuaua c                                               501
```

```
<210> SEQ ID NO 161
<211> LENGTH: 501
<212> TYPE: RNA
<213> ORGANISM: Diabrotica virgifera

<400> SEQUENCE: 161
ggaauauaau uaugaaauac gauuaaaguu uuggaaguuu gaugaaucua acaacaauu        60 ucaccuaaau accuccaucg aauauccgca ugaagauagc auuaauagua ugcuguuuca     120
```

```
accguguagu aaagaugaaa gacuucagug cguaaccguu ggagacgaca aaaauuuaa     180 aauauggcaa uuguccgaaa uugaaguagu cacagguacu caacuauccu ggcagugcuu     240
uggaguuggc uuuuaucgaa auuugccuug caaugcuuua ucauuuucaa uagaugdgguc    300 ucuauuugca acaggauucg gagaaauacu gacaguuugg acuucugaua cauguuugcu    360
uaaauguucu cuacuccauc cucuucauaa gaaacaauua aaguacauac aguuuggcua    420
cgguaaccaa ugccaucuac uugeugeggc uaguaaaaau caacuuageg uuuggaauau    480 ccuaacguua ucuaugacau c                                              501

<210> SEQ ID NO 162
<211> LENGTH: 501
<212> TYPE: RNA
<213> ORGANISM: Diabrotica virgifera

<400> SEQUENCE: 162
ggaagucguu gaaauuaaaa aacgacguca caggaggucg gugcaacaga uagauccgau     60
ggaggaaaaa agaaaaaagc uuuuagaauc acaucccuua caaguucaaa uaguggcaaa    120
guuaaaggau ggucccuuugc ugacuaucaa guuuuccuac cuaauaaaau uaaaaaucau    180
uacagucaug uccagcacga acugcucagc auguaaaaua acuggcaacu cagcuaggga    240
aguguuaacc ggagagaacc uucugaguga guuaguagaa gaugauaaug gccuagaaag    300 uccaaauccca auaacgaaau uucagauuaa gaagaucgga cuuacuucuu uucaaucguu    360 aguggccacag auccggauacg cauaaccauug ggcucaaaga guaugcggaa gagauuuucu    420
uaauaaaaaa auggauucgg augaauuagg cagaacuaau uagaaauuua aaugaaaauu    480
aauauuuaaa agauuggaau c                                              501

<210> SEQ ID NO 163
<211> LENGTH: 502
<212> TYPE: RNA
<213> ORGANISM: Diabrotica virgifera

<400> SEQUENCE: 163
gaucaaugga cgaugaagga aauaugaaaa aagaaucaaa ugcuagaaua guaagauggu    60
cugauggguc uuacagucua cauuuaggcu cugaaaucuu ugacguauau aaacaaccau    120
uacagggaga ccacaaccac uuguuuauuc gucaagguac agguuuacaa ggucaagcag    180
uauuccgaac aaaguugagc uuuaggccgc acucaacuga aaguuucacu cacagaaaga    240
ugacucuuuc uuuggcugac agaucuacca aaacaagugg uauuaaaauc augucgcaag    300
uuggugugga uccugauuua gacaaagcaa caagaauaaa gaaagaagaa gaaaaacuua    360
ggcaaucggc auccaaacca aaaacuacua gaaagaaguc cgacaaagcc ucuagggcac    420
uugaaaauac uuuuguuagg gaggaagaag guagugauga cgacggagca auuucucuug    480
cugcaauuaa aaguaaauau ac                                             502

<210> SEQ ID NO 164
<211> LENGTH: 502
<212> TYPE: RNA
<213> ORGANISM: Diabrotica virgifera

<400> SEQUENCE: 164
gcgaucaacu uauaaaacua aacaaccaaa cugcaggcag agauaaaaau gccaggcugc     60
ugcaguacuu gaguagguuu guauggcaca auuugcagaa aacucaaaaa caugguguag    120
uaagucugaa aaauuuggaa uuucaguuga guacuuucag gaaauuacuc agauuuggaa    180
```

```
gauuugccga aaguauauau acaacauuac cauucuucga gcaggaugaa gccacuauac    240
gcuauacugu gauuuaagc aaaauugcca auucguugu ucuuuggcu gaccacauac       300 uaugguuagg acgugcagac guguguacag uggacacgga gagaugguca cgucuaucca    360
acaaguauug guuauauucc auaacuauga auuuaguuag agauucuau gaaauuucua     420 auauuuuaaa aaguauaag gacucaauuu uacaaaauaa auucaguuca aaggaaaugc     480
uacauauuuu guuacgaagc uc                                             502
```

```
<210> SEQ ID NO 165
<211> LENGTH: 374
<212> TYPE: RNA
<213> ORGANISM: Diabrotica virgifera

<400> SEQUENCE: 165
gaugggcgag gaggaaauca caccaaauaa uaucaaagaa aaucagagug agaauaugaa    60
ugggaauaua aauggucaag aggaaaaucc accuccagaa gaaauggaua caaauggga     120 aaaugaugua aaugaagaug aucuggauga agacaaugau gacaugucgc cugaagaguu    180
ugcugcacuu gauccaccagu uagaugccuu aaauucugcu uuagaugaca uagaacagaa   240
aaaugauaau auacauucgc aguuacuaga acuacuccau gcuaacaggg aaauccggac    300
ucaauuacag caagauaaag cuagcacaga uaacagagaa gacguaaaua aaacaaauga    360
accaaaagca ugac                                                      374
```

```
<210> SEQ ID NO 166
<211> LENGTH: 500
<212> TYPE: RNA
<213> ORGANISM: Diabrotica virgifera

<400> SEQUENCE: 166
gcagguuauu aguacauuaa cgaaaguucu uaaauguaau cagagaagcu caacagaguu    60
uguuacgaac aucgaccggg aagguagagc caucgugaaa uguucaucuu uucagcacug    120
cugcgaucuu aaacaagaua ucgagaaguu uacgucccga cacggcaaca aaccuugaa    180 gguacuuguu aaccaugcuc aucuuauauc ucaucgaaua uuugcaggaa agauauuaaa    240
uuggcuagaa aaggcuuaaa uacaaggaga aggauucaga gcauuuuug ccgauguugu     300 gcugaagcca cagaauccag agccgugcau aauaaagggc auccuacaaa aagauuuagg    360
ccuuuggaag agcgcuagga gccaauggca ucgcuuguua auaucaggca ugaugcucga    420
guaugagaac aagaaagcuu uagcuaaaau auuuaccaaa aacuaugggc aaguaaugaa    480
agacuuuauc aaagaugauc                                                500
```

```
<210> SEQ ID NO 167
<211> LENGTH: 502
<212> TYPE: RNA
<213> ORGANISM: Diabrotica virgifera

<400> SEQUENCE: 167 gugaaauau acugcuagu guucuguaua gcaacuacac uuacauuauc uacggcacaa      60
uccuaugaag acaagagaug uaaguguaua ugccccagua uaccucagu aguaacgaau     120 aagacggaau cuagaaacca cacaucuagg auuuuauaca uuaccaaugu accaccaaau    180
aaaugcaauu gugaugaagu uauacuaccu aggauuaguc aagauauuau aggaaaagaa    240
caagaauuuu guccaagaug ugaaugcaaa uaugaaaaua gaaacacuac uauaauuaaa    300
```

```
guagugguga uuauaguaau uuggguuauu ucgauuuugg ucauauacau ggcauucuug    360
aucauacugg acccgcugcu gaacaagagg auuaaaggaa acuaccaaga gcauacaaau    420
gaagaggaug acguaucugc ugguccaaug ucccacaaca ugagcguaag aggaaacguc    480
uugaacagag uuggacauca ac                                            502

<210> SEQ ID NO 168
<211> LENGTH: 501
<212> TYPE: RNA
<213> ORGANISM: Diabrotica virgifera

<400> SEQUENCE: 168
ggcuguuaau ucauuuuaa ggcauguugc ggaauuacua aaguaugaau cagaugaaca     60
auuagaagaa uuguaucaga agacugcuug guauuucgaa gaaaaguaua agaagaauaa   120
agcuagugca uaugacuucu ucaaacaggc uguuuuagac cccaguauuu uagcagaaug   180
ugaauuagau gacaaaacaa agaagucuuu gcuuaguaac auuaagagaa agcuaacauc   240
ucaagcaguc aaaaucagag cugauauuga augugcuugu uaugguuaug aagguaucga   300
ugcuguuaaa acugcucuua aagcuggcuu ggcucuuuca acagaagaau uacccauuaa   360
aauaaaucuu uagcccccuc cucucuaugu uaugacuaca ucuacaccug aaaaacaaga   420
ugguuuaaaa guuuuaggag augcuauaga aaaagucaaa gcgacaauca cggaauuggg   480
uggaguauuu aauauucaaa c                                            501

<210> SEQ ID NO 169
<211> LENGTH: 500
<212> TYPE: RNA
<213> ORGANISM: Diabrotica virgifera

<400> SEQUENCE: 169
guauaagaag aauaaagcua gugcauauga cuucuucaaa caggcuguuu uagaccccag    60
uauuuuagca gaaugugaau uagaugacaa aacaaaagaa guuugcuuua guaacauuaa   120
gagaaagcua acaucucaag cagucaaaau cagagcugau auugaaugug cuguuuaugg   180
uuaugaaggu aucgaugcug uuaaaacugc ucuuaaagcu ggcuuggcuc uuucaacaga   240
agaauuaccc auuaaaauaa aucuuuagcu ccuccucuc uauguuauga cuacaucuac   300
accugaaaaa caagaugguu uaaaaguuuu aggagaugcu auagaaaaag ucaaagcgac   360
aaucacggaa uuggguggag uauuuaauau ucaaauggcu cccaagugg ucacagcuac   420 cgacgaagcc gaacucguca aacgaugga acgagcugaa ucgaaaacg cagaaguugc   480 uggcgacgac gacgaagaac                                              500

<210> SEQ ID NO 170
<211> LENGTH: 502
<212> TYPE: RNA
<213> ORGANISM: Diabrotica virgifera

<400> SEQUENCE: 170
gcguaauauc uaacaauuua ggaaguugug ccuccacauc uauagauccc aaucagguu     60 uagcuaguau gguuccugga guacaaacac cggguaugcu aacacccaca ggcgacaugg   120
aucugcgcaa aucggccaa gcaagaaaca cucugaugaa uguuaaacug ucacaaguau   180
cugacucugu aaccggucaa acaguuguug auccaaggg guaucuuacu gauuacaau    240 cuaugauacc cacuuaugga ggugacauua augcaucaa gaaagcuaga cuacuauuaa   300 aaucaguccag agaaacuaau ccaaaucauc caccugcuug gauugccagu gcuaggcuag   360
```

```
aggagguuac aggcaaaguc caagcagcua gaaaccuuau aaugaaaggc ugugaaguaa         420
auccccaaag cgaggaccua uggcuugaag cggcuagacu aaauccaccu gauaccgcua         480
aagcaaucau ugcucaagca gc                                                  502
```

<210> SEQ ID NO 171
<211> LENGTH: 496
<212> TYPE: RNA
<213> ORGANISM: Diabrotica virgifera

<400> SEQUENCE: 171

```
gacagcaaaa auuaauuuuc agguaaaaaa uaaagauauu cugcaaagug guauauuuaa          60
ucaaacuuua agggacuggc agaguaucca augugaaauc acagcgaaaa auuugaugua         120
cccagucuuu auuguggaag augaugaugu cguacaaccc auuaguagua ugccuggaau         180
uucaagguau ggaguaaaua aauuacguga ucauuuacaa gauguuguua aaauggacu          240 acaaucugug uuacuuuuug gaguqquaga aaaguugucc aaggaugauu ugcuaccca         300 cgcagauagc ucacaaaauc caguagucag ggcacuuccu aaacuaaaaa aauggutucc         360
uaaucugaca auagccugug auguuuguuu augcccuuac aguucccaug gacauugugg         420
aauacugaac aaugauggua guuuaaauaa uacugcuagu auccaaagaa uaucagaugu         480
agcucuagcu uaugcc                                                        496
```

<210> SEQ ID NO 172
<211> LENGTH: 502
<212> TYPE: RNA
<213> ORGANISM: Diabrotica virgifera

<400> SEQUENCE: 172

```
gggguguuau uuaucgaaaa acccgaucug guaaucugga gaagacuuca ccauucugga          60
ucaggucaau acgaauauaa aguguauggu acuuacaaug auguguagc cgaagauuuu         120 uugaauguuc aaguugauau ugacuauagg aggaagugg uacgagugc aguuauccuu          180 gaacacgcag agucugaucc uuugaagaau ucaacagcg augucauuua cugggaacuu         240
uuauggccuu ggcuguuugu gaaucgagau uacgucuuua acagacguua cuugauagac         300
aacacauuga acacuauauu cauccuaaac cggagcaccg aacauccaaa guuuccaaaa         360
uacgcagaaa aauucggau agcgacuau uggucgugua ugguaaucaa accguaugaa          420
ggagacauga cgaggccagg aauacaguuc gucuugaccu acuacgacaa cccaggcgug         480
aguauaccau ccucgguaac ac                                                 502
```

<210> SEQ ID NO 173
<211> LENGTH: 496
<212> TYPE: RNA
<213> ORGANISM: Diabrotica virgifera

<400> SEQUENCE: 173

```
gugguacagc aaucaaaugu aaacgauuau uuacuaaaaa aacaacaaga aaguccuaaa          60
gaauuaggcu cagaaugggc cgaacuugaa gaacuucaua auaaaaaauu guggcaucag         120
uugacucuaa aauugcugaa uuuuauuaag aaaccagaac uacagaagaa ugauaaccuc         180
auacaacugu acaauaacuu uauucaaagu uuugaaaaua aaucaauucc uuugucauug         240
guugaaauug uugcuauagu agccaacaa uucaaaaauc caaagaugc ugucgcuuuu         300 cuugaaaaga cugaaccuaa gguuaaaauu aauucagaug cccaaaacuu gugcaaagu          360
```

```
uuagcugggc agauauauau cgaaaaguug aacgauuuag augcuacuaa aaagauaauu    420
gaagaagugg aaucuacauu ggacaaugcu gaugguguua cuccaguuca uggaagauuu    480
uauuuacuug ccucac                                                    496
```

```
<210> SEQ ID NO 174
<211> LENGTH: 502
<212> TYPE: RNA
<213> ORGANISM: Diabrotica virgifera

<400> SEQUENCE: 174
guaguagcaa ucuuaaacac aggcuuguuc aaaaucuacc cagaucaaca ucauuuugga     60
guacaauuga uagaugaagg ugcagauaua uucgaugcca aaaucaaccu cgaagcccag    120
ugguguacgg aacauauuau agcagcaauc gagagaaaag guggguguau cacuuccgcu    180
uacuacgauc ucucacagucu gcaggcuaug guuaacagca agaaguuuuu ugaaagaggu    240
auuccaauac cccgcagaau gaugccuccc ccagacgcca uagaacacua cucagauccu    300
gcacagaggg gauauuuggc agaucccgag aagauauccc aagagcgucu aguccuagcc    360
cagaaauaug guuacagguu accaaaaaua gaagaagauc cugcauacga gauguuaaug    420
gaaaggaaag auccuaggca gauauucuau ggucuacauc ccggaugggu ggucaauuug    480
acggauaaga cuauacuuaa ac                                             502
```

```
<210> SEQ ID NO 175
<211> LENGTH: 502
<212> TYPE: RNA
<213> ORGANISM: Diabrotica virgifera

<400> SEQUENCE: 175
gaagugggua aacuaaaaau uagcaaaccu guuggacaaa aggcucaagu uucgcuuaca     60
uuaucuucag caauucuuaa uuugaaugag ccuggacaag aaaguauucc aaaggaucau    120
agauugaugu uauccacagu uacucaacaa acuuugggug ucuuucaca uguuacacca    180 acuaauauug auucuguggu accugaaacu gaaaagcugc acauggaagg caaaauagug    240
caaaaauugg aaugcaggcc auaugcagau aauuguuaca ugaaguugaa auuagaaucu    300
auuaggaaag cuucucuacc aguucgccaa gugaagcagu uagacagggu uguacaaaca    360
uacaagccag uaucugauca uaaaaauauu auugaguaca uggagagaaa gaaagcugaa    420
gguaaaaagg cucgugauga caaagaagcu guuuggaca uguuguuugc agcuuucgaa    480
aagcaccaau auuauaacau ac                                             502
```

```
<210> SEQ ID NO 176
<211> LENGTH: 501
<212> TYPE: RNA
<213> ORGANISM: Diabrotica virgifera

<400> SEQUENCE: 176
guaacaauca aagcucaaga ugaugccgac auaguaacgu uuauguuuga agccaaaaag     60
caggacaaga ucucagauua cgaaaugaaa cugaugaauu uggaccagga gcauuugggu    120
aucccagaaa cagauuucuc uugugucauc aggaugccug cagcugaauu cgcaagaaua    180
gucaaagauc uuucacaguu uggagaaucu aucguaaucu caugcacaaa agagggguguu    240 agguucucaa cuucuggaga uauuggcagu gcuaacauca aaauugccca gacaaguaau    300
uucgaaaagg aagaggaauc uguaagcaua gaaaugcaag aaccaguuac ucuuacuuuc    360
gcuugucagu auuugaauuc cuucaccaaa gccacaccuc uuacuaacgu ugugcagcua    420
```

| | |
|---|---|
| ucgaugucug acaauguacc uuuaguaguu gaauaucaaa uaccugauuu gggccauuug | 480 |
| agguacuacu uagcaccuaa c | 501 |

<210> SEQ ID NO 177
<211> LENGTH: 502
<212> TYPE: RNA
<213> ORGANISM: Diabrotica virgifera

<400> SEQUENCE: 177

| | |
|---|---|
| gaguaaugau gacacaguaa caaucaaagc ucaagaugau gccgacauag uaacguuuau | 60 |
| guuugaagcc aaaaagcagg acaagaucuc agauuacgaa augaaacuga ugaauuugga | 120 |
| ccaggagcau uggguaucc cagaaacaga uuucucuugu gucaucagga ugccugcagc | 180 |
| ugaauucgca agaauaguca aagaucuuuc acaguuugga gaaucuaucg uaaucucaug | 240 |
| cacaaaagag ggguuaggu ucucaacuuc uggagauauu ggcagugcua acaucaaaau | 300 |
| ugcccagaca aguaauuucg aaaaggaaga ggaaucugua agcauagaaa ugcaagaacc | 360 |
| aguuacucuu acuuucgcuu gucaguauuu gaauccuuc accaaagcca caccucuuac | 420 |
| uaacguugug cagcuaucga ugucugacaa uguaccuuua guaguugaau aucaaauacc | 480 |
| ugauuugggc cauuugaggu ac | 502 |

<210> SEQ ID NO 178
<211> LENGTH: 501
<212> TYPE: RNA
<213> ORGANISM: Diabrotica virgifera

<400> SEQUENCE: 178

| | |
|---|---|
| gaggaaucca gcucgaacag cgacagcucu gauaauucag uaaaauugcu ggaaaagcuc | 60 |
| acaaaagaaa gaauuagacu uggagaagaa aggaagaagc aaaaagaacu aaucaaagcu | 120 |
| acugaaacag cagaggagaa gagaaugagg cggcucguaa agaaggagaa caaagagaga | 180 |
| uccaggaaag agagaauggg cuggggauaac gaguauuuac auuauacaaa cagugacaau | 240 |
| ccuuucgggg auggaaacuu guugucuaca uuugugguggu ccaagaaguu aaacaaagaa | 300 |
| ggauugaaag guguuaguca agaagaaauc gaagcaauaa acaggaugaa acaagaagaa | 360 |
| aacaaaagag aacuggaaaa aguaaaaaag agacgucuag aaagagaauu agaaagacag | 420 |
| aagagggacg agaaacccca gaugcuccaa agaagcaagg aagcagcaca auuugaagag | 480 |
| ugggagaggc aagaagauaa c | 501 |

<210> SEQ ID NO 179
<211> LENGTH: 501
<212> TYPE: RNA
<213> ORGANISM: Diabrotica virgifera

<400> SEQUENCE: 179

| | |
|---|---|
| gaacagucug gaagaaauau uuuggacuac cagaaucagg cgaaaauguu auuucgaaaa | 60 |
| uuggggcacc aguccccugc uagauguuca auugaaacgg gaccuuauau auuccauuau | 120 |
| uuaauagaau acgaaguuug uuaccuagua uuaugugaaa aggcuuucuc aaaacgacug | 180 |
| gcuuacucau auuuggaaga uauagcacaa gaauccacg cacaauaugg caaagagug | 240 |
| aauacaguaa cuaggccuua uacauucaua gaguuugaca cauauaucca gaaagccaaa | 300 |
| aaacaguuug cagauucgag aucgagaagg aauuuaaaug ugauaaauaa ucagcuacac | 360 |
| gaugcccaaa ggauuauggu acaaaauaua gaugaugugc ugcagcgagg aacuguucua | 420 |

| | |
|---|---:|
| ucagaguugg acaccaaaac gcagaaucua uccauguuaa cggacaaaua caagaaggau | 480 |
| ucgacauacu ugaacacaaa c | 501 |

<210> SEQ ID NO 180
<211> LENGTH: 482
<212> TYPE: RNA
<213> ORGANISM: Diabrotica virgifera

<400> SEQUENCE: 180

| | |
|---|---:|
| gauggaugcu gaaacuggag aauuuuaccu agaccuugaa acuggagaaa uauccgaagc | 60 |
| ccccgcaguc caaaaugucg aaacggggga guacgaauau accagaacuu uuaaaauccc | 120 |
| aagcuacuac uacagaagau accagaaaag aaaagaaaaa accaacugca cuccacguaa | 180 |
| agcagauccc cuggagucac aguugauuac cgcggcuauc uuucuacuac cgacaaugau | 240 |
| auucuuccau cccaucaugc ucguuuugu ugcgugaua gaaauauuuu uacauacucg | 300 |
| cauucacaga agaacaaag aacuagaaga ucugccuuu uauuaccaga gcccauuaca | 360 |
| uggccuuaca aagagguau gugcuagaug uaaagacgaa aaagccaaga auaagaucgc | 420 |
| gaagcugcaa acaagcagc augagaaauu caagaauuac aucaaagggg uuguaacuua | 480 |
| ac | 482 |

<210> SEQ ID NO 181
<211> LENGTH: 501
<212> TYPE: RNA
<213> ORGANISM: Diabrotica virgifera

<400> SEQUENCE: 181

| | |
|---|---:|
| ggugaauaua augacucuga uauugaaugg gaacuguguu ucccccaagc acaaagauau | 60 |
| cuggaaaguu ucaugaguca ugcucaaaug aaaagcuuga ucauucuucu aacacuucau | 120 |
| aaaacuuuca uagaaccuca gacugcgcau uuaggucuca cggccgauca uauaagaaac | 180 |
| uucaucuuuu uggaauguga gucccauuau agugacuggg cagaacauag gcuagguauu | 240 |
| aaauuguuga aguacucaa acgucuucau acacaucuau cacaagcuaa accauguauu | 300 |
| ccagacuuuu uuguuaccaa uaaaaauacu uuaagugaag uaccuauuag aaaauaagaa | 360 |
| gagcucuaau ggcuuuggau gaaauuuuac aaucucccu gauguacuuc auaaaagccu | 420 |
| uacgaaaucu uagauauaca gacggggaaa auuucuuccc uccuuuaaau uuuaaacagu | 480 |
| ugcacgaucu gcuaaauaaa c | 501 |

<210> SEQ ID NO 182
<211> LENGTH: 502
<212> TYPE: RNA
<213> ORGANISM: Diabrotica virgifera

<400> SEQUENCE: 182

| | |
|---|---:|
| gccaauuau uuaaagauaa cgacgcaaaa uguguacuug gcuauuuaca aacuagacac | 60 |
| aagaaagaug auuccaguuu aucgucuuua uuuguuccug uucaaauuaa accgagugca | 120 |
| gaugacauaa auguuggagc agaacuuaca ggaacuuuga acaaaacaga uuuguuaaaa | 180 |
| guuuugaauua aguuuuauca gaaaaagaa auuaaggcau ugcuaguaga uaauggauua | 240 |
| gaucaguacc uucagcacca agccuaugug aguuccgaa gauauugccu agaagcacaa | 300 |
| aauuuaccag cagauaucca cguagucuuc ugugacauuc uacagggagc uggaaauauc | 360 |
| acugauauuu uccccuacuu ucuacgacau gccaaaauga uguuucccca ucucgacugc | 420 |
| auggaugauc uuagaaaaau uucugauuua agaucaccug cuaacuggua uccugaagca | 480 |

```
agggcuauua acagaaaaua ac                                              502

<210> SEQ ID NO 183
<211> LENGTH: 501
<212> TYPE: RNA
<213> ORGANISM: Diabrotica virgifera

<400> SEQUENCE: 183
ggagaacauu uaacucuaaa aauuaggucg aaaacauuug aagcaauguu aagacaggaa      60
auuggcuggu augaccaaaa aagcaaugga guuggggcac ugugugcacg ucuggcugga     120
gaugcuguag cuguccaagg ggcagcuggg ccacagauag gaacaacaau aaacuuuauu     180
ucaacauuca uacuuacgug uacguucucg uuuuauuuug aguggaggac aagcuuugug     240
cuuuuuucuu uguguccccgu aauauucuuu ucuguauauu uugagcagaa gguauuacaa    300
gaggaugcca cgaaaaacca aaaaauguua gaagcaucug caaaguuggc uguagaagcu     360
aucgguaaua uaagaacagu gguuucucua gguugugaaa aaguauuuau ggaacaguau     420
aucaaagagu uauuaccgua ucagaaaaug gcaagaaaaa agucacauua ucguggcaua     480
auaguagguu uagcuagaag c                                               501

<210> SEQ ID NO 184
<211> LENGTH: 490
<212> TYPE: RNA
<213> ORGANISM: Diabrotica virgifera

<400> SEQUENCE: 184
gauggauaau gaucuugaca gguccauucg cuuauuggaa aaugcuuuau cuaccucuaa      60
cagaggucuu uucaagaagu cauuuggaaa aucaaaguua gcuacugaca auauuucuaa     120
uguguccaua gcuucugcag augaugauuu aaggauauca ucaguaaaag cuuccuuacc     180
agcgauaaug cagugucuag gauacugcag ucugaucaaa cuguaacugg aaauguucuu     240
caagccagua cagcaccuug gaaaacggcu cuggauaguc uuuauaccga auuuuuugaa     300
auacuuacuu cacacucagg uggcuuugau uacuggaag uaguuaccga cuuagcuagg      360
uguugcucug augcccuuaa aguaauucag aguuugaagu cgaaggguagc aguucgcag     420 uuagaagaag aaauaaguuu agagaaggaa aggaauacau ggagauugcu uuuuauccuu     480
uaccaagauc                                                            490

<210> SEQ ID NO 185
<211> LENGTH: 508
<212> TYPE: RNA
<213> ORGANISM: Tomato Golden Mosaic Virus

<400> SEQUENCE: 185
gcucacaaaa gaugaagcgu uagagcaauu acagucaaua caacuaacuu cgaauaaacg      60
uuauaucaag auuugcagag agcuucacga gaauggggaa ccucauaucc augcccuuau     120
ccaacuugaa gggaaaguce agaucaccaa cgaacgacag uucgaccugg uaccccaac     180 caggucagca uauuuccauc cgaacauuca gggagcuaaa ucuaguuccg acgucaaauc     240
auacaucgac aaagauggag auacccucga augggagaa uccaaaucg acggcagauc      300 ugcuagggga ggccagcaga cugcaaacga uucauaugca aaggcgcuua acgcaguugg     360
agugcaagaa gcacuccaaa uuuuaaagga agaacaaccu agggauuuug uuaaagauuu     420
ucacaaucuc aagggguaacc uugagaagau auuuucaaag gcuccagaac cguggguucc     480
```

| | |
|---|---|
| uccauuucca cuuuccucau uuaauaac | 508 |

<210> SEQ ID NO 186
<211> LENGTH: 440
<212> TYPE: RNA
<213> ORGANISM: Tomato Golden Mosaic Virus

<400> SEQUENCE: 186

| | |
|---|---|
| gccagaggag uuacagacau gggcugauga uuauuugga aauggugccg cugcgcggac | 60 |
| uuuaagaccu aucaguauua ucaucgaagg ugauucaaga acuggaaaaa caaugugggc | 120 |
| ucguucauua ggaauucaua auuaucgag uggucaucua gauucaauu cuaggguua | 180 |
| cucaaauaau guuauguaca acgucauuga ugacguacca ccgcauuauc uaaagaugaa | 240 |
| acacuggaaa gagcucauug gggcccagac agacuggcag accaacugua aauacgggaa | 300 |
| acccauucaa auuaaaggug gcauuccauc aaucgugcua ugcaauccug gugagggggc | 360 |
| uagcuauaaa uacuaccucg acaaacagga aaacucacau cucaaggcgu ggacacuuca | 420 |
| caaugcaaaa uucgucuucc | 440 |

<210> SEQ ID NO 187
<211> LENGTH: 500
<212> TYPE: RNA
<213> ORGANISM: Cauliflower Mosaic Virus

<400> SEQUENCE: 187

| | |
|---|---|
| gaaucaacca gugcuggucg uaaccgucga cgucguccgc gucgugguuc ccgcuccgcc | 60 |
| cccuccuccg cggaugcuaa cuuuagaguc uugucgcagc agcuuucgcg acuuaauaag | 120 |
| acguuagcag cuggucgucc aacuauuaac cacccaaccu uuguagggag ugaacgcugu | 180 |
| agaccugggu acacguucac aucuauuacc cuaaagccac caaaaauaga ccgugggucu | 240 |
| uauuacggua aaagguuguu acuaccugau ucagucacgg aauaugauaa gaagcuuguu | 300 |
| ucgcgcauuc aaauucgagu uaacccuuug ccgaaauuug auucuaccgu gugggugaca | 360 |
| guccguaaag uuccugccuc cucggacuua uccguugccg ccaucucugc uauguucgcg | 420 |
| gacggagccu caccgguacu gguuuauacag uaugccgcau cuggagucca agccaacaac | 480 |
| aaacuguugu augaucuuuc | 500 |

<210> SEQ ID NO 188
<211> LENGTH: 501
<212> TYPE: RNA
<213> ORGANISM: Cauliflower Mosaic Virus

<400> SEQUENCE: 188

| | |
|---|---|
| gucguccaac uauuaaccac ccaaccuuug uagggaguga acgcuguaga ccuggguaca | 60 |
| cguucacauc uauuacccua aagccaccaa aaauagaccg uggguuuau acgguaaaa | 120 |
| gguuguuacu accugauuca gucacggaau augauaagaa gcuguuucg cgcauucaaa | 180 |
| uucgaguuaa cccuuugccg aaauuugauu cuaccgugug ggugacaguc cguaaaguuc | 240 |
| cugccuccuc ggacuuaucc guugccgcca ucucugcuau guucgcggac ggagccucac | 300 |
| cgguacuggu uuaucaguau gccgcaucug gaguccaagc caacaacaaa cuguuguaug | 360 |
| aucuuucggc gaugcgcgcu gauauaggug acaugagaaa guacgccguc ucguguauu | 420 |
| caaaagacga ugcgcucgag acggacgagc uaguacuuca guugacauc gagcaccaac | 480 |
| gcauucccac aucuggagug c | 501 |

<210> SEQ ID NO 189
<211> LENGTH: 501
<212> TYPE: RNA
<213> ORGANISM: Tomato Spotted Wilt Virus

<400> SEQUENCE: 189
gcauuguugc uuuguugaca caaggcaaag accuugaguu ugaggaagau cagaaucugg 60
uagcauucaa cuucaagacu uuuugucugg aaaaccuuga ccagaucaaa aagaugagcg 120
uuauuucaug ucugacauuc cugaagaauc gucagagcau aaugaagguu auuaagcaga 180
gugauuuuac uuuugguaaa auuaccauaa agaaaacuuc agacaggauu ggagccacug 240
acaugaccuu cagaaggcuu gauagcuuga ucagggucag gcuuguugag gaaacuggga 300
auucugagaa ucucaauacu aucaaaucua agauugcuuc ccacccuuug auucaagcuu 360
auggauuacc ucuugaugau gcaaagucug ugaggcuugc cauaaugcug ggagguagcu 420
uaccucuuau ugcuucaguu gauagcuuug agaugaucag uguugucuug gcuauauauc 480
aggaugcaaa auacaaggac c 501

<210> SEQ ID NO 190
<211> LENGTH: 501
<212> TYPE: RNA
<213> ORGANISM: Tomato Spotted Wilt Virus

<400> SEQUENCE: 190
gaccuucaga aggcuugaua gcuugaucag ggucaggcuu guugaggaaa cugggaauuc 60
ugagaaucuc aauacuauca aaucuaagau ugcuucccac ccuuugauuc aagcuuaugg 120
auuaccucuu gaugaugcaa agucugugag gcuugccaua augcugggag guagcuuacc 180
ucuuauugcu ucaguugaua gcuuugagau gaucaguguu gucuuggcua uauaucagga 240
ugcaaaauac aaggaccucg ggaucgaccc aaagaaguau gacaccaggg aagcuuuagg 300
aaaaguuugc acugugcuga aaagcaaagc auuugagaug aaugaagauc aggugaagaa 360
ggggaaagag uaugcugcua uacuuagcuc cagcaauccu aaugcuaaag gaaguauugc 420
uauggaacau uacagugaaa cucuuaacaa guucuaugaa auguuugggg uuaaaaaaca 480
ggcgaaacuc acagaacuug c 501

<210> SEQ ID NO 191
<211> LENGTH: 20
<212> TYPE: DNA
<213> ORGANISM: artificial Sequence
<220> FEATURE:
<223> OTHER INFORMATION: polynucleotide sequence or in vitro generated dsRNA

<400> SEQUENCE: 191
cccaggtcat catcatgaac 20

<210> SEQ ID NO 192
<211> LENGTH: 20
<212> TYPE: DNA
<213> ORGANISM: artificial Sequence
<220> FEATURE:
<223> OTHER INFORMATION: polynucleotide sequence or in vitro generated dsRNA

<400> SEQUENCE: 192
gagctcagca aacttgacag 20

<210> SEQ ID NO 193

```
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 193
aggctttcgc tgcgtgtt                                                       18

<210> SEQ ID NO 194
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 194
tggcccatcc aaactcaga                                                      19

<210> SEQ ID NO 195
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 195
gctcaagttc ttcggatgac                                                     20

<210> SEQ ID NO 196
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 196
acttcttcca gcagactagc                                                     20

<210> SEQ ID NO 197
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 197
gcaaccactc ccaaatactc                                                     20

<210> SEQ ID NO 198
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 198
cagggttgta cccaactttc                                                     20

<210> SEQ ID NO 199
<211> LENGTH: 20
```

```
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 199
tctggcatca caccttctac                                               20

<210> SEQ ID NO 200
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 200
ttctcacggt tagcctttgg                                               20

<210> SEQ ID NO 201
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 201
tgtcctgcca tctctatctc                                               20

<210> SEQ ID NO 202
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 202
acatccgaat ggtctctacg                                               20

<210> SEQ ID NO 203
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 203
cacaaccgtg cagtttacag                                               20

<210> SEQ ID NO 204
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 204
aaatgcgccc aagcatatcg                                               20

<210> SEQ ID NO 205
<211> LENGTH: 20
<212> TYPE: DNA
```

```
<213> ORGANISM: artificial Sequence
<220> FEATURE:
<223> OTHER INFORMATION: polynucleotide sequence or in vitro generated
      dsRNA

<400> SEQUENCE: 205
cagaggacga ggaatatgag                                                   20

<210> SEQ ID NO 206
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 206
ctagcagcat tgtcagtagg                                                   20

<210> SEQ ID NO 207
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 207
cggtgttcga cagcagctac                                                   20

<210> SEQ ID NO 208
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 208
cttcgccgcc aacaataccc                                                   20

<210> SEQ ID NO 209
<211> LENGTH: 22
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 209
gcgcaagttt ttcgtagatg ac                                                22

<210> SEQ ID NO 210
<211> LENGTH: 21
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 210
accatagtcc acagatgaca c                                                 21

<210> SEQ ID NO 211
<211> LENGTH: 20
<212> TYPE: DNA
<213> ORGANISM: artificial Sequence
```

```
<220> FEATURE:
<223> OTHER INFORMATION: polynucleotide sequence or in vitro generated
      dsRNA

<400> SEQUENCE: 211
gctgcgtgtt gtgcgttctg                                                    20

<210> SEQ ID NO 212
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 212
tcgtcgcgtg ctgtctgttc                                                    20

<210> SEQ ID NO 213
<211> LENGTH: 18
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 213
aggctttcgc tgcgtgtt                                                      18

<210> SEQ ID NO 214
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 214
tggcccatcc aaactcaga                                                     19

<210> SEQ ID NO 215
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 215
gctcaagttc ttcggatgac                                                    20

<210> SEQ ID NO 216
<211> LENGTH: 20
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 216
acttcttcca gcagactagc                                                    20

<210> SEQ ID NO 217
<211> LENGTH: 19
<212> TYPE: DNA
<213> ORGANISM: artificial Sequence
<220> FEATURE:
```

```
<223> OTHER INFORMATION: polynucleotide sequence or in vitro generated
      dsRNA

<400> SEQUENCE: 217
ggatgctact cgccagaca                                                  19

<210> SEQ ID NO 218
<211> LENGTH: 19
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 218
gtggtcagcc tgcttcaac                                                  19

<210> SEQ ID NO 219
<211> LENGTH: 22
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 219
gcgcaagttt ttcgtagatg ac                                              22

<210> SEQ ID NO 220
<211> LENGTH: 21
<212> TYPE: DNA
<213> ORGANISM: artificial Sequence
<220> FEATURE:
<223> OTHER INFORMATION: polynucleotide sequence or in vitro generated
      dsRNA

<400> SEQUENCE: 220
accatagtcc acagatgaca c                                               21

<210> SEQ ID NO 221
<211> LENGTH: 400
<212> TYPE: DNA
<213> ORGANISM: Spodoptera littoralis

<400> SEQUENCE: 221
cccacagaca agcccctgcg tcttcccctc caggacgtat acaaaatcgg tggtattggt     60
acggtgcccg taggcagagt tgaaactggt atcctcaagc ctggtaccat cgtcgtcttc    120
gcccccgcca acatcaccac tgaagtcaag tctgtggaga tgcaccacga agctctccaa    180
gaggccgtac ccggtgacaa cgttggtttc aacgtaaaga acgtttccgt caaggagttg    240
cgtcgtggtt acgtcgctgg tgactccaag aacaacccac ccaagggcgc cgccgatttc    300
acagcacagg tcatcgtgct caaccaccct ggtcaaatct caaacggata cacacctgtg    360
ctggattgcc acacagccca cattgcctgc aagttcgctg                          400

<210> SEQ ID NO 222
<211> LENGTH: 400
<212> TYPE: DNA
<213> ORGANISM: Zea mays

<400> SEQUENCE: 222
ccctcggaca agcccctgcg tctccccctc caggatgtgt acaagattgg tggtattgga     60
actgtgccag ttggtcgtgt ggagactggt gtcatcaagc ctggtatggt tgtcaccttt    120
```

```
ggtccaactg gcctgactac tgaggtgaag tctgttgaga tgcaccatga ggctcttcag    180
gaggcccttc ctggtgacaa tgttggcttc aacgtgaaga acgtcgctgt gaaggatatc    240
aagcgtggtt atgtggcctc caactccwag gatgaccctg ccaaggaggc tgccagcttc    300
acctcccagg tcatcatcat gaaccaccct gggcagatcg gtaacggtta tgccccagtg    360
ctggactgcc acacctccca tattgctgtc aagtttgctg                          400

<210> SEQ ID NO 223
<211> LENGTH: 443
<212> TYPE: DNA
<213> ORGANISM: Spodoptera littoralis

<400> SEQUENCE: 223
gaaatgggta agggttcctt caaatacgcc tgggtattgg acaaactgaa ggctgagcgt     60
gaacgtggta tcaccattga tattgctctg tggaagttcg aaaccgctaa atactatgtc    120
accattattg acgctcccgg acacagagat ttcatcaaga acatgatcac tggaacctcc    180
caggccgatt gcgccgtact cattgtcgcc gctggtaccg gtgaattcga ggctggtatc    240
tcgaagaacg gacagacccg tgagcacgct ctgctcgctt tcacactcgg tgtcaagcag    300
ctgattgtgg gcgtcaacaa aatggactcc actgagcccc catacagcga atcccgtttc    360
gaggaaatca agaaggaagt gtcctcctac atcaagaaga tcggttacaa cccagctgct    420
gtcgctttcg tacccatttc tgg                                            443

<210> SEQ ID NO 224
<211> LENGTH: 427
<212> TYPE: DNA
<213> ORGANISM: Zea mays

<400> SEQUENCE: 224
gaaatgaata agcgtgggtg ctcgacaagc tcaaggctga gcgtgagaga ggtatcacca     60
ttgatattgc tctgtggaag tttgagacca ccaagtacta ctgcacggtc attgatgccc    120
ctggacaccg tgacttcatc aagaacatga tcactggtac ctcccaggct gactgtgctg    180
tccttatcat tgactccacc actggtggtt ttgaggctgg tatctccaag gatggccaga    240
cccgtgaaca tgctctcctt gcgttcaccc ttggagtgaa gcagatgatt tgctgctgca    300
acaagatgga tgcaaccact cccaaatact ccaaggcacg ttatgaagag attgtgaagg    360
aagtctcatc ctacctcaag aaagttgggt acaaccctga taagattgcc tttgttccca    420
tttctgg                                                              427
```